US011932856B2

(12) United States Patent
Mali et al.

(10) Patent No.: US 11,932,856 B2
(45) **Date of Patent: *Mar. 19, 2024**

(54) RNA TARGETING OF MUTATIONS VIA SUPPRESSOR TRNAS AND DEAMINASES

(71) Applicant: The Regents of the University of California, Oakland, CA (US)

(72) Inventors: Prashant Mali, La Jolla, CA (US); Dhruva Katrekar, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 787 days.

This patent is subject to a terminal disclaimer.

(21) Appl. No.: 16/490,494

(22) PCT Filed: Mar. 2, 2018

(86) PCT No.: PCT/US2018/020762

§ 371 (c)(1),
(2) Date: Aug. 30, 2019

(87) PCT Pub. No.: WO2018/161032

PCT Pub. Date: Sep. 7, 2018

(65) Prior Publication Data

US 2020/0263180 A1 Aug. 20, 2020

Related U.S. Application Data

(60) Provisional application No. 62/551,732, filed on Aug. 29, 2017, provisional application No. 62/466,961, filed on Mar. 3, 2017.

(51) Int. Cl.

| | |
|---|---|
| ***C12N 15/113*** | (2010.01) |
| ***A61P 21/00*** | (2006.01) |
| ***C12N 9/78*** | (2006.01) |
| ***C12N 15/115*** | (2010.01) |
| *A61K 38/00* | (2006.01) |

(52) U.S. Cl.

CPC ............ *C12N 15/115* (2013.01); *A61P 21/00* (2018.01); *C12N 9/78* (2013.01); *C12Y 305/04* (2013.01); *A61K 38/00* (2013.01); *C12N 15/113* (2013.01); *C12N 15/1137* (2013.01); *C12N 2310/20* (2017.05); *C12N 2310/531* (2013.01); *C12N 2320/34* (2013.01)

(58) Field of Classification Search

CPC ...... C12N 15/115; C12N 9/78; C12N 15/113; C12N 15/1137; C12N 2310/20; C12N 2310/531; C12N 2320/34; A61P 21/00; C12Y 305/04; A61K 38/00

See application file for complete search history.

(56) References Cited

U.S. PATENT DOCUMENTS

| | | | |
|---|---|---|---|
| 5,759,833 A | 6/1998 | Shiba et al. | |
| 7,709,616 B2 | 5/2010 | Bentwich et al. | |
| 9,650,627 B1 | 5/2017 | Rosenthal et al. | |
| 9,745,576 B2 | 8/2017 | de Visser et al. | |
| 9,890,379 B2 | 2/2018 | De Kimp et al. | |
| 10,450,568 B2 | 1/2019 | Butler et al. | |
| 10,479,995 B2 | 11/2019 | Vargeese et al. | |
| 10,689,646 B2 | 6/2020 | De Kimp et al. | |
| 11,479,775 B2 * | 10/2022 | Mali ........................ | C12N 9/78 |
| 2002/0156042 A1 | 10/2002 | Panchal et al. | |
| 2007/0050146 A1 | 3/2007 | Bentwich et al. | |
| 2019/0040383 A1 | 2/2019 | Klein et al. | |
| 2019/0218552 A1 | 7/2019 | Turunen et al. | |
| 2020/0140857 A1 | 5/2020 | De Kimpe et al. | |
| 2020/0149043 A1 | 5/2020 | De Visser et al. | |
| 2020/0283755 A1 | 9/2020 | Zhang et al. | |
| 2020/0291383 A1 | 9/2020 | Mandel et al. | |

FOREIGN PATENT DOCUMENTS

| | | | |
|---|---|---|---|
| DE | 102015012522.2 | B3 | 6/2016 |
| EP | 3234134 | B1 | 10/2017 |
| EP | 3323890 | A1 | 5/2018 |
| EP | 3353299 | A1 | 3/2020 |
| EP | 3642342 | A1 | 4/2020 |
| EP | 3712269 | A1 | 9/2020 |
| GB | 1521987.6 | | 12/2015 |
| JP | 2002-508959 | A | 3/2002 |
| JP | 2016-182140 | A | 10/2016 |
| WO | 2013075035 | A1 | 5/2013 |
| WO | 2014011053 | A1 | 1/2014 |
| WO | 2015/120197 | A1 | 8/2015 |
| WO | 2005/094370 | A2 | 10/2015 |

(Continued)

OTHER PUBLICATIONS

Senis et al. (Biotechnol. J. 2014, 9:1402-1412). (Year: 2014).*
Fujisawa, Masaki, Office Action, Japan Patent Office, Application No. 2019-547704, dated Jan. 4, 2022.
Abudayyeh, 0. 0. et al., "C2c2 is a single-component programmable RNA-guided RNA-targeting CRISPR effector", Science, Aug. 5, 2016, 353(6299), pp. 1-23.
Abudayyeh, 0. 0. et al., "RNA targeting with CRISPR-Cas13a", Nature, Oct. 12, 2017, 550(7675), pp. 280-284.
Adamala, K. P., Martin-Alarcon, D. A & Boyden, E. S., "Programmable RNA-binding protein composed of repeats of a single modular unit", PNAS, Apr. 26, 2016, 113(19), E2579-E2588.
Aruscavage et al., "A phylogenetic analysis reveals an unusual sequence conservation within introns involved in RNA editing" RNA, Feb. 1, 2000, 6:257-269.

(Continued)

*Primary Examiner* — J. E. Angell
(74) *Attorney, Agent, or Firm* — Gavrilovich, Dodd & Lindsey LLP

(57) ABSTRACT

Aspects of the disclosure relate to a gene therapy approach for diseases, disorders, or conditions caused by mutation in the stop codon utilizing modified tRNA. At least 10-15% of all genetic diseases, including muscular dystrophy (e.g. Duchene muscular dystrophy), some cancers, beta thalassemia, Hurler syndrome, and cystic fibrosis, fall into this category. Not to be bound by theory, it is believed that this approach is safer than CRISPR approaches due to minimal off-target effects and the lack of genome level changes.

18 Claims, 32 Drawing Sheets

Specification includes a Sequence Listing.

(56) References Cited

FOREIGN PATENT DOCUMENTS

| | | | |
|---|---|---|---|
| WO | 2016094845 | A2 | 6/2016 |
| WO | 2016097212 | A1 | 6/2016 |
| WO | 2017/010556 | A | 1/2017 |
| WO | 2017050306 | A1 | 3/2017 |
| WO | 2017201091 | A1 | 11/2017 |
| WO | 2017220751 | A1 | 12/2017 |
| WO | 2018134301 | A1 | 1/2018 |
| WO | 2018041973 | A1 | 3/2018 |
| WO | 2019023680 | A1 | 1/2019 |
| WO | 2019071048 | A1 | 4/2019 |
| WO | 2019071274 | A1 | 4/2019 |
| WO | 2019/217944 | A1 | 11/2019 |
| WO | 2020/023655 | A1 | 1/2020 |
| WO | 2020001793 | A1 | 1/2020 |
| WO | 2020/074001 | A1 | 4/2020 |
| WO | 2020/154342 | A1 | 7/2020 |
| WO | 2020/154343 | A2 | 7/2020 |
| WO | 2020/154344 | A2 | 7/2020 |

OTHER PUBLICATIONS

Bidou, L., Allamand, V., Rousset, J .- P. & NAMY, 0., “Sense from nonsense: therapies for premature stop codon diseases”, Trends Mol. Med., Nov. 2012, vol. 18, Issue 11, pp. 679-688.

Bengtsson, N. E. et al., “Muscle-specific CRISPR/Cas9 dystrophin gene editing ameliorates pathophysiology in a mouse model for Duchenne muscular dystrophy”, Nat. Commun., Feb. 2017, 8(14454), pp. 1-10.

Bulfield, G., Siller, W. G., Wight, P. A. & Moore, K. J., “X chromosome-linked muscular dystrophy (mdx) in the mouse”, Proc. Natl. Acad. Sci. U.S. A., Feb. 1984, vol. 81, 1189-92.

Capecchi et al., “Altering the Genome by Homologous Recombination”, Science, Jun. 16, 1989, vol. 244, Issue 4910, pp. 1288-129.

Capone, J. P., Sharp, P.A. & Rajbhandary, U. L., “Amber, ochre and opal suppressor IRNA genes derived from a human serine tRNA gene”, The EMBO Journal, Jan. 1985, 4(1), pp. 213-221.

Chatterjee, A., Xiao, H., Bollong, M., Ai, H. & SCHULTZ, p. G., “Efficient viral delivery system for unnatural amino acid mutagenesis in mammalian cells”, PNAS, Jul. 16, 2013, vol. 110, No. 29, p. 11803-11808.

Chew, W. L. et al., “A multi-functional AAV-CRISPR-Cas9 and its host response”, Nat. Methods, Oct. 2016, 13 (10), pp. 868-887.

Cho, S. W. et al., “Analysis of off-target effects of CRISPR/Cas-derived RNA-guided endonucleases and nickases”, Genome Res., Jan. 2014, vol. 24, pp. 132-141.

Christian, M. et al., “Targeting DNA Double-Strand Breaks with TAL Effector Nucleases,” Genetics, Oct. 2010, vol. 186, Issue 2, pp. 757-761.

Cirak, S. et al., “Exon skipping and dystrophin restoration in patients with Duchenne muscular dystrophy after systemic phosphorodiamidate morpholino oligomer treatment: an open label, phase 2, dose escalation study,” Lancet, Aug. 13, 2011, 378, 595-605.

Cong, L., Ran, F., Cox, D., Lin, S. & Barretto, R., “Multiplex Genome Engineering Using CRISPR/Cas Systems”, Science, Feb. 15, 2013, vol. 339(6121), pp. 819-823.

Cox, D. B. T. et al., “RNA editing with CRISPR-Cas13”, Science, Nov. 24, 2017, vol. 358(6366), pp. 1019-1027.

Desterro et al., “Dynamic association of RNA-editing enzymes with the nucleolus”, J Cell Sci., May 2003; 116(Pt 9): 1805-18.

East-Seletsky, A et al., “Two Distinct RNase Activities of CRISPR-C2c2 Enable Guide RNA Processing and RNA Detection”, Nature, Oct. 13, 2016, 538(7624), 270-273.

East-Seletsky, A, O’connell, M. R., Burstein, D., Knott, G. J. & Doudna, J. A., “RNA Targeting by Functionally Orthogonal Type VI-A CRISPR-Cas Enzymes”, Mol. Cell, May 4, 2017, 66, Issue 3, pp. 373-383.

Ernst, R. J. et al., “Genetic code expansion in the mouse brain”, Nat Chem Biol., Oct. 2016, 12(10), pp. 776-778.

Fu, Y., Sander, J. D., Reyon, D., Cascio, V. M. & Joung, J. K., “Improving CRISPR-Cas nuclease specificity using truncated guide RNAs”, Nat. Biotechnol., Mar. 2014, 32(3), 279-284.

Fukuda et al., “Construction of a guide-RNA for site-directed RNA mutagenesis utilising intracellular A-to-I RNA editing”, Sci. Rep. , Feb. 2, 2017, 41478, pp. 1-49.

Gaudelli, N. M. et al., “Programmable base editing of A•T to G•C in genomic DNA without DNA cleavage”, Nov. 23, 2017, Nature, 551(7681), pp. 464-471.

Gautier, A et al., “Genetically Encoded Photocontrol of Protein Localization in Mammalian Cells”, J. Am. Chem. Soc. , Mar. 31, 2010, 132(12), 4086-4088.

Geslain, R. & Pan, T., “Functional Analysis of Human (RNA Isodecoders”, J Mol Biol, Feb. 26, 2010, vol. 396 (3), pp. 1-20.

Gootenberg, J. S. et al., “Nucleic acid detection with CRISPR-Cas13a/C2c2”, Science, Apr. 28, 2017, vol. 356 (6336), pp. 438-442.

Greiss, S. & Chin, J. W., “Expanding the Genetic Code of an Animal”, J American Chemical Society, Aug. 8, 2011, vol. 133(36), 14196-14199.

Grieger, J. C., Choi, V. W. & Samul Ski, R. J., “Production and characterization of adeno-associated viral vectors”, Nat. Protoc., Nov. 9, 2006, vol. 1, No. 3, 1412-1428.

Han, S et al., “Expanding the genetic code of Mus musculus”, Nat. Commun., Feb. 21, 2017, vol. 8(14568), pp. 1-7.

Hendel, A et al., “Chemically modified guide RNAs enhance CRISPR-Cas genome editing in human primary cells”, Nature Biotechnology, Sep. 2015, 33(9), pp. 985-989.

Higuchi et al., “RNA Editing of AMPA Receptor Subunit GluR-B: A Base-Paired Intron-Exon Structure Determines Position and Efficiency”, Cell, Dec. 31, 1993; 75: 1361-1370.

Hodges, P. E. & Rosenberg, L. E., “The spfash mouse: A missense mutation in the ornithine transcarbamylase gene also causes aberrant mRNA splicing”, Proc. Natl. Acad. Sci. USA, Jun. 1, 1989, vol. 86, No. 11, 4142-4146.

Jinek, M. et al., “A programmable dual RNA-guided DNA endonuclease in adaptive bacterial immunity,” Science, Aug. 17, 2012, vol. 337(6096), pp. 816-821.

Kim, K. et al., “Highly efficient RNA-guided base editing in mouse embryos”, Nat. Biotechnol., May 2017, vol. 35, No. 5, pp. 435-437.

Komor, A. C., Kim, Y. B., Packer, M. S., Zuris, J. A. & Liu, D. R., “Programmable editing of a target base in genomic DNA without double-stranded DNA cleavage”, Nature, Apr. 20, 2016, 533(7603), 420-424.

Kuttan, A. & Bass, B. L., “Mechanistic insights into editing-site specificity of ADARs”, PNAS, Nov. 5, 2012, 109, E3295-E3304.

Lennox et al., “Chemical modification and design of anit-miRNA oligonucleotides”, Gene Ther., Dec. 2011; 18 (12): 1111-20.

Li, K. et al., “Ochre Suppressor Transfer Rna Restored Dystrophin Expression in MDX Mice,” Life Sci., Jan. 1997, vol. 61(15), PL205-PL209.

Lomeli et al., “Control of Kinetic Properties of AMPA Receptor Channels by Nuclear RNA Editing” Science, Dec. 9, 1994, 266(5191): pp. 1709-1713.

Long, C. et al., “Prevention of muscular dystrophy in mice by CRISPR/Cas9-mediated editing of germline DNA”, Science, Sep. 5, 2014, vol. 345(6201), pp. 1184-1188.

Long, C. et al., “Postnatal genome editing partially restores dystrophin expression in a mouse model of muscular dystrophy”, Science, Jan. 22, 2016, vol. 351(6271), pp. 400-403.

Macbeth et al., “Evidence for auto-inhibition by the N terminus of hADAR2 and activation by dsRNA binding”, RNA, Oct. 2004, vol. 10, pp. 1563-1571.

Mah, J., “Current and emerging treatment strategies for Duchenne muscular dystrophy”, Neuropsychiatr. Dis. Treat., Jul. 22, 2016, vol. 12, 1795-1807.

Mali, P. et al., “RNA-Guided Human Genome Engineering via Cas9”, Science, Feb. 15, 2013, vol. 339(6121), pp. 823-826.

Malik V. et al., “Gentamicin-Induced Readthrough of Stop Codons in Duchenne Muscular Dystrophy”, Ann. Neurol., May 25, 2010, vol. 67(6), pp. 771-780.

Melcher, T. et al., “A mammalian RNA editing enzyme”, Nature, Feb. 1, 1996, vol. 379, pp. 460-464.

(56) References Cited

OTHER PUBLICATIONS

Montiel-Gonzalez et al., "Correction of mutations within the cystic fibrosis transmembrane conductance regulator by site-directed RNA editing", PNAS, Nov. 5, 2013, 110(45), pp. 18285-18290.
Mort, M., Ivanov, D., Cooper, D. N. & Chuzhanova, N.A., "A Meta-Analysis of Nonsense Mutations Causing Human Genetic Disease", Hum. Mutation, Aug. 1, 2008, 29(8), 1037-1047.
Nelson, C. E. et al., "In vivo genome editing improves muscle function in a mouse model of Duchenne muscular dystrophy," Science, Jan. 22, 2016, vol. 351(6271), pp. 403-407.
Nishikura, "Functions and Regulation of RNA Editing by ADAR Deaminases", Annu Rev Biochem., Oct. 12, 2010, 79, pp. 321-349.
Biddle et al., "Modification of Orthogonal tRNAs: Unexpected Consequences for Sense Codon Reassignment," Nucleic Acids Research, vol. 44, No. 21, pp. 10042-10050, Oct. 23, 2016.
Gatti, "Smrt Compounds Correct Nonsense Mutations in Primary Immunodeficiency and Other Genetic Models," Annals of the New York Academy of Sciences, vol. 1250, pp. 1-13, Feb. 2012.
Katrekar et al., "In vivo RNA Targeting of Point Mutations via Suppressor tRNAs and Adenosine Deaminases," BioRxiv, pp. 1-25, Oct. 27, 2017.
Thomas, Shane, International Search Report & Written Opinion, PCT/US2018/020762, United States Patent & Trademark Office, Jul. 17, 2018.
Mohri, Mineko, International Preliminary Examination Report on Patentability & Written Opinion, PCT/US2018/020762, The International Bureau of WIPO, Sep. 12, 2019.
Bordeira-Carrico et al., "Rescue of wild-type E-cadherin expression from nonsense-mutated cancer cells by a suppressor-tRNA", European Journal of Human Genetics, 2014, 22, 1085-1092.
Buvoli et al., "Suppression of Nonsense Mutations in Cell Culture and Mice by Multimerized Suppressor tRNA Genes", Mol Cell Biol., May 2000, 20(9): 3116-3124.
Chang et al., "Suppression of the nonsense mutation in homozygous BO thalassaemia", Nature, Oct. 18, 1979:281(5732):602-3.
Garncarz et al., "A high-throughput screen to identify enhancers of ADAR-mediated RNA-editing", RNA Biology, 2013, 10:2, 192-204.
Ho et al., "In vivo aminoacylation of human and Xenopus suppressor tRNAs constructed by site-specific mutagenesis", Proc Natl Acad Sci U S A, Apr. 1987, 84(8):2185-8.
Hudziak et al., "Establishment of Mammalian Cell Lines Containing Multiple Nonsense Mutations and Functional Suppressor tRNA Genes", Cell, Nov. 1982, vol. 31, 127-146.
Kimble et al., "Suppression of an amber mutation by microinjection of suppressor tRNA in C. elegans", Nature, , Sep. 3, 19820, 299 (5882):456-458.
Kiselev et al., Suppression of Nonsense Mutations in the Dystrophin Gene By a Suppressor tRNA Gene, Molecular Biology, vol. 36, No. 1, 2002, pp. 30-33.
Koukuntla et al., "U6 promoter-enhanced GlnUAG suppressor tRNA has higher suppression efficacy and can be stably expressed in 293 cells", J Gene Med, Feb. 2013, 15(2):93-101.
Aski et al., "An amber suppressor tRNA gene derived by site-specific mutagenesis: Cloning and function in mammalian cells", Proc. Natl. Acad. Sci. USA, Oct. 1982, vol. 79, pp. 5813-5817.
Lueck et al., "Engineered tRNA suppression of a CFTR nonsense mutation", bioRxiv, Nov. 19, 2016.
Lueck et al., "Engineered transfer RNAs for suppression of premature termination condons", Nature Commun., Feb. 2019. 18; 10(1)822.
Panchal et al. "Partial Functional Correction of Xeroderma Pigmentosum Group A Cells by Suppressor tRNA", Human Gene Therapy, 1999, vol. 10, No. 13, 2209-19.
Sako et al., "A novel therapeutic approach for genetic diseases by introduction of suppressor tRNA", Nucleic Acids Symposium Series , 2006, No. 50, 239-240.
Temple et al., "Construction of a functional human suppressor tRNA gene: an approach to gene therapy for B- thalassaemia", Nature, Apr. 1, 1982, 296, 537-540.
Woolf et al., "Toward the therapeutic editing of mutated RNA sequences", Proc. Natl. Acad. Sci. USA, Aug. 1995, vol. 92, pp. 8298-8302.
Daniel et al. "Editing inducer elements increases A-to-I editing efficiency in the mammalian transciptome," Genome Biology, 2017, 18:195, pp. 1-16.
Eggington et al., "Predicting sites of ADAR editing in double-stranded RNA," Nature Communications. Feb. 2011, 2:319, pp. 1-9.
Garncarz et al., "A high-throughput screen to identify enhancers of ADAR-mediated RNA editing," RNA Biology, Feb. 2013, 10:2, 192-204.
Katrekar et al., "In vivo RNA editing of point mutations via RNA-guided adenosine deaminases", Nature Methods, Mar. 2019, vol. 16, 239-242.
Lueck et al. "Engineered transfer RNA for suppression of premature termination codons," Nature Communications, 2019, 10:822, pp. 1-11.
Merkle et al., "Precise RNA editing by recruiting endogenous ADARs with antisense oligonucleotides," Nature Biotechnology, Jan. 27, 2019, 37(2): 133-138.
Andres, Serge, Extended European Search Report, European Patent Office, Application No. 18760638.9, dated Oct. 15, 2021.
Yamashita, Takenari et al., "Rescue of amyotrophic lateral sclerosis phenotype in a mouse model by intravenous AAV9-ADAR2 delivery to motor neurons", EMBO Mol Med, Nov. 2013, 5, pp. 1710-1719.
Nose et al., "Short-Chain Guide RNA for Site-Directed A-to-I RNA Editing", Nucleic Acid Therapeutics, Nov. 10, 2020; 00(00): 1-10.
O'Connell, M. R. et al., "Programmable RNA recognition and cleavage by CRISPR/Cas9", Nature, Dec. 11, 2014, 516(7530), 263-266.
Pinello, "Analyzing CRISPR genome editing experiments with CRISPResso", Nat. Biotechnol., Jul. 12, 2016, vol. 34(7), pp. 695-697.
Reider et al., "Tertiary structural elements determine the extent and specificity of messenger RNA editing", Nat. Commun., Feb. 2013; 4: 2232, pp. 1-11.
Robinson-Hamm, J. N. & Gersbach, C. A., "Gene therapies that restore dystrophin expression for the treatment of Duchenne muscular dystrophy", Hum. Genet., Sep. 2016, 135(9), 1029-1040.
Rueter, S. M., et al., "Glutamate Receptor RNA Editing in Vitro by Enzymatic Conversion of Adenosine to Inosine", Science, Mar. 10, 1995, vol. 267(5203), pp. 1491-1494.
Schade et al., "A 6 bp Z-DNA hairpin binds two Za domains from the human RNA editing enzyme ADAR1", Febs Letters, Sep. 3, 1999, 458, 27-31.
Schaefer, K. A et al., "Unexpected mutations after CRISPR-Cas9 editing in vivo", Nature, May 30, 2017, 14(6), pp. 547-548.
Schneider et al., "Optimal guideRNAs for re-directing deaminase activity of hADAR1 and hADAR2 in trans" Nucleic Acids Research, Apr. 17, 2014, vol. 42, No. 10, e87, pp. 1-9.
Sicinski, P. et al., "The Molecular Basis of Muscular Dystrophy in the mdx Mouse: A Point Mutation", Science, Jun. 1989, 244(4912), 1578-80.
Stefl et al., "A novel RNA pentaloop fold involved in targeting ADAR2", RNA, May 2005, vol. 11(5), pp. 592-597.
Svoboda et al., "Hairpin RNA: a secondary structure of primary importance", Cell. Mol. Life Sci., Mar. 29, 2006, (7-8), pp. 901-908.
Tabebordbar, M. et al., "In vivo gene editing in dystrophic mouse muscle and muscle stem cells#", Science, Jan. 22, 2016, vol. 351(6271), pp. 407-411.
Takata, M. et al., "Homologous recombination and non-homologous end-joining pathways of DNA double-strand break repair have overlapping roles in the maintenance of chromosomal integrity in vertebrate cells", EMBO J., Sep. 15, 1998, vol. 17, Issue 18, pp. 5497-5508.
Tan, M. H. et al., "Dynamic landscape and regulation of RNA editing in mammals", Nature, Oct. 11, 2017, 550 (7675), 249-254.
Tuerk, C et al., "CUUCGG hairpins: Extraordinarily stable RNA secondary structures associated with various biochemical processes (hairpin stability/sequence analysis/reverse transcriptase)", Proc. Natl. Acad. Sci. USA, Biochemistry, Mar. 1988, vol. 85, pp. 1364-1368.

(56) References Cited

OTHER PUBLICATIONS

Urnov, F. D. et al., "Highly efficient endogenous human gene correction using designed zinc-finger nucleases," Nature, Jun. 2005, 435, pp. 646-651.
Urnov, F. D., Rebar, E. J., Holmes, M. C., Zhang, H. S. & Gregory, P. D., "Genome editing with engineered zinc finger nucleases", Nat. Rev. Genet., Sep. 2010, 11, pp. 636-646.
Varani, G., Cheong, C. & Tinoco, I., "Structure of an Unusually Stable RNA Hairpint," Biochemistry, Apr. 2, 1991, 30(13), 3280-3289.
Vogel et al., "Improving Site-Directed RNA Editing In vitro and in Cell Culture by Chemical Modification of the GuideRNA", Angewandte Chemie, May 28, 2014, 53(24), pp. 6267-6271.
Wagner, K. R. et al., "Gentamicin Treatment of Duchenne and Becker Muscular Dystrophy Due to Nonsense Mutations", Ann. Neurol., Jun. 5, 2001, vol. 49, Issue 6, pp. 706-711.
Wang, D. et al., "Adenovirus-Mediated Somatic Genome Editing of Pten by CRISPR/Cas9 in Mouse Liver in Spite of Cas9-Specific Immune Responses", Hum. Gene Ther., Jun. 17, 2015, vol. 26, No. 7, pp. 432-442.
Wang, L., Brock, A., Herberich, B. & Schultz, P. G., "Expanding the Genetic Code of *Escherichia coli*", Science, May 2001, vol. 292(5516), pp. 498-500.
Welch, E. M. et al., "PTC124 targets genetic disorders caused by nonsense mutations", Nature, May 3, 2007, vol. 447, 87-91.
Wettengel, J. et al., "Harnessing human ADAR2 for RNA repair—Recoding a PINK1 mutation rescues mitophagy," Oct. 7, 2016, Nucleic Acids Res., vol. 45, Issue 5, pp. 2797-2808, 2017.
Wong et al., "Substrate recognition by ADAR1 and ADAR2", RNA, Jun. 1, 2001, 7(6), pp. 846-858.
Yang, Y. et al., "A dual AAV system enables the Cas9-mediated correction of a metabolic liver disease in newborn mice," Nat. Biotechnol., Mar. 2016, 34(3), 334-338.
Fujisawa, Masaki, Final Office Action, Application No. 2019-547704, Japan Patent Office, dated Oct. 18, 2022.
Bass, B. L., "RNA Editing by Adenosine Deaminases that Act on RNA", Annual Review of Biochemistry, Jul. 2002, 71 (1), 817-846.
Casey, J. L., "Control of ADAR1 Editing of Hepatitis Delta virus RNAs", Adenosine Deaminases Acting on RNA (ADARs) and A-to-I Editing, Jan. 1, 2011, 123-143.
Chang, J., Sigal, L. J., Lerro, A., & Taylor, J., "Replication of the Human Hepatitis Delta Virus Genome is Initiated in Mouse Hepatocytes Following Intravenous Injection of Naked DNA or RNA Sequences", Journal of Virology, Apr. 1, 2001, 75(7), 3469-3473.
Gallo, A., & Locatelli, F., "ADARs: allies or enemies? The importance of A-to-I RNA editing in human disease: from cancer to HIV-1", Biological Reviews, Jun. 20, 2011, 87(1), 95-110.
Modahl, L. E., & Lai, M. M., "Transcription of Hepatitis Delta Antigen mRNA Continues throughout Hepatitis Delta Virus (HDV) Replication: a New Model of HDV RNA Transcription and Replication", Journal of Virology, Jul. 1, 1998, 72(7), 5449-5456.
Nishikura, K., "Editor meets silencer: crosstalk between RNA editing and RNA interference", Nature Reviews Molecular and Cellular Biology, Dec. 1, 2006, 7, 919-31.

* cited by examiner

FIGURE 5

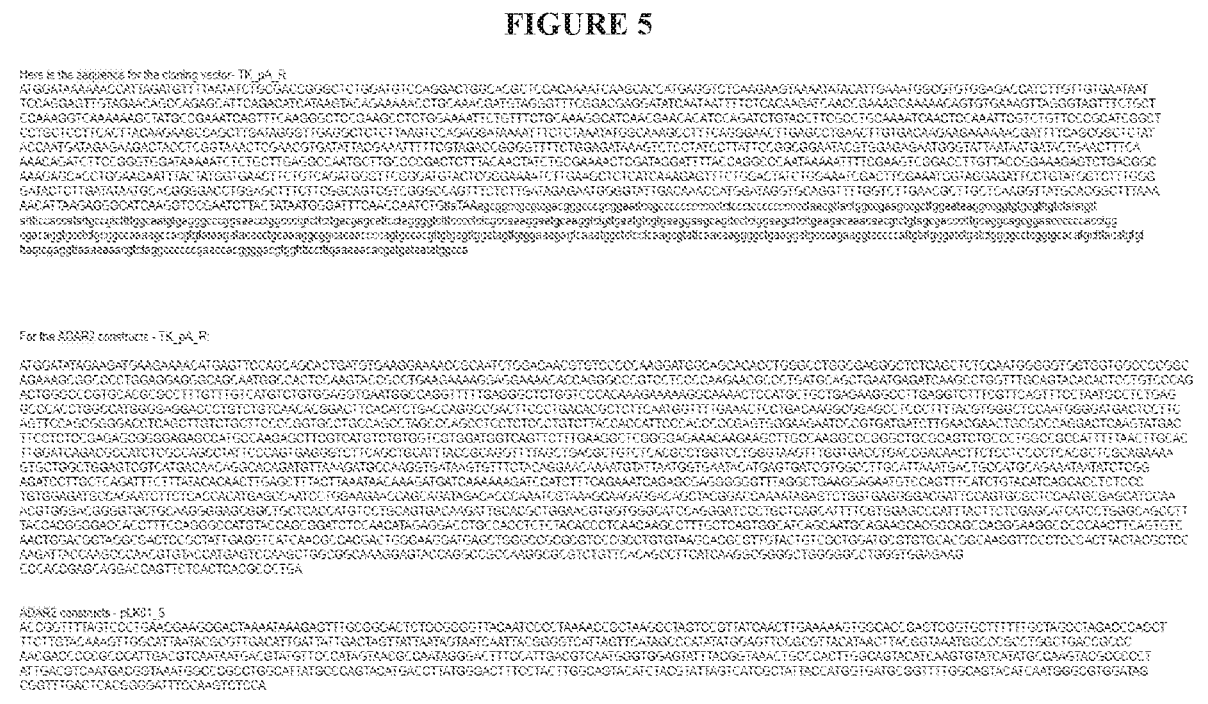

Here is the sequence for the cloning vector- TK_pA_R

[illegible]

For the ADAR2 constructs - TK_pA_R:

[illegible]

ADAR2 constructs - pLK01_5

[illegible]

FIGURE 9
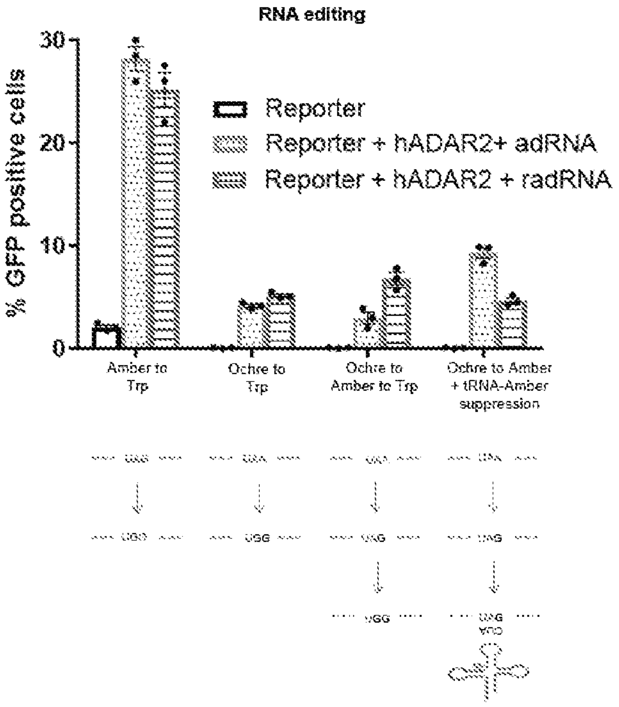
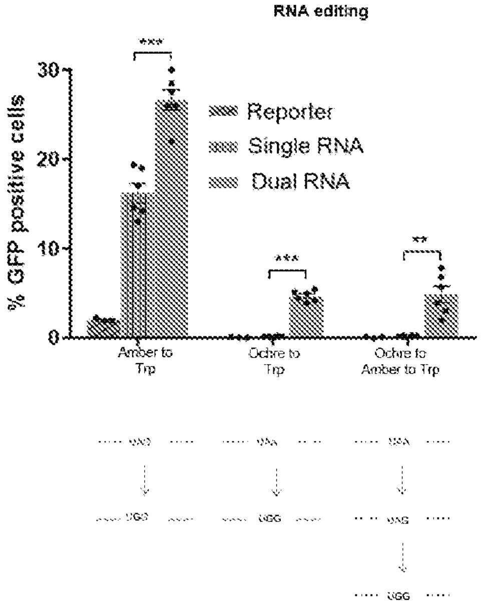

FIGURE 10
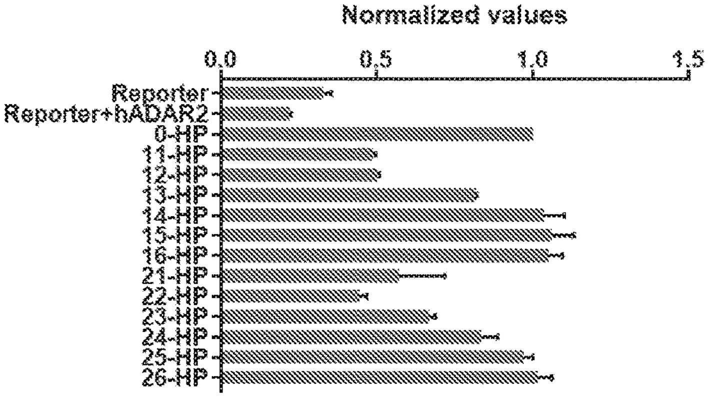
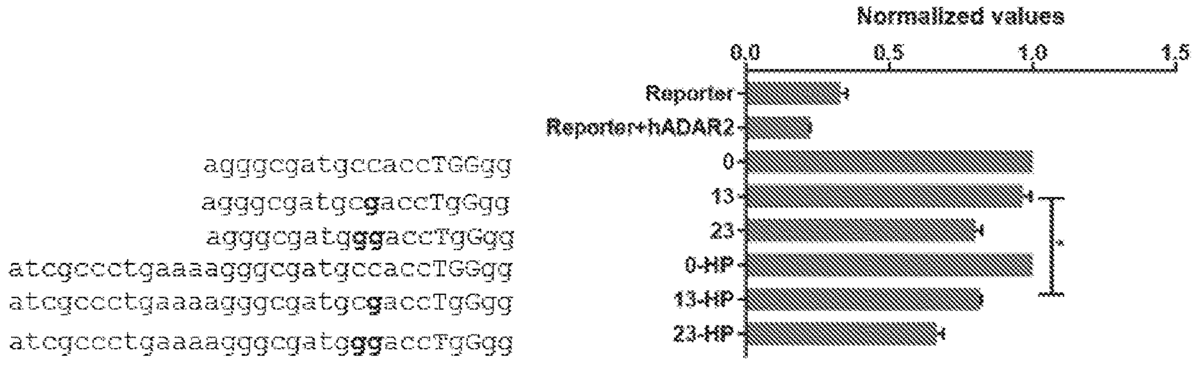

FIGURE 12
(a)
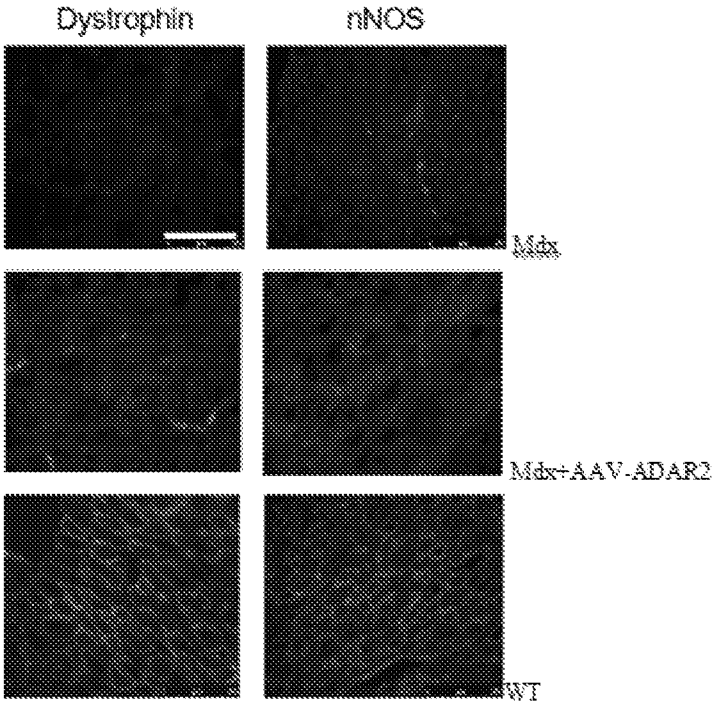
(b)
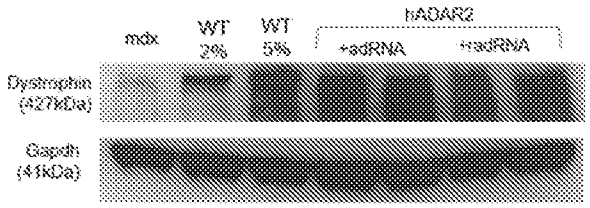
(c)
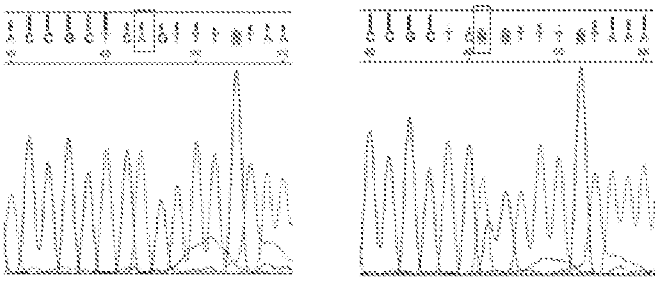

FIGURE 18
a
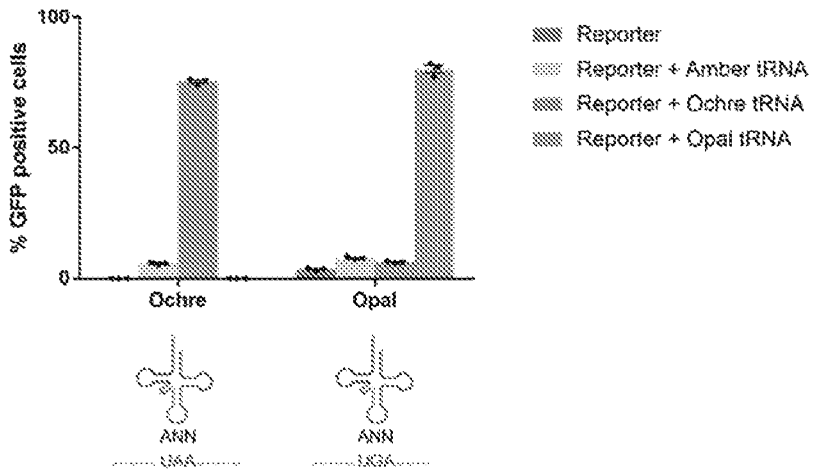
b
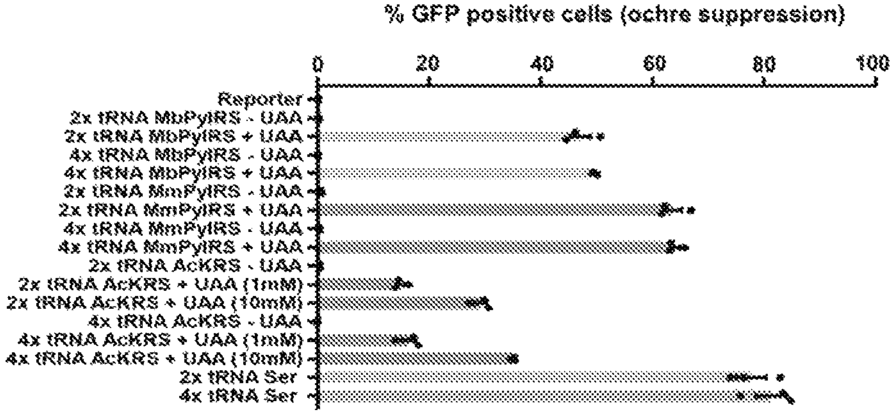

FIGURE 22
a
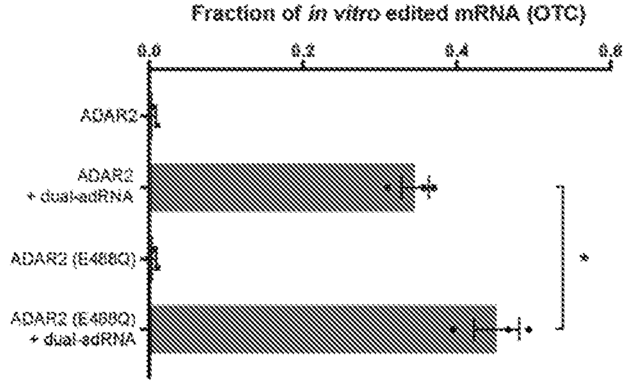
b
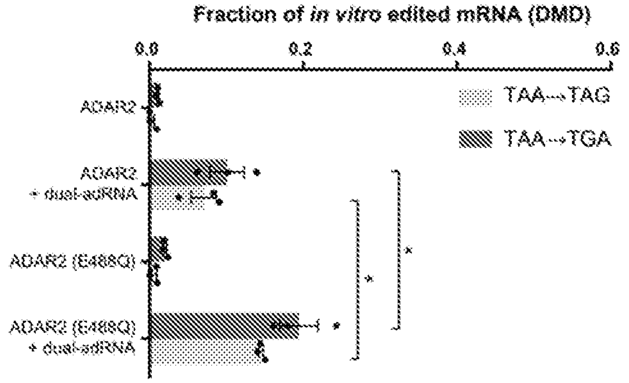

FIGURE 23
a
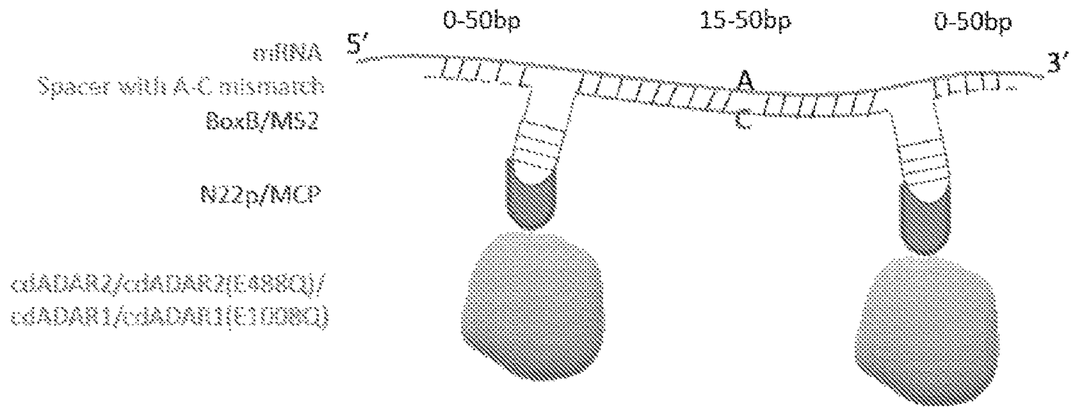
b
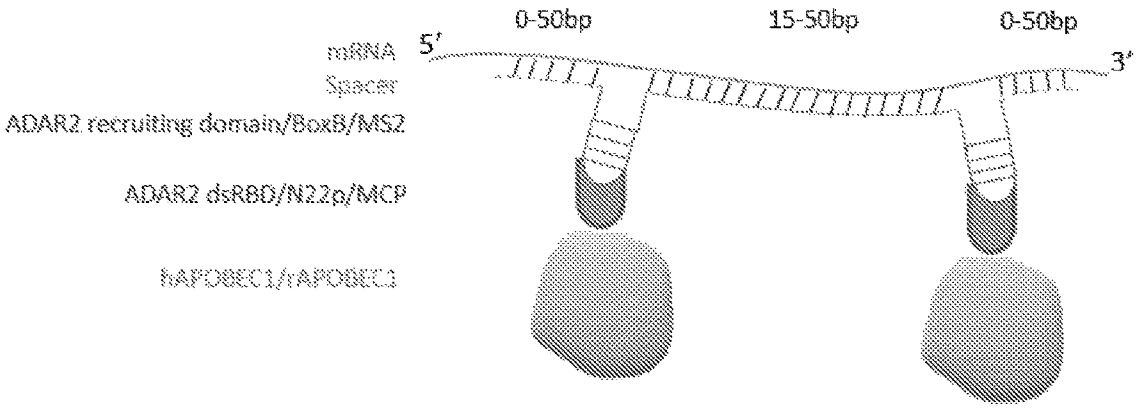

FIGURE 23 contd.
c
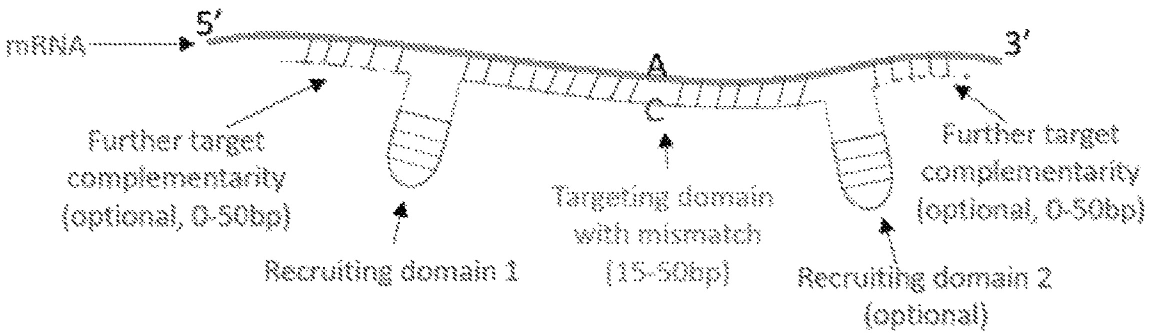
d
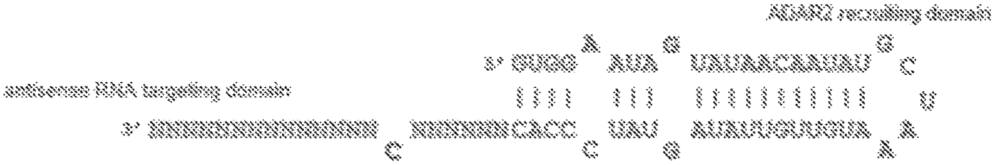

FIGURE 24
a
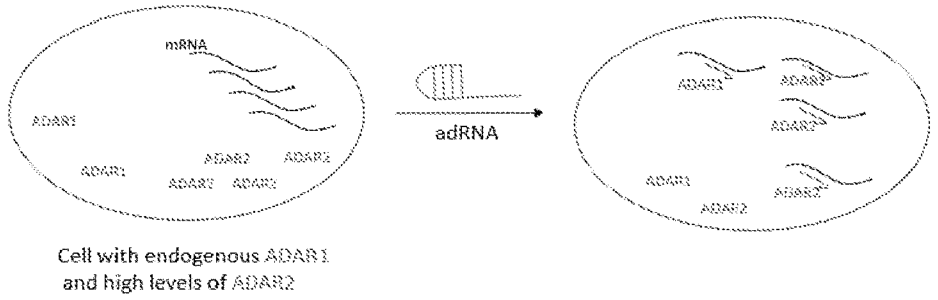
b
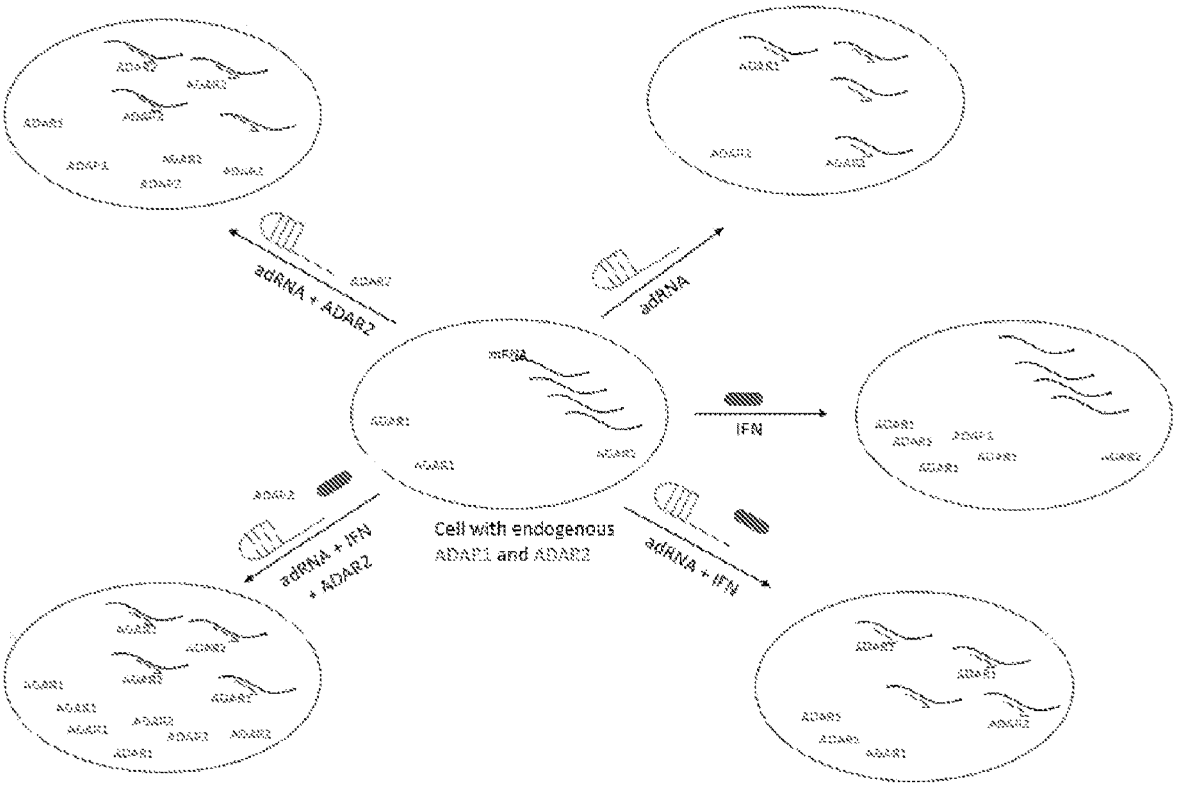

FIGURE 29

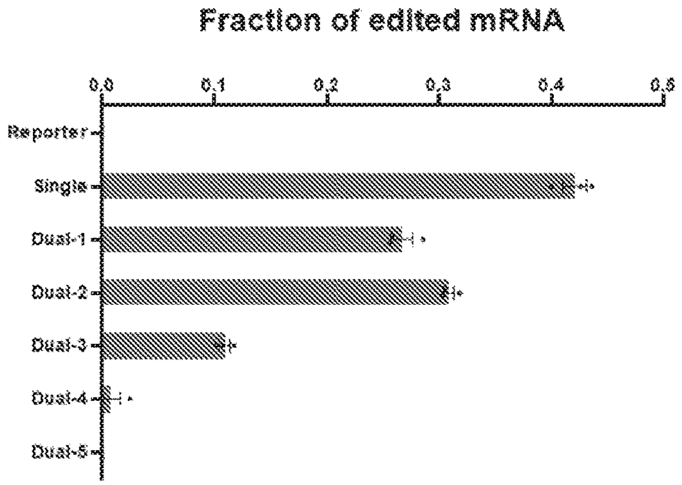

Single:

GTGGAATAGTATAACAATATGCTAAATGTTGTTATAGTATCCCACACAAACCGAGCGGTGTCTGT

Dual 1:

GTGGAATAGTATAACAATATGCTAAATGTTGTTATAGTATCCCACCAAACCGAGCGGTGTCTGTGGTGGAATAGTATAACAAT
ATGCTAAATGTTGTTATAGTATCCCAC

Dual 2:

GTGGAATAGTATAACAATATGCTAAATGTTGTTATAGTATCCCACTACAAACCGAGCGGTGTCTGGTGGAATAGTATAACAAT
ATGCTAAATGTTGTTATAGTATCCCAC

Dual 3:

GTGGAATAGTATAACAATATGCTAAATGTTGTTATAGTATCCCACTTTACAAACCGAGCGGTGTCGTGGAATAGTATAACAAT
ATGCTAAATGTTGTTATAGTATCCCAC

Dual 4:

GTGGAATAGTATAACAATATGCTAAATGTTGTTATAGTATCCCACGTTTTACAAACCGAGCGGTGGTGGAATAGTATAACAAT
ATGCTAAATGTTGTTATAGTATCCCAC

Dual 5:

GTGGAATAGTATAACAATATGCTAAATGTTGTTATAGTATCCCACAAGTTTTACAAACCGAGCGGGTGGAATAGTATAACAAT
ATGCTAAATGTTGTTATAGTATCCCAC

RNA TARGETING OF MUTATIONS VIA SUPPRESSOR TRNAS AND DEAMINASES

CROSS REFERENCE TO RELATED APPLICATION

This application is a U.S. National Stage Application filed under 35 U.S.C. § 371 and claims priority to International Application No. PCT/US2018/020762, filed Mar. 2, 2018, which claims priority under 35 U.S.C. 119(e) to U.S. Ser. No. 62/466,961, filed Mar. 3, 2017, and U.S. Ser. No. 62/551,732, filed Aug. 29, 2017, the entirety of each of which are incorporated by reference herein.

STATEMENT REGARDING GOVERNMENT SUPPORT

This invention was made with government support under Grant No. R01HG009285 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 25, 2019, is named 00015-365US1_SL.txt and is 220,085 bytes in size.

BACKGROUND

Aspects of the disclosure relate to a gene therapy approach for diseases, disorders, or conditions caused by mutation in the stop codon using modified tRNA. At least 10-15% of all genetic diseases, including muscular dystrophy (e.g. Duchene muscular dystrophy), some cancers, beta thalassemia, Hurler syndrome, and cystic fibrosis, fall into this category. Not to be bound by theory, it is believed that this approach is safer than CRISPR or TALEN approaches due to minimal off-target effects and the lack of genome level changes.

SUMMARY

Aspects of the disclosure relate to a method for restoring expression of a protein comprising a point mutation in an RNA sequence encoding the protein in a subject in need thereof, the method comprising, or alternatively consisting essentially of, or yet further consisting of administering to the subject a vector encoding one or more tRNA having an anticodon sequence that recognizes a codon comprising the point mutation to the subject, optionally wherein the point mutation results in a premature stop codon, optionally wherein the point mutation results in a premature stop codon. In some embodiments, the point mutation results in a nonsense mutation having the DNA sequence TAA and the RNA sequence UAA. In some embodiments, the tRNA is an endogenous tRNA with a modified anticodon stem recognizing the codon comprising the point mutation. In further embodiments, the tRNA is charged with a serine. In some embodiments, the tRNA is an orthogonal tRNA charged with a non-canonical amino acid. In further embodiments, the vector further comprises a corresponding tRNA synthetase. In some embodiments, the corresponding synthetase is *E. coli* Glutaminyl-tRNA synthetase. In some embodiments involving an orthogonal tRNA, the non-canonical amino acid is pyrrolysine. In further embodiments, the pyrrolysine is administered to the subject by introduction into the diet of the subject. In some embodiments, the vector encodes two tRNA having an anticodon sequence that recognizes the codon comprising the point mutation. In some embodiments, the protein is dystrophin. In a further aspect, the subject is a human and is optionally a pediatric patient.

Further method aspects relate to a treating a disease, disorder, or condition characterized by the presence of a point mutation in an RNA sequence encoding a protein associated with the disease, disorder, or condition in a subject in need thereof, the method comprising, or alternatively consisting essentially of, or yet further consisting of, administering to the subject a vector encoding one or more tRNA having an anticodon sequence that recognizes a codon comprising the point mutation to the subject, optionally wherein the point mutation results in a premature stop codon. In some embodiments, the point mutation results in a nonsense mutation having the DNA sequence TAA and the RNA sequence UAA. In some embodiments, the tRNA is an endogenous tRNA with a modified anticodon stem recognizing the codon comprising the point mutation. In further embodiments, the tRNA is charged with a serine. In some embodiments, the tRNA is an orthogonal tRNA charged with a non-canonical amino acid. In further embodiments, the vector further comprises a corresponding tRNA synthetase. In some embodiments, the corresponding synthetase is *E. coli* Glutaminyl-tRNA synthetase. In some embodiments involving an orthogonal tRNA, the non-canonical amino acid is pyrrolysine. In further embodiments, the pyrrolysine is introduced in the diet of the subject. In some embodiments, the vector encodes two tRNA having an anticodon sequence that recognizes the codon comprising the point mutation. In some embodiments, the disease, disorder, or condition is selected from the group consisting of the diseases, disorders, and conditions listed in Table 1, optionally characterized by the presence of a nonsense mutation and/or a premature stop codon. In some embodiments, the protein is dystrophin. In further embodiments, the disease, disorder, or condition is muscular dystrophy. In still further embodiments, the disease disorder or condition is Duchenne muscular dystrophy. In some embodiments, the subject is a human and is optionally a pediatric patient.

Still further aspects disclosed herein relate to a vector encoding one or more tRNA having an anticodon sequence that recognizes a codon comprising a point mutation in an RNA sequence encoding a protein, optionally wherein the point mutation results in a premature stop codon. In some embodiments, the point mutation results in a nonsense mutation having the DNA sequence TAA and the RNA sequence UAA. In some embodiments, the tRNA is an endogenous tRNA with a modified anticodon stem recognizing the codon comprising the point mutation. In further embodiments, the tRNA is charged with a serine. In some embodiments, the tRNA is an orthogonal tRNA charged with a non-canonical amino acid. In further embodiments, the vector further comprises a corresponding tRNA synthetase. In some embodiments, the corresponding synthetase is *E. coli* Glutaminyl-tRNA synthetase. In some embodiments involving an orthogonal tRNA, the non-canonical amino acid is pyrrolysine. In some embodiments, the vector encodes two tRNA having an anticodon sequence that recognizes the codon comprising the point mutation. In some embodiments, the vector is an AAV vector, optionally an AAV8 vector. In some embodiments, the protein is dystrophin. In a further aspect, the subject is a human and is optionally a pediatric patient.

In another aspect, the disclosure relates to a method for restoring expression of a protein comprising a point mutation in an RNA sequence encoding the protein in a subject in need thereof comprising administering one or more vectors encoding an ADAR based RNA editing system comprising one or more forward guide RNAs for the ADAR ("adRNAs") and one or more corresponding reverse guide RNAs for the ADAR ("radRNAs") to the subject, wherein the ADAR based RNA editing system specifically edits the point mutation. In some embodiments, the point mutation results in a nonsense mutation having the DNA sequence TAA and the RNA sequence UAA. In some embodiments, the ADAR based RNA editing system converts UAA to UIA and, optionally, further UIA to UII. In some embodiments, the ADAR based RNA editing system converts UAA to UAI. In some embodiments, optionally those involving nonsense or missense mutations, the RNA targeted in mRNA. In further embodiments, the one or more vector further encodes a tRNA that targets an amber codon. In some embodiments, the protein is dystrophin. In some embodiments, the point mutation results in a splice site or missense mutation having the DNA sequence CAG and the RNA sequence CAG. In some embodiments, the ADAR based RNA editing system converts CAG to CIG. In some embodiments, optionally those involving splice site mutations, the RNA targeted is pre-mRNA. In some embodiments, the protein is ornithine transcabamylase. In some embodiments, the ADAR based editing system further comprises ADAR1, ADAR2, the E488Q and E100Q mutants each thereof, a fusion protein comprising the catalytic domain of an ADAR and a domain which associates with an RNA hairpin motif, a fusion protein comprising the catalytic domain of an ADAR and a dead Cas9, or a fusion protein comprising the double stranded binding domain of an ADAR and an APOBEC. In further embodiments, the domain which associates with an RNA hairpin motif is selected from the group of an MS2 bacteriophage coat protein (MCP) and an N22 peptide. In some embodiments, the method further comprises administering an effective amount of an interferon to enhance endogenous ADAR1 expression. In still further embodiments, the interferon is interferon α. In some embodiments, the adRNA comprises one or more RNA hairpin motifs. In some embodiments, the one or more RNA hairpin motifs are selected from the group of an MS2 stem loop and a BoxB loop and/or are stabilized by replacing A-U with G-C. In some embodiments, the adRNA is stabilized through the incorporation of one or more of 2'-O-methyl, 2'-O-methyl 3'phosphorothioate, or 2'-O-methyl 3'thioPACE at either or both termini of the adRNA. In a further aspect, the subject is a human and is optionally a pediatric patient.

Further method aspects relate to a method of treating a disease, disorder, or condition characterized by the presence of a point mutation in an RNA sequence encoding a protein associated with the disease, disorder, or condition in a subject in need thereof, the method comprising, or alternatively consisting essentially of, or yet further consisting of, administering to the subject one or more vectors encoding an ADAR based RNA editing system comprising one or more forward guide RNAs for the ADAR ("adRNAs") and one or more corresponding reverse guide RNAs for the ADAR ("radRNAs") to the subject, wherein the ADAR based RNA editing system specifically edits the point mutation. In some embodiments, the point mutation results in a nonsense mutation having the DNA sequence TAA and the RNA sequence UAA. In some embodiments, the ADAR based RNA editing system converts UAA to UIA and, optionally, further UIA to UM In some embodiments, the ADAR based RNA editing system converts UAA to UAI. In some embodiments, optionally those involving nonsense or missense mutations, the RNA targeted in mRNA. In further embodiments, the one or more vector further encodes a tRNA that targets an amber codon. In some embodiments, the protein is dystrophin. In some embodiments, the point mutation results in a splice site or missense mutation having the DNA sequence CAG and the RNA sequence CAG. In some embodiments, the ADAR based RNA editing system converts CAG to CIG. In some embodiments, optionally those involving splice site mutations, the RNA targeted is pre-mRNA. In some embodiments, the protein is ornithine transcabamylase. In some embodiments, the ADAR based editing system further comprises ADAR1, ADAR2, the E488Q and E100Q mutants each thereof, a fusion protein comprising the catalytic domain of an ADAR and a domain which associates with an RNA hairpin motif, a fusion protein comprising the catalytic domain of an ADAR and a dead Cas9, or a fusion protein comprising the double stranded binding domain of an ADAR and an APOBEC. In further embodiments, the domain which associates with an RNA hairpin motif is selected from the group of an MS2 bacteriophage coat protein (MCP) and an N22 peptide. In some embodiments, the method further comprises administering an effective amount of an interferon to enhance endogenous ADAR1 expression. In still further embodiments, the interferon is interferon α. In some embodiments, the adRNA comprises one or more RNA hairpin motifs. In some embodiments, the one or more RNA hairpin motifs are selected from the group of an MS2 stem loop and a BoxB loop and/or are stabilized by replacing A-U with G-C. In some embodiments, the adRNA is stabilized through the incorporation of one or more of 2'-O-methyl, 2'-O-methyl 3'phosphorothioate, or 2'-O-methyl 3'thioPACE at either or both termini of the adRNA. In some embodiments, the disease, disorder, or condition is selected from the group consisting of the diseases, disorders, and conditions listed in Table 1. In further embodiments, the protein is dystrophin and the disease, disorder, or condition is muscular dystrophy. In still further embodiments, the disease disorder or condition is Duchenne muscular dystrophy. In some embodiments, the subject is a human and is optionally a pediatric patient.

Additional aspects relate to a recombinant expression system comprising one or more vectors encoding an ADAR based RNA editing system comprising one or more forward guide RNAs for the ADAR ("adRNAs") and one or more corresponding reverse guide RNAs for the ADAR ("radRNAs") to the subject, wherein the ADAR based RNA editing system specifically edits a point mutation in an RNA sequence encoding a protein. In some embodiments, the point mutation results in a nonsense mutation having the DNA sequence TAA and the RNA sequence UAA. In some embodiments, the ADAR based RNA editing system converts UAA to UIA and, optionally, further UIA to UII. In some embodiments, the ADAR based RNA editing system converts UAA to UAI. In some embodiments, optionally those involving nonsense or missense mutations, the RNA targeted in mRNA. In further embodiments, the one or more vector further encodes a tRNA that targets an amber codon. In some embodiments, the protein is dystrophin. In some embodiments, the point mutation results in a splice site or missense mutation having the DNA sequence CAG and the RNA sequence CAG. In some embodiments, the ADAR based RNA editing system converts CAG to CIG. In some embodiments, optionally those involving splice site mutations, the RNA targeted is pre-mRNA. In some embodiments, the protein is ornithine transcabamylase. In some embodiments, the ADAR based editing system further comprises ADAR1, ADAR2, the E488Q and E100Q mutants each thereof, a fusion protein comprising the catalytic domain of an ADAR and a domain which associates with an RNA hairpin motif, a fusion protein comprising the catalytic domain of an ADAR and a dead Cas9, or a fusion protein comprising the double stranded binding domain of an ADAR and an APOBEC. In further embodiments, the domain which associates with an RNA hairpin motif is selected from the group of an MS2 bacteriophage coat protein (MCP) and an N22 peptide. In some embodiments, the adRNA comprises one or more RNA hairpin motifs. In some embodiments, the one or more RNA hairpin motifs are selected from the group of an MS2 stem loop and a BoxB loop and/or are stabilized by replacing A-U with G-C. In some embodiments, the adRNA is stabilized through the incorporation of one or more of 2'-O-methyl, 2'-O-methyl 3'phosphorothioate, or 2'-O-methyl 3'thioPACE at either or both termini of the adRNA. In a further aspect, the subject is a human and is optionally a pediatric patient.

Still further aspects relate to a composition comprising any one or more of the vectors disclosed herein and optionally one or more carriers, such as a pharmaceutically acceptable carrier. In some embodiments, the composition further comprises an effective amount of an interferon to enhance endogenous ADAR1 expression. In still further embodiments, the interferon is interferon α.

Some aspects disclosed herein relate to methods for restoring expression of a protein in a subject in need thereof, the method comprising, or alternatively consisting essentially of, or yet further consisting of, administering to the subject a tRNA having an anticodon sequence that recognizes a mutation in an RNA sequence encoding the protein or a vector encoding one or more of said tRNA to the subject. In some embodiments, the mutation is a nonsense mutation, optionally a premature stop codon. In some embodiments, the nonsense mutation is TAA in DNA and UAA in RNA. In some embodiments, the tRNA is a modified endogenous tRNA charged with a canonical amino acid. In some embodiments, the canonical amino acid is serine. In some embodiments, the tRNA is an orthogonal tRNA charged with a non-canonical amino acid. In some embodiments, the orthogonal tRNA has a corresponding synthetase. In some embodiments, the corresponding synthetase is *E. coli* Glutaminyl-tRNA synthetase. In some embodiments, the non-canonical amino acid is introduced or administered to the subject (e.g. through food), allowing for the induction of the orthogonal tRNA activity. In some embodiments, the non-canonical amino acid is pyrrolysine. In some embodiments, the tRNA targets an amber codon. In some embodiments, the tRNA targets an ochre codon. In some embodiments, the tRNA targets an opal codon. In some embodiments, the protein is dystrophin. In a further aspect, the subject is a human and is optionally a pediatric patient.

Further aspects disclosed herein relate to methods of a disease, disorder, or condition characterized by a protein deficiency in a subject in need thereof, the method comprising, or alternatively consisting essentially or, or yet further consisting of administering a tRNA having an anticodon sequence that recognizes a mutation in an RNA sequence encoding the protein or a vector encoding one or more of said tRNA to the subject. In some embodiments, the mutation is a nonsense mutation, optionally a premature stop codon. In some embodiments, the nonsense mutation is TAA in DNA and UAA in RNA. In some embodiments, the tRNA is a modified endogenous tRNA charged with a canonical amino acid. In some embodiments, the canonical amino acid is serine. In some embodiments, the tRNA is an orthogonal tRNA charged with a non-canonical amino acid. In some embodiments, the orthogonal tRNA has a corresponding synthetase. In some embodiments, the corresponding synthetase is *E. coli* Glutaminyl-tRNA synthetase. In some embodiments, the non-canonical amino acid is administered or introduced to the subject (e.g. through food), allowing for the induction of the orthogonal tRNA activity. In some embodiments, the non-canonical amino acid is pyrrolysine. In some embodiments, the tRNA targets an amber codon. In some embodiments, the tRNA targets an ochre codon. In some embodiments, the tRNA targets an opal codon. In some embodiments, the protein deficiency is a dystrophin deficiency. In some embodiments, the disease, disorder, or condition is muscular dystrophy. In some embodiments, the muscular dystrophy is Duchene muscular dystrophy. In a further aspect, the subject is a human and is optionally a pediatric patient.

Other aspects relate to a vector encoding one or more tRNA having an anticodon sequence that recognizes a mutation in an RNA sequence encoding the protein. In some embodiments, the mutation is a nonsense mutation, optionally a premature stop codon. In some embodiments, the nonsense mutation is TAA in DNA and UAA in RNA. In some embodiments, the tRNA is a modified endogenous tRNA charged with a canonical amino acid. In some embodiments, the canonical amino acid is serine. In some embodiments, the tRNA is an orthogonal tRNA charged with a non-canonical amino acid. In some embodiments, the orthogonal tRNA has a corresponding synthetase. In some embodiments, the corresponding synthetase is *E. coli* Glutaminyl-tRNA synthetase. In some embodiments, the vector further comprises the corresponding synthetase. In some embodiments, the non-canonical amino acid is introduced or administered to the subject (e.g. through food), allowing for the induction of the orthogonal tRNA activity. In some embodiments, the non-canonical amino acid is pyrrolysine. In some embodiments, the tRNA targets an amber codon. In some embodiments, the tRNA targets an ochre codon. In some embodiments, the tRNA targets an opal codon. In some embodiments, the protein is dystrophin. In some embodiments, the mutation is a nonsense mutation, optionally a premature stop codon. In some embodiments, the vector is an Adeno-Associated Virus (AAV) vector. In some embodiments, the AAV vector is an AAV8 vector.

Additional aspects of this disclosure relate to on-demand, in vivo production of therapeutic proteins, such as, but not limited to, (i) insulin; (ii) neutralizing antibodies for viruses (e.g. HIV, HCV, HPV, influenza) and bacteria (e.g. Staph Aureus; drug resistant strains). Such method aspects comprise administering to a subject a vector encoding the therapeutic protein with a mutation in its sequence and a tRNA having an anticodon sequence that recognizes the mutation in the RNA sequence encoding the therapeutic protein or a vector encoding one or more of said tRNA. Accordingly, any of the methods and vectors disclosed hereinabove relating to a tRNA having an anticodon sequence that recognizes a mutation in an RNA sequence encoding the protein or a vector encoding one or more of said tRNA may be applied to this aspect, as well.

Some aspects disclosed herein relate to methods for restoring expression of a protein in a subject in need thereof comprising administering an ADAR2 based RNA editing system comprising an ADAR2, one or more forward guide RNAs for the ADAR2 ("adRNAs"), and one or more corresponding reverse guide RNAs for the ADAR2 ("radR- NAs") to the subject, wherein the ADAR2 based RNA editing system specifically edits a mutation in an RNA sequence encoding the protein or one or more vectors encoding said ADAR2, adRNAs, radRNAs. In some embodiments, the ADAR2 based RNA editing system changes adenosine (A) to inosine (I), which is read during translation as guanosine (G). In some embodiments, the mutation is a nonsense mutation. In some embodiments, the nonsense mutation is TAA in DNA and UAA in RNA. In some embodiments, the ADAR2 based RNA editing system causes point mutations at one or more adenosines (A) in the nonsense mutation. In some embodiments, the ADAR2 based RNA editing system converts UAA to UIA (read as UGA). In further embodiments, the ADAR2 based RNA editing system converts UIA (read as UGA) to UII (read as UGG). In some embodiments, the ADAR2 based RNA editing system converts UAA to UAI (read as UAG). In some embodiments, the method further comprises administering a tRNA, such as one disclosed hereinabove, that recognizes the codon encoded by the ADAR2 edited sequence. In some embodiments, the tRNA is a modified endogenous tRNA charged with a canonical amino acid. In some embodiments, the canonical amino acid is serine. In some embodiments, the tRNA is an orthogonal tRNA charged with a non-canonical amino acid. In some embodiments, the orthogonal tRNA has a corresponding synthetase. In some embodiments, the corresponding synthetase is *E. coli* Glutaminyl-tRNA synthetase. In some embodiments, the non-canonical amino acid is introduced to the subject (e.g. through food), allowing for the induction of the orthogonal tRNA activity. In some embodiments, the non-canonical amino acid is pyrrolysine. In some embodiments, the tRNA targets an amber codon. In some embodiments, the tRNA targets an ochre codon. In some embodiments, the tRNA targets an opal codon. In some embodiments, the protein deficiency is a dystrophin deficiency. In some embodiments, the disease, disorder, or condition is muscular dystrophy. In some embodiments, the muscular dystrophy is Duchene muscular dystrophy.

Further aspects disclosed herein relate to methods of a disease, disorder, or condition characterized by a protein deficiency in a subject in need thereof comprising administering an ADAR2 based RNA editing system comprising an ADAR2, one or more forward guide RNAs for the ADAR2 ("adRNAs"), and one or more corresponding reverse guide RNAs for the ADAR2 ("radRNAs") to the subject, wherein the ADAR2 based RNA editing system specifically edits a mutation in an RNA sequence encoding the protein or one or more vectors encoding said ADAR2, adRNAs, radRNAs. In some embodiments, the ADAR2 based RNA editing system changes adenosine (A) to inosine (I), which is read during translation as guanosine (G). In some embodiments, the mutation is a nonsense mutation. In some embodiments, the nonsense mutation is TAA. In some embodiments, the ADAR2 based RNA editing system causes point mutations at one or more adenosines (A) in the nonsense mutation. In some embodiments, the ADAR2 based RNA editing system converts UAA to UIA (read as UGA). In further embodiments, the ADAR2 based RNA editing system converts UIA (read as UGA) to UII (read as UGG). In some embodiments, the ADAR2 based RNA editing system converts UAA to UAI (read as UAG). In some embodiments, the method further comprises administering a tRNA, such as one disclosed hereinabove, that recognizes the codon encoded by the ADAR2 edited sequence. In some embodiments, the tRNA is a modified endogenous tRNA charged with a canonical amino acid. In some embodiments, the canonical amino acid is serine. In some embodiments, the tRNA is an orthogonal tRNA charged with a non-canonical amino acid. In some embodiments, the orthogonal tRNA has a corresponding synthetase. In some embodiments, the corresponding synthetase is *E. coli* Glutaminyl-tRNA synthetase. In some embodiments, the non-canonical amino acid is introduced to the subject (e.g. through food), allowing for the induction of the orthogonal tRNA activity. In some embodiments, the non-canonical amino acid is pyrrolysine. In some embodiments, the tRNA targets an amber codon. In some embodiments, the tRNA targets an ochre codon. In some embodiments, the tRNA targets an opal codon. In some embodiments, the protein deficiency is a dystrophin deficiency. In some embodiments, the disease, disorder, or condition is muscular dystrophy. In some embodiments, the muscular dystrophy is Duchene muscular dystrophy.

Other aspects relate to a recombinant expression system comprising one or more vectors encoding an ADAR2 based RNA editing system comprising one or more of an ADAR2, one or more forward guide RNAs for the ADAR2 ("adRNAs"), and one or more corresponding reverse guide RNAs for the ADAR2 ("radRNAs"), wherein the ADAR2 based RNA editing system specifically edits a mutation in an RNA sequence encoding a protein. In some embodiments, the ADAR2 changes adenosine (A) to inosine (I), which is read during translation as guanosine (G). In some embodiments, one adRNA/radRNA pair guides the conversion of UAA to UIA (read as UGA). In further embodiments, a second adRNA/radRNA pair guides the conversion of UIA (read as UGA) to UII (read as UGG). In some embodiments, one adRNA/radRNA pair guides the conversion of UAA to UAI (read as UAG). In some embodiments, the one or more vectors or an additional vector further encodes a tRNA, such as one disclosed hereinabove, that recognizes the codon encoded by the ADAR2 edited sequence. In some embodiments, the tRNA is a modified endogenous tRNA charged with a canonical amino acid. In some embodiments, the canonical amino acid is serine. In some embodiments, the tRNA is an orthogonal tRNA charged with a non-canonical amino acid. In some embodiments, the orthogonal tRNA has a corresponding synthetase. In some embodiments, the corresponding synthetase is *E. coli* Glutaminyl-tRNA synthetase. In some embodiments, the non-canonical amino acid is introduced to the subject (e.g. through food), allowing for the induction of the orthogonal tRNA activity. In some embodiments, the non-canonical amino acid is pyrrolysine. In some embodiments, the tRNA targets an amber codon. In some embodiments, the tRNA targets an ochre codon. In some embodiments, the tRNA targets an opal codon. In some embodiments, the protein is dystrophin. In some embodiments, the mutation is a nonsense mutation. In some embodiments, the vector is an Adeno-Associated Virus (AAV) vector. In some embodiments, the AAV vector is an AAV8 vector.

Additional aspects of this disclosure relate to on-demand, in vivo production of therapeutic proteins, such as, but not limited to, (i) insulin; (ii) neutralizing antibodies for viruses (e.g. HIV, HCV, HPV, influenza) and bacteria (e.g. Staph Aureus; drug resistant strains). Such method aspects comprise administering to a subject a vector encoding the therapeutic protein with a mutation in its sequence and an ADAR2 based RNA editing system comprising an ADAR2, one or more forward guide RNAs for the ADAR2 ("adRNAs"), and one or more corresponding reverse guide RNAs for the ADAR2 ("radRNAs"), wherein the ADAR2 based RNA editing system specifically edits a mutation in an RNA sequence encoding the protein or one or more vectors encoding said ADAR2, adRNAs, radRNAs. Accordingly, any of the methods and vectors disclosed hereinabove relating to an ADAR2 based RNA editing system specifically edits a mutation in an RNA sequence encoding the protein or a vector encoding one or more vectors encoding said ADAR2, adRNAs, radRNAs.

PARTIAL SEQUENCE LISTING mU6, tRNA(U25C) Amber
tcccggggtttccgccaTTTTTTGGTACTGAGtCGCCCaGTCTCAGATAGATCCGACGCCGCCAT
CTCTAGGCCCGCGCCGGCCCCCTCGCACAGACTTGTGGGAGAAGCTCGGCTACTCCC
CTGCCCCGGTTAATTTGCATATAATATTTCCTAGTAACTATAGAGGCTTAATGTGCG
ATAAAAGACAGATAATCTGTTCTTTTTAATACTAGCTACATTTTACATGATAGGCTTG
GATTTCTATAAGAGATACAAATACTAAATTATTATTTTAAAAAACAGCACAAAAGG
AAACTCACCCTAACTGTAAAGTAATTGTGTGTTTTGAGACTATAAATATCCCTTGGA
GAAAAGCCTTGTTTGggaaacctgatcatgtagatcgaaCggactCTAaatccgttcagccgggttagattcccggggttt
ccgccaTTTTTTCCTAGACCCAGCTTTCTTGTACAAAGTTGG (SEQ ID NO: 1)

mU6, tRNA(U25C) Ochre
tcccggggtttccgccaTTTTTTGGTACTGAGtCGCCCaGTCTCAGATAGATCCGACGCCGCCAT
CTCTAGGCCCGCGCCGGCCCCCTCGCACAGACTTGTGGGAGAAGCTCGGCTACTCCC
CTGCCCCGGTTAATTTGCATATAATATTTCCTAGTAACTATAGAGGCTTAATGTGCG
ATAAAAGACAGATAATCTGTTCTTTTTAATACTAGCTACATTTTACATGATAGGCTTG
GATTTCTATAAGAGATACAAATACTAAATTATTATTTTAAAAAACAGCACAAAAGG
AAACTCACCCTAACTGTAAAGTAATTGTGTGTTTTGAGACTATAAATATCCCTTGGA
GAAAAGCCTTGTTTGggaaacctgatcatgtagatcgaaCggactTTAaatccgttcagccgggttagattcccggggttt
ccgccaTTTTTTCCTAGACCCAGCTTTCTTGTACAAAGTTGG (SEQ ID NO: 2)

mU6, tRNA(U25C) Opal
tcccggggtttccgccaTTTTTTGGTACTGAGtCGCCCaGTCTCAGATAGATCCGACGCCGCCAT
CTCTAGGCCCGCGCCGGCCCCCTCGCACAGACTTGTGGGAGAAGCTCGGCTACTCCC
CTGCCCCGGTTAATTTGCATATAATATTTCCTAGTAACTATAGAGGCTTAATGTGCG
ATAAAAGACAGATAATCTGTTCTTTTTAATACTAGCTACATTTTACATGATAGGCTTG
GATTTCTATAAGAGATACAAATACTAAATTATTATTTTAAAAAACAGCACAAAAGG
AAACTCACCCTAACTGTAAAGTAATTGTGTGTTTTGAGACTATAAATATCCCTTGGA
GAAAAGCCTTGTTTGggaaacctgatcatgtagatcgaaCggactTCAaatccgttcagccgggttagattcccggggttt
ccgccaTTTTTTCCTAGACCCAGCTTTCTTGTACAAAGTTGG (SEQ ID NO: 3)

MmPylRS (AfIII)
CAGCCTCCGGACTCTAGAGGATCGAACCCTTAAGgccaccATGGATAAGAAACCTTTG
AACACTCTCATTAGTGCGACAGGGCTCTGGATGTCCCGAACGGGGACTATACACAA
GATAAAACACCATGAGGTCTCAAGGAGCAAAATCTATATCGAGATGGCATGCGGCG
ACCATCTTGTGGTAAATAATAGTAGGTCCTCCAGGACGGCAAGAGCACTCCGACATC
ACAAGTACAGAAAAACCTGCAAACGGTGTAGGGTATCCGACGAAGACTTGAACAAA
TTTTTGACTAAGGCCAACGAGGATCAAACTTCTGTCAAAGTGAAAGTGGTTTCTGCT
CCTACCCGAACTAAGAAGGCCATGCCCAAGTCCGTGGCAAGGGCACCCAAGCCACT
CGAAAATACTGAGGCCGCTCAGGCCCAACCATCCGGTAGTAAGTTCAGTCCAGCCA
TACCCGTAAGTACCCAAGAATCTGTCAGTGTGCCGGCCTCAGTTTCCACATCTATAA
GTTCAATTTCTACAGGAGCGACGGCCTCCGCCCTCGTCAAGGGTAACACAAACCCG
ATAACTTCTATGAGTGCCCCCGTACAGGCATCCGCACCAGCACTGACGAAGTCTCAA
ACTGATAGGCTGGAAGTGCTCTTGAATCCGAAGGACGAGATATCTCTTAACTCCGGT
AAACCTTTCCGGGAGCTGGAAAGTGAACTTCTCAGCCGGCGAAAAAAAGACCTCCA
GCAAATTTACGCAGAGGAAAGGGAGAACTATCTGGGGAAGTTGGAACGAGAGATC
ACCCGATTCTTTGTCGATCGCGGATTTTTGGAGATTAAAAGCCCAATTCTCATCCCCC
TTGAATATATCGAACGAATGGGAATCGACAATGATACGGAGTTGTCCAAGCAGATT
TTCCGCGTAGACAAGAACTTTTGTCTTCGACCCATGCTCGCTCCGAACCTCTACAATT
ACTTGAGAAAGTTGGACAGAGCGCTCCCGGACCCGATCAAGATATTTGAGATCGGT
CCTTGTTATAGAAAGGAGAGTGATGGAAAAGAACACCTCGAAGAGTTCACGATGCT
GAACTTCTGCCAAATGGGTTCTGGCTGCACACGGGAGAATCTCGAAAGCATCATTAC
AGATTTCCTTAACCATCTGGGGATAGACTTTAAAATAGTGGGTGACAGCTGTATGGT
ATACGGAGATACCTTGGACGTAATGCACGGGGATCTTGAGCTTTCCTCCGCCGTGGT
TGGACCTATACCGTTGGACCGGGAGTGGGGAATCGACAAACCGTGGATAGGCGCCG
GTTTCGGCCTTGAAAGACTCCTCAAAGTCAAGCATGATTTCAAAAACATAAAACGG
GCTGCTCGCTCCGAATCTTATTACAACGGTATAAGTACGAACCTGTGATAATAGCTT
AAGGGTTCGATCCCTACtGGTTAGTAATGAGTTTA (SEQ ID NO: 4)

tRNAs
Amber suppression:
ggaaacctgatcatgtagatcgaatggactctaaatccgttcagccgggttagattcccggggtttccgcca (SEQ ID NO: 5)

Amber suppression (2):
ggggggtggatcgaatagatcacacggactctaaattcgtgcaggcgggtgaaactcccgtactccccgcca (SEQ ID NO: 6)

Ochre supression
ggaaacctgatcatgtagatcgaatggactttaaatccgttcagccgggttagattcccggggtttccgcca (SEQ ID NO: 7)

Opal suppression:
ggaaacctgatcatgtagatcgaatggacttcaaatccgttcagccgggttagattcccggggtttccgcca (SEQ ID NO: 8)

Synthetase:
ATGGATAAAAAACCATTAGATGTTTTAATATCTGCGACCGGGCTCTGGATGTCCAGG
ACTGGCACGCTCCACAAAATCAAGCACCATGAGGTCTCAAGAAGTAAAATATACAT -continued

PARTIAL SEQUENCE LISTING

TGAAATGGCGTGTGGAGACCATCTTGTTGTGAATAATTCCAGGAGTTGTAGAACAGC
CAGAGCATTCAGACATCATAAGTACAGAAAAACCTGCAAACGATGTAGGGTTTCGG
ACGAGGATATCAATAATTTTCTCAGAAGATCAACCGAAAGCAAAAACAGTGTGAAA
GTTAGGGTAGTTTCTGCTCCAAAGGTCAAAAAAGCTATGCCGAAATCAGTTTCAAGG
GCTCCGAAGCCTCTGGAAAATTCTGTTTCTGCAAAGGCATCAACGAACACATCCAGA
TCTGTACCTTCGCCTGCAAAATCAACTCCAAATTCGTCTGTTCCCGCATCGGCTCCTG
CTCCTTCACTTACAAGAAGCCAGCTTGATAGGGTTGAGGCTCTCTTAAGTCCAGAGG
ATAAAATTTCTCTAAATATGGCAAAGCCTTTCAGGGAACTTGAGCCTGAACTTGTGA
CAAGAAGAAAAAACGATTTTCAGCGGCTCTATACCAATGATAGAGAAGACTACCTC
GGTAAACTCGAACGTGATATTACGAAATTTTTCGTAGACCGGGGTTTTCTGGAGATA
AAGTCTCCTATCCTTATTCCGGCGGAATACGTGGAGAGAATGGGTATTAATAATGAT
ACTGAACT1TCAAAACAGATCTTCCGGGTGGATAAAAATCTCTGCTTGAGGCCAATG
CTTGCCCCGACTCTTTACAACTATCTGCGAAAACTCGATAGGATTTTACCAGGCCCA
ATAAAAATTTTCGAAGTCGOACCTTGTTACCOGAAAGAGTCTGACGGCAAAGAGCA
CCTGGAAGAATTTACTATGGTGAACTTCTGTCAGATGGGTTCGGGATGTACTCGGGA
AAATCTTGAAGCTCTCAICAAAGAGTTTCTGGACTATCTGGAAATCGACTTCGAAAT
CGTAGGAGATTCCTGTATGGTCTTTGGGGATACTCTTGATATAATGCACGGGGACCT
GGAGCTTTCTTCGGCAGTCGTCGGGCCAGTTTCTCTTGATAGAGAATGGGGTATTGA
CAAACCATGGATAGGTGCAGGTTTTGGTCTTGAACGCTTGCTCAAGGTTATGCACGG
CTTTAAAAACATTAAGAGGGCATCAAGGTCCGAATCTTACTATAATGGGATTTCAAC
CAATCTGTAA (SEQ ID NO: 9)

EGFP:
atggtgagcaagggcgaggagctgttcaccggggtggtgcccatcctggtcgagctggacggcgacgtaaacggecacaagttcagcgt
gtccggcgagggcgagggcgatgccacctacggcaagctgaccctgaagttcatctgcaccaccggcaagctgcccgtgccctggccc
accctcgtgaccaccctgacctacggcgtgcagtgcttcagccgctaccccgaccacatgaagcagcacgacttcttcaagtccgccatgc
ccgaaggctacgtccaggagcgcaccatcttcttcaaggacgacggcaactacaagacccgcgccgaggtgaagttcgagggcgacac
cctggtgaaccgcatcgagctgaagggcatcgacttcaaggaggacggcaacatcctggggcacaagctggagtacaactacaacagcc
acaacgtctatatcatggccgacaagcagaagaacggcatcaaggtgaacttcaagatccgccacaacatcgaggacggcagcgtgcag
ctcgccgaccactaccagcagaacacccccatcggcgacggccccgtgctgctgcccgacaaccactacctgagcacccagtccgccct
gagcaaagaccccaacgagaagcgcgatcacatggtcctgctggagttcgtgaccgccgccgggatcactctcggcatggacgagctgt
acaagtaa (SEQ ID NO: 10)

EGFP Amber:
Atggtgagcaagggcgaggagctgttcaccggggtggtgcccatcctggtcgagctggacggcgacgtaaacggccacaagttcagcg
tgtccggcgagggcgagggcgatgccacctagggcaagctgaccctgaagttcatctgcaccaccggcaagctgcccgtgccctggcc
caccctcgtgaccaccctgacctacggcgtgcagtgcttcagccgctaccccgaccacatgaagcagcacgacttcttcaagtccgccatg
cccgaaggctacgtccaggagcgcaccatcttcttcaaggacgacggcaactacaagacccgcgccgaggtgaagttcgagggcgaca
ccctggtgaaccgcatcgagctgaagggcatcgacttcaaggaggacggcaacatcctggggcacaagctggagtacaactacaacagc
cacaacgtctatatcatggccgacaagcagaagaacggcatcaaggtgaacttcaagatccgccacaacatcgaggacggcagcgtgca
gctcgccgaccactaccagcagaacacccccatcggcgacggccccgtgctgctgcccgacaaccactacctgagcacccagtccgcc
ctgagcaaagaccccaacgagaagcgcgatcacatggtcctgctggagttcgtgaccgccgccgggatcactctcggcatggacgagct
gtacaagtaatga (SEQ ID NO: 11)

EGFP Ochre:
atggtgagcaagggcgaggagctgttcaccggggtggtgcccatcctggtcgagctggacggcgacgtaaacggccacaagttcagcgt
gtccggcgagggcgagggcgatgccacctaaggcaagctgaccctgaagttcatctgcaccaccggcaagctgcccgtgccctggccc
accctcgtgaccaccctgacctacggcgtgcagtgcttcagccgctaccccgaccacatgaagcagcacgacttcttcaagtccgccatgc
ccgaaggctacgtceaggagcgcaccatcttcttcaaggacgacggcaactacaagacccgcgccgaggtgaagttcgagggcgacac
cctggtgaaccgcatcgagctgaagggcatcgacttcaaggaggacggcaacatcctggggcacaagetggagtacaactacaacagcc
acaacgtctatatcatggccgacaagcagaagaacggcatcaaggtgaacttcaagatccgccacaacatcgaggacggcagcgtgcag
ctcgccgaccactaccagcagaacacccccatcggcsacggccccgtgagctgcccgacaaccactacagagcacccagtccgccct
gagcaaagaccccaacgagaagcgcgatcacatggtcctgaggagttcgtgaccgccgccgggatcactetcggcatggacgagetgt
acaagtaatga (SEQ ID NO: 12)

EGFP Opa1:
Atggtgagcaagggcgaggagctgttcaccggggtggtgcccatcctggtcgagctggacggcgacgtaaacggccacaagttcagcg
tgtccggcgagggcgagggcgatgccacctgaggcaagctgaccctgaagttcatctgcaccaccggcaagctgcccgtgccctggcc
caccctcgtgaccaccctgacctacggcgtgcagtgcttcagccgctaccccgaccacatgaagcagcacgacttcttcaagtccgccatg
cccgaaggctacgtccaggagcgcaccatcttcttcaaggacgacggcaactacaagacccgcgccgaggtgaagttcgagggcgaca
ccctggtgaaccgcatcgagctgaagggcatcgacttcaaggaggacggcaacatcctggggcacaagctggagtacaactacaacagc
cacaacgtctatatcatggccgacaagcagaagaacggcatcaaggtgaacttcaagatccgccacaacatcgaggacggcagcgtgca
gctcgccgaccactaccagcagaacacccccatcggcgacggccccgtgctgctgcccgacaaccactacctgagcacccagtccgcc
ctgagcaaagaccccaacgagaagcgcgatcacatggtcctgctggagttcgtgaccgccgccgggatcactctcggcatggacgagct
gtacaagtaatga (SEQ ID NO: 13)

MbPylRS 10 20 30 40 50
MDKKPLDVLI SATGLWMSRT GTLHKIKHHE VSRSKIYIEM ACGDHLVVNN 60 70 80 90 100
SRSCRTARAF RHHKYRKTCK RCRVSDEDIN NFLTRSTESK NSVKVRVVSA 110 120 130 140 150
PKVKKAMPKS VSRAPKPLEN SVSAKASTNT SRSVPSPAKS TPNSSVPASA 160 170 180 190 200

-continued

| PARTIAL SEQUENCE LISTING |
|---|

```
PAPSLTRSQL DRVEALLSPE DKISLNMAKP FRELEPELVT RRKNDFQRLY

       210        220        230        240        250
TNDREDYLGK LERDITKFFV DRGFLEIKSP ILIPAEYVER MGINNDTELS

       260        270        280        290        300
KQIFRVDKNL CLRPMLAPTL YNYLRKLDRI LPGPIKIFEV GPCYRKESDG

       310        320        330        340        350
KEHLEEFTMV NFCQMGSGCT RENLEALIKE FLDYLEIDFE IVGDSCMVYG

       360        370        380        390        400
DTLDIMHGDL ELSSAVVGPV SLDREWGIDK PWIGAGFGLE RLLKVMHGFK

NIKRASRSES YYNGISTNL (SEQ ID NO: 14)

MmPylRS (uniprot)
        10         20         30         40         50
MDKKPLNTLI SATGLWMSRT GTIHKIKHHE VSRSKIYIEM ACGDHLVVNN

        60         70         80         90        100
SRSSRTARAL RHHKYRKTCK RCRVSDEDLN KFLTKANEDQ TSVKVKVVSA

       110        120        130        140        150
PTRTKKAMPK SVARAPKPLE NTEAAQAQPS GSKFSPAIPV STQESVSVPA

       160        170        180        190        200
SVSTSISSIS TGATASALVK GNTNPITSMS APVQASAPAL TKSQTDRLEV

       210        220        230        240        250
LLNPKDEISL NSGKPFRELE SELLSRRKKD LQQIYAEERE NYLGKLEREI

       260        270        280        290        300
TRFFVDRGFL EIKSPILIPL EYIERMGIDN DTELSKQIFR VDKNFCLRPM

       310        320        330        340        350
LAPNLYNYLR KLDRALPDPI KIFEIGPCYR KESDGKEHLE EFTMLNFCQM

       360        370        380        390        400
GSGCTRENLE SIITDFLNHL GIDFKIVGDS CMVYGDTLDV MHGDLELSSA

       410        420        430        440        450
VVGPIPLDRE WGIDKPWIGA GFGLERLLKV KHDFKNIKRA ARSESYYNGI

STNL (SEQ ID NO: 15)
```

PylT* (Amber)
ggaaacctgatcatgtagatcgaaCggactCTAaatccgttcagccgggttagattcccggggtttccgccaTTTTTT
(SEQ ID NO: 16)

PylT* (Ochre)
ggaaacctgatcatgtagatcgaaCggactTTAaatccgttcagccgggttagattcccggggTTTccgccaTTTTTT
(SEQ ID NO: 17)

PylT* (Opal)
ggaaacctgatcatgtagatcgaaCggactTCAaatccgttcagccgggttagattcccggggtttccgccaTTTTTT
(SEQ ID NO: 18)

Mouse U6 primers
tcccggggtttccgccaTTTTTTGGTACTGAGtCGCCCaGTCTCAGAT (SEQ ID NO: 19)

CAAACAAGGCTTTTCTCCAAGGGATAT (SEQ ID NO: 20)

tRNA (U25C) Amber_F:
CCTTGGAGAAAAGCCTTGTTTGggaaacctgatcatgtagatcgaacggactCTAaatccgttcagccggg
(SEQ ID NO: 21)

Common reverse:
PylT
ggaaacctgatcatgtagatcgaatggactCTAaatccgttcagccgggttagattcccggggTTTccgcca (SEQ ID NO: 22)

PylT* (U25C)
ggaaacctgatcatgtagatcgaaCggactCTAaatccgttcagccgggttagattcccggggtttccgcca (SEQ ID NO: 23)

-continued

PARTIAL SEQUENCE LISTING

1. Arg tRNA (opal) (E-Cadherin paper)
GGCCGCGTGGCCTAATGGATAAGGCGTCTGACTTCAGA*<u>TCA</u>*GAAGATTGCAGGT
TCGAGTCCTGCCGCGGTCG (SEQ ID NO: 24)

2. Arg tRNA (opal) (Xeroderma paper)
GACCACGTGGCCTAATGGATAAGGCGTCTGACTTCAGA*<u>TCA</u>*GAAGATTGAGGGT
TCGAATCCCTTCGTGGTTA (SEQ ID NO: 25)

3. Serine tRNA (amber)
GTAGTCGTGGCCGAGTGGTTAAGGCGATGGACT*<u>CTA</u>*AATCCATTGGGGTTTCCCC
GCGCAGGTTCGAATCCTGCCGACTACG (SEQ ID NO: 26)

4. Leucine tRNA (amber)
GTCAGGATGGCCGAGTGGTCTAAGGCGCCAGACT*<u>CTA</u>*GTTCTGGTCTCCAATGGA
GGCGTGGGTTCGAATCCCACTTCTGACA (SEQ ID NO: 27)

Forward:
TTGTGGAAAGGACGAAACACC (SEQ ID NO: 28)

Reverse:
ACAAGAAAGCTGGGTCTAGGCTAGCAAAAAA (SEQ ID NO: 29)

tRNA_Leu_Am_F (overlaps with vector, bold; anti-codon sequences, bold underline):
TTGTGGAAAGGACGAAACACCGGTCAGGATGGCCGAGTGGTCTAAGGCGCCAGAC
T*<u>CTA</u>*GTTCTGGTCTCCAATGG (SEQ ID NO: 30)

tRNA_Leu_Oc_F (overlaps with vector, bold; anti-codon sequences, bold underline):
TTGTGGAAAGGACGAAACACCGGTCAGGATGGCCGAGTGGTCTAAGGCGCCAGAC
T*<u>TTA</u>*GTTCTGGTCTCCAATGG (SEQ ID NO: 31)

tRNA_Leu_Op_F (overlaps with vector, bold; anti-codon sequences, bold underline):
TTGTGGAAAGGACGAAACACCGGTCAGGATGGCCGAGTGGTCTAAGGCGCCAGAC
T*<u>TCA</u>*GTTCTGGTCTCCAATGG (SEQ ID NO: 32)

tRNA_Leu_R (overlaps with vector, bold; anti-codon sequences, bold underline):
ACAAGAAAGCTGGGTCTAGGCTAGCAAAAAATGTCAGAAGTGGGATTCGAACCC
ACGCCTCCATTGGAGACCAGAAC (SEQ ID NO: 33)

tRNA_Ser_Am_F (overlaps with vector, bold; anti-codon sequences, bold underline):
TTGTGGAAAGGACGAAACACCGGTAGTCGTGGCCGAGTGGTTAAGGCGATGGACT
*<u>CTA</u>*AATCCATTGGGGTTTCC (SEQ ID NO: 34)

tRNA_Ser_Oc_F (overlaps with vector, bold; anti-codon sequences, bold underline):
TTGTGGAAAGGACGAAACACCGGTAGTCGTGGCCGAGTGGTTAAGGCGATGGACT
*<u>TTA</u>*AATCCATTGGGGTTTCC (SEQ ID NO: 35)

tRNA_Ser_Op (overlaps with vector, bold; anti-codon sequences, bold underline)F:
TTGTGGAAAGGACGAAACACCGGTAGTCGTGGCCGAGTGGTTAAGGCGATGGACT
*<u>TCA</u>*AATCCATTGGGGTTTCC (SEQ ID NO: 36)

tRNA_Ser_R (overlaps with vector, bold; anti-codon sequences, bold underline):
ACAAGAAAGCTGGGTCTAGGCTAGCAAAAAACGTAGTCGGCAGGATTCGAACCT
GCGCGGGGAAACCCCAATGGATT (SEQ ID NO: 37)

tRNA_Arg_Am_F (overlaps with vector, bold; anti-codon sequences, bold underline):
TTGTGGAAAGGACGAAACACCGGACCACGTGGCCTAATGGATAAGGCGTCTGACT
*<u>TCA</u>*GATCAGAAGATTGAGGGTT (SEQ ID NO: 38)

tRNA_Arg_Oc_F (overlaps with vector, bold; anti-codon sequences, bold underline):
TTGTGGAAAGGACGAAACACCGGACCACGTGGCCTAATGGATAAGGCGTCTGACT
*<u>TTA</u>*GATCAGAAGATTGAGGGTT (SEQ ID NO: 39)

tRNA_Arg_Op_F (overlaps with vector, bold; anti-codon sequences, bold underline):
TTGTGGAAAGGACGAAACACCGGACCACGTGGCCTAATGGATAAGGCGTCTGACT
*<u>TCA</u>*GATCAGAAGATTGAGGGTT (SEQ ID NO: 40)

tRNA_Arg_R (overlaps with vector, bold; anti-codon sequences, bold underline):
ACAAGAAAGCTGGGTCTAGGCTAGCAAAAAATAACCACGAAGGGATTCGAACCC
TCAATCTTCTGATC (SEQ ID NO: 41)

mU6_tRNA_ser_oc:
GTACTGAGtCGCCCaGTCTCAGATAGATCCGACGCCGCCATCTCTAGGCCCGCGCCGG
CCCCCTCGCACAGACTTGTGGGAGAAGCTCGGCTACTCCCCTGCCCCGGTTAATTTG
CATATAATATTTCCTAGTAACTATAGAGGCTTAATGTGCGATAAAAGACAGATAATC
TGTTCTTTTTAATACTAGCTACATTTTACATGATAGGCTTGGATTTCTATAAGAGATA
CAAATACTAAATTATTATTTTAAAAAACAGCACAAAAGGAAACTCACCCTAACTGTA -continued

PARTIAL SEQUENCE LISTING

AAGTAATTGTGTGTTTTGAGACTATAAATATCCCTTGGAGAAAAGCCTTGTTTGGTA
GTCGTGGCCGAGTGGTTAAGGCGATGGACTTTAAATCCATTGGGGTTTCCCCGCGCA
GGTTCGAATCCTGCCGACTACGTTTTTT (SEQ ID NO: 42)

mU6_tRNA_ser_oc_Nhe1_insert_F:
AATCCTGCCGACTACGTTTTTTGTACTGAGtCGCCCAGTCT (SEQ ID NO: 43)

adRNA (premature stop codon target, bold; edited bases, bold underline):
Sequential edits:
TTTGAAAGAGCAATAAAAT (SEQ ID NO: 44)

CTTTGAAAGAGCAATAGAA (SEQ ID NO: 45)

Dual edits:
TTTGAAAGAGCAATAAAAT (SEQ ID NO: 46)

radRNA (premature stop codon target, bold; edited bases, bold underline):
Sequential edits:
AtaaAATGGCTTCAACTAT (SEQ ID NO: 47)

AAtagAATGGCTTCAACTA (SEQ ID NO: 48)

Dual edits:
AAtaaAATGGCTTCAACTA (SEQ ID NO: 49)

OTC target (edited bases, bold):
TCACAGACACCGCTCAGTTTGT (SEQ ID NO: 50)

Optimization of the length of adRNA and distance of the edit from the ADAR2 recruiting domain (Length of adRNA-distance of edit from ADAR2 recruiting domain):
16-5: atgccaccTGGggcaa (SEQ ID NO: 51)

16-6: tgccaccTGGggcaag (SEQ ID NO: 52)

16-7: gccaccTGGggcaagc (SEQ ID NO: 53)

18-6: gatgccaccTGGggcaag (SEQ ID NO: 54)

20-6: gcgatgccaccTGGggcaag (SEQ ID NO: 55)

ADAR2 recruiting region v1:
GGGTGGAATAGTATAACAATATGCTAAATGTTGTTATAGTATCCCACCT
(SEQ ID NO: 56)

ADAR2 recruiting region v2:
GTGGAATAGTATAACAATATGCTAAATGTTGTTATAGTATCCCAC (SEQ ID NO: 57)

Hairpin (3') (FIG. 8): GGGCCCTCTTCAGGGCCCTCTAGA (SEQ ID NO: 58)

Hairpin (3') (FIG. 10): atcgccctgaaaag (SEQ ID NO: 59)

Toe hold (5'): gccaccTGGgg (SEQ ID NO: 60)

List of suppressor tRNA sequences:

| Suppressor tRNAs | Sequence (5' to 3') |
|---|---|
| Serine | GTAGTCGTGGCCGAGTGGTTAAGGCGATGGACTNNNAATCCATTGG GGTTTCCCCGCGCAGGTTCGAATCCTGCCGACTACG (SEQ ID NO: 61) |
| Leucine | GTCAGGATGGCCGAGTGGTCTAAGGCGCCAGACTNNNGTTCTGGTC TCCAATGGAGGCGTGGGTTCGAATCCCACTTCTGACA (SEQ ID NO: 62) |
| Arginine | GACCACGTGGCCTAATGGATAAGGCGTCTGACTNNNGATCAGAAG ATTGAGGGTTCGAATCCCTTCGTGGTTA (SEQ ID NO: 63) |

NNN—anticodon

In endogenous tRNA, the tRNA is modified to recognize the codon comprising the point mutation by including the complementary sequence at the NNN position noted herein above. As clarified in more detail below, the NNN sequences in amber, ochre, and opal tRNA are as follows: Amber: NNN=CTA; Ochre: NNN=TCA; Opal: NNN=TTA.

List of primers for next generation sequencing (NGS) analyses.

| Name | Sequence (5' to 3') |
|---|---|
| NGS_DMD_F1 | GTGTTACTGAATATGAAATAATGGAGGA (SEQ ID NO: 64) |
| NGS_DMD_R1 | ATTTCTGGCATATTTCTGAAGGTG (SEQ ID NO: 65) |
| NGS_DMD_F2 | CTCTCTGTACCTTATCTTAGTGTTACTGA (SEQ ID NO: 66) |
| NGS_DMD_R2 | CTCTTCAAATTCTGACAGATATTTCTGGC (SEQ ID NO: 67) |

-continued

| Name | Sequence (5' to 3') |
|---|---|
| NGS_OTC_F | ACCCTTCCTTTCTTACCACACA (SEQ ID NO: 68) |
| NGS_OTC_R | CAGGGTGTCCAGATCTGATTGTT (SEQ ID NO: 69) |
| NGS_OTC_R2 | CTTCTCTTTTAAACTAACCCATCAGAGTT (SEQ ID NO: 70) |

List of adRNA antisense sequences and corresponding ADAR2 recruiting scaffold used for in vivo RNA editing studies. In some embodiments, the recruiting scaffold v2—disclosed in the preceding paragraph, is used with these sequences.

| Name | adRNA antisense sequence (3' to 5') |
|---|---|
| OTC | TGTCTGTGGCGAGCCAAACA (SEQ ID NO: 71) |
| DMD | ACTTTCTCGTTACCTTACCG (SEQ ID NO: 72) |

MCP-*Linker*-ADAR1-NLS (optional sequence in brackets)

(SEQ ID NO: 73)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGS*KAERMGFTEVTPVTGASLRRTMLLLSRSPEA

QPKTLPLTGSTFHDQIAMLSHRCFNTLTNSFQPSLLGRKILAAIIMKKDSEDMGVVVSLG

TGNRCVKGDSLSLKGETVNDCHAEIISRRGFIRFLYSELMKYNSQTAKDSIFEPAKGGEK

LQIKKTVSFHLYISTAPCGDGALFDKSCSDRAMESTESRHYPVFENPKQGKLRTKVENG

EGTIPVESSDIVPTWDGIRLGERLRTMSCSDKILRWNVLGLQGALLTHFLQPIYLKSVTLG

YLFSQGHLTRAICCRVTRDGSAFEDGLRHPFIVNHPKVGRVSIYDSKRQSGKTKETSVN

WCLADGYDLEILDGTRGTVDGPRNELSRVSKKNIFLLFKKLCSFRYRRDLLRLSYGEAK

KAARDYETAKNYFKKGLKDMGYGNWISKPQEEKNFYLCPVGSGSGSGPKKRKV[AA]*

MCP-*Linker*-ADAR2 (optional sequence in brackets)

(SEQ ID NO: 74)

MGPKKKRKVAAGSGSGSMASNFTQFVLVDNGGTGDVTVAPSNFANGVAEWISSNSR

SQAYKVTCSVRQSSAQKRKYTIKVEVPKVATQTVGGVELPVAAWRSYLNMELTIPI

FATNSDCELIVKAMQGLLKDGNPIPSAIAANSGIY*GGSGGSGGS*MLHLDQTPSRQPIPS

EGLQLHLPQVLADAVSRLVLGKFGDLTDNFSSPHARRKVLAGVVMTTGTDVKDAKVIS

VSTGTKCINGEYMSDRGLALNDCHAEIISRRSLLRFLYTQLELYLNNKDDQKRSIFQKSE

RGGFRLKENVQFHLYISTSPCGDARIFSPHEPILEEPADRHPNRKARGQLRTKIESGEGTIP

VRSNASIQTWDGVLQGERLLTMSCSDKIARWNVVGIQGSLLSIFVEPIYFSSIILGSLYHG

DHLSRAMYQRISNIEDLPPLYTLNKPLLSGISNAEARQPGKAPNFSVNWTVGDSAIEVIN

ATTGKDELGRASRLCKHALYCRWMRVHGKVPSHLLRSKITKPNVYHESKLAAKEYQA

AKARLFTAFIKAGLGAWVEKPTEQDQFSLT[P]*

N22p-*Linker*-ADAR1-NLS (optional sequence in brackets)

(SEQ ID NO: 75)

MGNARTRRRERRAEKQAQWKAANGGGGTSGSGSGS*PAGGGAPGSGGGS*KAERMGF

TEVTPVTGASLRRTMLLLSRSPEAQPKTLPLTGSTFHDQIAMLSHRCFNTLTNSFQPSLLG

-continued

RKILAAIIMKKDSEDMGVVVSLGTGNRCVKGDSLSLKGETVNDCHAEIISRRGFIRFLYS

ELMKYNSQTAKDSIFEPAKGGEKLQIKKTVSFHLYISTAPCGDGALFDKSCSDRAMESTE

SRHYPVFENPKQGKLRTKVENGEGTIPVESSDIVPTWDGIRLGERLRTMSCSDKILRWNV

LGLQGALLTHFLQPIYLKSVTLGYLFSQGHLTRAICCRVTRDGSAFEDGLRHPFIVNHPK

VGRVSIYDSKRQSGKTKETSVNWCLADGYDLEILDGTRGTVDGPRNELSRVSKKNIFLL

FKKLCSFRYRRDLLRLSYGEAKKAARDYETAKNYFKKGLKDMGYGNWISKPQEEKNF

YLCPVGSGSGSGPKKRKV[AA]*

Nuclear Localization Sequence-*Linker*-N22p-*Linker*-ADAR2
(optional sequence in brackets)

(SEQ ID NO: 76)

[MG]PKKKRKVAA*GSGSGS*MGNARTRRRERRAEKQAQWKAANGGGGTSGSGSGS*P*

*AGGGAPGSGGGS*MLHLDQTPSRQPIPSEGLQLHLPQVLADAVSRLVLGKFGDLTDNFSSP

HARRKVLAGVVMTTGTDVKDAKVISVSTGTKCINGEYMSDRGLALNDCHAEIISRRSLL

RFLYTQLELYLNNKDDQKRSIFQKSERGGFRLKENVQFHLYISTSPCGDARIFSPHEPILE

EPADRHPNRKARGQLRTKIESGEGTIPVRSNASIQTWDGVLQGERLLTMSCSDKIARWN

VVGIQGSLLSIFVEPIYFSSIILGSLYHGDHLSRAMYQRISNIEDLPPLYTLNKPLLSGISNA

EARQPGKAPNFSVNWTVGDSAIEVINATTGKDELGRASRLCKHALYCRWMRVHGKVP

SHLLRSKITKPNVYHESKLAAKEYQAAKARLFTAFIKAGLGAWVEKPTEQDQFSLT[P]*

MCP-*Linker*-ADAR1(E1008Q)-NLS (optional sequence in brackets)

(SEQ ID NO: 77)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGS*KAERMGFTEVTPVTGASLRRTMLLLSRSPEA

QPKTLPLTGSTFHDQIAMLSHRCFNTLTNSFQPSLLGRKILAAIIMKKDSEDMGVVVSLG

TGNRCVKGDSLSLKGETVNDCHAEIISRRGFIRFLYSELMKYNSQTAKDSIFEPAKGGEK

LQIKKTVSFHLYISTAPCGDGALFDKSCSDRAMESTESRHYPVFENPKQGKLRTKVENG

QGTIPVESSDIVPTWDGIRLGERLRTMSCSDKILRWNVLGLQGALLTHFLQPIYLKSVTL

GYLFSQGHLTRAICCRVTRDGSAFEDGLRHPFIVNHPKVGRVSIYDSKRQSGKTKETSVN

WCLADGYDLEILDGTRGTVDGPRNELSRVSKKNIFLLFKKLCSFRYRRDLLRLSYGEAK

KAARDYETAKNYFKKGLKDMGYGNWISKPQEEKNFYLCPVGSGSGSGPKKRKV[AA]*

Nuclear Localization Sequence-*Linker*-MCP-*Linker*-ADAR2(E488Q) (optional sequence in brackets)

(SEQ ID NO: 78)

[MG]PKKKRKVAA*GSGSGS*MASNFTQFVLVDNGGTGDVTVAPSNFANGVAEWISSNS

RSQAYKVTCSVRQSSAQKRKYTIKVEVPKVATQTVGGVELPVAAWRSYLNMELTI

PIFATNSDCELIVKAMQGLLKDGNPIPSAIAANSGIY*GGSGGSGGS*MLHLDQTPSRQPI

PSEGLQLHLPQVLADAVSRLVLGKFGDLTDNFSSPHARRKVLAGVVMTTGTDVKDAKV

ISVSTGTKCINGEYMSDRGLALNDCHAEIISRRSLLRFLYTQLELYLNNKDDQKRSIFQKS

ERGGFRLKENVQFHLYISTSPCGDARIFSPHEPILEEPADRHPNRKARGQLRTKIESGQGT

IPVRSNASIQTWDGVLQGERLLTMSCSDKIARWNVVGIQGSLLSIFVEPIYFSSIILGSLYH

GDHLSRAMYQRISNIEDLPPLYTLNKPLLSGISNAEARQPGKAPNFSVNWTVGDSAIEVI

NATTGKDELGRASRLCKHALYCRWMRVHGKVPSHLLRSKITKPNVYHESKLAAKEYQ

AAKARLFTAFIKAGLGAWVEKPTEQDQFSLT[P]*

-continued

N22p-*Linker*-ADAR1(E1008Q) (optional sequence in brackets)

(SEQ ID NO: 79)

MGNARTRRRERRAEKQAQWKAANGGGGTSGSGSGS*PAGGGAPGSGGGS*KAERMGF
TEVTPVTGASLRRTMLLLSRSPEAQPKTLPLTGSTFHDQIAMLSHRCFNTLTNSFQPSLLG
RKILAAIIMKKDSEDMGVVVSLGTGNRCVKGDSLSLKGETVNDCHAEIISRRGFIRFLYS
ELMKYNSQTAKDSIFEPAKGGEKLQIKKTVSFHLYISTAPCGDGALFDKSCSDRAMESTE
SRHYPVFENPKQGKLRTKVENGQGTIPVESSDIVPTWDGIRLGERLRTMSCSDKILRWN
VLGLQGALLTHFLQPIYLKSVTLGYLFSQGHLTRAICCRVTRDGSAFEDGLRHPFIVNHP
KVGRVSIYDSKRQSGKTKETSVNWCLADGYDLEILDGTRGTVDGPRNELSRVSKKNIFL
LFKKLCSFRYRRDLLRLSYGEAKKAARDYETAKNYFKKGLKDMGYGNWISKPQEEKN
FYLCPVGSGSGSGPKKRKV[AA]*

Nuclear Localization Sequence-*Linker*-N22p-*Linker*-ADAR2(E488Q)

(SEQ ID NO: 80)

[MG]PKKKRKVAA*GSGSGS*MGNARTRRRERRAEKQAQWKAANGGGGTSGSGSGS*P
AGGGAPGSGGGS*MLHLDQTPSRQPIPSEGLQLHLPQVLADAVSRLVLGKFGDLTDNFSSP
HARRKVLAGVVMTTGTDVKDAKVISVSTGTKCINGEYMSDRGLALNDCHAEIISRRSLL
RFLYTQLELYLNNKDDQKRSIFQKSERGGFRLKENVQFHLYISTSPCGDARIFSPHEPILE
EPADRHPNRKARGQLRTKIESGQGTIPVRSNASIQTWDGVLQGERLLTMSCSDKIARWN
VVGIQGSLLSIFVEPIYFSSIILGSLYHGDHLSRAMYQRISNIEDLPPLYTLNKPLLSGISNA
EARQPGKAPNFSVNWTVGDSAIEVINATTGKDELGRASRLCKHALYCRWMRVHGKVP
SHLLRSKITKPNVYHESKLAAKEYQAAKARLFTAFIKAGLGAWVEKPTEQDQFSLT[P]*

Nuclear Localization Sequence-*Linker*-MCP-*Linker*-hAPOPEC1

(SEQ ID NO: 81)

[MG]PKKKRKVAA*GSGSGS***MASNFTQFVLVDNGGTGDVTVAPSNFANGVAEWISSNS
RSQAYKVTCSVRQSSAQKRKYTIKVEVPKVATQTVGGVELPVAAWRSYLNMELTI
PIFATNSDCELIVKAMQGLLKDGNPIPSAIAANSGIY***GGSGGSGGS*MTSEKGPSTGDPT
LRRRIEPWEFDVFYDPRELRKEACLLYEIKWGMSRKIWRSSGKNTTNHVEVNFIKKFTSE
RDFHPSMSCSITWFLSWSPCWECSQAIREFLSRHPGVTLVIYVARLFWHMDQQNRQGLR
DLVNSGVTIQIIVIRASEYYHCWRNFVNYPPGDEAHWPQYPPLWMMLYALELHCIILSLPP
CLKISRRWQNHLTFFRLHLQNCHYQTIPPHILLATGLIHPSVAWR*

Nuclear Localization Sequence-*Linker*-MCP-*Linker*-rAPOBEC1

(SEQ ID NO: 82)

[MG]PKKKRKVAA*GSGSGS***MASNFTQFVLVDNGGTGDVTVAPSNFANGVAEWISSNS
RSQAYKVTCSVRQSSAQKRKYTIKVEVPKVATQTVGGVELPVAAWRSYLNMELTI
PIFATNSDCELIVKAMQGLLKDGNPIPSAIAANSGIY***GGSGGSGGS*MSSETGPVAVDPT
LRRRIEPHEFEVFFDPRELRKETCLLYEINWGGRHSIWRHTSCINTNKHVEVNFIEKFTTER
YFCPNTRCSITWFLSWSPCGECSRAITEFLSRYPHVTLFIYIARLYHHADPRNRQGLRDLI
SSGVTIQIMTEQESGYCWRNFVNYSPSNEAHWPRYPHLWVRLYVLELYCIILGLPPCLNI
LRRKQPQLTFFTIALCISCHYQRLPPHILWATGLK* dsRBD-*Linker*-rAPOBEC1

(SEQ ID NO: 83)

**MDIEDEENMSSSSTDVKENRNLDNVSPKDGSTPGPGEGSQLSNGGGGGPGRKRPLE
EGSNGHSKYRLKKRRKTPGPVLPKNALMQLNEIKPGLQYTLLSQTGPVHAPLFVM
SVEVNGQVFEGSGPTKKKAKLHAAEKALRSFVQFPNASEAHLAMGRTLSVNTDFT
SDQADFPDTLFNGFETPDKAEPPFYVGSNGDDSFSSSGDLSLSASPVPASLAQPPLPV**

-continued

LPPFPPPSGKNPVMILNELRPGLKYDFLSESGESHAKSFVMSVVVDGQFFEGSGRNK

KLAKARAAQSALAAIFN*GGSGGSGGS*MSSETGPVAVDPTLRRRIEPHEFEVFFDPRELR

KETCLLYEINWGGRHSIWRHTSQNTNKHVEVNFIEKFTTERYFCPNTRCSITWFLSWSPC

GECSRAITEFLSRYPHVTLFIYIARLYHHADPRNRQGLRDLISSGVTIQIMTEQESGYCWR

NFVNYSPSNEAHWPRYPHLWVRLYVLELYCIILGLPPCLNILRRKQPQLTFFTIALQSCH

YQRLPPHILWATGLK* dsRBD-*Linker*-hAPOBEC1

(SEQ ID NO: 84)

MDIEDEENMSSSSTDVKENRNLDNVSPKDGSTPGPGEGSQLSNGGGGGPGRKRPLE

EGSNGHSKYRLKKRRKTPGPVLPKNALMQLNEIKPGLQYTLLSQTGPVHAPLFVM

SVEVNGQVFEGSGPTKKKAKLHAAEKALRSFVQFPNASEAHLAMGRTLSVNTDFT

SDQADFPDTLFNGFETPDKAEPPFYVGSNGDDSFSSSGDLSLSASPVPASLAQPPLPV

LPPFPPPSGKNPVMILNELRPGLKYDFLSESGESHAKSFVMSVVVDGQFFEGSGRNK

KLAKARAAQSALAAIFN*GGSGGSGGS*MTSEKGPSTGDPTLRRRIEPWEFDVFYDPRELR

KEACLLYEIKWGMSRKIWRSSGKNTTNHVEVNFIKKFTSERDFHPSMSCSITWFLSWSPC

WECSQAIREFLSRHPGVTLVIYVARLFWHMDQQNRQGLRDLVNSGVTIQIMRASEYYH

CWRNFVNYPPGDEAHWPQYPPLWMMLYALELHCIILSLPPCLKISRRWQNHLTFFRLHL

QNCHYQTIPPHILLATGLIHPSVAWR*

MCP-*Linker*-ADAR1-NES (SEQ ID NO: 85)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGS*KAERMGFTEVTPVTGASLRRTMLLLSRSPEA

QPKTLPLTGSTFHDQIAMLSHRCFNTLTNSFQPSLLGRKILAAIIMKKDSEDMGVVVSLG

TGNRCVKGDSLSLKGETVNDCHAEIISRRGFIRFLYSELMKYNSQTAKDSIFEPAKGGEK

LQIKKTVSFHLYISTAPCGDGALFDKSCSDRAMESTESRHYPVFENPKQGKLRTKVENG

EGTIPVESSDIVPTWDGIRLGERLRTMSCSDKILRWNVLGLQGALLTHFLQPIYLKSVTLG

YLFSQGHLTRAICCRVTRDGSAFEDGLRHPFIVNHPKVGRVSIYDSKRQSGKTKETSVN

WCLADGYDLEILDGTRGTVDGPRNELSRVSKKNIFLLFKKLCSFRYRRDLLRLSYGEAK

KAARDYETAKNYFKKGLKDMGYGNWISKPQEEKNFYLCPVGSGSGSLPPLERLTL*

MCP-*Linker*-ADAR2-NLS (SEQ ID NO: 86)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGS*QLHLPQVLADAVSRLVLGKFGDLTDNFSSPH

ARRKVLAGVVMTTGTDVKDAKVISVSTGTKCINGEYMSDRGLALNDCHAEIISRRSLLR

FLYTQLELYLNNKDDQKRSIFQKSERGGFRLKENVQFHLYISTSPCGDARIFSPHEPILEEP

ADRHPNRKARGQLRTKIESGEGTIPVRSNASIQTWDGVLQGERLLTMSCSDKIARWNVV

GIQGSLLSIFVEPIYFSSIILGSLYHGDHLSRAMYQRISNIEDLPPLYTLNKPLLSGISNAEA

RQPGKAPNFSVNWTVGDSAIEVINATTGKDELGRASRLCKHALYCRWMRVHGKVPSH

LLRSKITKPNVYHESKLAAKEYQAAKARLFTAFIKAGLGAWVEKPTEQDQFSLTGSGSG

SPKKKRKV*

-continued

MCP-*Linker*-ADAR2-NES (SEQ ID NO: 87)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGS*QLHLPQVLADAVSRLVLGKFGDLTDNFSSPH

ARRKVLAGVVMTTGTDVKDAKVISVSTGTKCINGEYMSDRGLALNDCHAEIISRRSLLR

FLYTQLELYLNNKDDQKRSIFQKSERGGFRLKENVQFHLYISTSPCGDARIFSPHEPILEEP

ADRHPNRKARGQLRTKIESGEGTIPVRSNASIQTWDGVLQGERLLTMSCSDKIARWNVV

GIQGSLLSIFVEPIYFSSIILGSLYHGDHLSRAMYQRISNIEDLPPLYTLNKPLLSGISNAEA

RQPGKAPNFSVNWTVGDSAIEVINATTGKDELGRASRLCKHALYCRWMRVHGKVPSH

LLRSKITKPNVYHESKLAAKEYQAAKARLFTAFIKAGLGAWVEKPTEQDQFSLTGSGSG

SLPPLERLTL*

MCP-*Linker*-rAPOBEC1-NLS (SEQ ID NO: 88)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGSSGSETPGTSESATPES*MSSETGPVAVDPTLRR

RIEPHEFEVFFDPRELRKETCLLYEINWGGRHSIWRHTSQNTNKHVEVNFIEKFT

TERYFCPNTRCSITWFLSWSPCGECSRAITEFLSRYPHVTLFIYIARLYHHADPRNRQGLR

DLISSGVTIQIMTEQESGYCWRNFVNYSPSNEAHWPRYPHLWVRLYVLELYCIILGLPPC

LNILRRKQPQLTFFTIALCISCHYQRLPPHILWATGLKGSGSGSPKKKRKV*

MCP-*Linker*-rAPOBEC1-NES (SEQ ID NO: 89)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGSSGSETPGTSESATPES*MSSETGPVAVDPTLRR

RIEPHEFEVFFDPRELRKETCLLYEINWGGRHSIWRHTSQNTNKHVEVNFIEKFTTERYFC

PNTRCSITWFLSWSPCGECSRAITEFLSRYPHVTLFIYIARLYHHADPRNRQGLRDLISSG

VTIQIMTEQESGYCWRNFVNYSPSNEAHWPRYPHLWVRLYVLELYCIILGLPPCLNILRR

KQPQLTFFTIALQSCHYQRLPPHILWATGLKGSGSGSLPPLERLTL*

MCP-*Linker*-hAPOBEC1-NLS (SEQ ID NO: 90)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGSSGSETPGTSESATPES*MTSEKGPSTGDPTLRRR

IEPWEFDVFYDPRELRKEACLLYEIKWGMSRKIWRSSGKNTTNHVEVNFIKKFTSERDF

HPSMSCSITWFLSWSPCWECSCIAIREFLSRHPGVTLVIYVARLFWHMDQQNRQGLRDLV

NSGVTIQIMRASEYYHCWRNFVNYPPGDEAHWPQYPPLWMMLYALELHCIILSLPPCLK

ISRRWQNHLTFFRLHLCINCHYQTIPPHILLATGLIHPSVAWRGSGSGSPKKKRKV*

MCP-*Linker*-hAPOBEC1-NES (SEQ ID NO: 91)

MASNFTQFVLVDNGGTGDVTVAPSNFANGIAEWISSNSRSQAYKVTCSVRQSSAQN

RKYTIKVEVPKGAWRSYLNMELTIPIFATNSDCELIVKAMQGLLKDGNPIPSAIAAN

SGIYGGSGSGAGSGS*PAGGGAPGSGGGSSGSETPGTSESATPES*MTSEKGPSTGDPTLRRR

IEPWEFDVFYDPRELRKEACLLYEIKWGMSRKIWRSSGKNTTNHVEVNFIKKFTSERDF

-continued

HPSMSCSITWFLSWSPCWECSQAIREFLSRHPGVTLVIYVARLFWHMDQQNRQGLRDLV

NSGVTIQIMRASEYYHCWRNFVNYPPGDEAHWPQYPPLWMMLYALELHCIILSLPPCLK

ISRRWQNHLTFFRLHLQNCHYQTIPPHILLATGLIHPSVAWRGSGSGSLPPLERLTL*

Alternate spacer (can be used in place of GGSGGSGGS (SEQ ID NO: 92)):

(SEQ ID NO: 93)

*SGSETPGTSESATPES*

3XNLS-4x1N-cdADAR2

(SEQ ID NO: 94)

MPKKKRKVDPKKKRKVDPKKKRKVGSYPYDVPDYAGSNARTRRRERRAEKQAQ

WKAANGGGGSGGGGSGGGGSNARTRRRERRAEKQAQWKAANGGGGSGGGGSG

GGGSNARTRRRERRAEKQAQWKAANGGGGSGGGGSGGGGSNARTRRRERRAEK

QAQWKAANLHLDQTPSRQPIPSEGLQLHLPQVLADAVSRLVLGKFGDLTDNFSSPHAR

RKVLAGVVMTTGTDVKDAKVISVSTGTKCINGEYMSDRGLALNDCHAEIISRRSLLRFL

YTQLELYLNNKDDQKRSIFQKSERGGFRLKENVQFHLYISTSPCGDARIFSPHEPILEEPA

DRHPNRKARGQLRTKIESGEGTIPVRSNASIQTWDGVLQGERLLTMSCSDKIARWNVVG

IQGSLLSIFVEPIYFSSIILGSLYHGDHLSRAMYQRISNIEDLPPLYTLNKPLLSGISNAEAR

QPGKAPNFSVNWTVGDSAIEVINATTGKDELGRASRLCKHALYCRWMRVHGKVPSHLL

RSKITKPNVYHESKLAAKEYQAAKARLFTAFIKAGLGAWVEKPTEQDQFSLTP

N22p-hAPOBEC1

(SEQ ID NO: 95)

MPKKKRKVDGSGNARTRRRERRAEKQAQWKAANGGGGTSGSGSGSPAGGGAPG

SGGGSMTSEKGPSTGDPTLRRRIEPWEFDVFYDPRELRKEACLLYEIKWGMSRKIWRSS

GKNTTNHVEVNFIKKFTSERDFHPSMSCSITWFLSWSPCWECSQAIREFLSRHPGVTLVI

YVARLFWHMDQQNRQGLRDLVNSGVTIQIMRASEYYHCWRNFVNYPPGDEAHWPQY

PPLWMMLYALELHCIILSLPPCLKISRRWQNHLTFFRLHLQNCHYQTIPPHILLATGLIHP

SVAWR

3XNLS-4x1N-hAPOBEC1

(SEQ ID NO: 96)

MPKKKRKVDPKKKRKVDPKKKRKVGSYPYDVPDYAGSNARTRRRERRAEKQAQ

WKAANGGGGSGGGGSGGGGSNARTRRRERRAEKQAQWKAANGGGGSGGGGSG

GGGSNARTRRRERRAEKQAQWKAANGGGGSGGGGSGGGGSNARTRRRERRAEK

QAQWKAANMTSEKGPSTGDPTLRRRIEPWEFDVFYDPRELRKEACLLYEIKWGMSRKI

WRSSGKNTTNHVEVNFIKKFTSERDFHPSMSCSITWFLSWSPCWECSQAIREFLSRHPGV

TLVIYVARLFWHMDQQNRQGLRDLVNSGVTIQIMRASEYYHCWRNFVNYPPGDEAHW

PQYPPLWMMLYALELHCIILSLPPCLKISRRWQNHLTFFRLHLQNCHYQTIPPHILLATGL

IHPSVAWR

C-terminal ADAR2 (residues 1-138 deleted)

(SEQ ID NO: 97)

MLRSFVQFPNASEAHLAMGRTLSVNTDFTSDQADFPDTLFNGFETPDKAEPPFYVGSNG

DDSFSSSGDLSLSASPVPASLAQPPLPVLPPFPPPSGKNPVMILNELRPGLKYDFLSESGES

HAKSFVMSVVVDGQFFEGSGRNKKLAKARAAQSALAAIFNLHLDQTPSRQPIPSEGLQL

HLPQVLADAVSRLVLGKFGDLTDNFSSPHARRKVLAGVVMTTGTDVKDAKVISVSTGT

KCINGEYMSDRGLALNDCHAEIISRRSLLRFLYTQLELYLNNKDDQKRSIFQKSERGGFR

LKENVQFHLYISTSPCGDARIFSPHEPILEEPADRHPNRKARGQLRTKIESGEGTIPVRSNA

SIQTWDGVLQGERLLTMSCSDKIARWNVVGIQGSLLSIFVEPIYFSSIILGSLYHGDHLSR

-continued

AMYQRISNIEDLPPLYTLNKPLLSGISNAEARQPGKAPNFSVNWTVGDSAIEVINATTGK

DELGRASRLCKHALYCRWMRVHGKVPSHLLRSKITKPNVYHESKLAAKEYQAAKARL

FTAFIKAGLGAWVEKPTEQDQFSLTP*

MS2-RNA:
Single:
(SEQ ID NO: 98)
NNNNNNNNNNNNNNNNNNNNggccAACATGAGGATCACCCATGTCTGCAGggcc Dual:
(SEQ ID NO: 99)
aACATGAGGATCACCCATGTcNNNNNNNNNNNNNNNNNNNNaACATGAGGATCACC CATGTc BoxB RNA:
Single:
(SEQ ID NO: 100)
NNNNNNNNNNNNNNNNNNNNgggccctgaagaagggccc Dual:
(SEQ ID NO: 101)
ggGCCCTGAAGAAGGGCccNNNNNNNNNNNNNNNNNNNNggGCCCTGAAGAAGGGCcc PP7-RNA:
(SEQ ID NO: 102)
NNNNNNNNNNNNNNNNNNNNccggagcagacgatatggcgtcgctccgg Dual Hairpin RNA:
(SEQ ID NO: 103)
TGGAATAGTATAACAATATGCTAAATGTTGTTATAGTATCCCAC

NNNNNNNGTGGAATAGTATAACAATATGCTAAATGTTGTTATAGTATCCCAC

A-U to G-C substitutions in adRNA
v1:
(SEQ ID NO: 104)
GGGTGGAATAGTATAACAATATGCTAAATGTTGTTATAGTATCCCACCT

*NNNCNNNNNNNNNNNNNNNN* v2:
(SEQ ID NO: 105)
GTGGAATAGTATAACAATATGCTAAATGTTGTTATAGTATCCCAC

*NNNNNNCNNNNNNNNNNNNNN* v3:
(SEQ ID NO: 106)
GTGGAAGAGGAGAACAATATGCTAAATGTTGTTCTCGTCTCCCAC
*NNNNNNCNNNNNNNNNNNNNNN* v4:
(SEQ ID NO: 107)
GGGTGGAAGAGGAGAACAATATGCTAAATGTTGTTCTCGTCTCCCACCT

*NNNCNNNNNNNNNNNNNNNN* v5:
(SEQ ID NO: 108)
GGTGAAGAGGAGAACAATATGCTAAATGTTGTTCTCGTCTCCACC

*NNNNNNCNNNNNNNNNNNNNNN* v6:
(SEQ ID NO: 109)
GGTGAAGAGGAGAACAATATGCTAAATGTTGTTCTCGTCTCCACC

*NNNNNNNCNNNNNNNNNNNNNN* v7:
(SEQ ID NO: 110)
GTGGAAGAGGAGAACAATAGGCTAAACGTTGTTCTCGTCTCCCAC

*NNNNNNCNNNNNNNNNNNNNNN*

-continued v8:
(SEQ ID NO: 111)
GGGTGGAAGAGGAGAACAATAGGCTAAACGTTGTTCTCGTCTCCCACCT

*NNNCNNNNNNNNNNNNNNNN* v9:
(SEQ ID NO: 112)
GGTGAAGAGGAGAACAATAGCTAAACGTTGTTCTCGTCTCCACC

*NNNNNNCNNNNNNNNNNNNNNN* v10:
(SEQ ID NO: 113)
GGTGAAGAGGAGAACAATAGCTAAACGTTGTTCTCGTCTCCACC

*NNNNNNNCNNNNNNNNNNNNN* v11:
(SEQ ID NO: 114)
GGTGTCGAGAATAGTATAACCAATATGCTAAATGTTGTTATAGTATCCTCGACACC

*NNNNNNNCNNNNNNNNNNN* v12:
(SEQ ID NO: 115)
GGTGTCGAGAAGAGGATGACAATATGCTAAATGTTGTTCTCGTCTCCTCGACACC

*NNNNNNNCNNNNNNNNNNN* v13:
(SEQ ID NO: 116)
GGTGTCGAGAAGAGGAGAACAATAGGCTAAACGTTGTTCTCGTCTCCTCGACACC

*NNNNNNNCNNNNNNNNNNN* dCas9Cj-NES-*Linker*-cdADAR2(E488Q)
(SEQ ID NO: 117)
MARILAFAIGISSIGWAFSENDELKDCGVRIFTKVENPKTGESLALPRRLARSARKR

LARRKARLNHLKIILIANEFKLNYEDYQSFDESLAKAYKGSLISPYELRFRALNELLS

KQDFARVILHIAKRRGYDDIKNSDDKEKGAILKAIKQNEEKLANYQSVGEYLYKEY

FQKFKENSKEFTNVRNKKESYERCIAQSFLKDELKLIFKKQREFGFSFSKKFEEEVL

SVAFYKRALKDFSHLVGNCSFFTDEKRAPKNSPLAFMFVALTRIINLLNNLKNTEGI

LYTKDDLNALLNEVLKNGTLTYKQTKKLLGLSDDYEFKGEKGTYFIEFKKYKEFI

KALGEHNLSQDDLNEIAKDITLIKDEIKLKKALAKYDLNQNQIDSLSKLEFKDHLNI

SFKALKLVTPLMLEGKKYDEACNELNLKVAINEDKKDFLPAFNETYYKDEVTNPV

VLRAIKEYRKVLNALLKKYGKVHKINIELAREVGKNHSQRAKIEKEQNENYKAKK

DAELECEKLGLKINSKNILKLRLFKEQKEFCAYSGEKIKISDLQDEKMLEIDAIYPYS

RSFDDSYMNKVLVFTKQNQEKLNQTPFEAFGNDSAKWQKIEVLAKNLPTKKQKRI

LDKNYKDKEQKNFKDRNLNDTRYIARLVLNYTKDYLDFLPLSDDENTKLNDTQKG

SKVHVEAKSGMLTSALRHTWGFSAKDRNNHLHHAIDAVIIAYANNSIVKAFSDFKK

EQESNSAELYAKKISELDYKNKRKFFEPFSGFRQKVLDKIDEIFVSKPERKKPSGAL

HEETFRKEEEFYQSYGGKEGVLKALELGKIRKVNGKIVKNGDMFRVDIFKHKKTN

KFYAVPIYTMDFALKVLPNKAVARSKKGEIKDWILMDENYEFCFSLYKDSLILIQT

KDMQEPEFVYYNAFTSSTVSLIVSKIIDNKFETLSKNQKILFKNANEKEVIAKSIGIQ

NLKVFEKYIVSALGEVTKAEFRQREDFKKSGLPPLERLTL*GSGGGG*SQLHLPQVLAD

AVSRLVLGKFGDLTDNFSSPHARRKVLAGVVMTTGTDVKDAKVISVSTGTKCINGEYM

SDRGLALNDCHAEIISRRSLLRFLYTQLELYLNNKDDQKRSIFQKSERGGFRLKENVQFH

LYISTSPCGDARIFSPHEPILEEPADRHPNRKARGQLRTKIESGQGTIPVRSNASIQTWDGV

-continued

LQGERLLTMSCSDKIARWNVVGIQGSLLSIFVEPIYFSSIILGSLYHGDHLSRAMYQRISNI

EDLPPLYTLNKPLLSGISNAEARQPGKAPNFSVNWTVGDSAIEVINATTGKDELGRASRL

CKHALYCRWMRVHGKVPSHLLRSKITKPNVYHESKLAAKEYQAAKARLFTAFIKAGLG

AWVEKPTEQDQFSLT

Single and dual ADAR2 recruiting domain:

Single:

(SEQ ID NO: 118)

GTGGAATAGTATAACAATATGCTAAATGTTGTTATAGTATCCCACACAAACCGA

GCGGTGTCTGT

Dual 1:

(SEQ ID NO: 119)

GTGGAATAGTATAACAATATGCTAAATGTTGTTATAGTATCCCACCAAACCGAG

CGGTGTCTGTGGTGGAATAGTATAACAATATGCTAAATGTTGTTATAGTATCCCAC

Dual 2:

(SEQ ID NO: 120)

GTGGAATAGTATAACAATATGCTAAATGTTGTTATAGTATCCCACTACAAACCG

AGCGGTGTCTGGTGGAATAGTATAACAATATGCTAAATGTTGTTATAGTATCCCAC

Dual 3:

(SEQ ID NO: 121)

GTGGAATAGTATAACAATATGCTAAATGTTGTTATAGTATCCCACTTTACAAACC

GAGCGGTGTCGTGGAATAGTATAACAATATGCTAAATGTTGTTATAGTATCCCAC

Dual 4:

(SEQ ID NO: 122)

GTGGAATAGTATAACAATATGCTAAATGTTGTTATAGTATCCCACGTTTTACAAA

CCGAGCGGTGGTGGAATAGTATAACAATATGCTAAATGTTGTTATAGTATCCCAC

Dual 5:

(SEQ ID NO: 123)

GTGGAATAGTATAACAATATGCTAAATGTTGTTATAGTATCCCACAAGTTTTACA

AACCGAGCGGGTGGAATAGTATAACAATATGCTAAATGTTGTTATAGTATCCCAC

BRIEF DESCRIPTION OF THE DRAWINGS

(FIG. 2A) Relative efficiencies of the suppressor tRNAs derived from arginine, serine and leucine towards the amber, ochre and opal stop codons; Representative images showing the restoration of GFP expression in the presence of the Ser tRNAAmber (FIG. 2B) Comparison of the suppression efficiencies of the single or dual pyrrolysyl tRNAs towards amber, ochre and opal stop codons in the presence of 2 mM UAA; Representative images showing the relative GFP restoration using single and dual pyrrolysyl tRNAAmber in the presence of 2 mM UAA.

FIG. 5 shows sequences used to generate the ADAR2 constructs (SEQ ID NOS 164-166, respectively, in order of appearance).

FIG. 9 shows in vitro restoration of GFP expression using the editing systems described herein.

FIG. 10 shows the results of optimization of hairpins with mismatches (SEQ ID NOS 167-172, respectively, in order of appearance). The first number in the shorthand for each category on the Y-axis is the number of mismatches and the second number is the number of bases it is from the target. For example, 13 is 1 mismatch, 3 bases away from the target.

FIG. 12A-C show results of (FIG. 12A) immunostaining, (FIG. 12B) Western blot, and (FIG. 12C) in vitro OTC mRNA editing assays (SEQ ID NOS 173-174, respectively, in order of appearance).

(FIG. 16A) Activity of arginine, serine and leucine suppressor tRNAs targeting amber, ochre and opal stop codons (n=3 independent replicates). (FIG. 16B) Orthogonal tRNA/aaRS (MbPylRS)

based suppression of amber, ochre and opal stop codons in the presence of one or two copies of the pyrrolysyl-tRNA delivered via an AAV vector and in the presence of 1 mM NE-Boc-L-Lysine (n=3 independent replicates) (p-values 0.022, 0.002, 0.027 respectively). (FIG. 16C) ADAR2 based RNA editing efficiencies of amber and ochre stop codons, in one-step, two-steps, or in combination with suppressor tRNAs (n=3 independent replicates). (FIG. 16D) ADAR2 based RNA editing efficiencies of amber and ochre stop codons in the presence of one or two copies of the adRNA, delivered via an AAV vector (n=3 or 6 independent replicates) (p-values 0.0003, 0.0001, 0.0015 respectively).

(FIG. 17A) Schematic of the DNA and RNA targeting approaches to restore dystrophin expression in mdx mice: (i) a dual gRNA-CRISPR based approach leading to in frame excision of exon 23; (ii) tRNA suppression of the ochre codon; and (iii) ADAR2 based editing of the ochre codon. (FIG. 17B) Immunofluorescence staining for dystrophin and nNOS in controls and treated samples (scale bar: 250 μm). (FIG. 17C) In vivo TAA→TGG/TAG/TGA RNA editing efficiencies in corresponding treated adult mdx mice (n=3 or 4 mice). (FIG. 17D) Schematic of the OTC locus in spf$^{ash}$ mice which have a G→A point mutation at a donor splice site or missense in the last nucleotide of exon 4, and approach for correction of mutant OTC mRNA via ADAR2 mediated RNA editing (FIG. 17E) In vivo A→G RNA editing efficiencies in corresponding treated adult spf$^{ash}$ mice (n=3 or 4 mice).

FIG. 18A-B show in vitro tRNA suppression evaluation and optimization: (FIG. 18A) Specificity of modified serine suppressor tRNAs for ochre and opal stop codons (n=3 independent replicates). (FIG. 18B) Ochre stop codon suppression efficiency utilizing three different aaRS: MbPylRS, MmPylRS and AcKRS, and two or four copies of the pyrroysyl-tRNA, or serine suppressor tRNA, all delivered using an AAV vector. MbPylRS, MmPylRS: 1 mM Nε-Boc-L-Lysine; AcKRS: 1 or 10 mM Nε-Acetyl-L-Lysine (n=3 independent replicates).

(FIG. 19A) GFP expression is restored when adRNA/radRNA has two mismatches corresponding to the two adenosines in the ochre stop codon. Presence of a single mismatch results in the formation of an amber or opal stop codon (n=3 independent replicates) (SEQ ID NOS 175-179, respectively, in order of appearance). (FIG. 19B) Panel of adRNA designs used (SEQ ID NOS 180-181, respectively, in order of appearance). (FIG. 19C) Optimization of adRNA antisense region using adRNA design 1: length and distance from the ADAR2 recruiting region were systematically varied, and editing efficiency calculated as a ratio of Sanger peak heights G/(A+G) (n=3 independent replicates) (SEQ ID NOS 182-206, respectively, in order of appearance).

(FIG. 20A) Progressively increasing restoration of dystrophin expression over time in mdx mice treated with AAV8-dual-serine-ochre-tRNA. (FIG. 20B) UAA inducible nNOS localization in mdx mice treated with AAV8-dual-pyrrolysine-ochre-tRNA-MbPylRS. (FIG. 20C) Western blot for dystrophin shows partial recovery of dystrophin expression in the mdx mice treated with a serine tRNA ochre, the pyrrolysyl-tRNA ochre and administered with the UAA, as well as in Cas9/gRNAs treated samples.

(FIG. 21A) Representative Sanger sequencing plot showing 12.7% editing of the ochre stop codon (TAA→TGG) in a fragment of the mdx dystrophin mRNA expressed in HEK 293T cells (quantified using NGS) (SEQ ID NOS 207-208, respectively, in order of appearance). (FIG. 21B) Representative example of in vivo RNA editing analyses of treated mdx mouse (quantified using NGS) (SEQ ID NOS 209-216, respectively, in order of appearance). (FIG. 21C) Representative Sanger sequencing plot showing 29.7% correction of the point mutation in a fragment of the spf$^{ash}$ OTC mRNA expressed in HEK 293T cells (quantified using NGS) (SEQ ID NOS 217-218, respectively, in order of appearance). (FIG. 21D) Representative example of in vivo RNA editing analyses of treated spf$^{ash}$ mouse (quantified using NGS) (SEQ ID NOS 219-226, respectively, in order of appearance).

FIG. 22A-B show in vitro editing efficiency of ADAR2-E488Q. ADAR2-E488Q enables higher efficiency than the ADAR2 in the in vitro editing of: (FIG. 22A) a fragment of spf$^{ash}$ OTC mRNA expressed in HEK293T cells (n=3 independent replicates) (p-value 0.037), and (FIG. 22B) a fragment of mdx dystrophin mRNA expressed in HEK293T cells (n=3 independent replicates) (p-values 0.048, 0.012 respectively). Efficiency was calculated as a ratio of Sanger peak heights G/(A+G).

FIG. 23A-D show schematics of (FIG. 23A) MCP or N22 fusions with ADAR1 or ADAR2, (FIG. 23B) recruitment of APOBEC by adRNA, (FIG. 23C) a more general adRNA architecture, and (FIG. 23D) the structure of the v2 adRNA scaffold after folding (SEQ ID NO: 227).

FIG. 24A-B show schematics of optional embodiments in which (FIG. 24A) endogenous ADAR2 can be used in the methods disclosed herein in tissues with high endogenous ADAR2, e.g., brain, lung, and spleen and (FIG. 24B) ADAR1 and/or ADAR2 levels can be increased in tissues with low levels of endogenous ADAR1 and ADAR2. Clockwise from the left, (1) delivery of adRNA and ADAR2 would result in high levels of RNA editing, (2) delivery of adRNA alone is likely to bring about little or no editing due to the low levels of endogenous ADAR1 and ADAR2, (3) treatment of cells with IFNs will lead to an increase in the ADAR1 (p150) levels but is unlikely to bring about any editing of the RNA target in the absence of the adRNA; (4) treatment of cells with IFNs with the addition of adRNA will lead to elevated levels of ADAR1 (p150) and in the presence of adRNA, is likely to lead to high levels of target RNA editing, (5) treatment of cells with IFNs with the addition of adRNA and ADAR2 will lead to elevated levels of ADAR1 expression, and high levels of RNA editing.

FIG. 29 shows the fraction of edited mRNA with single versus dual ADAR2 recruiting domains and the corresponding sequences (SEQ ID NOS 118-123, respectively, in order of appearance).

DETAILED DESCRIPTION

Figure 1:
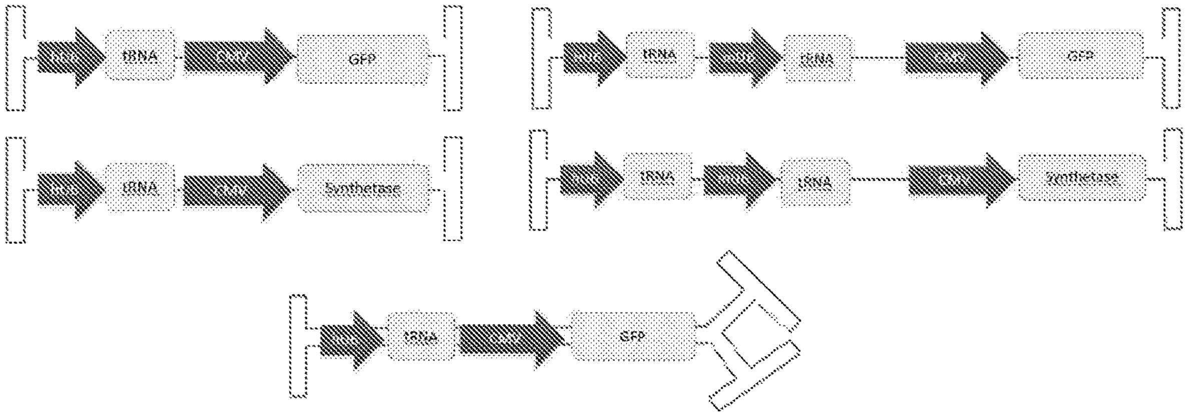
FIG. 1 is a schematic of the vector constructs developed for the delivery of the modified endogenous or orthogonal tRNA.
Figure 2:
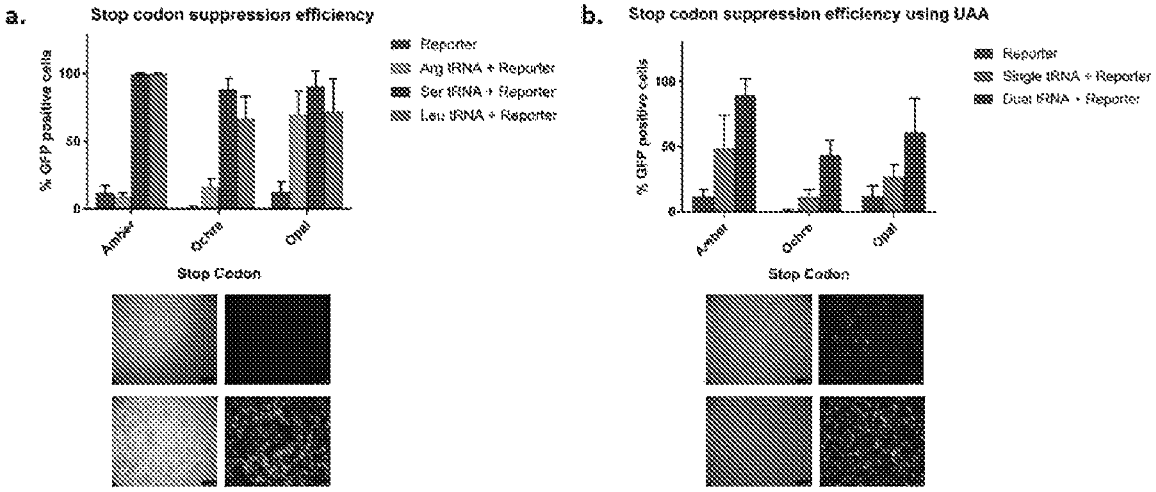
FIG. 2A-B show suppression efficiencies of the tRNA constructs.
Figure 3:
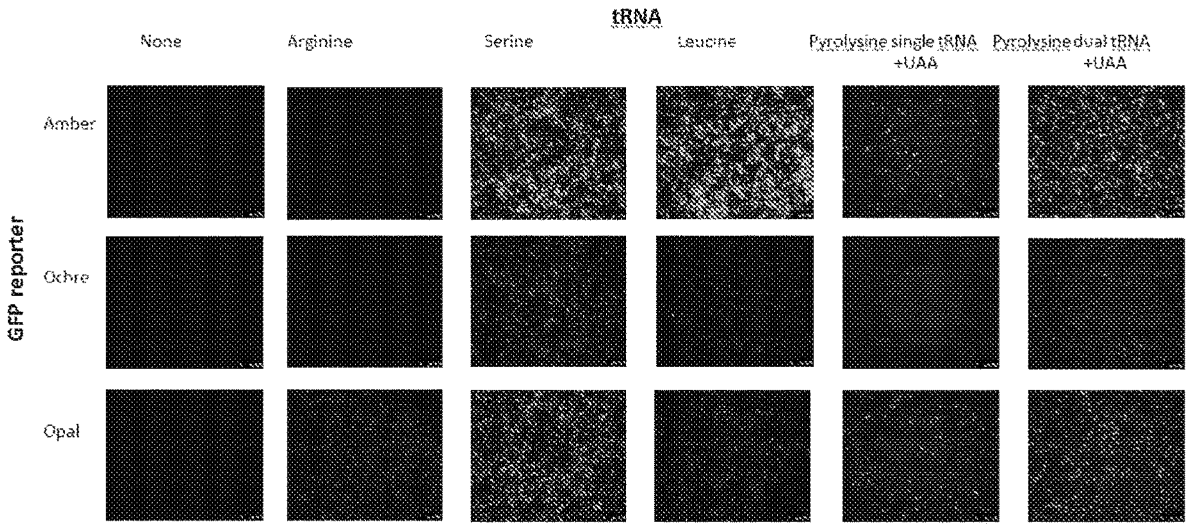
FIG. 3 shows the GFP reporter results for dystrophin with various tRNA and amino acids.
Figure 4:
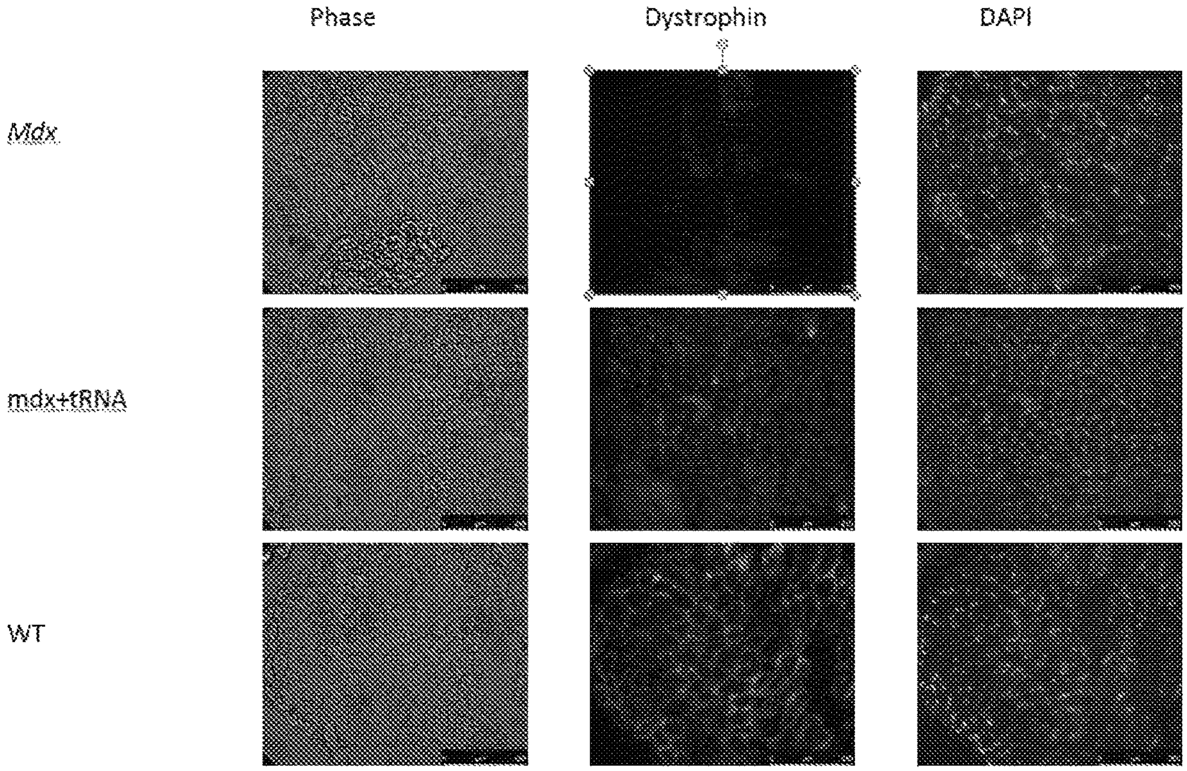
FIG. 4 shows the results of the dystrophin restoration experiments performed in mdx mice.

Unless defined otherwise, all technical and scientific terms used herein have the same meanings as commonly understood by one of ordinary skill in the art to which this invention belongs. All nucleotide sequences provided herein are presented in the 5' to 3' direction. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR* 1*: A Practical Approach* (IRL Press at Oxford University Press); MacPherson et al. (1995) *PCR* 2*: A Practical Approach*; Harlow and Lane eds. (1999) *Antibodies, A Laboratory Manual; Freshney* (2005) i Culture of Animal Cells: A Manual of Basic Technique, 5th edition; Gait ed. (1984) *Oligonucleotide Synthesis; U.S. Pat. No.* 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

The terminology used in the description herein is for the purpose of describing particular embodiments only and is not intended to be limiting of the invention. All publications, patent applications, patents and other references mentioned herein are incorporated by reference in their entirety.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

Definitions

As used in the specification and claims, the singular form "a", "an" and "the" include plural references unless the context clearly dictates otherwise. For example, the term "a polypeptide" includes a plurality of polypeptides, including mixtures thereof.

The term "about," as used herein when referring to a measurable value such as an amount or concentration and the like, is meant to encompass variations of 20%, 10%, 5%, 1%, 0.5%, or even 0.1% of the specified amount.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. As used herein, the term "fusion protein" refers to a protein comprised of domains from more than one naturally occurring or recombinantly produced protein, where generally each domain serves a different function. In this regard, the term "linker" refers to a protein fragment that is used to link these domains together—optionally to preserve the conformation of the fused protein domains and/or prevent unfavorable interactions between the fused protein domains which may compromise their respective functions.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. In some embodiments, the polynucleotide may comprise one or more other nucleotide bases, such as inosine (I), a nucleoside formed when hypoxanthine is attached to ribofuranose via a β-N9-glycosidic bond, resulting in the chemical structure:

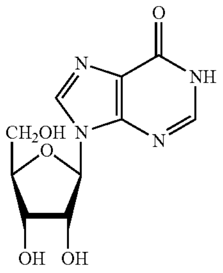

Inosine is read by the translation machinery as guanine (G). The term "polynucleotide sequence" is the alphabetical representation of a polynucleotide molecule. This alphabetical representation can be input into databases in a computer having a central processing unit and used for bioinformatics applications such as functional genomics and homology searching.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The terms "equivalent" or "biological equivalent" are used interchangeably when referring to a particular molecule, biological, or cellular material and intend those having minimal homology while still maintaining desired structure or functionality.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the term "functional" may be used to modify any molecule, biological, or cellular material to intend that it accomplishes a particular, specified effect.

As used herein, the terms "treating," "treatment" and the like are used herein to mean obtaining a desired pharmacologic and/or physiologic effect. The effect may be prophylactic in terms of completely or partially preventing a disease, disorder, or condition or sign or symptom thereof, and/or may be therapeutic in terms of a partial or complete cure for a disorder and/or adverse effect attributable to the disorder.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The term "Cas9" refers to a CRISPR associated endonuclease referred to by this name (for example, UniProtKB G3ECR1 (CAS9_STRTR)) as well as dead Cas9 or dCas9, which lacks endonuclease activity (e.g., with mutations in both the RuvC and HNH domain). The term "Cas9" may further refer to equivalents of the referenced Cas9 having at least about 60%, 65%, 70%, 75%, 80%, 85%, 90%, 95%, or 99% identity thereto, including but not limited to other large Cas9 proteins. In some embodiments, the Cas9 is derived from *Campylobacter jejuni* or another Cas9 otrholog 1000 amino acids or less in length.

The term "vector" refers to a polynucleotide (usually DNA) used to artificially carry foreign genetic material to another cell where it can be replicated or expressed. Non-limiting exemplary vectors include plasmids, viral vectors, cosmids, and artificial chromosomes. Such vectors may be derived from a variety of sources, including bacterial and viral sources. A non-limiting exemplary viral source for a plasmid is adeno-associated virus.

As used herein, the term "recombinant expression system" refers to a genetic construct or constructs for the expression of certain genetic material formed by recombination; the term "construct" in this regard is interchangeable with the term "vector" as defined herein.

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11, sequentially numbered, are disclosed in the prior art. Non-limiting exemplary serotypes useful for the purposes disclosed herein include any of the 11 serotypes, e.g., AAV2 and AAV8.

The term "lentivirus" as used herein refers to a member of the class of viruses associated with this name and belonging to the genus lentivirus, family Retroviridae. While some lentiviruses are known to cause diseases, other lentivirus are known to be suitable for gene delivery. See, e.g., Tomas et al. (2013) Biochemistry, Genetics and Molecular Biology: "Gene Therapy—Tools and Potential Applications," ISBN 978-953-51-1014-9, DOI: 10.5772/52534.

As used herein the term "restoring" in relation to expression of a protein refers to the ability to establish expression of full length protein where previously protein expression was truncated due to mutation.

The term "mutation" as used herein, refers to an alteration to a nucleic acid sequence encoding a protein relative to the consensus sequence of said protein. "Missense" mutations result in the substitution of one codon for another; "nonsense" mutations change a codon from one encoding a particular amino acid to a stop codon. Nonsense mutations often result in truncated translation of proteins. "Silent" mutations are those which have no effect on the resulting protein. As used herein the term "point mutation" refers to a mutation affecting only one nucleotide in a gene sequence. "Splice site mutations" are those mutations present pre-mRNA (prior to processing to remove introns) resulting in mistranslation and often truncation of proteins from incorrect delineation of the splice site.

"Messenger RNA" or "mRNA" is a nucleic acid molecule that is transcribed from DNA and then processed to remove non-coding sections known as introns. The resulting mRNA is exported from the nucleus (or another locus where the DNA is present) and translated into a protein. The term "pre-mRNA" refers to the strand prior to processing to remove non-coding sections.

"Transfer ribonucleic acid" or "tRNA" is a nucleic acid molecule that helps translate mRNA to protein. tRNA have a distinctive folded structure, comprising three hairpin loops; one of these loops comprises a "stem" portion that encodes an anticodon. The anticodon recognizes the corresponding codon on the mRNA. Each tRNA is "charged with" an amino acid corresponding to the mRNA codon; this "charging" is accomplished by the enzyme tRNA synthetase. Upon tRNA recognition of the codon corresponding to its anticodon, the tRNA transfers the amino acid with which it is charged to the growing amino acid chain to form a polypeptide or protein. Endogenous tRNA can be charged by endogenous tRNA synthetase. Accordingly, endogenous tRNA are typically charged with canonical amino acids. Orthogonal tRNA, derived from an external source, require a corresponding orthogonal tRNA synthetase. Such orthogonal tRNAs may be charged with both canonical and non-canonical amino acids. In some embodiments, the amino acid with which the tRNA is charged may be detectably labeled to enable detection in vivo. Techniques for labeling are known in the art and include, but are not limited to, click chemistry wherein an azide/alkyne containing unnatural amino acid is added by the orthogonal tRNA/synthetase pair and, thus, can be detected using alkyne/azide comprising fluorophore or other such molecule.

The term "stop codon" intends a three nucleotide contiguous sequence within messenger RNA that signals a termination of translation. Non-limiting examples include in RNA, UAG, UAA, UGA and in DNA TAG, TAA or TGA. Unless otherwise noted, the term also includes nonsense mutations within DNA or RNA that introduce a premature stop codon, causing any resulting protein to be abnormally shortened. tRNA that correspond to the various stop codons are known by specific names: amber (UAG), ochre (UAA), and opal (UGA).

"Canonical amino acids" refer to those 20 amino acids found naturally in the human body shown in the table below with each of their three letter abbreviations, one letter abbreviations, structures, and corresponding codons:

| non-polar, aliphatic residues | | | | |
|---|---|---|---|---|
| Glycine | Gly | G | 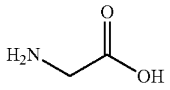 | GGU GGC GGA GGG |
| Alanine | Ala | A | 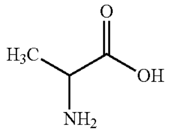 | GCU GCC GCA GCG |

-continued
| | | | | |
|---|---|---|---|---|
| Valine | Val | V | 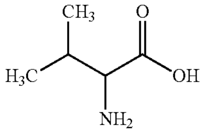 | GUU GUC GUA GUG |
| Leucine | Leu | L | 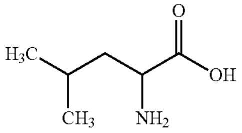 | UUA UUG CUU CUC CUA CUG |
| Isoleucine | Ile | I | 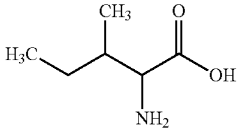 | AUU AUC AUA |
| Proline | Pro | P | 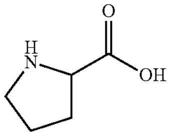 | CCU CCC CCA CCG |
| | | aromatic residues | | |
| Phenylalanine | Phe | F | 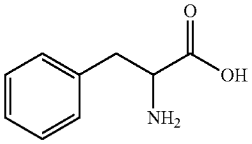 [SMILES: NC(Cc1ccccc1)C(=O)O] | UUU UUC |
| Tyrosine | Tyr | Y | 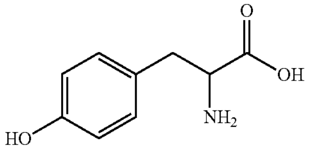 [SMILES: NC(Cc1ccc(O)cc1)C(=O)O] | UAU UAC |
| Tryptophan | Trp | W | 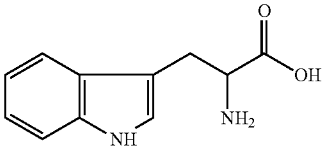 [SMILES: NC(Cc1c[nH]c2ccccc12)C(=O)O] | UGG |
| | | polar, non-charged residues | | |
| Serine | Ser | S | 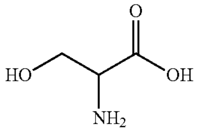 | UCU UCC UCA UCG AGU AGC |
| Threonine | Thr | T | 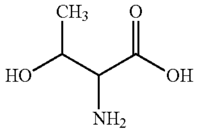 | ACU ACC ACA ACG |
| Cysteine | Cys | C | 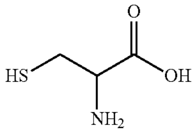 | UGU UGC |

-continued

| | | | | |
|---|---|---|---|---|
| Methionine | Met | M | 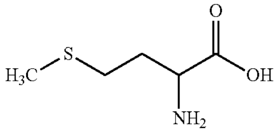 | AUG |
| Asparagine | Asn | N | 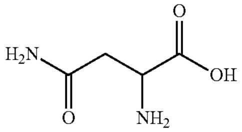 | AAU AAC |
| Glutamine | Gln | Q | 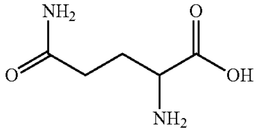 | CAA CAG |
| positively charged residues | | | | |
| Lysine | Lys | K | 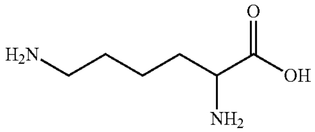 | AAA AAG |
| Arginine | Arg | R | 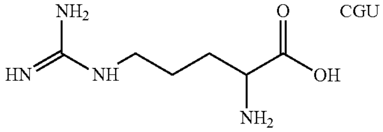 | CGU CGC CGA CGG AGA AGG |
| Histidine | His | H | 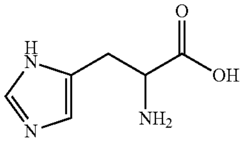 [SMILES: NC(Cc1cnc[nH]1)C(=O)O] | CAU CAC |
| negatively charged residues | | | | |
| Aspartate | Asp | D | 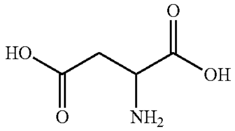 | GAU GAC |
| Glutamate | Glu | E | 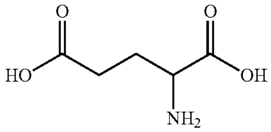 | GAA GAG |

The term "non-canonical amino acids" refers to those synthetic or otherwise modified amino acids that fall outside this group, typically generated by chemical synthesis or modification of canonical amino acids (e.g. amino acid analogs). The present disclosure employs proteinogenic non-canonical amino acids in some of the methods and vectors disclosed herein. A non-limiting exemplary non-canonical amino acid is pyrrolysine (Pyl or O), the chemical structure of which is provided below:

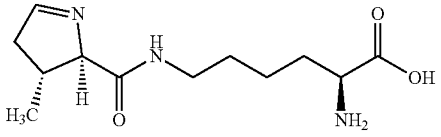 [SMILES: C[C@@H]1CC=N[C@H]1C(=O)NCCCC[C@H](N)C(=O)O]

Inosine (I) is another exemplary non-canonical amino acid, which is commonly found in tRNA and is essential for proper translation according to "wobble base pairing." The structure of inosine is provided above.

The term "ADAR" as used herein refers to an adenosine deaminase that can convert adenosines (A) to inosines (I) in an RNA sequence. ADAR1 and ADAR2 are two exemplary species of ADAR that are involved in mRNA editing in vivo. Non-limiting exemplary sequences for ADAR1 may be found under the following reference numbers: HGNC: 225; Entrez Gene: 103; Ensembl: ENSG 00000160710; OMIM: 146920; UniProtKB: P55265; and GeneCards: GC01M154554, as well as biological equivalents thereof. Non-limiting exemplary sequences for ADAR2 may be found under the following reference numbers: HGNC: 226; Entrez Gene: 104; Ensembl: ENSG00000197381; OMIM: 601218; UniProtKB: P78563; and GeneCards: GC21P045073, as well as biological equivalents thereof. Further non-limitined exemplary sequences of the catalytic domain are provided hereinabove. The forward and reverse RNA used to direct site-specific ADAR editing are known as "adRNA" and "radRNA," respectively. The catalytic domains of ADAR1 and ADAR2 are comprised in the sequences provided herein below.

ADAR1 catalytic domain:

(SEQ ID NO: 124)

KAERMGFTEVTPVTGASLRRTMLLLSRSPEAQPKTLPLTGSTFHDQIAML

SHRCFNTLTNSFQPSLLGRKILAAIIMKKDSEDMGVVVSLGTGNRCVKGD

SLSLKGETVNDCHAEIISRRGFIRFLYSELMKYNSQTAKDSIFEPAKGGE

KLQIKKTVSFHLYISTAPCGDGALFDKSCSDRAMESTESRHYPVFENPKQ

GKLRTKVENGEGTIPVESSDIVPTWDGIRLGERLRTMSCSDKILRWNVLG

LQGALLTHFLQPIYLKSVTLGYLFSQGHLTRAICCRVTRDGSAFEDGLRH

PFIVNHPKVGRVSIYDSKRQSGKTKETSVNWCLADGYDLEILDGTRGTVD

GPRNELSRVSKKNIFLLFKKLCSFRYRRDLLRLSYGEAKKAARDYETAKN

YFKKGLKDMGYGNWISKPQEEKNFYLCPV

ADAR2 catalytic domain:

(SEQ ID NO: 125)

QLHLPQVLADAVSRLVLGKEGDLTDNESSPHARRKVLAGVVMTTGTDVKD

AKVISVSTGTKCINGEYMSDRGLALNDCHAEIISRRSLLRFLYTQLELYL

NNKDDQKRSIFQKSERGGFRLKENVQFHLYISTSPCGDARIFSPHEPILE

EPADRHPNRKARGQLRTKIESGEGTIPVRSNASIQTWDGVLQGERLLTMS

CSDKIARWNVVGIQGSLLSIFVEPIYFSSIILGSLYHGDHLSRAMYQRIS

NIEDLPPLYTLNKPLLSGISNAEARQPGKAPNFSVNWTVGDSAIEVINAT

TGKDELGRASRLCKHALYCRWMRVHGKVPSHLLRSKITKPNVYHESKLAA

KEYQAAKARLFTAFIKAGLGAWVEKPTEQDQFSLT

The double stranded RNA binding domains (dsRBD) of an ADAR is comprised in the sequence provided herein below.

ADAR dsRBD:

(SEQ ID NO: 126)

MDIEDEENMSSSSTDVKENRNLDNVSPKDGSTPGPGEGSQLSNGGGGGPG

RKRPLEEGSNGHSKYRLKKRRKTPGPVLPKNALMQLNEIKPGLQYTLLSQ

-continued

TGPVHAPLFVMSVEVNGQVFEGSGPTKKKAKLHAAEKALRSFVQFPNASE

AHLAMGRTLSVNTDFTSDQADFPDTLFNGFETPDKAEPPFYVGSNGDDSF

SSSGDLSLSASPVPASLAQPPLPVLPPFPPPSGKNPVMILNELRPGLKYD

FLSESGESHAKSFVMSVVVDGQFFEGSGRNKKLAKARAAQSALAAIFN

It is appreciated that further mutations can be made to the sequence of the ADAR and/or its various domains. For example, Applicants have generated E488Q and E1008Q mutants of both ADAR1 and ADAR2, as well as a "promiscuous" variant of ADAR2—resulting from a C-terminal deletion. This "promiscuous" variant is known as such because it demonstrated promiscuity in edited reads with several As close to a target sequence showing an A to G conversion (verified across 2 different loci). The sequence of this variant is provided herein below.

"Promiscuous" ADAR2 variant:

(SEQ ID NO: 127)

MLRSFVQFPNASEAHLAMGRTLSVNTDFTSDQADFPDTLFNGFETPDKAE

PPFYVGSNGDDSFSSSGDLSLSASPVPASLAQPPLPVLPPFPPPSGKNPV

MILNELRPGLKYDFLSESGESHAKSFVMSVVVDGQFFEGSGRNKKLAKAR

AAQSALAAIFNLHLDQTPSRQPIPSEGLQLHLPQVLADAVSRLVLGKFGD

LTDNFSSPHARRKVLAGVVMTTGTDVKDAKVISVSTGTKCINGEYMSDRG

LALNDCHAEIISRRSLLRFLYTQLELYLNNKDDQKRSIFQKSERGGFRLK

ENVQFHLYISTSPCGDARIFSPHEPILEEPADRHPNRKARGQLRTKIESG

EGTIPVRSNASIQTWDGVLQGERLLTMSCSDKIARWNVVGIQGSLLSIFV

EPIYFSSIILGSLYHGDHLSRAMYQRISNIEDLPPLYTLNKPLLSGISNA

EARQPGKAPNFSVNWTVGDSAIEVINATTGKDELGRASRLCKHALYCRWM

RVHGKVPSHLLRSKITKPNVYHESKLAAKEYQAAKARLFTAFIKAGLGAW

VEKPTEQDQFSLTP*

Not to be bound by theory, a C-terminal deletion in ADAR1 may produce the same or similar effect.

The term "deficiency" as used herein refers to lower than normal (physiologically acceptable) levels of a particular agent. In context of a protein, a deficiency refers to lower than normal levels of the full length protein.

The term "dystrophin" as used herein refers to the protein corresponding with that name and encoded by the gene Dmd; a non-limiting example of which is found under UniProt Reference Number P11532 (for humans) and P11531 (for mice).

Figure 31:
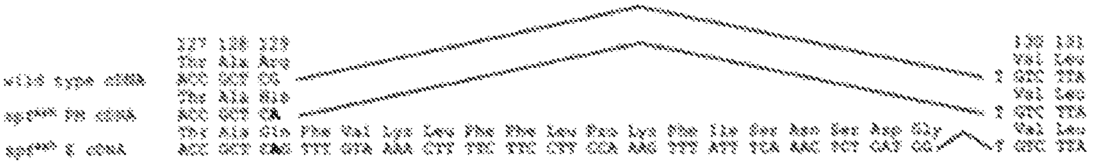
FIG. 31 shows alternative splice variants of OTC and is taken from Hodges, P. E. & Rosenberg, L. E. The spfash mouse: a missense mutation in the ornithine transcarbamylase gene also causes aberrant mRNA splicing. *Proc. Natl. Acad. Sci. U.S.A* 86, 4142-4146 (1989) (SEQ ID NOS 270-275, respectively, in order of appearance).

The term "ornithine transcarbamylase" or "OTC" as used herein refers to the protein corresponding with that name and encoded by the gene Otc; a non-limiting example of which is found under UniProt Reference Number P00480 (for humans) and P11725 (for mice). OTC deficiency is an X-linked genetic condition resulting in high concentrations of ammonia in blood. In some cases, OTC deficiency is caused by a G→A splice site mutation in the donor splice site of exon 4 that results in mis-splicing of the pre-mRNA. This mutation results in the formation of a protein that either is elongated or bears a point mutation. There is a 15-20 fold reduction in the OTC protein levels. The FIG. 31 (taken from Hodges, P. E. & Rosenberg, L. E. The spfash mouse: a missense mutation in the ornithine transcarbamylase gene also causes aberrant mRNA splicing. *Proc. Natl. Acad. Sci.*

*U.S.A* 86, 4142-4146 (1989)) shows the alternative forms produced. The sequences thereof are provided below:

```
OTC pre-mRNA (wild type):
                                        (SEQ ID NO: 128)
.....CTCACAGACCGCTCGGTTTGTAAAACTTTTCTTC.....

OTC pre-mRNA mutant:
                                        (SEQ ID NO: 129)
.....CTCACAGACCGCTCAGTTTGTAAAACTTTTCTTC.....

OTC mRNA (incorrectly spliced mutant):
                                        (SEQ ID NO: 130)
.....CTCACAGACACCGCTCAGTTTGTAAAACTTTTCTTC.....

OTC mRNA (correctly spliced, mutant):
                                        (SEQ ID NO: 131)
.....CTCACAGACACCGCTCATGTCTTATCTAGCATGACA.....

OTC mRNA (correctly spliced, wild type):
                                        (SEQ ID NO: 132)
.....CTCACAGACACCGCTCGTGTCTTATCTAGCATGACA.....
```

As shown above, a correct splice variant may be produced when the mutation is present; however, such production results in a missense mutation, which also can contribute to OTC deficiency.

The terms "hairpin," "hairpin loop," "stem loop," and/or "loop" used alone or in combination with "motif" is used in context of an oligonucleotide to refer to a structure formed in single stranded oligonucleotide when sequences within the single strand which are complementary when read in opposite directions base pair to form a region whose conformation resembles a hairpin or loop.

As used herein, the term "domain" refers to a particular region of a protein or polypeptide and is associated with a particular function. For example, "a domain which associates with an RNA hairpin motif" refers to the domain of a protein that binds one or more RNA hairpin. This binding may optionally be specific to a particular hairpin. For example, the M2 bacteriophage coat protein (MCP) is capable of specifically binding to particular stem-loop structures, including but not limited to the MS2 stem loop. See, e.g. Peabody, D. S., "The RNA binding site of bacteriophage MS2 coat protein." *EMBO J.* 12(2):595-600 (1993); Corrigan and Chubb, "Biophysical Methods in Cell Biology" *Methods in Cell Biology* (2015). Similarly, λ N22—referred to herein as "N22 peptide" is capable of specifically binding to particular stem-loop structures, including but not limited to BoxB stem loops. See, e.g., Cilley and Williamson, "Analysis of bacteriophage N protein and peptide binding to boxB RNA using polyacrylamide gell coelectrophoresis (PACE)." *RNA* 3(1):57-67 (1997). The sequences of both MCP and MS2 stem loop and N22 peptide and BoxB loop are provided hereinabove in context of fusion proteins with an ADAR (MCP, N22 peptide) and use in adRNA (MS2 stem loop, BoxB loop), respectively.

The term "APOBEC" as used herein refers to any protein that falls within the family of evolutionarily conserved cytidine deaminases involved in mRNA editing—catalyzing a C to U conversion—and equivalents thereof. In some aspects, the term APOBEC refers to any one of APOBEC1, APOBEC2, APOBEC3A, APOBEC3B, APOBEC3C, APOBEC3E, APOBEC3F, APOBEC3G, APOBEC3H, APOBEC4, or equivalents each thereof. Non-limiting exemplary sequences of fusion proteins comprising one or more APOBEC domains are provided herein both fused to an ADAR domain or fused to alternative domains to render them suitable for use in an RNA editing system. To this end, APOBECs can be considered an equivalent of ADAR—catalyzing editing albeit by a different conversion. Thus, not to be bound by theory, Applicants believe that all embodiments contemplated herein for use with an ADAR based editing system may be adapted for use in an APOBEC based RNA editing system.

As used herein, the term "interferon" refers to a group of signaling proteins known to be associated with the immune response. In context of this application, the interferons of interest are those that result in enhanced expression of an ADAR. The correlation between interferon α and ADAR1 is well known, and, thus, the present disclosure contemplates use of interferon α as a means of increasing endogenous ADAR1 expression. Commercial sources of isolated or recombinant interferon α include but are not limited to Sigma-Aldrich, R&D Systems, Abcam, and Thermo Fisher Scientific. Alternatively, interferon α may be produced using a known vector and given protein sequence, e.g. Q6QNB6 (human IFNA).

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge. Additionally, an equivalent polynucleotide is one that hybridizes under stringent conditions to the reference polynucleotide or its complement or in reference to a polypeptide, a polypeptide encoded by a polynucleotide that hybridizes to the reference encoding polynucleotide under stringent conditions or its complementary strand. Alternatively, an equivalent polypeptide or protein is one that is expressed from an equivalent polynucleotide.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

Modes of Carrying Out the Disclosure

Point mutations underlie many genetic diseases. In this regard, while programmable DNA nucleases have been used to repair mutations, their use for gene therapy poses multiple challenges: one, efficiency of homologous recombination is typically low in cells; two, an active nuclease presents a risk of introducing permanent off-target mutations; and three, prevalent programmable nucleases typically comprise elements of non-human origin raising the potential of in vivo immunogenicity. In light of these, approaches to instead directly target RNA, and use of molecular machinery native to the host would be highly desirable. Towards this, Applicants have engineered and optimized two complementary approaches, referred together hereon as tRiAD, based on the use of tRNAs in codon suppression and adenosine deaminases in RNA editing. Specifically, by delivering modified endogenous tRNAs or the RNA editing enzyme ADAR and an associated guiding RNA (adRNA) via adeno-associated viruses, Applicants enabled premature stop codon read-through and correction in the mdx mouse model of muscular dystrophy that harbors a nonsense mutation in the dystrophin gene. Additionally, Applicants engineered ADAR2 mediated correction of a point mutation in liver RNA of the $spf^{ash}$ mouse model of ornithine transcarbamylase (OTC) deficiency. Taken together, the results disclosed herein establish the use of suppressor tRNAs and ADAR2 for in vivo RNA targeting, and this integrated tRiAD approach is robust, genomically scarless, and potentially non-immunogenic, as it utilizes effector RNAs and human proteins.

Aspects of the disclosure relate to a tRNA based protein editing system optionally alone or in combination with an ADAR based RNA editing system comprising one or more forward guide RNAs for the ADAR ("adRNAs") and one or more corresponding reverse guide RNAs for the ADAR ("radRNAs") to the subject, wherein the ADAR based RNA editing system specifically edits a point mutation in an RNA sequence encoding a gene.

The tRNA based protein editing system may comprise endogenous modified tRNA and/or orthogonal tRNA in order to prevent off target editing of proteins. In this regard, systems for the control of these tRNA are disclosed herein below.

The adRNA architecture for use in the ADAR based RNA editing system is relatively simple, comprising a RNA targeting domain, complementary to the target and, optionally, one or two recruiting domains (also referred to as aptamers) that recruit RNA binding domains of various proteins. The optional recruiting domains are positioned at the 5' and/or 3' ends of the RNA targeting domain. A schematic of adRNA bound to its mRNA target is provided in FIG. 23C. In some embodiments, the adRNA features an A-C mismatch, which prompts editing function of the ADAR. A similar framework can be used to target pre-mRNA, prior to intron processing by adapting the scaffold to target the pre-mRNA present in the nucleus. This approach is taken in the non-limiting exemplary methods involving OTC deficiency—involving a splice site mutation, whereas an mRNA editing approach is taken in the non-limiting exemplary methods involving dystrophin deficiency—involving a nonsense mutation.

Figure 19:
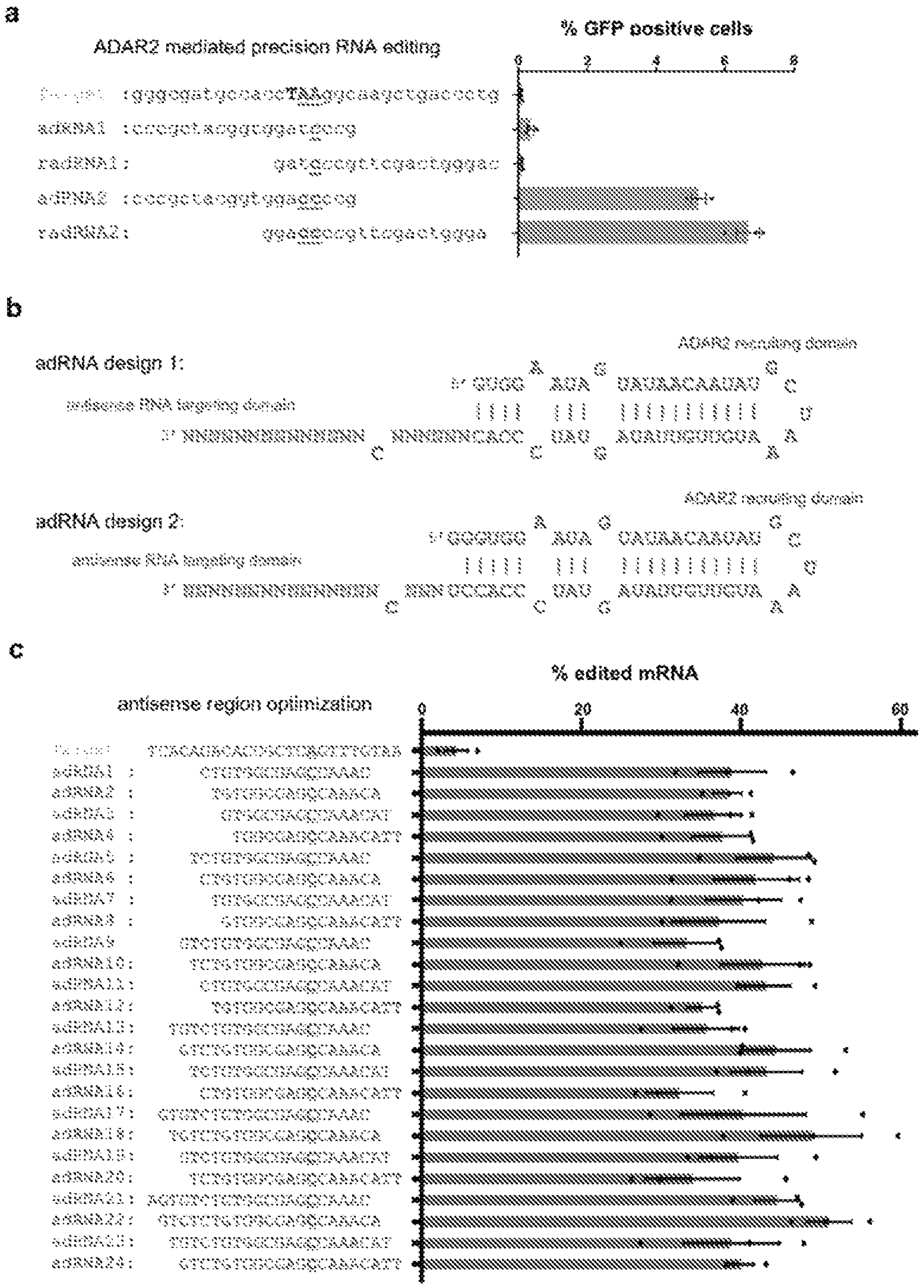
FIG. 19A-C shows in vitro ADAR2 mediated site-specific RNA editing evaluation and optimization.

Applicants tested a series of scaffolds, shown in FIG. 19C, to recruit RNA binding domains of the ADARs. The sequences provided in the figure represent the recruiting domain and the italicized Ns represent the nucleotides complimentary to the target. The C is the mismatch that prompts the editing function. Sequences of varying length and mismatch position may be tested to determine the best adRNA for the desired target. For example, residues in the recruiting domain of the adRNAs generated by Applicants were modified as follows (5'-3'):

v1:

(SEQ ID NO: 104)
GGGTGGAATAGTATAACAATATGCTAAATGTTGTTATAGTATCCCACCT *NNNCNNNNNNNNNNNNNNNN* v2:

(SEQ ID NO: 105)
GTGGAATAGTATAACAATATGCTAAATGTTGTTATAGTATCCCAC *NNNNNNCNNNNNNNNNNNNN*

-continued v3:

(SEQ ID NO: 106)
GTGGAAGAGGAGAACAATATGCTAAATGTTGTTCTCGTCTCCCAC *NNNNNNCNNNNNNNNNNNNNN* v4:

(SEQ ID NO: 107)
GGGTGGAAGAGGAGAACAATATGCTAAATGTTGTTCTCGTCTCCCACCT *NNNCNNNNNNNNNNNNNNNN* v5:

(SEQ ID NO: 108)
GGTGAAGAGGAGAACAATATGCTAAATGTTGTTCTCGTCTCCACC *NNNNNNCNNNNNNNNNNNNNN* v6:

(SEQ ID NO: 109)
GGTGAAGAGGAGAACAATATGCTAAATGTTGTTCTCGTCTCCACC *NNNNNNNCNNNNNNNNNNNNN* v7:

(SEQ ID NO: 110)
GTGGAAGAGGAGAACAATAGGCTAAACGTTGTTCTCGTCTCCCAC *NNNNNNCNNNNNNNNNNNNNN* v8:

(SEQ ID NO: 111)
GGGTGGAAGAGGAGAACAATAGGCTAAACGTTGTTCTCGTCTCCCACCT *NNNCNNNNNNNNNNNNNNNN* v9:

(SEQ ID NO: 112)
GGTGAAGAGGAGAACAATAGCTAAACGTTGTTCTCGTCTCCACC *NNNNNNCNNNNNNNNNNNNNN* v10:

(SEQ ID NO: 113)
GGTGAAGAGGAGAACAATAGCTAAACGTTGTTCTCGTCTCCACC *NNNNNNNCNNNNNNNNNNNN* v11:

(SEQ ID NO: 114)
GGTGTCGAGAATAGTATAACCAATATGCTAAATGTTGTTATAGTATCCTCGACACC *NNNNNNNCNNNNNNNNNN* v12:

(SEQ ID NO: 115)
GGTGTCGAGAAGAGGATGACAATATGCTAAATGTTGTTCTCGTCTCCTCGACACC *NNNNNNNCNNNNNNNNNN* v13:

(SEQ ID NO: 116)
GGTGTCGAGAAGAGGAGAACAATAGGCTAAACGTTGTTCTCGTCTCCTCGACACC *NNNNNNNCNNNNNNNNNN*

The structure of V2 after folding is provided as FIG. 23D.
And the corresponding radRNAs were generated as follows:

(SEQ ID NO: 133)
*NNNNNNNNNNNNNNNNCNNN* TCCACCCTATGATATTGTTGTAAATCGTATAACAATATGATAAGGTGGG (SEQ ID NO: 134)
*NNNNNNNNNNNNNCNNNNNN* CACCCTATGATATTGTTGTAAATCGTATAACAATATGATAAGGTG (SEQ ID NO: 135)
*NNNNNNNNNNNNNNCNNNNNN* CACCCTCTGCTCTTGTTGTAAATCGTATAACAAGAGGAGAAGGTG (SEQ ID NO: 136)
*NNNNNNNNNNNNNNNNCNNN* TCCACCCTCTGCTCTTGTTGTAAATCGTATAACAAGAGGAGAAGGTGGG (SEQ ID NO: 137)
*NNNNNNNNNNNNNNCNNNNNN* CCACCTCTGCTCTTGTTGTAAATCGTATAACAAGAGGAGAAGTGG (SEQ ID NO: 138)
*NNNNNNNNNNNNNCNNNNNNN* CCACCTCTGCTCTTGTTGTAAATCGTATAACAAGAGGAGAAGTGG (SEQ ID NO: 139)
*NNNNNNNNNNNNNNCNNNNNN* CACCCTCTGCTCTTGTTGCAAATCGGATAACAAGAGGAGAAGGTG (SEQ ID NO: 140)
*NNNNNNNNNNNNNNNNCNNN* TCCACCCTCTGCTCTTGTTGCAAATCGGATAACAAGAGGAGAAGGTGGG (SEQ ID NO: 141)
*NNNNNNNNNNNNNNCNNNNNN* CCACCTCTGCTCTTGTTGCAAATCGGATAACAAGAGGAGAAGTGG (SEQ ID NO: 142)
*NNNNNNNNNNNNNCNNNNNNN* CCACCTCTGCTCTTGTTGCAAATCGGATAACAAGAGGAGAAGTGG

Figure 16:
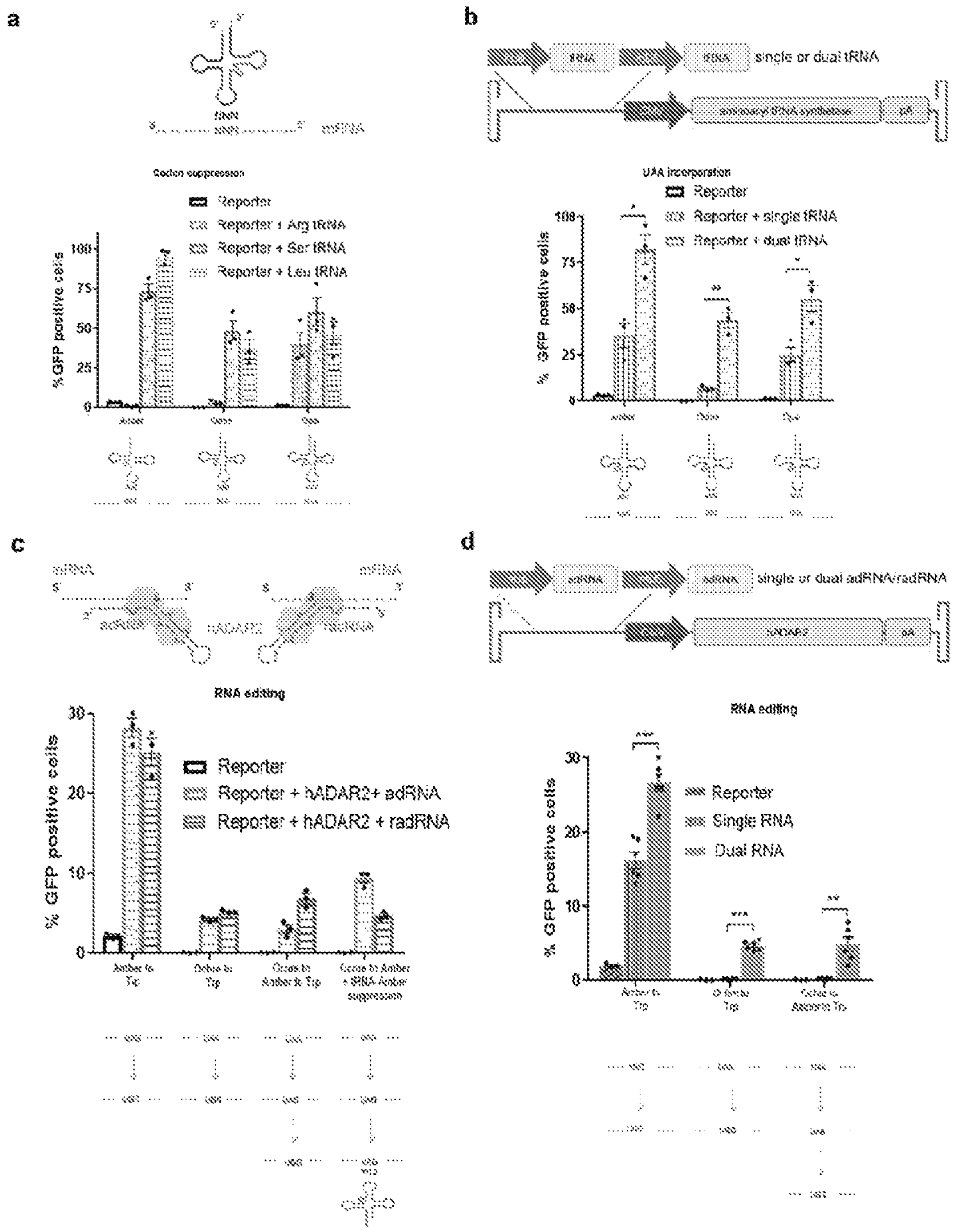
FIG. 16A-D shows in vitro suppression and editing of stop codons in GFP reporter mRNA.

-continued (SEQ ID NO: 143)
*NNNNNNNNNNCNNNNNNN* CCACAGCTCCTCTGCTCTTGTTGCAAATCGGATAACAAGAGGAGAAGAGCTGTGG (SEQ ID NO: 144)
*NNNNNNNNNNCNNNNNNN* CCACAGCTCCTCTGCTCTTGTTGTAAATCGTATAACAAGAGGAGAAGAGCTGTGG (SEQ ID NO: 145)
*NNNNNNNNNNCNNNNNNN* CCACAGCTCCTATGATATTGTTGTAAATCGTATAACAATATGATAAGAGCTGTGG A schematic of the resulting adRNA and radRNA pairings to the target mRNA is shown in FIG. 16C.

An alternative scaffold framework was also applied by Applicants using two ADAR recruiting domains (black font) on either side of the targeting domain while varying the position of the C mismatch in the targeting domain (italicized Ns).

(SEQ ID NO: 146)
TGGAATAGTATAACAATATGCTAAATGTTGTTATAGTATCCCAC

*NNNNNNNNNNNNNNNNNNNN*GTGGAATAGTATAACAATATGC

TAAATGTTGTTATAGTATCCCAC

These non-limiting exemplary scaffolds provide a template for the engineering of adRNA and radRNA for particular targets and may be optimized based on comparative efficacy studies carried out according to the exemplary methods disclosed herein.

In some embodiments, the ADAR based editing system further comprises ADAR1, ADAR2, the E488Q and E100Q mutants each thereof, a fusion protein comprising the catalytic domain of an ADAR and a domain which associates with an RNA hairpin motif, a fusion protein comprising the catalytic domain of an ADAR and a dead Cas9, or a fusion protein comprising the double stranded binding domain of an ADAR and an APOBEC. In further embodiments, the domain which associates with an RNA hairpin motif is selected from the group of an MS2 bacteriophage coat protein (MCP) and an N22 peptide. In some embodiments, the adRNA comprises one or more RNA hairpin motifs. In some embodiments, the one or more RNA hairpin motifs are selected from the group of an MS2 stem loop and a BoxB loop.

Not to be bound by theory, Applicants believe the double stranded RNA binding motif from ADARs may bind to several double stranded RNA sequences and could thus have possible off target effects. To avoid such effects, Applicants contemplate the use of exogenous protein domains to recognize RNA hairpin motifs in the adRNA. Both ADAR1 and ADAR2 consist of RNA binding domains and a catalytic domain that catalyzes the conversion of adenosine to inosine. The catalytic domain can be uncoupled from the RNA binding domain. Our aim is to achieve high editing efficiency of the targeted adenosine while reducing off target effects and thus are exploring alternative RNA binding domains. Applicants have fused the catalytic domain of the ADAR1 or ADAR2 to different RNA binding domains such as the MCP, N22 or a dead CjCas9 (or other RNA targeting CRISPRs such as from SaCas9, CRISPR-Cas13 etc.). Upon the addition of appropriate guide RNAs (adRNAs), the fusion proteins are recruited to the target, further catalyzing an adenosine to inosine change. The dead CjCas9 (and other CRISPRs by extension) in this case basically serves as a RNA binding domain that can in turn be tethered to effectors.

The domains are fused to the ADAR catalytic domain to generate ADAR specifically targeting the particular adRNA comprising the RNA hairpin motifs. For example, Applicants have used a MS2 bacteriophage coat protein (MCP) fused to either the catalytic domain of ADAR1 or ADAR2 and their respective mutants E488Q and E1008Q, while using a MS2 stem loop on the RNA to recruit the fusion protein (FIG. 23A). Analogous to this system, Applicants have also utilized a N22 peptide fused to the catalytic domains of ADAR1 or ADAR2 (and their mutants) while making use of a boxB aptamer to recruit the fusion protein. Thus, one or two copies of ADAR may be recruited based on the addition of single or dual hairpins (MS2/BoxB loops) (FIG. 23A). PP7 hairpins are also contemplated for use in the same manner.

A non-limiting framework sequence for the recruitment of MCP-based fusion proteins, where the C mismatch may be varied within the targeting domain, is provided herein below (with the lower case letters representing those linkers that help stabilize the underlined hairpins):

Single recruiting domain (underlined):

(SEQ ID NO: 98)
*NNNNNNNNNNNNNNNNNNNN*ggccAACATGAGGATCACCCATGTCTGCAGg gcc

Two recruiting domains (underlined):
(SEQ ID NO: 99)
aACATGAGGATCACCCATGTc*NNNNNNNNNNNNNNNNNNNN*aACATGAGGA

TCACCCATGTc

An analogous non-limiting framework sequence is provided for the N22-based fusion proteins:

Single recruiting domain (underlined):

(SEQ ID NO: 100)
*NNNNNNNNNNNNNNNNNNNN*gggccctgaagaagggccc

Two recruiting domains (underlined):
(SEQ ID NO: 101)
ggGCCCTGAAGAAGGGCcc*NNNNNNNNNNNNNNNNNNNN*ggGCCCTGAAGA

AGGGCcc

Another approach is to recruitment domains in the adRNA associated with Cas9 and couple a dead Cas9 to the ADAR catalytic domain, thus, rendering the same effect of specific recruitment. A non-limiting framework sequence for the recruitment is provided for Cas9-based fusion proteins:

Psp dCas13a recruitment (mismatch position can be varied)

(SEQ ID NO: 147)
CAACATTATCGGGGAGTTTTGACCTCCAAGGTGTTGNNNNNNNNNNNNNNNN

NNNNNNNNNNNNNNNNNNNNNNNNNNNNNNNNNNN

Cj dCas9 recruitment (mismatch position can be varied)

(SEQ ID NO: 148)
NNNNNNNNNNNNNNNNNNNNNNgttttagtccctgaaaagggactaaaata aagagtttgcgggactctgcggggttacaatcccctaaaaccgcttttttt APOBECs also have RNA editing function (FIG. 23B). Thus, they may be used in the alternative or in addition to the ADAR based editing system. For example, Applicants have created MCP/N22 peptide fusions with APOBECs to engineer targeted C→T RNA editing. In addition, Applicants have fused the double stranded RNA binding domains (dsRBD) of the ADAR2 with APOBECs as a result of which the APOBECs can be recruited by the adRNA.

The addition of Nuclear Localization Signals (NLS) to the fusion protein could help target nuclear RNA (i.e. pre-mRNA) while addition of Nuclear Export Signals (NES) to the fusion protein could help target cytoplasmic RNA in any of the embodiments disclosed herein. This method is useful when editing for splice site mutations, which result in incorrect processing of introns in the pre-mRNA and, thus, results in incorrect mRNA for translation. OTC deficiency is example where targeting pre-mRNA with adRNA scaffolds can be useful, since the majority of aberrant OTC expression comes from the splice site mutation resulting in a truncated OTC protein. Further addition of RNA localization tags to the adRNA will enable targeting RNA in specific cellular compartments.

In further embodiments where the adRNA comprises one or more RNA hairpin motifs, the one or more RNA hairpin motifs are stabilized by replacing A-U with G-C. In some embodiments, the adRNA is stabilized through the incorporation of one or more of 2'-O-methyl, 2'-O-methyl 3'phosphorothioate, or 2'-O-methyl 3'thioPACE at either or both termini of the adRNA.

More generally, can be appreciated that the RNA targeting domains of adRNAs are designed such that they are complementary to the target mRNA while containing C mismatch at the position of the target adenosine. The recruiting domains of the adRNA are constant. BY way of non-limiting example:

Example target: OTC mRNA (mutation underlined)

(SEQ ID NO: 149)
5'-AAAGTCTCACAGACACCGCTCAGTTTGTAAAACTTTTCTTC-3' adRNA v2 (targeting domain length 20 bp, mismatch position after 6 bases):

(SEQ ID NO: 149)
5'-AAAGTCTCACAGACACCGCTCAGTTTGTAAAACTTTTCTTC-3'

(SEQ ID NO: 150)
5'-GTGGAATAGTATAACAATATGCTAAATGTTGTTATAGTATCCCACTGT CTGTGGCGAGCCAACA-3' adRNA v2 (targeting domain length 21 bp, mismatch position after 6 bases):

(SEQ ID NO: 149)
5'-AAAGTCTCACAGACACCGCTCAGTTTGTAAAACTTTTCTTC-3'

(SEQ ID NO: 151)
5'-GTGGAATAGTATAACAATATGCTAAATGTTGTTATAGTATCCCACGTG TCTGTGGCGAGCCAAACA-3' radRNA v2 (targeting domain length 20 bp, mismatch position after 6 bases):

(SEQ ID NO: 149)
3'-CTTCTTTTCAAAATGTTTGACTCGCCACAGACACTCTGAAA-5'

(SEQ ID NO: 152)
5'-AAGTTTTACAAACCGAGCGGCACCCTATGATATTGTTGTAAATCGTAT AACAATATGATAAGGTG-3' adRNA dual (targeting domain length 20 bp, mismatch position after 5, 14 bases):

(SEQ ID NO: 149)
3'-CTTCTTTTCAAAATGTTTGACTCGCCACAGACACTCTGAAA-5'

(SEQ ID NO: 153)
5'TGGAATAGTATAACAATATGCTAAATGTTGTTATAGTATCCCACCAAAC CGAGCGGTGTCTGTGGTGGAATAGTATAACAATATGCTAAATGTTGTTATA GTATCCCAC-3' adRNA MS2 (targeting domain length 20 bp, mismatch position after 14 bases)

(SEQ ID NO: 149)
3'-CTTCTTTTCAAAATGTTTGACTCGCCACAGACACTCTGAAA-5'

(SEQ ID NO: 154)
5'-CAAACCGAGCGGTGTCTGTGggccAACATGAGGATCACCCATGTCTGC AGggcc-3' adRNA MS2 dual (targeting domain length 20 bp, mismatch position after 5, 14 bases)

(SEQ ID NO: 149)
3'-CTTCTTTTCAAAATGTTTGACTCGCCACAGACACTCTGAAA-5'

(SEQ ID NO: 155)
5'-aACATGAGGATCACCCATGTcCAAACCGAGCGGTGTCTGTGaACATGA GGATCACCCATGTc-3' adRNA BoxB (targeting domain length 20 bp, mismatch position after 14 bases)

(SEQ ID NO: 149)
3'-CTTCTTTTCAAAATGTTTGACTCGCCACAGACACTCTGAAA-5'

(SEQ ID NO: 156)
5'-CAAACCGAGCGGTGTTCTGTGgggccctgaagaagggccc-3' adRNA BoxB dual (targeting domain length 20 bp, mismatch position after 5, 14 bases)

(SEQ ID NO: 149)
3'-CTTCTTTTCAAAATGTTTGACTCGCCACAGACACTCTGAAA-5'

(SEQ ID NO: 157)
5'-ggGCCCTGAAGAAGGGccCAAACCGAGCGGTGTCTGTGggGCCCTGAA GAAGGGCcc-3'

A coordinate or alternate approach to preventing off-target effects is to make use of endogenous ADAR. ADAR2 is highly expressed in tissues such as the brain, lung and spleen while ADAR1 is ubiquitously expressed with general expression levels being higher than ADAR1. Thus, Applicants propose two avenues in order to engineer RNA editing by endogenous ADARs. First, ADAR1 expression can be stimulated by molecules such as interferons, e.g., interferon α. Second, scaffolds may be engineered specifically for recruiting ADAR1 and are carrying out experiments with the v1-v13 scaffolds as well as some chemically modified scaffolds disclosed herein above. Making use of the endogenous ADARs as opposed to overexpression could help limit the off-target effects.

Recombinant Expression Systems and Vectors

Aspects of the disclosure relate to vectors and recombinant expression systems.

For example, some aspects relate to a vector encoding one or more tRNA having an anticodon sequence that recognizes a codon comprising a point mutation in an RNA sequence encoding a protein, optionally wherein the point mutation results in a premature stop codon. In some embodiments, the point mutation results in a nonsense mutation having the DNA sequence TAA and the RNA sequence UAA. In some embodiments, the tRNA is an endogenous tRNA with a modified anticodon stem recognizing the codon comprising the point mutation. In further embodiments, the tRNA is charged with a serine. In some embodiments, the tRNA is an orthogonal tRNA charged with a non-canonical amino acid. In further embodiments, the vector further comprises a corresponding tRNA synthetase. In some embodiments, the corresponding synthetase is *E. coli* Glutaminyl-tRNA synthetase. In some embodiments involving an orthogonal tRNA, the non-canonical amino acid is pyrrolysine. In some embodiments, the vector encodes two tRNA having an anticodon sequence that recognizes the codon comprising the point mutation. In some embodiments, the vector is an AAV vector, optionally an AAV8 vector. In some embodiments, the protein is dystrophin.

Further aspects relate to a recombinant expression system comprising one or more vectors encoding an ADAR based RNA editing system comprising one or more forward guide RNAs for the ADAR ("adRNAs") and one or more corresponding reverse guide RNAs for the ADAR ("radRNAs") to the subject, wherein the ADAR based RNA editing system specifically edits a point mutation in an RNA sequence encoding a protein. In some embodiments, the point mutation results in a nonsense mutation, optionally a premature stop codon, having the DNA sequence TAA and the RNA sequence UAA. In some embodiments, the ADAR based RNA editing system converts UAA to UIA and, optionally, further UIA to UII. In some embodiments, the ADAR based RNA editing system converts UAA to UAI. In some embodiments, the point mutation results in a splice site or missense mutation having the DNA sequence CAG and the RNA sequence CAG. In some embodiments, the ADAR based RNA editing system converts CAG to CIG. In further embodiments, the one or more vector further encodes a tRNA that targets an amber codon. In some embodiments, the ADAR based editing system further comprises ADAR1, ADAR2, the E488Q and E100Q mutants each thereof, a fusion protein comprising the catalytic domain of an ADAR and a domain which associates with an RNA hairpin motif, a fusion protein comprising the catalytic domain of an ADAR and a dead Cas9, or a fusion protein comprising the double stranded binding domain of an ADAR and an APOBEC. In further embodiments, the domain which associates with an RNA hairpin motif is selected from the group of an MS2 bacteriophage coat protein (MCP) and an N22 peptide. In some embodiments, the adRNA comprises one or more RNA hairpin motifs. In some embodiments, the one or more RNA hairpin motifs are selected from the group of an MS2 stem loop and a BoxB loop and/or are stabilized by replacing A-U with G-C. In some embodiments, the adRNA is stabilized through the incorporation of one or more of 2'-O-methyl, 2'-O-methyl 3'phosphorothioate, or 2'-O-methyl 3'thioPACE at either or both termini of the adRNA.

In general methods of packaging genetic material such as RNA into one or more vectors is well known in the art. For example, the genetic material may be packaged using a packaging vector and cell lines and introduced via traditional recombinant methods.

In some embodiments, the packaging vector may include, but is not limited to retroviral vector, lentiviral vector, adenoviral vector, and adeno-associated viral vector (optionally AAV8). The packaging vector contains elements and sequences that facilitate the delivery of genetic materials into cells. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter.

The retroviral packaging plasmid may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell. Similar vector based systems may employ other vectors such as sleeping beauty vectors or transposon elements.

The resulting packaged expression systems may then be introduced via an appropriate route of administration, discussed in detail with respect to the method aspects disclosed herein.

Compositions

Further aspects relate to a composition comprising any one or more of the vectors disclosed herein. In some embodiments, the composition further comprises an effective amount of an interferon to enhance endogenous ADAR1 expression. In still further embodiments, the interferon is interferon α.

Briefly, pharmaceutical compositions of the present disclosure including but not limited to any one of the claimed compositions may comprise a target cell population as described herein, in combination with one or more pharmaceutically or physiologically acceptable carriers, diluents or excipients.

Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

Such compositions may also comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Administration of the compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art. In a further aspect, the cells and composition of the disclosure can be administered in combination with other treatments.

The vectors, recombinant expression systems, and/or compositions are administered to the host using methods known in the art. This administration of the compositions of the disclosure can be done to generate an animal model of the desired disease, disorder, or condition for experimental and screening assays.

Briefly, pharmaceutical compositions of the present disclosure including but not limited to any one of the claimed compositions may comprise one or more vectors or recombinant expression systems as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Pharmaceutical compositions of the present disclosure may be administered in a manner appropriate to the disease, disorder, or condition to be treated or prevented. The quantity and frequency of administration will be determined by such factors as the condition of the patient, and the type and severity of the patient's disease, although appropriate dosages may be determined by clinical trials.

Methods of Restoring Protein Expression

Aspects of the disclosure relate to methods of restoring protein expression.

For example, some aspects of the disclosure relate to a method for restoring expression of a protein comprising a point mutation in an RNA sequence encoding the protein in a subject in need thereof comprising administering a vector encoding one or more tRNA having an anticodon sequence that recognizes a codon comprising the point mutation to the subject, optionally wherein the point mutation results in a premature stop codon. In some embodiments, the point mutation results in a nonsense mutation having the DNA sequence TAA and the RNA sequence UAA. In some embodiments, the tRNA is an endogenous tRNA with a modified anticodon stem recognizing the codon comprising the point mutation. In further embodiments, the tRNA is charged with a serine. In some embodiments, the tRNA is an orthogonal tRNA charged with a non-canonical amino acid. In further embodiments, the vector further comprises a corresponding tRNA synthetase. In some embodiments, the corresponding synthetase is *E. coli* Glutaminyl-tRNA synthetase. In some embodiments involving an orthogonal tRNA, the non-canonical amino acid is pyrrolysine. In further embodiments, the pyrrolysine is introduced in the diet of the subject. In some embodiments, the vector encodes two tRNA having an anticodon sequence that recognizes the codon comprising the point mutation. In some embodiments, the protein is dystrophin.

Other aspects relate to a recombinant expression system comprising one or more vectors encoding an ADAR based RNA editing system comprising one or more forward guide RNAs for the ADAR ("adRNAs") and one or more corresponding reverse guide RNAs for the ADAR ("radRNAs") to the subject, wherein the ADAR based RNA editing system specifically edits a point mutation in an RNA sequence encoding a protein. In some embodiments, the point mutation results in a nonsense mutation, optionally a premature stop codon, having the DNA sequence TAA and the RNA sequence UAA. In some embodiments, the ADAR based RNA editing system converts UAA to UIA and, optionally, further UIA to UM In some embodiments, the ADAR based RNA editing system converts UAA to UAI. In some embodiments, optionally those involving nonsense or missense mutations, the RNA targeted in mRNA. In further embodiments, the one or more vector further encodes a tRNA that targets an amber codon. In some embodiments, the protein is dystrophin. In some embodiments, the point mutation results in a splice site or missense mutation having the DNA sequence CAG and the RNA sequence CAG. In some embodiments, the ADAR based RNA editing system converts CAG to CIG. In some embodiments, optionally those involving splice site mutations, the RNA targeted is pre-mRNA. In some embodiments, the ADAR based editing system further comprises ADAR1, ADAR2, the E488Q and E100Q mutants each thereof, a fusion protein comprising the catalytic domain of an ADAR and a domain which associates with an RNA hairpin motif, a fusion protein comprising the catalytic domain of an ADAR and a dead Cas9, or a fusion protein comprising the double stranded binding domain of an ADAR and an APOBEC. In further embodiments, the domain which associates with an RNA hairpin motif is selected from the group of an MS2 bacteriophage coat protein (MCP) and an N22 peptide. In some embodiments, the adRNA comprises one or more RNA hairpin motifs. In some embodiments, the one or more RNA hairpin motifs are selected from the group of an MS2 stem loop and a BoxB loop and/or are stabilized by replacing A-U with G-C. In some embodiments, the adRNA is stabilized through the incorporation of one or more of 2'-O-methyl, 2'-O-methyl 3'phosphorothioate, or 2'-O-methyl 3'thioPACE at either or both termini of the adRNA.

In either case, the assessment of whether protein expression is "restored" is achieved through any means of protein quantification when compared to a baseline. The baseline may optionally be calculated based on a prior level in the subject or as the normal level in the population, adjusted for the subjects age, ethnicity, and other relevant demographic information. Techniques of quantifying protein expression are well known in the art and may, optionally, utilize a control or a threshold value for comparison to the baseline value. Methods known in the art for such studies include but are not limited to qRTPCR, ELISA, Western blot, protein immunostaining, spectroscopy and/or spectrometry based methods, and other assays typically conducted to determine the amount of protein expression in a sample from the subject. Alternatively, the "restoration" effect may be determined based on a clinical outcome. For example, aberrant dystrophin levels are linked to muscular dystrophy symptoms. Thus, the restoration of expression may be outwardly determined based on clinical signals such as a reduction or reversal of these symptoms. For dystrophin, improvement in muscle strength can be one such indicator. Thus, physicians may carry out strength measurements to determine outcome. Another example is ornithine transcarbamylase (OTC); aberrant OTC levels are a result of a rare X-linked genetic disorder resulting in excessive accumulation of ammonia in the blood (due to nitrogen accumulation). Thus, a relevant clinical outcome would be a decrease in ammonia in a biological sample, such as blood or urine. Similarly, clinical signals associated with and expression of proteins downstream of the protein of interest may be relevant indicators of "restoration" where the protein of interest is involved in a particular pathway.

Methods of Treatment

Point mutations are implicated in a number of diseases, disorders, and conditions. Non-limiting examples are provided in Table 1 below.

TABLE 1

| Protein/Disease, Disorder, or Condition | Associated Point Mutation |
|---|---|
| G to A point mutations or premature stop codons | |
| Dihydropyrimidine dehydrogenase deficiency | NM_000110.3(DPYD): c.1905 + 1G > A |
| Noonan syndrome | NM_005633.3(SOS1): c.2536G > A (p.Glu846Lys) |
| Lynch syndrome | NM_000251.2(MSH2): c.212 − 1G > A |
| Breast-ovarian cancer, familial 1 | NM_007294.3(BRCA1): c.963G > A (p.Trp321Ter) |
| Cystic fibrosis | NM_000492.3(CFTR): c.57G > A (p.Trp19Ter) |
| Anemia, due to G6PD deficiency | NM_000402.4(G6PD): c.292G > A (p.Val98Met) |
| AVPR2 Nephrogenic diabetes insipidus, X-linked | NM_000054.4(AVPR2): c.878G > A (p.Trp293Ter) |
| FANCC Fanconi anemia, complementation group C | NM_000054.4(AVPR2): c.878G > A (p.Trp293Ter) |
| FANCC Fanconi anemia, complementation group C | NM_000136.2(FANCC): c.1517G > A (p.Trp506Ter) |
| IL2RG X-linked severe combined immunodeficiency | NM_000206.2(IL2RG): c.710G > A (p.Trp237Ter) |
| F8 Hereditary factor VIII deficiency disease | NM_000132.3(F8): c.3144G > A (p.Trp1048Ter) |
| LDLR Familial hypercholesterolemia | NM_000527.4(LDLR): c.1449G > A (p.Trp483Ter) |
| CBS Homocystinuria due to CBS deficiency | NM_000071.2(CBS): c.162G > A (p.Trp54Ter) |
| HBB betaThalassemia | NM_000518.4(HBB): c.114G > A (p.Trp38Ter) |
| ALDOB Hereditary fructosuria | NM_000035.3(ALDOB): c.888G > A (p.Trp296Ter) |
| DMD Duchenne muscular dystrophy | NM_004006.2(DMD): c.3747G > A (p.Trp1249Ter) |
| SMAD4 Juvenile polyposis syndrome | NM_005359.5(SMAD4): c.906G > A (p.Trp302Ter) |
| BRCA2 Familial cancer of breast\|Breast-ovarian cancer, familial 2 | NM_000059.3(BRCA2): c.582G > A (p.Trp194Ter) |
| GRIN2A Epilepsy, focal, with speech disorder and with or without mental retardation | NM_000833.4(GRIN2A): c.3813G > A (p.Trp1271Ter) |
| SCN9A Indifference to pain, congenital, autosomal recessive | NM_002977.3(SCN9A): c.2691G > A (p.Trp897Ter) |
| TARDBP Amyotrophic lateral sclerosis type 10 | NM_007375.3(TARDBP): c.943G > A (p.Ala315Thr) |
| CFTR Cystic fibrosis\|Hereditary pancreatitis\|not provided\|ataluren response - Efficacy | NM_000492.3(CFTR): c.3846G > A (p.Trp1282Ter) |
| UBE3A Angelman syndrome | NM_130838.1(UBE3A): c.2304G > A (p.Trp768Ter) |
| SMPD1 Niemann-Pick disease, type A | NM_000543.4(SMPD1): c.168G > A (p.Trp56Ter) |
| USH2A Usher syndrome, type 2A | NM_206933.2(USH2A): c.9390G > A (p.Trp3130Ter) |
| MEN1 Hereditary cancer-predisposing syndrome | NM_130799.2(MEN1): c.1269G > A (p.Trp423Ter) |
| C8orf37 Retinitis pigmentosa 64 | NM_177965.3(C8orf37): c.555G > A (p.Trp185Ter) |
| MLH1 Lynch syndrome | NM_000249.3(MLH1): c.1998G > A (p.Trp666Ter) |
| TSC2 Tuberous sclerosis 2\|Tuberous sclerosis syndrome 46 | NM_000548.4(TSC2): c.2108G > A (p.Trp703Ter) |
| NF1 Neurofibromatosis, type 1 | NM_000267.3(NF1): c.7044G > A (p.Trp2348Ter) |
| MSH6 Lynch syndrome | NM_000179.2(MSH6): c.3020G > A (p.Trp1007Ter) |
| SMN1 Spinal muscular atrophy, type II\|Kugelberg-Welander disease | NM_000344.3(SMN1): c.305G > A (p.Trp102Ter) |
| SH3TC2 Charcot-Marie-Tooth disease, type 4C | NM_024577.3(SH3TC2): c.920G > A (p.Trp307Ter) |
| DNAH5 Primary ciliary dyskinesia | NM_001369.2(DNAH5): c.8465G > A (p.Trp2822Ter) |
| MECP2 Rett syndrome | NM_004992.3(MECP2): c.311G > A (p.Trp104Ter) |
| ADGRV1 Usher syndrome, type 2C | NM_032119.3(ADGRV1): c.7406G > A (p.Trp2469Ter) |
| AHI1 Joubert syndrome 3 | NM_017651.4(AHI1): c.2174G > A (p.Trp725Ter) |

TABLE 1-continued

| Protein/Disease, Disorder, or Condition | Associated Point Mutation |
|---|---|
| PRKN Parkinson disease 2 | NM_004562.2(PRKN): c.1358G > A (p.Trp453Ter) |
| COL3A1 Ehlers-Danlos syndrome, type 4 | NM_000090.3(COL3A1): c.3833G > A (p.Trp1278Ter) |
| BRCA1 Familial cancer of breast\|Breast-ovarian cancer, familial 1 | NM_007294.3(BRCA1): c.5511G > A (p.Trp1837Ter) |
| MYBPC3 Primary familial hypertrophic cardiomyopathy | NM_000256.3(MYBPC3): c.3293G > A (p.Trp1098Ter) |
| APC Familial adenomatous polyposis 1 | NM_000038.5(APC): c.1262G > A (p.Trp421Ter) |
| BMPR2 Primary pulmonary hypertension | NM_001204.6(BMPR2): c.893G > A (p.W298*) |
| T to C point mutations | |
| Wilson disease | NM_000053.3(ATP7B): c.3443T > C (p.Ile1148Thr) |
| Leukodystrophy, hypomyelinating, 2 | NM_020435.3(GJC2): c.857T > C (p.Met286Thr) |
| Alport syndrome, X-linked recessive | NM_000495.4(COL4A5): c.438 + 2T > C |
| Leigh disease | NC_012920.1: m.9478T > C |
| Gaucher disease, type 1 | NM_001005741.2(GBA): c.751T > C (p.Tyr251His) |
| Renal dysplasia, retinal pigmentary dystrophy, cerebellar ataxia and skeletal dysplasia | NM_014714.3(IFT140): c.4078T > C (p.Cys1360Arg) |
| Marfan syndrome | NM_000138.4(FBN1): c.3793T > C (p.Cys1265Arg) |
| Deficiency of UDPglucose-hexose-1-phosphate uridylyltransferase | NM_000155.3(GALT): c.482T > C (p.Leu161Pro) |
| Familial hypercholesterolemia | NM_000527.4(LDLR): c.694 + 2T > C |
| Episodic pain syndrome, familial, 3 | NM_001287223.1(SCN11A): c.1142T > C (p.Ile381Thr) |
| Navajo neurohepatopathy | NM_002437.4(MPV17): c.186 + 2T > C |
| Congenital muscular dystrophy, LMNA-related | NM_170707.3(LMNA): c.1139T > C (p.Leu380Ser) |
| Hereditary factor VIII deficiency disease | NM_000132.3(F8): c.5372T > C (p.Met1791Thr) |
| Insulin-dependent diabetes mellitus secretory diarrhea syndrome | NM_014009.3(FOXP3): c.970T > C (p.Phe324Leu) |
| Hereditary factor IX deficiency disease | NM_000133.3(F9): c.1328T > C (p.Ile443Thr) |
| Familial cancer of breast, Breast-ovarian cancer, familial 2, Hereditary cancerpredisposing syndrome | NM_000059.3(BRCA2): c.316 + 2T > C |
| Cardiac arrhythmia | NM_000238.3(KCNH2): c.1945 + 6T > C |
| Tangier disease | NM_005502.3(ABCA1): c.4429T > C (p.Cys1477Arg) |
| Dilated cardiomyopathy IAA | NM_001103.3(ACTN2): c.683T > C (p.Met228Thr) |
| Mental retardation 3, X-linked | NM_005334.2(HCFC1): c. −970T > C |
| Limb-girdle muscular dystrophy, type 2B | NM_003494.3(DYSF): c.1284 + 2T > C |
| Macular dystrophy, vitelliform, 5 | NM_016247.3(IMPG2): c.370T > C (p.Phe124Leu) |
| Retinitis pigmentosa | NM_000322.4(PRPH2): c.736T > C (p.Trp246Arg) |

Further non-limiting examples include Ornithine Transcarbamylase Deficiency, Nougaret night blindness, Usher syndrome, Atrial Fibrillation, Duchenne Muscular Dyrstrophy, Wilson disease, hereditary tyrosinemia, and some cancers carrying a A→G mutation in genes such as B-catenin.

Thus, aspects of this disclosure relate to the treatment of certain diseases, disorders, and conditions involving point mutations.

For example, some method aspects relate to a treating a disease, disorder, or condition characterized by the presence of a point mutation in an RNA sequence encoding a protein associated with the disease, disorder, or condition in a subject in need thereof comprising administering a vector encoding one or more tRNA having an anticodon sequence that recognizes a codon comprising the point mutation to the subject, optionally wherein the point mutation results in a premature stop codon. In some embodiments, the point mutation results in a nonsense mutation having the DNA sequence TAA and the RNA sequence UAA. In some embodiments, the tRNA is an endogenous tRNA with a modified anticodon stem recognizing the codon comprising the point mutation. In further embodiments, the tRNA is charged with a serine. In some embodiments, the tRNA is an orthogonal tRNA charged with a non-canonical amino acid. In further embodiments, the vector further comprises a corresponding tRNA synthetase. In some embodiments, the corresponding synthetase is *E. coli* Glutaminyl-tRNA synthetase. In some embodiments involving an orthogonal tRNA, the non-canonical amino acid is pyrrolysine. In further embodiments, the pyrrolysine is introduced in the diet of the subject. In some embodiments, the vector encodes two tRNA having an anticodon sequence that recognizes the codon comprising the point mutation. In some embodiments, the disease, disorder, or condition is selected from the group consisting of the diseases, disorders, and conditions listed in Table 1, optionally characterized by the presence of a nonsense mutation and/or a premature stop codon. In some embodiments, the protein is dystrophin. In further embodiments, the disease, disorder, or condition is muscular dystrophy. In still further embodiments, the disease disorder or condition is Duchenne muscular dystrophy.

Additional method aspects relate to a method of treating a disease, disorder, or condition by the presence of a point mutation in an RNA sequence encoding a protein associated with the disease, disorder, or condition in a subject in need thereof comprising administering one or more vectors encoding an ADAR based RNA editing system comprising one or more forward guide RNAs for the ADAR ("adRNAs") and one or more corresponding reverse guide RNAs for the ADAR ("radRNAs") to the subject, wherein the ADAR based RNA editing system specifically edits the point mutation. In some embodiments, the point mutation results in a nonsense mutation, optionally a premature stop codon, having the DNA sequence TAA and the RNA sequence UAA. In some embodiments, the ADAR based RNA editing system converts UAA to UIA and, optionally, further UIA to UII. In some embodiments, the ADAR based RNA editing system converts UAA to UAI. In some embodiments, optionally those involving nonsense or missense mutations, the RNA targeted in mRNA. In further embodiments, the one or more vector further encodes a tRNA that targets an amber codon. In some embodiments, the protein is dystrophin. In some embodiments, the point mutation results in a splice site or missense mutation having the DNA sequence CAG and the RNA sequence CAG. In some embodiments, the ADAR based RNA editing system converts CAG to CIG. In some embodiments, optionally those involving splice site mutations, the RNA targeted is pre-mRNA. In some embodiments, the ADAR based editing system further comprises ADAR1, ADAR2, the E488Q and E100Q mutants each thereof, a fusion protein comprising the catalytic domain of an ADAR and a domain which associates with an RNA hairpin motif, a fusion protein comprising the catalytic domain of an ADAR and a dead Cas9, or a fusion protein comprising the double stranded binding domain of an ADAR and an APOBEC. In further embodiments, the domain which associates with an RNA hairpin motif is selected from the group of an MS2 bacteriophage coat protein (MCP) and an N22 peptide. In some embodiments, the method further comprises administering an effective amount of an interferon to enhance endogenous ADAR1 expression. In still further embodiments, the interferon is interferon α. In some embodiments, the adRNA comprises one or more RNA hairpin motifs. In some embodiments, the one or more RNA hairpin motifs are selected from the group of an MS2 stem loop and a BoxB loop and/or are stabilized by replacing A-U with G-C. In some embodiments, the adRNA is stabilized through the incorporation of one or more of 2'-O-methyl, 2'-O-methyl 3'phosphorothioate, or 2'-O-methyl 3'thioPACE at either or both termini of the adRNA. In some embodiments, the disease, disorder, or condition is selected from the group consisting of the diseases, disorders, and conditions listed in Table 1. In further embodiments, the protein is dystrophin and the disease, disorder, or condition is muscular dystrophy. In still further embodiments, the disease disorder or condition is Duchenne muscular dystrophy.

An ordinary skilled artisan will appreciate that the doses and route of administration employed in these methods may vary based on the subject and the disease, disorder, or condition to be treated. Based on knowledge in the art such suitable doses and routes may be selected based on the subject's age, ethnicity, and other relevant demographic factors.

Kits

In one particular aspect, the present disclosure provides kits for performing any of the methods disclosed herein as well as instructions for carrying out the methods of the present disclosure and/or administering the vectors, recombinant expression systems, and compositions disclosed herein.

The kit can also comprise agents necessary for the preservation of those components comprised therein, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components can be packaged in a manner customary for use by those of skill in the art. For example, these suggested kit components may be provided in solution or as a liquid dispersion or the like.

EXAMPLES

The following examples are non-limiting and illustrative of procedures which can be used in various instances in carrying the disclosure into effect. Additionally, all reference disclosed herein are incorporated by reference in their entirety.

Example 1—Design of tRNA Constructs

The tRNA constructs were designed along the lines of the schematics in FIG. 1 to recognize the nonsense mutation TAA. Both modified endogenous and orthogonal tRNA were generated. The constructs were validated in vitro using a GFP harboring nonsense mutation. It was determined that two copies of the tRNA should be include in each AAV vector for both modified endogenous and orthogonal tRNAs. MbPyl sythetase was selected for use with the orthogonal tRNA. The AAV vectors were generated comprising the tRNA and GFP (as well as the synthetase, where orthogonal tRNA was used). The sequences used in these constructs are provided in the Sequence Listing above.

Example 2—Restoration of Full Length Dystrophin in Mdx Mice

The anticodon stem of the human serine tRNA is modified such that it recognizes the nonsense codon (TAA). No endogenous tRNA can recognize a stop codon and translation terminates when the ribosome reaches a stop codon. Mdx mice bear a nonsense mutation (TAA) in the gene coding for dystrophin as a result of which they lack full length dystrophin expression. AAVs are used to deliver two copies of the modified tRNAs into the mouse muscle which in turn allows for the stop codon readthrough enabling the expression of full length dystrophin.

The calf muscles of mdx mice were injected with 1E12 particles of AAV8 carrying 2 copies of the modified serine tRNA and a GFP gene. These mice were then sacrificed after a month and the calf muscles were harvested. The muscles were sectioned and stained with an antibody against dystrophin. A clear restoration of dystrophin expression was noticed. In addition, the muscle morphology improved too.

Applicants have, thus, demonstrated activity of our vectors in vitro using a GFP gene harboring a stop codon. In addition Applicants have demonstrated restoration of dystrophin expression in mdx mouse muscles. Within a span of one month after injecting the mdx mice with AAVs carrying two copies of the serine tRNA, Applicants observed restoration of dystrophin expression in the calf muscle via Immunohistochemistry. Applicants also noted an improved muscle morphology.

This experiment is repeated with the orthogonal tRNA, introducing the pyrrolysine through the mouse feed, and is again replicated with both tRNAs in a larger population of mice.

Example 3—Diet Regulable Production of Therapeutic Proteins

Applicants aim at achieving on-demand, in vivo production of therapeutics such as (i) insulin; (ii) neutralizing antibodies for viruses (e.g. HIV, HCV, HPV, influenza) and bacteria (e.g. staph aureus; drug resistant strains) by the skeletal muscle.

The desired transgenes are delivered to the muscle via AAVs (or lentiviruses) along with an orthogonal tRNA/tRNA synthetase pair. These transgenes contain a premature termination codon (stop codon) that will prevent the full length protein from being expressed. For an on demand synthesis of the therapeutics, an appropriate unnatural amino acid is consumed in the diet, which in turn is incorporated by the orthogonal tRNA/tRNA synthetase at the premature termination site, enabling synthesis of the desired therapeutics.

Example 4—ADAR2 Based RNA Editing

Applicants suspected that ADAR2 (adenosine deaminase that acts on RNA) to correct mutations at the mRNA level. Applicants used Adeno-Associated Viruses to deliver the ADAR2 and a adRNA (forward ADAR2 guide) or radRNA (reverse ADAR2 guide) that direct the enzyme to the mutation in an attempt to restore the expression of dystrophin in the mdx mouse models of DMD, by editing the nonsense mutation. Applicants also applied this technology to the mouse model of the metabolic disorder Ornithine Transcarbamylase (OTC) deficiency.

As compared to nucleases, ADARs make site specific Adenosine to Inosine (A→I) changes in the mRNA with Inosine being read as a Guanosine (G) during translation and are thereby safe from creating permanent off target effects. Also, since they make edits at the mRNA level, the altered proteins are expressed only transiently. The use of nucleases in adult OTC-deficient mice led to large deletions that proved to be lethal to the animals. The use of ADARs might circumvent this problem. This could be a readily translatable solution for several disorders characterized by point mutations. In addition, the origin of the ADAR2 is human, thereby minimizing the immune response generated by the body against it. Applicants also combine the idea of tRNA suppression with ADAR2 based RNA editing. In addition, Applicants designed hairpin loops (3' overlap) and toe-holds (5' overlap) that help improve the specificity of the adRNA/radRNA. Applicants also go on to optimize the lengths of the adRNA for efficient A→I editing as well as the ADAR2 recruiting domain of the adRNA/radRNA.

Existing studies have made use of nucleases such as Cas9 to delete the mutated region of the Dystrophin/OTC genes and replaced it with a functional copy, for the treatment of DMD or OTC deficiency caused by a point mutation. For DMD, existing therapies include the use of corticosteroids that delay the symptoms of the disorder. Other strategies include the premature stop codon readthrough by making use of drugs such as Ataluren or Gentamycin. Another strategy is that of exon skipping which results in a truncated protein, however able to reduce the severity of the DMD phenotype. Another approach is the delivery of a u-dystrophin gene. Clinical trials for OTC deficiency have been attempted making use of adenoviral vectors to deliver OTC cDNA in patients. Other avenues for treatment include use of sodium phenylbutyrate which helps increase the waste nitrogen excretion.

The use of ADAR2 as an engineered RNA editing enzyme has been demonstrated only in vitro.

Applicants utilized adRNAs and radRNAs comprised of two domains, one complementary to the target sequence and the other an ADAR2 recruiting domain. Applicants utilized AAVs to deliver these adRNAs/radRNAs along with the ADAR2 enzyme. Mdx mice bear a nonsense mutation (TAA) in the gene coding for dystrophin. Applicants packaged two copies of the adRNAs/radRNAs or a combination of adRNA/radRNA+tRNA along with the ADAR2 enzyme into the AAV and deliver it into the Tibialis Anterior (TA) muscle. Applicants utilized three alternative strategies to restore dystrophin expression:

(1) adRNAs/radRNAs that can edit both the adenosines in the 'TAA' to inosines;

(2) a sequential approach whereby the first adRNA/radRNA converts TAA→TGA and the next adRNA/radRNA converts it to TGG, restoring expression; and (3) a combination of adRNAs/radRNAs and a tRNA whereby the adRNA/radRNA converts the TAA into TAG and the tRNA suppression of the amber codon (TAG) restores dystrophin expression.

Applicants also delivered two copies of the adRNA targeting the OTC G→A mutation in spf-ash mice along with the ADAR2 to the liver via retro-orbital injections.

Figure 6:
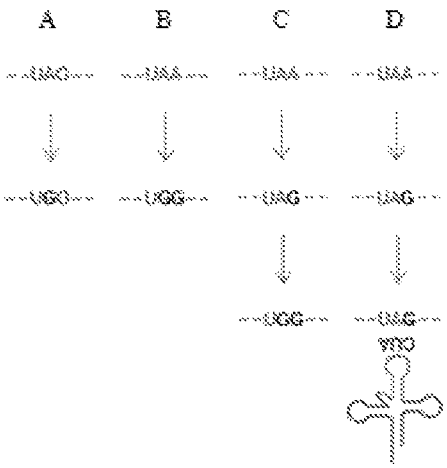
FIG. 6 shows non-limiting examples of RNA level point mutations to a codon that can be made by ADAR2.
Figure 7:
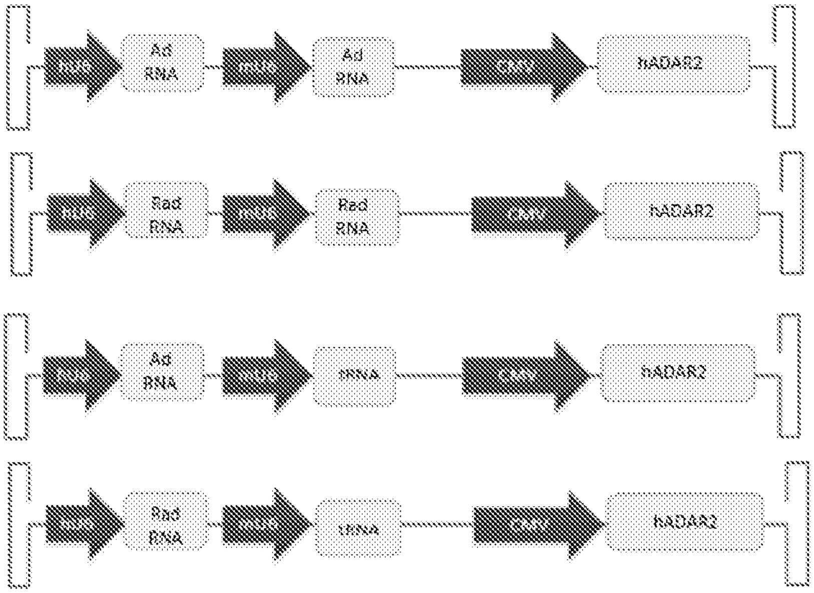
FIG. 7 shows exemplary schematics of constructs that may be used in an ADAR2 based RNA editing system.
Figure 8:
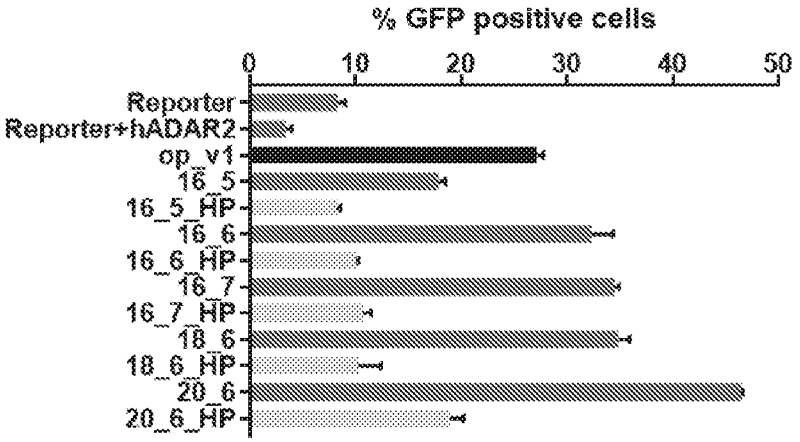
FIG. 8 shows the results of optimization of the length of adRNA and distance of the edit from the ADAR2 recruiting domain. The first number in the shorthand for each category on the Y-axis is the length of adRNA and the second number (following the dash) is the distance of edit from ADAR2 recruiting domain. 20-6 with ADAR2 recruiting region v2 gave us the best results.
Figure 11:
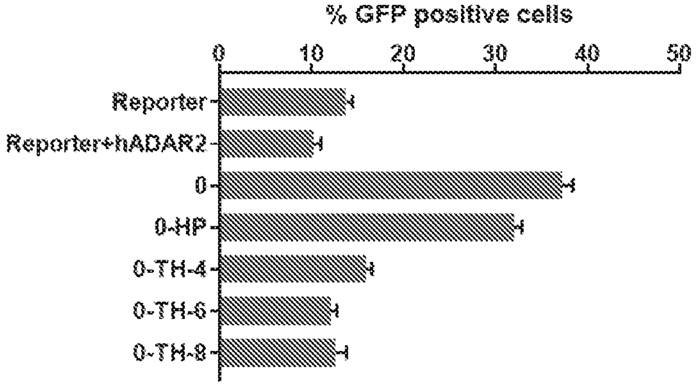
FIG. 11 shows the results of varying lengths of toe hold, guide RNA sequences with no mismatches to the target.
Figure 13:
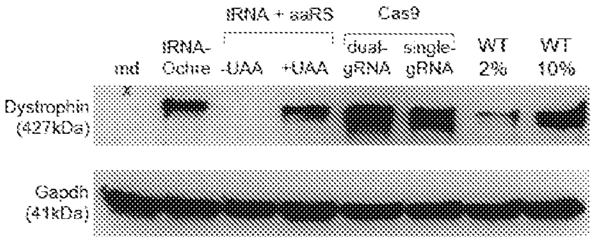
FIG. 13 is a Western blot that shows the restoration of dystrophin expression using suppressor tRNA, in comparison with the Cas9 based approaches.
Figure 14:
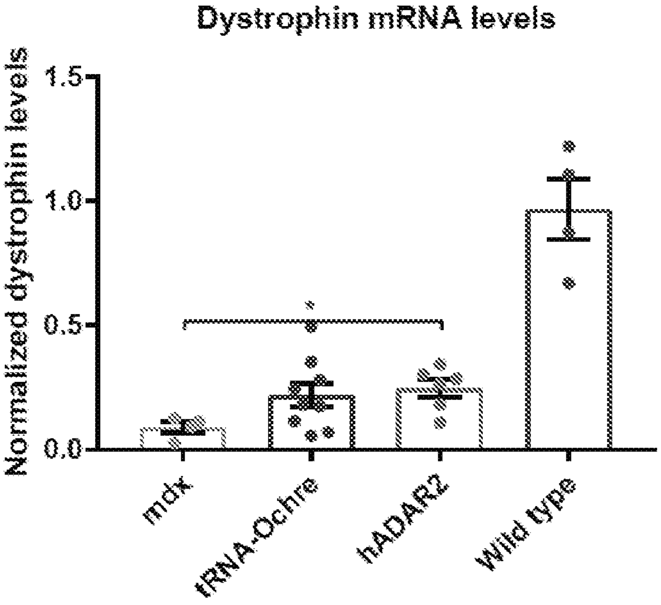
FIG. 14 shows normalized dystrophin mRNA levels.
Figure 15:
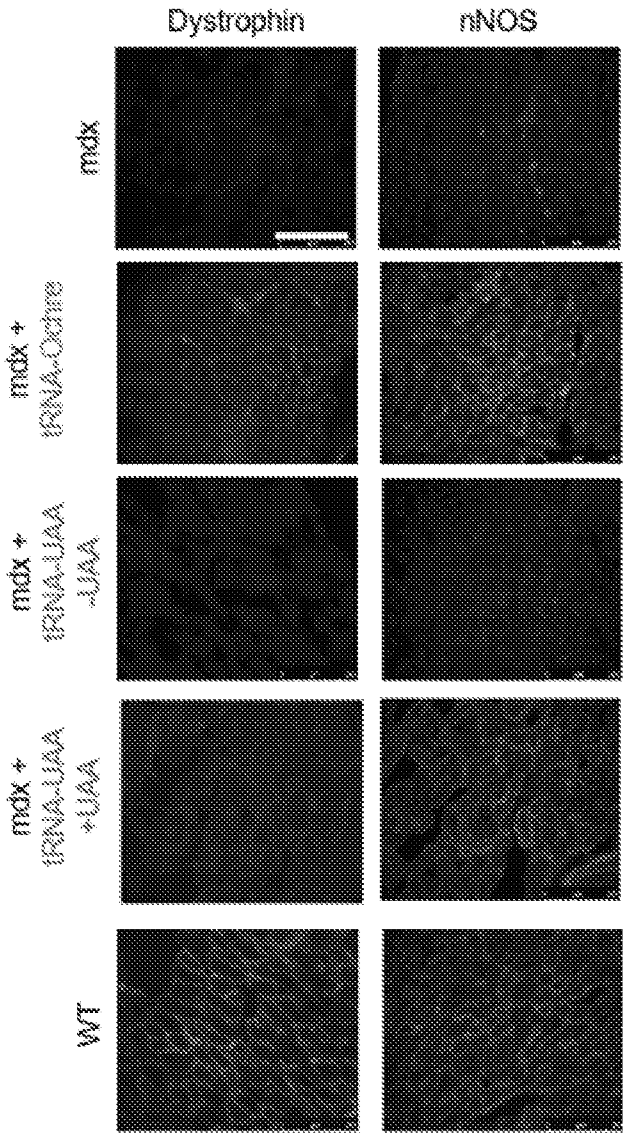
FIG. 15 shows results of immunostaining.

The system works by editing an Adenosine to Inosine which is read as a Guanosine during translation. This can be used to correct point mutations as well as restore expression by editing premature stop codons. In FIG. 6: A. An Amber stop codon can be converted to a tryptophan codon by a single edit. B. Ochre stop codon—both edits made in a single step. C. Ochre stop codon—Sequential editing. D. Ochre stop codon—ADAR2 editing in combination with suppressor tRNA.

The following 10 steps represent the workflow to test these constructs:

1. Design and clone ADAR2 constructs—adRNA and radRNA.
2. In vitro validation of constructs using a GFP harboring a nonsense mutation.
3. Modification of constructs—decision to clone two copies of the adRNA/radRNA. Creation of vectors harboring one copy of a adRNA/radRNA and a copy of a serine suppressor tRNA.
4. Generation of AAV8 vectors carrying ADAR2 and adRNAs/radRNAs or suppressor tRNAs.
6. TA/Gastrocnemius injections of mdx mice—1E12 particles of AAV8 carrying the ADAR2 and with adRNAs/radRNAs or suppressor tRNA were injected.
7. The mice were sacrificed 6 weeks after injections and the TA/gastrocnemimus were harvested. Immunohistochemistry performed to detect dystrophin. Some evidence of restoration of dystrophin.
8. qPCR, Western blots and NGS were carried out.
9. Vectors were optimized to improve efficiency. adRNA lengths varied, location of the edit varied.
10. Steps 4-8 repeated with optimized vectors.

Applicants designed adRNA and radRNAs against a premature stop codon in GFP and demonstrated robust restoration of expression (FIG. 5). For the ochre stop codon (TAA), two A→G edits are needed to restore expression. Applicants constructed a single ad/radRNA targeting both As or a two ad/radRNAs that target a single A in a sequential manner. Applicants also constructed an adRNA/radRNA+suppressor tRNA vector combining RNA editing with tRNA suppression.

In vitro RNA editing showed robust restoration of GFP expression after which AAVs bearing the ADAR2 and adRNA/radRNAs were generated to target the nonsense mutation in dystrophin in mdx mice.

The Tibialis Anterior (TA) or gastrocnemius muscles of mdx mice were injected with 1E12 particles of AAV8 carrying ADAR2 and two copies of the adRNA/radRNA or one copy of the adRNA/radRNA and a suppressor tRNA. These mice were sacrificed after 6 weeks and the appropriate muscles were harvested. The muscles were sectioned and stained with an antibody against dystrophin. Partial restoration of dystrophin expression was noticed.

In general, Applicants noticed a fractional restoration of dystrophin expression via Immunostaining. However, western blots and NGS did not show any evidence of editing/restoration of dystrophin expression.

Potential applications of the system include targeting point mutations for the treatment of disorders such as but not restricted to DMD, OTC deficiency, Wilson's disease and hereditary tysosinemia type 1. It could also be used to create alternate start codons, enabling the co-existence of a protein and its N-terminal truncated form.

Example 5—ADAR Editing in Mouse Models

Genome engineering methodologies coupled with rapidly advancing synthetic biology toolsets are enabling powerful capabilities to perturb genomes for deciphering function, programming novel function, and repairing aberrant function. In particular, programmable DNA nucleases, such as meganucleases, zinc finger nucleases (ZFNs), transcription activator-like effector nucleases (TALENs), and CRISPR-Cas, have been widely used to engineer genomes across a range of organisms. Their use in gene therapy however poses at least three major challenges: one, the efficiency of homologous recombination versus non-homologous end joining is typically low, particularly in post-mitotic cells that comprise the vast majority of the adult body; two, an active nuclease always poses the threat of introducing permanent off-target mutations, thus presenting formidable challenges in both engineering exquisite nuclease specificity without compromising activity, as well as ensuring tight regulation of the nuclease dose and duration in target cells; and three, prevalent programmable nucleases are of prokaryotic origin or bear domains that are of non-human origin raising a significant risk of immunogenicity in in vivo therapeutic applications. The recent advent of base editing approaches is opening an exciting alternative strategy for gene targeting, but demonstrated approaches rely on CRISPR-Cas systems that are of prokaryotic origin. Thus for genomic mutations that lead to alteration in protein function, such as in disease causing gene mutations, approaches to instead directly target RNA would be highly desirable. Leveraging the aspect that single-stranded RNA as compared to double-stranded DNA, is generally more accessible to oligonucleotide mediated targeting without a need for additional enabling proteins, and building on the advances in tRNA mediated codon suppression and genetic code expansion, as well as adenosine deaminase mediated RNA editing, Applicants have engineered and optimized an integrated platform for RNA targeting, and demonstrate its efficacy in in vitro and in vivo applications.

Vector Design and Construction

To construct the GFP reporters—GFP-Amber, GFP-Ochre and GFP-Opal, three gene blocks were synthesized with 'TAG', 'TAA' and 'TGA' respectively replacing the Y39 residue of the wild type GFP and were cloned downstream of a CAG promoter. One, two, or four copies of the endogenous suppressor tRNAs were cloned into an AAV vector containing a human U6 and mouse U6 promoter. Pyrrolysyl tRNAs and adRNAs/radRNAs were similarly cloned into an AAV vector containing a human U6 and mouse U6 promoter along with a CMV promoter driving the expression of MbPylRS/MmPylRS/AcKRS or hADAR2 respectively.

Mammalian Cell Culture and Transfection

All HEK 293T cells were grown in Dulbecco's Modified Eagle Medium supplemented with 10% FBS and 1% Antibiotic-Antimycotic (Thermo Fisher) in an incubator at 37° C. and 5% $CO_2$ atmosphere. All in vitro transfection experiments were carried out in HEK 293T cells using the commercial transfection reagent Lipofectamine 2000 (Thermo Fisher). All in vitro suppression and editing experiments were carried out in 24 well plates using 500 ng of reporter plasmid and 1000 ng of the suppressor tRNA/aaRS plasmid or the adRNA/ADAR2 plasmid. Cells were transfected at 30% confluence. Cells were harvested 48 and 72 hours post transfection for quantification of suppression and editing respectively. The UAAs Nε-Boc-L-Lysine (Chemimpex) and Nε-Acetyl-L-Lysine (Sigma) were added to the media at the desired concentration before transfection.

Production of AAV Vectors

Virus was prepared using the protocol from the Gene Transfer, Targeting and Therapeutics (GT3) core at the Salk Institute of Biological Studies (La Jolla, CA). AAV8 particles were produced using HEK 293T cells via the triple transfection method and purified via an iodixanol gradient. Confluency at transfection was about 80%. Two hours prior to transfection, DMEM supplemented with 10% FBS was added to the HEK 293T cells. Each virus was produced in 5×15 cm plates, where each plate was transfected with 7.5 ug of pXR-8, 7.5 of ug recombinant transfer vector, 7.5 ug of pHelper vector using PEI (1 ug/uL linear PEI in 1×DPBS pH 4.5, using HCl) at a PEI:DNA mass ratio of 4:1. The mixture was incubated for 10 minutes at RT and then applied dropwise onto the cell media. The virus was harvested after 72 hours and purified using an iodixanol density gradient ultracentrifugation method. The virus was then dialyzed with 1×PBS (pH 7.2) supplemented with 50 mM NaCl and 0.0001% of Pluronic F68 (Thermo Fisher) using 50 kDA filters (Millipore), to a final volume of ~1 mL and quantified by qPCR using primers specific to the ITR region, against a standard (ATCC VR-1616).

```
AAV-ITR-F:
                                  (SEQ ID NO: 158)
5'-CGGCCTCAGTGAGCGA-3'
and

AAV-ITR-R:
                                  (SEQ ID NO: 159)
5'-GGAACCCCTAGTGATGGAGTT-3'.
```

RNA Isolation and Next Generation Sequencing Library Preparation

RNA from gastrocnemius or TA muscles of mdx mice or livers of spf$^{ash}$ mice was extracted using the RNeasy Plus Universal Mini Kit (Qiagen), according to the manufacturer's protocol. Next generation sequencing libraries were prepared as follows. cDNA was synthesized using the Protoscript II First Strand cDNA synthesis Kit (New England Biolabs). Briefly, 500 ng of input cDNA was amplified by PCR with primers that amplify 150 bp surrounding the sites of interest using KAPA Hifi HotStart PCR Mix (Kapa Biosystems). PCR products were gel purified (Qiagen Gel Extraction kit), and further purified (Qiagen PCR Purification Kit) to eliminate byproducts. Library construction was done with NEBNext Multiplex Oligos for Illumina kit (NEB). 10 ng of input DNA was amplified with indexing primers. Samples were then pooled and loaded on an Illumina Miseq (150 single-end run) at 5 nM concentrations. Data analysis was performed using CRISPResso.

Animal Experiments

AAV Injections: All animal procedures were performed in accordance with protocols approved by the Institutional Animal Care and Use Committee (IACUC) of the University of California, San Diego. All mice were acquired from Jackson labs. AAVs were injected into the gastrocnemius or TA muscle of mdx mice (6-10 weeks old) using 2.5E+12 vg/muscle. AAVs were injected into spf$^{ash}$ (10-12 weeks old) mice via retro-orbital injections using 3E+12 vg/mouse.

UAA Administration:

Mice were fed water containing 20 mg/ml Nε-Boc-L-Lysine (Chemimpex) for one month. Mice were also administered the 30 mg Nε-Boc-L-Lysine via IP injections, thrice a week.

Immunofluorescence

Harvested gastrocnemius or TA muscles were placed in molds containing OCT compound (VWR) and flash frozen in liquid nitrogen. 20 μm sections were cut onto pre-treated histological slides. Slides were fixed using 4% Paraformaldehyde. Dystrophin was detected with a rabbit polyclonal antibody against the N-terminal domain of dystrophin (1:100, Abcam 15277) followed by a donkey anti-rabbit Alexa 546 secondary antibody (1:250, Thermo Fisher).

Statistical Analysis

All statistical analyses were performed using the software Graphpad Prism and p-values were computed by unpaired two-tailed t tests.

Results

Applicants focused first on establishing the system for targeting nonsense mutations. This was motivated by the fact that nonsense mutations are responsible for 11% of all described gene lesions causing inheritable human disease, and close to 20% of disease-associated single base substitutions that affect the coding regions of genes. Specifically, we explored two independent but complementary approaches to directly target nonsense mutations. First, Applicants focused on engineering robust nonsense codon suppression via suppressor tRNAs. Although the use of suppressor tRNAs for premature stop codon read-through of endogenous non-sense mutations has been attempted in vivo in mice, these prior studies relied only on plasmid delivery and the use of robust and optimized delivery formats was not explored. Additionally, the potential use of un-natural amino acid (UAA) based inducible in vivo suppression of a disease-causing endogenous nonsense mutation has not been explored either. Towards this, Applicants first modified the anticodon stems of serine, arginine and leucine tRNAs to create suppressor tRNAs targeting all three stop codons, amber, opal and ochre, and evaluated these constructs in cells using GFP reporters harboring corresponding nonsense mutations. Among these, the serine suppressor tRNA demonstrated the most consistent and robust results (FIG. 16A, FIG. 18A). To also engineer UAA mediated inducible codon suppression, we next utilized the pyrrolysyl-tRNA/aminoacyl tRNA synthetase (aaRS) pair from *Methanosarcina barkeri* (MbPylRS)[32, 33] and cloned it into AAV vectors. This enabled programmable incorporation of UAAs at a stop codon. Notably, Applicants found that adding a second copy of the tRNA into the expression vector significantly boosted suppression efficiencies (FIG. 18B). Applicants further systematically evaluated additional aminoacyl tRNA synthetases from *Methanosarcina mazei* (MmPylRS)[34] and an Nε-acetyl-lysyl-tRNA synthetase (AcKRS), and also explored varying the number of tRNAs copies per vector to up to four (FIG. 18B).

As suppressor tRNA based approaches can lead to the read-through of other non-target stop codons, concurrently Applicants also engineered a system for sequence-specific targeted RNA editing via adenosine deaminase enzymes. Specifically, adenosine to inosine (A to I) editing is a common post-transcriptional modification in RNA, catalyzed by adenosine deaminases acting on RNA (ADARs). Inosine is a deaminated form of adenosine and is biochemically recognized as guanine. Recently, multiple studies have demonstrated the engineering of ADAR2 mediated targeting in vitro, and a study also demonstrated correction of the nonsense mutation in CFTR in *xenopus* oocytes. Building on this, Applicants engineered here a system for sequence-specific targeted RNA editing in vitro and in vivo, utilizing the human ADAR2 enzyme and an associated ADAR2 guide RNA (adRNAs) engineered from its naturally occurring substrate GluR2 pre-mRNA. This ADAR2 guiding RNA comprises an ADAR-recruiting domain and a programmable antisense region that is complementary to a specified target RNA sequence. Applicants first evaluated the RNA editing efficiency of this system in vitro by co-transfecting the constructs with GFP reporters harboring a non-sense amber or ochre mutation at Y39. Specifically, Applicants utilized two editing approaches to engineer the editing of both adenosines in the ochre stop codon: a one-step mechanism where both the adenosines are edited simultaneously or a two-step mechanism wherein editing takes place sequentially. In addition, we also explored the possibility of conversion of an ochre codon to an amber codon followed by amber suppression to restore GFP expression. All three approaches enabled restoration of GFP expression (FIG. 16C, FIG. 19A). Applicants next constructed AAV vectors to deliver the adRNA or a reverse oriented adRNA (radRNA) along with the ADAR2 enzyme. Similar to tRNA mediated codon suppression, addition of a second copy of the adRNA/radRNA significantly improved the targeting efficiency (FIG. 19D). Applicants further systematically evaluated modified ADAR recruiting domains, and a range of RNA targeting antisense designs of varying lengths and the number of nucleotides intervening the target A and the R/G motif of the adRNA[26], yielding a panel of efficient adRNA designs (FIG. 19B-C).

Based on the above in vitro optimizations, Applicants next tested the system for in vivo RNA targeting. Applicants focused first on the mdx mouse model for Duchenne muscular dystrophy (DMD)[35] which bears an ochre stop site in exon 23 of the dystrophin gene. Recent studies utilizing the CRISPR-Cas9 system have shown promising results in the prevention[38] and partial functional recovery of DMD by making changes in exon 23 at the DNA level in the mdx mouse. We thus concurrently evaluated three approaches (FIG. 17A): one, suppressor tRNAs derived from modified endogenous tRNAs or pyrrolysyl tRNAs for nonsense codon suppression; two, ADAR2 based correction of the nonsense mutation; and, three, CRISPR-Cas9 based genome targeting to benchmark the RNA targeting approaches.

Figure 17:
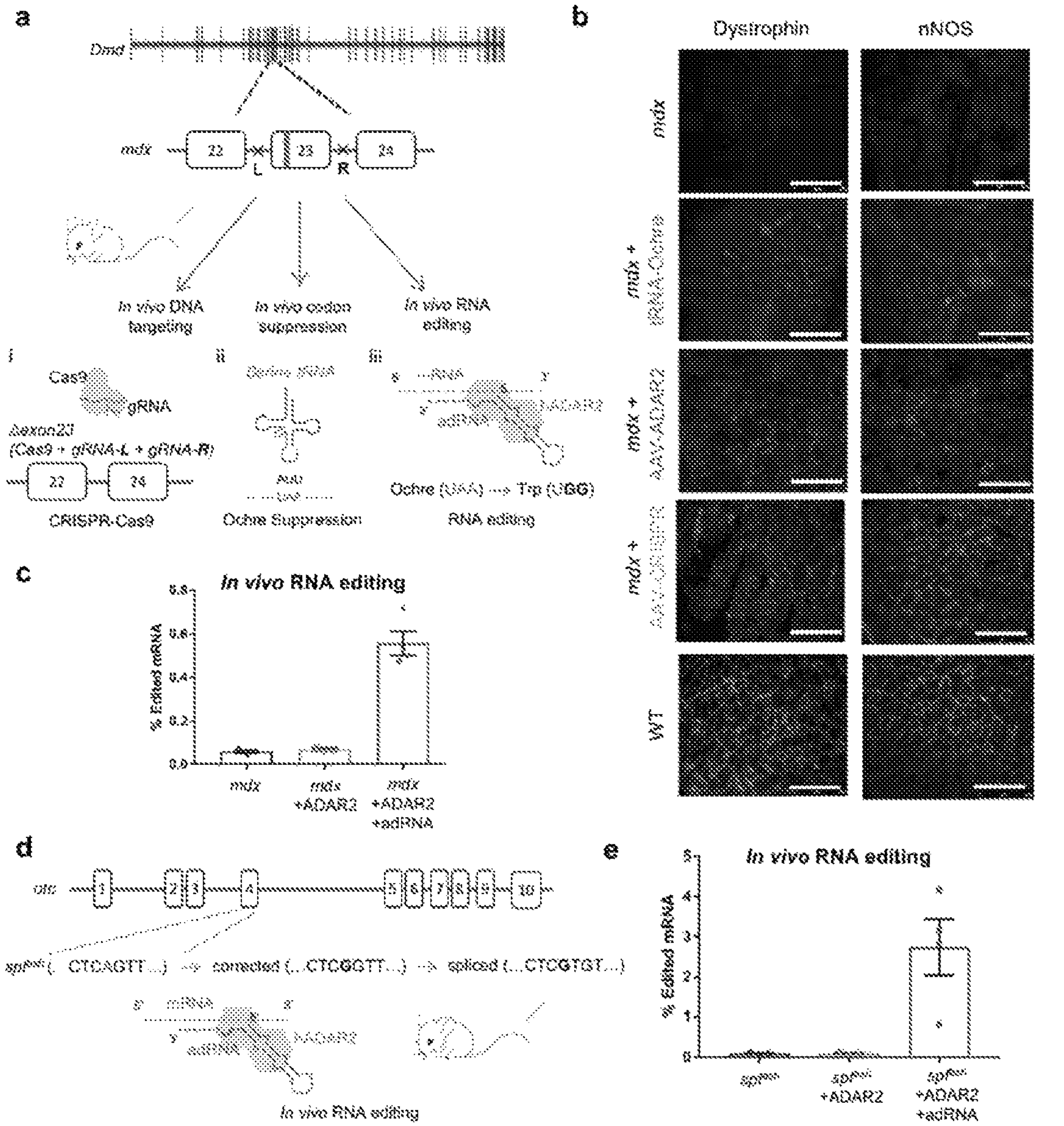
FIG. 17A-E shows in vivo RNA targeting in mouse models of human disease.
Figure 20:
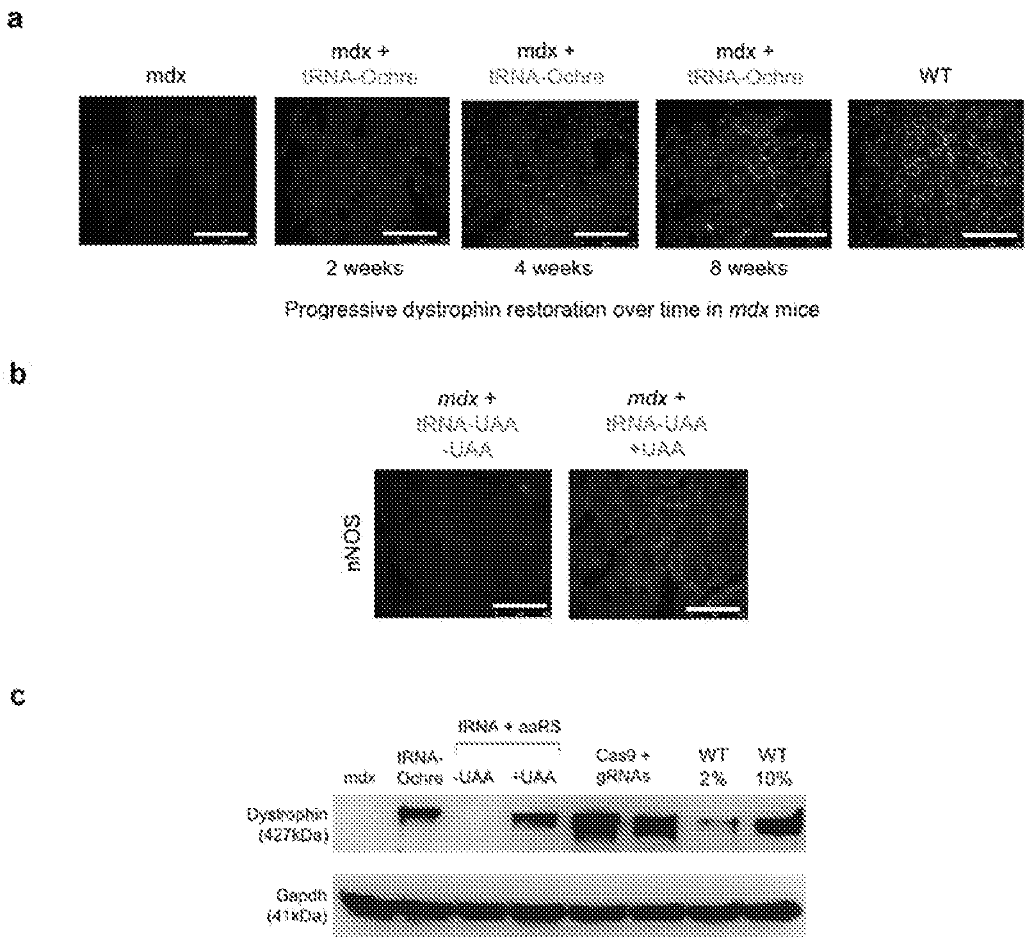
FIG. 20A-C shows in vivo targeting of dystrophin mRNA via suppressor tRNAs.

Corresponding, Applicants first designed an AAV carrying two copies of the serine suppressor tRNA targeting the ochre stop codon, and the tibalis anterior (TA) or gastrocnemius of mdx mice were injected with the same. Mice muscles were harvested after 2, 4, and 8 weeks. Progressively improved restoration of dystrophin expression was seen over time, with the mice harvested after 8 weeks showing the greatest degree of restoration (FIG. 17B, FIG. 20A). In addition, neuronal nitric oxide synthase (nNOS) activity was restored at the sarcolemma which is absent in mdx mice due to the absence of the nNOS binding site in the mutant dystrophin protein (FIG. 17B). To further make the system inducible, a vector carrying two copies of the pyrrolysyl-tRNA targeting the ochre stop codon and MbPylRS was also constructed and injected into the TA or gastrocnemius of mdx mice, and the mice were divided into two groups: one that was administered the pyrrolysine UAA and a control group that was not. Expectedly only mice that were provided the UAA showed nNOS localization at the sarcolemma (FIG. 20B), and restoration of dystrophin expression (FIG. 20C).

Figure 21:
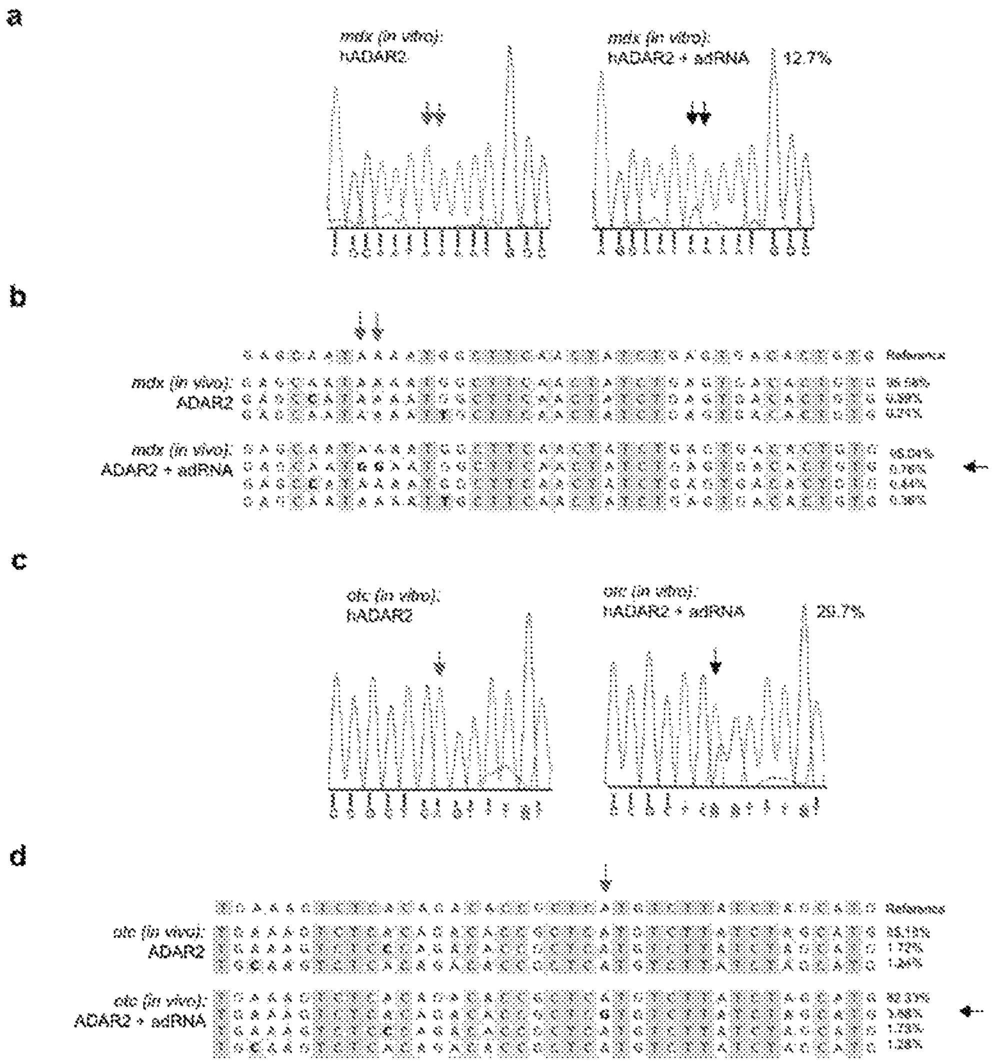
FIG. 21A-D show in vitro and in vivo editing of dystrophin and OTC mRNA.
Figure 25:
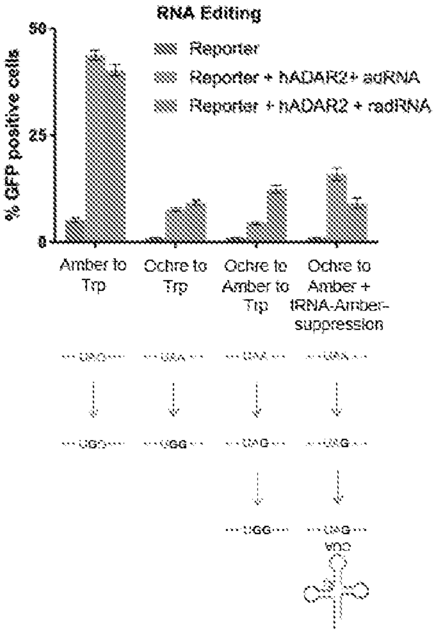
FIG. 25 shows the rate of UAA to UAG conversion. The UAA is converted to UAG via ADAR2 based editing and addition of suppressor tRNA targeting the UAG stop codon led to partial restoration of GFP expression
Figure 26:
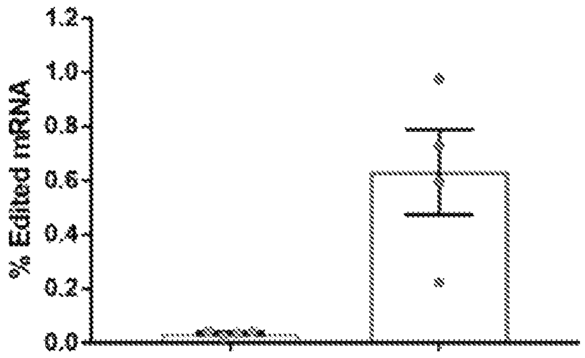
FIG. 26 shows the results of in vivo RNA editing in the mdx mouse model of muscular dystrophy.
Figure 27:
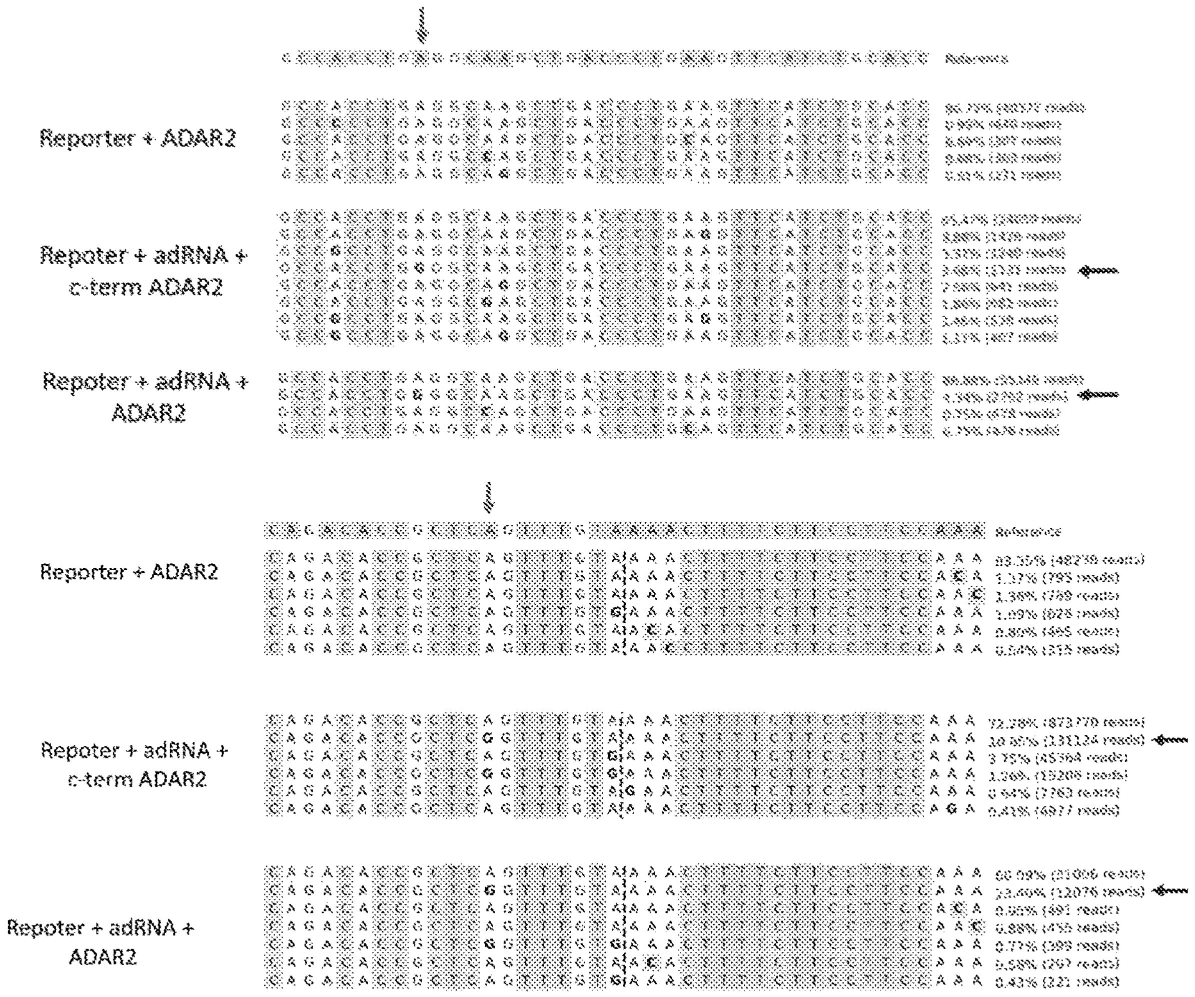
FIG. 27 shows the resulting edited sequences resulting from use of the promiscuous C-terminal ADAR2 (SEQ ID NOS 228-264, respectively, in order of appearance).

Next, Applicants evaluated the ADAR2 based site-specific RNA editing approach in this mouse model. To test the efficiency of this system in editing both adenosines in the ochre stop codon in mdx DMD mRNA, Applicants first optimized the constructs in vitro with a reporter plasmid bearing a fragment of the mdx DMD mRNA in HEK293T cells. Sanger sequencing and NGS analysis confirmed successful targeting (FIG. 21A). Applicants next packaged the optimized constructs into AAV8, and injected the tibialis anterior (TA) or gastrocnemius of mdx mice. Eight weeks post injection, TA and gastrocnemius muscles were collected from mdx mice, wild type mice, and mice treated with adRNA targeting and non-targeting controls. IHC revealed clear restoration of dystrophin expression (FIG. 17B). In addition, nNOS activity was also restored at the sarcolemma (FIG. 17B). RNA editing rates (TAA→TGG/TAG/TGA) of 0.5-0.7% were observed in treated mice (FIG. 17C, FIG. 21B). Applicants also note that the mdx mice showed no mRNA with a TAA→TGG change while the treated mice showed up to 0.42% TAA→TGG edited mRNA. Applicants note that corresponding DNA editing rates via CRISPR-Cas9 in published in vivo targeting studies were about 2%[39]. To further benchmark the tRiAD approach, we thus also targeted the mdx mice via CRISPR based genome editing of the nonsense mutation. Applicants injected vectors bearing dual-gRNAs to excise exon 23 codon, and expectedly, this led to restoration of dystrophin expression in a subset of the muscle cells (FIG. 17B).

Finally, we also evaluated the ADAR2 mediated RNA editing approach in an independent mouse model of human disease. Specifically, we focused on the male sparse fur ash ($spf^{ash}$) mouse model of ornithine transcarbamylase (OTC) deficiency. The $spf^{ash}$ mice have a G→A point mutation in the last nucleotide of the fourth exon of the OTC gene, which leads to OTC mRNA deficiency and production of mutant protein[43]. Recent studies have demonstrated the use of CRISPR-Cas9 and homologous recombination based strategies for robust correction of this mutation in neonatal mice. However, gene correction via homology-directed repair (HDR) in adult mice was inefficient and led to genomic deletions which proved to be lethal as they compromised liver function in targeted mice. To test the effectiveness of the system in editing the point mutation in $spf^{ash}$ OTC mRNA (FIG. 17D), Applicants first evaluated our constructs in vitro with a plasmid bearing a fragment of the $spf^{ash}$ OTC mRNA in HEK293T cells. Sanger sequencing and next generation sequencing (NGS) analysis confirmed robust RNA editing efficiencies (FIG. 21C). Applicants next packaged the constructs into AAV8, which has high liver tropism[44], and injected 10-12 week old $spf^{ash}$ mice. Four weeks post injection, Applicants collected liver samples from $spf^{ash}$, wild-type litter mates, and $spf^{ash}$ mice treated with the ADAR2 targeting and non-targeting vectors and evaluated editing efficiency via NGS. Notably, significant RNA editing rates in the range of 0.8-4.2% were observed in treated mice in the spliced OTC mRNA (FIG. 17E, FIG. 21D), further confirming the utility of this approach for in vivo editing of endogenous RNA in adult mice.

Taken together, Applicants' results establish the use of suppressor tRNAs and ADAR2 as potential strategies for in vivo RNA targeting of point mutations. Specifically, by optimizing delivery, Applicants first demonstrated robust and inducible stop codon read-through via the use of suppressor tRNAs. The delivery of modified endogenous suppressor tRNAs for premature stop read-through has several potential advantages: it lacks the toxicity associated with read-through drugs such as gentamycin and can be used to bring about efficient stop codon read-through in post-mitotic cells. In addition, being of endogenous origin, it is not likely to elicit a strong immune response. Additionally, the inducibility enabled by the UAA based systems, albeit non-native, could provide tight regulation over the expression of genes. Localized injections of the UAA into the target muscle could further help improve the efficiency of the system in future studies. Notably, Applicants did not observe any overt toxicity via this approach in the mdx targeting studies. Applicants however note too that an important caveat to this strategy, analogous to the read-through drugs, is that suppressor tRNA based approaches will lead to the read-through of other non-target stop codons. In this regard, Applicants thus also demonstrated ADAR2 based site-specific correction of point mutations in RNA in two independent mouse models. Applicants note that potential off-targets in RNA are limited as compared to DNA, as the transcriptome is only a small subset of the genome. Secondly, even if off-targets exist, the presence of an A within the target window is required for the enzyme to create an off-target A→G change. Lastly, the off-target effects will be transient. Thus, overall off-target effects due to a RNA editing enzyme such as ADAR2 are likely to be limited, although enzyme processivity, promiscuity, and off-target hybridization of the antisense domain of the adRNA need to be studied thoroughly. ADAR2 being of human origin is also less likely to elicit an immune response, while enabling more site-specific editing of RNA compared to the suppressor tRNA approach.

Applicants also note that compared to the tRiAD based RNA targeting approaches above, CRISPR based genome targeting approaches currently show faster kinetics and greater degree of mutant protein restoration. Applicants however anticipate that systematic engineering and directed evolution of the ADAR2 could help improve the editing efficiency and also eliminate the intrinsic biases of the ADAR2 for certain sequences, coupled with insights from studies unearthing novel regulators of ADAR2 providing cues to improve its stability. In this regard, Applicants tested the ADAR2-E488Q mutant and noted that it enabled higher editing efficiency than the wild type ADAR2 for both the DMD and OTC mRNA fragments expressed in vitro (FIG. 22). The demonstration of site-specific A→G mRNA editing in vivo also opens up the door to future site-specific C→T editing via targeted recruitment of cytosine deaminases, thereby potentially expanding the repertoire of RNA editing tools. However, an important consideration while targeting RNA for gene therapy via the use of non-integrating vectors such as AAVs, is the necessity for periodic re-administration of the effector constructs due to the typically limited half-life of edited mRNAs. Secondly, RNA folding, intrinsic half-life, localization, and RNA binding proteins might also impact accessibility of target sites in the RNA. For instance, in this example, the short half-life of mutant dystrophin RNA, and the need to target the transient pre-mRNA in OTC potentially negatively impact overall editing efficiencies. Chemical and structural modifications in tRNAs and adR- NAs while taking cues from the specificity studies on sgRNAs[49], or coupling of shielding proteins, or recently demonstrated programmable RNA binding proteins and RNA-targeting CRISPR-Cas systems, might help improve RNA stability and specificity, and improve the efficiency of the above approaches. With progressive improvements, Applicants thus anticipate this integrated tRiAD toolset will have broad implications in both applied life sciences as well as fundamental research.

Example 6—ADAR and APOBEC Editing Efficacy

Figure 28:
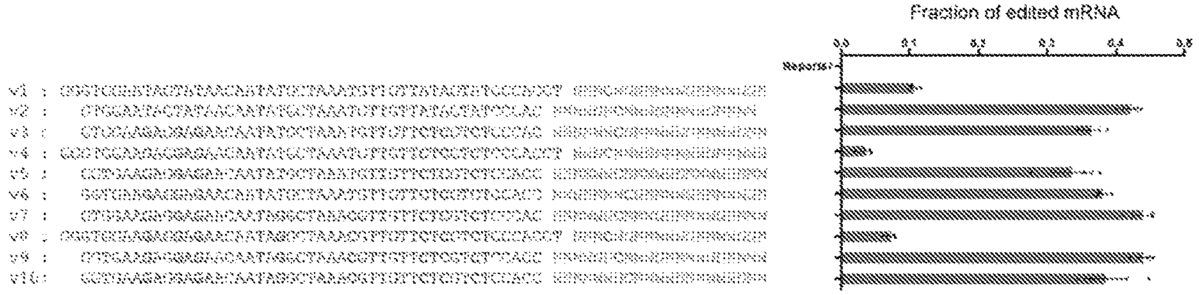
FIG. 28 shows editing efficiency of the stabilized scaffolds (SEQ ID NOS 104-113, respectively, in order of appearance).
Figure 30:
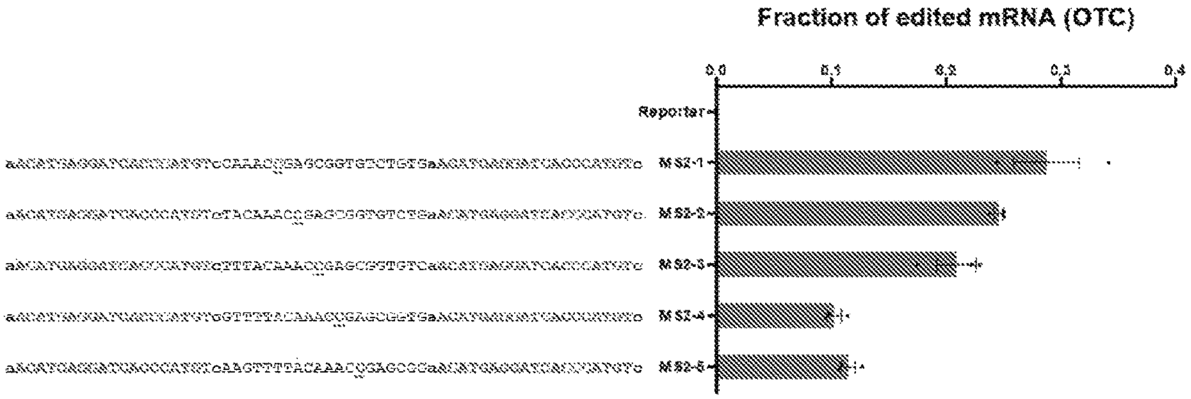
FIG. 30 shows the fraction of edited mRNA with various MCP-ADAR scaffolds (SEQ ID NOS 265-269, respectively, in order of appearance).

A number of ADAR scaffolds—both dual and single—were tested for efficacy in recruiting ADAR in a cell line where ADAR2 was overexpressed (FIG. 28 and FIG. 29). Further assessments were made for MCP-ADAR fusion scaffolds (FIG. 30). Endogenous mRNA target editing efficiency was assessed using scaffold v2. SEQ ID NOS 160-163 are disclosed below.

| mRNA | Target | #1 | #2 | #3 | Average |
|---|---|---|---|---|---|
| RAB7A | GGGAAATCCAGCTAGC GGCA | 32.0% | 34.1% | 30.2% | 32.1% |
| RAB7A | GGGAAAACTGTCTAGT TCCC | 28.2% | 27.5% | 23.0% | 26.2% |
| CCNB1 | TAATTGACTGGCTAGT ACAG | 23.8% | 17.2% | 21.1% | 20.7% |
| CCNB1 | GAGCTTTTTGCTTAGC ACTG | 15.1% | 18.4% | 17.4% | 17.0% |

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

REFERENCES

Welch, E. M. et al. PTC124 targets genetic disorders caused by nonsense mutations. Nature 447, 87-91 (2007).

Mah, J. Current and emerging treatment strategies for Duchenne muscular dystrophy. Neuropsychiatr. Dis. Treat. Volume 12, 1795-1807 (2016).

Tabebordbar, M. et al. In vivo gene editing in dystrophic mouse muscle and muscle stem cells. Science (80.). 351, 407-411 (2016).

Nelson, C. E. et al. In vivo genome editing improves muscle function in a mouse model of Duchenne muscular dystrophy. Science (80.). 351, (2016).

Cirak, S. et al. Exon skipping and dystrophin restoration in patients with Duchenne muscular dystrophy after systemic phosphorodiamidate morpholino oligomer treatment: an open label, phase 2, dose escalation study. Lancet 378, 595-605 (2011).

Malik, V. et al. Gentamicin induced readthrough of stop codons in Duchenne muscular dystrophy. Ann. Neurol. 67, NANA (2010).

Wagner, K. R. et al. Gentamicin treatment of Duchenne and Becker muscular dystrophy due to nonsense mutations. Ann. Neurol. 49, 706-11 (2001).

Yang, Y. et al. A dual AAV system enables the Cas9-mediated correction of a metabolic liver disease in newborn mice. Nat. Biotechnol. 34, 334-338 (2016).

Wettengel, J. et al. Harnessing human ADAR2 for RNA repair—Recoding a PINK1 mutation rescues mitophagy. Nucleic Acids Res. gkw911 (2016).

Fukuda, M. et al. Construction of a guide-RNA for site-directed RNA mutagenesis utilising intracellular A-to-I RNA editing 1-49.

Hendel, A. et al. Chemically modified guide RNAs enhance CRISPR-Cas genome editing in human primary cells. Nature Biotechnology, 33(9), pp. 985-989 (2015).

Jinek, M. et al. A Programmable Dual-RNA-Guided DNA Endonuclease in Adaptive Bacterial Immunity. Science (80-.). 337, 816-821 (2012).

Christian, M. et al. Targeting DNA Double-Strand Breaks with TAL Effector Nucleases. Genetics 186, 757-761 (2010).

Urnov, F. D. et al. Highly efficient endogenous human gene correction using designed zinc-finger nucleases. Nature 435, 646-651 (2005).

Urnov, F. D., Rebar, E. J., Holmes, M. C., Zhang, H. S. & Gregory, P. D. Genome editing with engineered zinc finger nucleases. Nat. Rev. Genet. 11, 636-646 (2010).

Mali, P. et al. RNA-guided human genome engineering via Cas9. Science 339, 823-6 (2013).

Cong, L., Ran, F., Cox, D., Lin, S. & Barretto, R. Multiplex Genome Engineering Using CRISPR/Cas Systems. Science (80-.). 819, (2013).

Mario, R. et al. Altering the genome by Homologous Recombination. Sci. Virol. Sci. Theor. Appl. Genet. Arch. Tierz. Kexue Tongbao K. Ozato al. Cell Differ. Aquac. Trans. Am. Fish. Soc 244, 1288-1292 (1989).

Takata, M. et al. Homologous recombination and non-homologous end-joining pathways of DNA double-strand break repair have overlapping roles in the maintenance of chromosomal integrity in vertebrate cells. EMBO J. 17, 5497-508 (1998).

Cho, S. W. et al. Analysis of off-target effects of CRISPR/Cas-derived RNA-guided endonucleases and nickases. Genome Res. 24, 132-41 (2014).

Schaefer, K. A. et al. Unexpected mutations after CRISPR—Cas9 editing in vivo Digenome-seq web tool for profiling CRISPR specificity. Nature 14, 547-548 (2017).

Wang, D. et al. Adenovirus-Mediated Somatic Genome Editing of Pten by CRISPR/Cas9 in Mouse Liver in Spite of Cas9-Specific Immune Responses. Hum. Gene Ther. 26, 432-42 (2015).

Chew, W. L. et al. A multifunctional AAV—CRISPR-Cas9 and its host response. Nat. Methods 13, 868-874 (2016).

Komor, A. C., Kim, Y. B., Packer, M. S., Zuris, J. A. & Liu, D. R. Programmable editing of a target base in genomic DNA without double-stranded DNA cleavage. Nature 533, 420-424 (2016).

Gaudelli, N. M. et al. Programmable base editing of A.T to G.C in genomic DNA without DNA cleavage. (2017). doi:10.1038/nature24644

Kim, K. et al. Highly efficient RNA-guided base editing in mouse embryos. Nat. Biotechnol. 9, 12-15 (2017).

Capone, J. P., Sharp, P. A. & RajBhandary, U. L. Amber, ochre and opal suppressor tRNA genes derived from a human serine tRNA gene. EMBO J. 4, 213-21 (1985).

Geslain, R. & Pan, T. Functional analysis of human tRNA isodecoders. doi:10.1016/j.jmb.2009.12.018

Panchal, R. G., Wang, S., Mcdermott, J. & Link, C. J. Partial Functional Correction of Xeroderma Pigmentosum Group A Cells by Suppressor tRNA. Hum. Gene Ther. 10, 2209-2219 (1999).

Buvoli, M., Buvoli, A. & Leinwand, L. A. Suppression of nonsense mutations in cell culture and mice by multimerized suppressor tRNA genes. Mol. Cell. Biol. 20, 3116-24 (2000).

Wang, L., Brock, A., Herberich, B. & Schultz, P. G. Expanding the Genetic Code of *Escherichia coli*. Science (80-.). 292, (2001).

Ernst, R. J. et al. Genetic code expansion in the mouse brain. 1-5 (2016). doi:10.1038/nchembio.2160

Han, S. et al. Expanding the genetic code of *Mus musculus*. Nat. Commun. 8, 14568 (2017).

Melcher, T. et al. A mammalian RNA editing enzyme. Nature 379, 460-464 (1996).

Rueter, S. M., Burns, C. M., Coode, S. A., Mookherjee, P. & Emeson, R. B. Glutamate receptor RNA editing in vitro by enzymatic conversion of adenosine to inosine. Science 267, 1491-4 (1995).

Montiel-Gonzalez, M. F., Vallecillo-Viejo, I., Yudowski, G. A. & Rosenthal, J. J. C. Correction of mutations within the cystic fibrosis transmembrane conductance regulator by site-directed RNA editing. Proc. Natl. Acad. Sci. U.S.A 110, 18285-90 (2013).

Wettengel, J., Reautschnig, P., Geisler, S., Kahle, P. J. & Stafforst, T. Harnessing human ADAR2 for RNA repair—Recoding a PINK1 mutation rescues mitophagy. Nucleic Acids Res. gkw911 (2016). doi:10.1093/nar/gkw911

Fukuda, M. et al. Construction of a guide-RNA for site-directed RNA mutagenesis utilising intracellular A-to-I RNA editing. Sci. Rep. 7, 41478 (2017).

Mort, M., Ivanov, D., Cooper, D. N. & Chuzhanova, N. A. A meta-analysis of nonsense mutations causing human genetic disease. Hum. Mutat. 29, 1037-1047 (2008).

Bidou, L., Allamand, V., Rousset, J.-P. & Namy, O. Sense from nonsense: therapies for premature stop codon diseases. Trends Mol. Med. 18, 679-688 (2012).

Li, K. et al. OCHRE SUPPRESSOR TRANSFER RNA RESTORED DYSTROPHIN EXPRESSION IN MDX MICE. Life Sci. 61, PL205-PL209 (1997).

Kiselev, A. V. et al. Suppression of nonsense mutations in the Dystrophin gene by a suppressor tRNA gene|Ispol'zovanie gena supressornoi tRNK dlia ispravleniia nonsens-mutatsii v gene distrofina. Mol. Biol. 36, 43-47 (2002).

Gautier, A. et al. Genetically Encoded Photocontrol of Protein Localization in Mammalian Cells. J. Am. Chem. Soc. 132, 4086-4088 (2010).

Chatterjee, A., Xiao, H., Bollong, M., Ai, H. & Schultz, P. G. Efficient viral delivery system for unnatural amino acid mutagenesis in mammalian cells. 110, 11803-11808 (2013).

Greiss, S. & Chin, J. W. Expanding the Genetic Code of an Animal. 2, 14196-14199 (2011).

Robinson-Hamm, J. N. & Gersbach, C. A. Gene therapies that restore dystrophin expression for the treatment of Duchenne muscular dystrophy. Hum. Genet. 135, 1029-1040 (2016).

Bulfield, G., Siller, W. G., Wight, P. A. & Moore, K. J. X chromosome-linked muscular dystrophy (mdx) in the mouse. Proc. Natl. Acad. Sci. U.S.A 81, 1189-92 (1984).

Sicinski, P. et al. The molecular basis of muscular dystrophy in the mdx mouse: a point mutation. Science 244, 1578-80 (1989).

Long, C. et al. Prevention of muscular dystrophy in mice by CRISPR/Cas9-mediated editing of germline DNA. Science (80-.). 345, 1184-1188 (2014).

Nelson, C. E. et al. In vivo genome editing improves muscle function in a mouse model of Duchenne muscular dystrophy. Science (80-.). 351, (2016).

Tabebordbar, M. et al. In vivo gene editing in dystrophic mouse muscle and muscle stem cells. Science (80-.). 351, 407-411 (2016).

Long, C. et al. Postnatal genome editing partially restores dystrophin expression in a mouse model of muscular dystrophy. Science (80-.). 351, 400-403 (2016).

Bengtsson, N. E. et al. Muscle-specific CRISPR/Cas9 dystrophin gene editing ameliorates pathophysiology in a mouse model for Duchenne muscular dystrophy. Nat. Commun. 8, 14454 (2017).

Hodges, P. E. & Rosenberg, L. E. The spfash mouse: a missense mutation in the ornithine transcarbamylase gene also causes aberrant mRNA splicing. Proc. Natl. Acad. Sci. U.S.A 86, 4142-4146 (1989).

Yang, Y. et al. A dual AAV system enables the Cas9-mediated correction of a metabolic liver disease in newborn mice. Nat. Biotechnol. 34, 334-338 (2016).

Kuttan, A. & Bass, B. L. Mechanistic insights into editing-site specificity of ADARs. Proc. Natl. Acad. Sci. 109, E3295-E3304 (2012).

Tan, M. H. et al. Dynamic landscape and regulation of RNA editing in mammals. Nature 550, 249-254 (2017).

Varani, G., Cheong, C. & Tinoco, I. Structure of an Unusually Stable RNA Hairpint. Biochemistry 30, 3280-3289 (1991).

Tuerk, C. et al. CUUCGG hairpins: Extraordinarily stable RNA secondary structures associated with various biochemical processes (hairpin stability/sequence analysis/reverse transcriptase). Biochemistry 85, 1364-1368 (1988).

Fu, Y., Sander, J. D., Reyon, D., Cascio, V. M. & Joung, J. K. Improving CRISPR-Cas nuclease specificity using truncated guide RNAs. Nat. Biotechnol. 32, 279-84 (2014).

Adamala, K. P., Martin-Alarcon, D. A. & Boyden, E. S. Programmable RNA-binding protein composed of repeats of a single modular unit. Proc. Natl. Acad. Sci. 113, E2579-E2588 (2016).

East-Seletsky, A. et al. Two distinct RNase activities of CRISPR-C2c2 enable guide-RNA processing and RNA detection. Nature (2016). doi:10.1038/nature19802

Abudayyeh, O. O. et al. C2c2 is a single-component programmable RNA-guided RNA-targeting CRISPR effector. Science 353, aaf5573 1-9 (2016).

O'Connell, M. R. et al. Programmable RNA recognition and cleavage by CRISPR/Cas9. Nature 516, 263-266 (2014).

Abudayyeh, O. O. et al. RNA targeting with CRISPR-Cas13. Nature (2017). doi:10.1038/nature24049

Cox, D. B. T. et al. RNA editing with CRISPR-Cas13. Science eaaq0180 (2017). doi:10.1126/science.aaq0180

Gootenberg, J. S. et al. Nucleic acid detection with CRISPR-Cas13a/C2c2. Science (80-.). 356, 438-442 (2017).

East-Seletsky, A., O'Connell, M. R., Burstein, D., Knott, G. J. & Doudna, J. A. RNA Targeting by Functionally Orthogonal Type VI-A CRISPR-Cas Enzymes. Mol. Cell 66, 373-383.e3 (2017).

Grieger, J. C., Choi, V. W. & Samulski, R. J. Production and characterization of adeno-associated viral vectors. Nat. Protoc. 1, 1412-1428 (2006).

Analyzing CRISPR genome-editing experiments with CRISPResso. Nat. Biotechnol. 34, (2016).

What is claimed is:

1. A pharmaceutical composition in unit dose form comprising:

(a) a DNA vector encoding a guide RNA, wherein the guide RNA:

(i) comprises an antisense region that hybridizes to a target RNA, and (ii) has two recruiting domains or no recruiting domains, wherein the two recruiting domains are recognized by an adenosine deaminase acting on RNA (ADAR) enzyme, and (b) a pharmaceutically acceptable excipient, diluent, or carrier, wherein the pharmaceutical composition does not encode or contain an exogenously added ADAR enzyme, wherein an endogenous ADAR enzyme present in endogenous amounts in a cell, when contacted with the guide RNA and the target RNA, deaminates an adenosine in the target RNA, and wherein the guide RNA, by leveraging endogenous ADAR enzyme in endogenous amounts, results in reduced off-target editing relative to pharmaceutical compositions that encode or contain exogenously added ADAR enzyme.

2. The pharmaceutical composition of claim 1, wherein upon hybridization, the antisense region and the target RNA form a mismatch corresponding to a cytosine of the antisense region and the adenosine of the target RNA.

3. The pharmaceutical composition of claim 2, wherein the mismatch is centrally positioned with respect to the antisense region.

4. The pharmaceutical composition of claim 1, wherein the DNA vector is an AAV vector.

5. The pharmaceutical composition of claim 4, wherein the AAV vector is an AAV2 vector, an AAV5 vector, an AAV8 vector, or an AAV9 vector.

6. The pharmaceutical composition of claim 1, wherein the endogenous ADAR enzyme is an ADAR2 enzyme.

7. The pharmaceutical composition of claim 1, wherein the guide RNA does not comprise a chemical modification.

8. The pharmaceutical composition of claim 1, wherein the guide RNA has two recruiting domains.

9. The pharmaceutical composition of claim 1, wherein the recruiting domain comprises a sequence that has at least about 90% sequence identity to SEQ ID NO:180 or SEQ ID NO:181.

10. The pharmaceutical composition of claim 1, wherein the antisense region comprises a length of from about 50 nucleotides to about 150 nucleotides.

11. The pharmaceutical composition of claim 10, wherein the antisense region comprises a length of about 50 nucleotides.

12. The pharmaceutical composition of claim 10, wherein the antisense region comprises a length of about 100 nucleotides.

13. The pharmaceutical composition of claim 1, wherein the target RNA comprises a nonsense mutation or a missense mutation.

14. The pharmaceutical composition of claim 13, wherein the nonsense mutation or the missense mutation is implicated in a disease.

15. The pharmaceutical composition of claim 14, wherein the disease comprises muscular dystrophy.

16. The pharmaceutical composition of claim 1, wherein the pharmaceutically acceptable carrier comprises a phosphate buffer.

17. The pharmaceutical composition of claim 1, formulated for parenteral administration.

18. The pharmaceutical composition of claim 1, wherein the guide RNA has no recruiting domains.

* * * * *

SEQUENCE LISTING

<160> NUMBER OF SEQ ID NOS: 275

<210> SEQ ID NO 1
<211> LENGTH: 473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tcccggggtt tccgccattt tttggtactg agtcgcccag tctcagatag atccgacgcc     60
gccatctcta ggcccgcgcc ggccccctcg cacagacttg tgggagaagc tcggctactc    120
ccctgccccg gttaatttgc atataatatt tcctagtaac tatagaggct taatgtgcga    180
taaaagacag ataatctgtt ctttttaata ctagctacat tttacatgat aggcttggat    240
ttctataaga gatacaaata ctaaattatt attttaaaaa acagcacaaa aggaaactca    300
ccctaactgt aaagtaattg tgtgttttga gactataaat atcccttgga gaaaagcctt    360
gtttgggaaa cctgatcatg tagatcgaac ggactctaaa tccgttcagc cgggttagat    420
tcccggggtt tccgccattt tttcctagac ccagctttct tgtacaaagt tgg           473

<210> SEQ ID NO 2
<211> LENGTH: 473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
tcccggggtt tccgccattt tttggtactg agtcgcccag tctcagatag atccgacgcc     60
gccatctcta ggcccgcgcc ggccccctcg cacagacttg tgggagaagc tcggctactc    120
ccctgccccg gttaatttgc atataatatt tcctagtaac tatagaggct taatgtgcga    180
taaaagacag ataatctgtt ctttttaata ctagctacat tttacatgat aggcttggat    240
ttctataaga gatacaaata ctaaattatt attttaaaaa acagcacaaa aggaaactca    300
ccctaactgt aaagtaattg tgtgttttga gactataaat atcccttgga gaaaagcctt    360
gtttgggaaa cctgatcatg tagatcgaac ggactttaaa tccgttcagc cgggttagat    420
tcccggggtt tccgccattt tttcctagac ccagctttct tgtacaaagt tgg           473

<210> SEQ ID NO 3

<211> LENGTH: 473
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3

```
tcccggggtt tccgccattt tttggtactg agtcgcccag tctcagatag atccgacgcc     60
gccatctcta ggcccgcgcc ggccccctcg cacagacttg tgggagaagc tcggctactc    120
ccctgccccg gttaatttgc atataatatt tcctagtaac tatagaggct taatgtgcga    180
taaaagacag ataatctgtt ctttttaata ctagctacat tttacatgat aggcttggat    240
ttctataaga gatacaaata ctaaattatt attttaaaaa acagcacaaa aggaaactca    300
ccctaactgt aaagtaattg tgtgttttga gactataaat atcccttgga gaaaagcctt    360
gtttgggaaa cctgatcatg tagatcgaac ggacttcaaa tccgttcagc cgggttagat    420
tcccggggtt tccgccattt tttcctagac ccagctttct tgtacaaagt tgg           473
```

<210> SEQ ID NO 4
<211> LENGTH: 1449
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4

```
cagcctccgg actctagagg atcgaaccct taaggccacc atggataaga aacctttgaa     60
cactctcatt agtgcgacag ggctctggat gtcccgaacg gggactatac acaagataaa    120
acaccatgag gtctcaagga gcaaaatcta tatcgagatg gcatgcggcg accatcttgt    180
ggtaaataat agtaggtcct ccaggacggc aagagcactc cgacatcaca agtacagaaa    240
aacctgcaaa cggtgtaggg tatccgacga agacttgaac aaatttttga ctaaggccaa    300
cgaggatcaa acttctgtca aagtgaaagt ggtttctgct cctacccgaa ctaagaaggc    360
catgcccaag tccgtggcaa gggcacccaa gccactcgaa aatactgagg ccgctcaggc    420
ccaaccatcc ggtagtaagt tcagtccagc catacccgta agtacccaag aatctgtcag    480
tgtgccggcc tcagtttcca catctataag ttcaatttct acaggagcga cggcctccgc    540
cctcgtcaag ggtaacacaa acccgataac ttctatgagt gccccccgtac aggcatccgc    600
accagcactg acgaagtctc aaactgatag gctggaagtg ctcttgaatc cgaaggacga    660
gatatctctt aactccggta aacctttccg ggagctggaa agtgaacttc tcagccggcg    720
aaaaaaagac ctccagcaaa tttacgcaga ggaaagggag aactatctgg ggaagttgga    780
acgagagatc acccgattct ttgtcgatcg cggatttttg gagattaaaa gcccaattct    840
catccccctt gaatatatcg aacgaatggg aatcgacaat gatacggagt tgtccaagca    900
gattttccgc gtagacaaga acttttgtct tcgacccatg ctcgctccga acctctacaa    960
ttacttgaga aagttggaca gagcgctccc ggacccgatc aagatatttg agatcggtcc   1020
ttgttataga aaggagagtg atggaaaaga acacctcgaa gagttcacga tgctgaactt   1080
ctgccaaatg ggttctggct gcacacggga gaatctcgaa agcatcatta cagatttcct   1140
taaccatctg ggatagact ttaaaatagt gggtgacagc tgtatggtat acggagatac    1200
cttggacgta atgcacgggg atcttgagct ttcctccgcc gtggttggac ctataccgtt   1260
ggaccgggag tggggaatcg acaaaccgtg gataggcgcc ggtttcggcc ttgaaagact   1320
```

cctcaaagtc aagcatgatt tcaaaaacat aaaacgggct gctcgctccg aatcttatta 1380
caacggtata agtacgaacc tgtgataata gcttaagggt tcgatcccta ctggttagta 1440
atgagttta 1449

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
ggaaacctga tcatgtagat cgaatggact ctaaatccgt tcagccgggt tagattcccg 60
gggtttccgc ca 72

<210> SEQ ID NO 6
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
ggggggtgga tcgaatagat cacacggact ctaaattcgt gcaggcgggt gaaactcccg 60
tactccccgc ca 72

<210> SEQ ID NO 7
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
ggaaacctga tcatgtagat cgaatggact ttaaatccgt tcagccgggt tagattcccg 60
gggtttccgc ca 72

<210> SEQ ID NO 8
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
ggaaacctga tcatgtagat cgaatggact tcaaatccgt tcagccgggt tagattcccg 60
gggtttccgc ca 72

<210> SEQ ID NO 9
<211> LENGTH: 1260
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atggataaaa aaccattaga tgttttaata tctgcgaccg ggctctggat gtccaggact 60

```
ggcacgctcc acaaaatcaa gcaccatgag gtctcaagaa gtaaaatata cattgaaatg    120
gcgtgtggag accatcttgt tgtgaataat tccaggagtt gtagaacagc cagagcattc    180
agacatcata agtacagaaa aacctgcaaa cgatgtaggg tttcggacga ggatatcaat    240
aattttctca caagatcaac cgaaagcaaa aacagtgtga aagttagggt agtttctgct    300
ccaaaggtca aaaaagctat gccgaaatca gtttcaaggg ctccgaagcc tctggaaaat    360
tctgtttctg caaaggcatc aacgaacaca tccagatctg taccttcgcc tgcaaaatca    420
actccaaatt cgtctgttcc cgcatcggct cctgctcctt cacttacaag aagccagctt    480
gatagggttg aggctctctt aagtccagag gataaaattt ctctaaatat ggcaaagcct    540
ttcagggaac ttgagcctga acttgtgaca agaagaaaaa acgattttca gcggctctat    600
accaatgata gagaagacta cctcggtaaa ctcgaacgtg atattacgaa atttttcgta    660
gaccggggtt ttctggagat aaagtctcct atccttattc cggcggaata cgtggagaga    720
atgggtatta ataatgatac tgaactttca aaacagatct tccgggtgga taaaaatctc    780
tgcttgaggc caatgcttgc cccgactctt tacaactatc tgcgaaaact cgataggatt    840
ttaccaggcc caataaaaat tttcgaagtc ggaccttgtt accggaaaga gtctgacggc    900
aaagagcacc tggaagaatt tactatggtg aacttctgtc agatgggttc gggatgtact    960
cgggaaaatc ttgaagctct catcaaagag tttctggact atctggaaat cgacttcgaa   1020
atcgtaggag attcctgtat ggtctttggg gatactcttg atataatgca cggggacctg   1080
gagctttctt cggcagtcgt cgggccagtt tctcttgata gagaatgggg tattgacaaa   1140
ccatggatag gtgcaggttt tggtcttgaa cgcttgctca aggttatgca cggctttaaa   1200
aacattaaga gggcatcaag gtccgaatct tactataatg ggatttcaac caatctgtaa   1260
```

<210> SEQ ID NO 10
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 11
<211> LENGTH: 723

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
atggtgagca agggcgagga gctgttcacc ggggtggtgc ccatcctggt cgagctggac 60
ggcgacgtaa acggccacaa gttcagcgtg tccggcgagg gcgagggcga tgccacctag 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720
tga 723

<210> SEQ ID NO 12
<211> LENGTH: 723
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
atggtgagca agggcgagga gctgttcacc ggggtggtgc ccatcctggt cgagctggac 60
ggcgacgtaa acggccacaa gttcagcgtg tccggcgagg gcgagggcga tgccacctaa 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720
tga 723

<210> SEQ ID NO 13
<211> LENGTH: 723
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13

```
atggtgagca agggcgagga gctgttcacc ggggtggtgc ccatcctggt cgagctggac     60

ggcgacgtaa acggccacaa gttcagcgtg tccggcgagg gcgagggcga tgccacctga    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtaa    720

tga                                                                  723
```

<210> SEQ ID NO 14
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205
```

```
Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu


<210> SEQ ID NO 15
<211> LENGTH: 454
<212> TYPE: PRT
<213> ORGANISM: Methanosarcina mazei

<400> SEQUENCE: 15

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160
```

-continued

```
Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450
```

<210> SEQ ID NO 16
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16

```
ggaaacctga tcatgtagat cgaacggact ctaaatccgt tcagccgggt tagattcccg     60

gggtttccgc catttttt                                                   78
```

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
ggaaacctga tcatgtagat cgaacggact ttaaatccgt tcagccgggt tagattcccg 60
gggtttccgc catttttt 78

<210> SEQ ID NO 18
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
ggaaacctga tcatgtagat cgaacggact tcaaatccgt tcagccgggt tagattcccg 60
gggtttccgc catttttt 78

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tcccggggtt tccgccattt tttggtactg agtcgcccag tctcagat 48

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
caaacaaggc ttttctccaa gggatat 27

<210> SEQ ID NO 21
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
ccttggagaa aagccttgtt tgggaaacct gatcatgtag atcgaacgga ctctaaatcc 60
gttcagccgg g 71

<210> SEQ ID NO 22
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
ggaaacctga tcatgtagat cgaatggact ctaaatccgt tcagccgggt tagattcccg 60
gggtttccgc ca 72

<210> SEQ ID NO 23
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
ggaaacctga tcatgtagat cgaacggact ctaaatccgt tcagccgggt tagattcccg 60
gggtttccgc ca 72

<210> SEQ ID NO 24
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
ggccgcgtgg cctaatggat aaggcgtctg acttcagatc agaagattgc aggttcgagt 60
cctgccgcgg tcg 73

<210> SEQ ID NO 25
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gaccacgtgg cctaatggat aaggcgtctg acttcagatc agaagattga gggttcgaat 60
cccttcgtgg tta 73

<210> SEQ ID NO 26
<211> LENGTH: 82
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
gtagtcgtgg ccgagtggtt aaggcgatgg actctaaatc cattggggtt tccccgcgca 60
ggttcgaatc ctgccgacta cg 82

<210> SEQ ID NO 27
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gtcaggatgg ccgagtggtc taaggcgcca gactctagtt ctggtctcca atggaggcgt 60
gggttcgaat cccacttctg aca 83

<210> SEQ ID NO 28
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 28
ttgtggaaag gacgaaacac c 21

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
acaagaaagc tgggtctagg ctagcaaaaa a 31

<210> SEQ ID NO 30
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
ttgtggaaag gacgaaacac cggtcaggat ggccgagtgg tctaaggcgc cagactctag 60
ttctggtctc caatgg 76

<210> SEQ ID NO 31
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
ttgtggaaag gacgaaacac cggtcaggat ggccgagtgg tctaaggcgc cagactttag 60
ttctggtctc caatgg 76

<210> SEQ ID NO 32
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
ttgtggaaag gacgaaacac cggtcaggat ggccgagtgg tctaaggcgc cagacttcag 60
ttctggtctc caatgg 76

<210> SEQ ID NO 33
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
acaagaaagc tgggtctagg ctagcaaaaa atgtcagaag tgggattcga acccacgcct 60
ccattggaga ccagaac 77

<210> SEQ ID NO 34
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ttgtggaaag gacgaaacac cggtagtcgt ggccgagtgg ttaaggcgat ggactctaaa 60
tccattgggg tttcc 75

<210> SEQ ID NO 35
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
ttgtggaaag gacgaaacac cggtagtcgt ggccgagtgg ttaaggcgat ggactttaaa 60
tccattgggg tttcc 75

<210> SEQ ID NO 36
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
ttgtggaaag gacgaaacac cggtagtcgt ggccgagtgg ttaaggcgat ggacttcaaa 60
tccattgggg tttcc 75

<210> SEQ ID NO 37
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
acaagaaagc tgggtctagg ctagcaaaaa acgtagtcgg caggattcga acctgcgcgg 60
ggaaacccca atggatt 77

<210> SEQ ID NO 38
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
ttgtggaaag gacgaaacac cggaccacgt ggcctaatgg ataaggcgtc tgacttcaga 60
tcagaagatt gagggtt 77

<210> SEQ ID NO 39
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
ttgtggaaag gacgaaacac cggaccacgt ggcctaatgg ataaggcgtc tgactttaga 60
tcagaagatt gagggtt 77

<210> SEQ ID NO 40
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
ttgtggaaag gacgaaacac cggaccacgt ggcctaatgg ataaggcgtc tgacttcaga 60
tcagaagatt gagggtt 77

<210> SEQ ID NO 41
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
acaagaaagc tgggtctagg ctagcaaaaa ataaccacga agggattcga accctcaatc 60
ttctgatc 68

<210> SEQ ID NO 42
<211> LENGTH: 429
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
gtactgagtc gcccagtctc agatagatcc gacgccgcca tctctaggcc cgcgccggcc 60
ccctcgcaca gacttgtggg agaagctcgg ctactcccct gccccggtta atttgcatat 120
aatatttcct agtaactata gaggcttaat gtgcgataaa agacagataa tctgttcttt 180
ttaatactag ctacatttta catgataggc ttggatttct ataagagata caaatactaa 240
attattattt taaaaaacag cacaaaagga aactcaccct aactgtaaag taattgtgtg 300
ttttgagact ataaatatcc cttggagaaa agccttgttt ggtagtcgtg gccgagtggt 360
taaggcgatg gactttaaat ccattggggt ttccccgcgc aggttcgaat cctgccgact 420
acgttttt 429

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
aatcctgccg actacgtttt ttgtactgag tcgcccagtc t 41

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
tttgaaagag caataaaat 19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
ctttgaaaga gcaatagaa 19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
tttgaaagag caataaaat 19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
ataaaatggc ttcaactat 19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
aatagaatgg cttcaacta 19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
aataaaatgg cttcaacta 19

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
tcacagacac cgctcagttt gt 22

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
atgccacctg gggcaa 16

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
tgccacctgg ggcaag 16

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
gccacctggg gcaagc 16

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
gatgccacct ggggcaag 18

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
gcgatgccac ctggggcaag 20

<210> SEQ ID NO 56
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
gggtggaata gtataacaat atgctaaatg ttgttatagt atcccacct 49

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
gtggaatagt ataacaatat gctaaatgtt gttatagtat cccac 45

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
gggccctctt cagggccctc taga 24

<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
atcgccctga aaag 14

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
gccacctggg g 11

<210> SEQ ID NO 61
<211> LENGTH: 82
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (34)..(36)

<223> OTHER INFORMATION: a, c, t, g, unknown or other

<400> SEQUENCE: 61
gtagtcgtgg ccgagtggtt aaggcgatgg actnnnaatc cattggggtt tccccgcgca 60
ggttcgaatc ctgccgacta cg 82

<210> SEQ ID NO 62
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (35)..(37)
<223> OTHER INFORMATION: a, c, t, g, unknown or other

<400> SEQUENCE: 62
gtcaggatgg ccgagtggtc taaggcgcca gactnnngtt ctggtctcca atggaggcgt 60
gggttcgaat cccacttctg aca 83

<210> SEQ ID NO 63
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (34)..(36)
<223> OTHER INFORMATION: a, c, t, g, unknown or other

<400> SEQUENCE: 63
gaccacgtgg cctaatggat aaggcgtctg actnnngatc agaagattga gggttcgaat 60
cccttcgtgg tta 73

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gtgttactga atatgaaata atggagga 28

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
atttctggca tatttctgaa ggtg 24

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ctctctgtac cttatcttag tgttactga 29

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
ctcttcaaat tctgacagat atttctggc 29

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
acccttcctt tcttaccaca ca 22

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
cagggtgtcc agatctgatt gtt 23

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
cttctctttt aaactaaccc atcagagtt 29

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
tgtctgtggc gagccaaaca 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72 acttttctcgt taccttaccg 20

<210> SEQ ID NO 73
<211> LENGTH: 585
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (584)..(585)
<223> OTHER INFORMATION: May or may not be present

<400> SEQUENCE: 73

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Lys Ala Glu
    130                 135                 140

Arg Met Gly Phe Thr Glu Val Thr Pro Val Thr Gly Ala Ser Leu Arg
145                 150                 155                 160

Arg Thr Met Leu Leu Leu Ser Arg Ser Pro Glu Ala Gln Pro Lys Thr
                165                 170                 175

Leu Pro Leu Thr Gly Ser Thr Phe His Asp Gln Ile Ala Met Leu Ser
            180                 185                 190

His Arg Cys Phe Asn Thr Leu Thr Asn Ser Phe Gln Pro Ser Leu Leu
        195                 200                 205

Gly Arg Lys Ile Leu Ala Ala Ile Ile Met Lys Lys Asp Ser Glu Asp
    210                 215                 220

Met Gly Val Val Val Ser Leu Gly Thr Gly Asn Arg Cys Val Lys Gly
225                 230                 235                 240

Asp Ser Leu Ser Leu Lys Gly Glu Thr Val Asn Asp Cys His Ala Glu
                245                 250                 255

Ile Ile Ser Arg Arg Gly Phe Ile Arg Phe Leu Tyr Ser Glu Leu Met
            260                 265                 270

Lys Tyr Asn Ser Gln Thr Ala Lys Asp Ser Ile Phe Glu Pro Ala Lys
        275                 280                 285

Gly Gly Glu Lys Leu Gln Ile Lys Lys Thr Val Ser Phe His Leu Tyr
    290                 295                 300

Ile Ser Thr Ala Pro Cys Gly Asp Gly Ala Leu Phe Asp Lys Ser Cys
305                 310                 315                 320
```

Ser Asp Arg Ala Met Glu Ser Thr Glu Ser Arg His Tyr Pro Val Phe
325 330 335

Glu Asn Pro Lys Gln Gly Lys Leu Arg Thr Lys Val Glu Asn Gly Glu
340 345 350

Gly Thr Ile Pro Val Glu Ser Ser Asp Ile Val Pro Thr Trp Asp Gly
355 360 365

Ile Arg Leu Gly Glu Arg Leu Arg Thr Met Ser Cys Ser Asp Lys Ile
370 375 380

Leu Arg Trp Asn Val Leu Gly Leu Gln Gly Ala Leu Leu Thr His Phe
385 390 395 400

Leu Gln Pro Ile Tyr Leu Lys Ser Val Thr Leu Gly Tyr Leu Phe Ser
405 410 415

Gln Gly His Leu Thr Arg Ala Ile Cys Cys Arg Val Thr Arg Asp Gly
420 425 430

Ser Ala Phe Glu Asp Gly Leu Arg His Pro Phe Ile Val Asn His Pro
435 440 445

Lys Val Gly Arg Val Ser Ile Tyr Asp Ser Lys Arg Gln Ser Gly Lys
450 455 460

Thr Lys Glu Thr Ser Val Asn Trp Cys Leu Ala Asp Gly Tyr Asp Leu
465 470 475 480

Glu Ile Leu Asp Gly Thr Arg Gly Thr Val Asp Gly Pro Arg Asn Glu
485 490 495

Leu Ser Arg Val Ser Lys Lys Asn Ile Phe Leu Leu Phe Lys Lys Leu
500 505 510

Cys Ser Phe Arg Tyr Arg Arg Asp Leu Leu Arg Leu Ser Tyr Gly Glu
515 520 525

Ala Lys Lys Ala Ala Arg Asp Tyr Glu Thr Ala Lys Asn Tyr Phe Lys
530 535 540

Lys Gly Leu Lys Asp Met Gly Tyr Gly Asn Trp Ile Ser Lys Pro Gln
545 550 555 560

Glu Glu Lys Asn Phe Tyr Leu Cys Pro Val Gly Ser Gly Ser Gly Ser
565 570 575

Gly Pro Lys Lys Arg Lys Val Ala Ala
580 585

<210> SEQ ID NO 74
<211> LENGTH: 560
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (560)..(560)
<223> OTHER INFORMATION: May or may not be present

<400> SEQUENCE: 74

Met Gly Pro Lys Lys Lys Arg Lys Val Ala Ala Gly Ser Gly Ser Gly
1 5 10 15

Ser Met Ala Ser Asn Phe Thr Gln Phe Val Leu Val Asp Asn Gly Gly
20 25 30

Thr Gly Asp Val Thr Val Ala Pro Ser Asn Phe Ala Asn Gly Val Ala
35 40 45

Glu Trp Ile Ser Ser Asn Ser Arg Ser Gln Ala Tyr Lys Val Thr Cys
50 55 60

-continued

```
Ser Val Arg Gln Ser Ser Ala Gln Lys Arg Lys Tyr Thr Ile Lys Val
65                  70                  75                  80

Glu Val Pro Lys Val Ala Thr Gln Thr Val Gly Gly Val Glu Leu Pro
                85                  90                  95

Val Ala Ala Trp Arg Ser Tyr Leu Asn Met Glu Leu Thr Ile Pro Ile
            100                 105                 110

Phe Ala Thr Asn Ser Asp Cys Glu Leu Ile Val Lys Ala Met Gln Gly
        115                 120                 125

Leu Leu Lys Asp Gly Asn Pro Ile Pro Ser Ala Ile Ala Ala Asn Ser
    130                 135                 140

Gly Ile Tyr Gly Gly Ser Gly Gly Ser Gly Gly Ser Met Leu His Leu
145                 150                 155                 160

Asp Gln Thr Pro Ser Arg Gln Pro Ile Pro Ser Glu Gly Leu Gln Leu
                165                 170                 175

His Leu Pro Gln Val Leu Ala Asp Ala Val Ser Arg Leu Val Leu Gly
            180                 185                 190

Lys Phe Gly Asp Leu Thr Asp Asn Phe Ser Ser Pro His Ala Arg Arg
        195                 200                 205

Lys Val Leu Ala Gly Val Val Met Thr Thr Gly Thr Asp Val Lys Asp
    210                 215                 220

Ala Lys Val Ile Ser Val Ser Thr Gly Thr Lys Cys Ile Asn Gly Glu
225                 230                 235                 240

Tyr Met Ser Asp Arg Gly Leu Ala Leu Asn Asp Cys His Ala Glu Ile
                245                 250                 255

Ile Ser Arg Arg Ser Leu Leu Arg Phe Leu Tyr Thr Gln Leu Glu Leu
            260                 265                 270

Tyr Leu Asn Asn Lys Asp Asp Gln Lys Arg Ser Ile Phe Gln Lys Ser
        275                 280                 285

Glu Arg Gly Gly Phe Arg Leu Lys Glu Asn Val Gln Phe His Leu Tyr
    290                 295                 300

Ile Ser Thr Ser Pro Cys Gly Asp Ala Arg Ile Phe Ser Pro His Glu
305                 310                 315                 320

Pro Ile Leu Glu Glu Pro Ala Asp Arg His Pro Asn Arg Lys Ala Arg
                325                 330                 335

Gly Gln Leu Arg Thr Lys Ile Glu Ser Gly Glu Gly Thr Ile Pro Val
            340                 345                 350

Arg Ser Asn Ala Ser Ile Gln Thr Trp Asp Gly Val Leu Gln Gly Glu
        355                 360                 365

Arg Leu Leu Thr Met Ser Cys Ser Asp Lys Ile Ala Arg Trp Asn Val
    370                 375                 380

Val Gly Ile Gln Gly Ser Leu Leu Ser Ile Phe Val Glu Pro Ile Tyr
385                 390                 395                 400

Phe Ser Ser Ile Ile Leu Gly Ser Leu Tyr His Gly Asp His Leu Ser
                405                 410                 415

Arg Ala Met Tyr Gln Arg Ile Ser Asn Ile Glu Asp Leu Pro Pro Leu
            420                 425                 430

Tyr Thr Leu Asn Lys Pro Leu Leu Ser Gly Ile Ser Asn Ala Glu Ala
        435                 440                 445

Arg Gln Pro Gly Lys Ala Pro Asn Phe Ser Val Asn Trp Thr Val Gly
    450                 455                 460

Asp Ser Ala Ile Glu Val Ile Asn Ala Thr Thr Gly Lys Asp Glu Leu
465                 470                 475                 480

Gly Arg Ala Ser Arg Leu Cys Lys His Ala Leu Tyr Cys Arg Trp Met
```

```
                485                 490                 495

Arg Val His Gly Lys Val Pro Ser His Leu Leu Arg Ser Lys Ile Thr
            500                 505                 510

Lys Pro Asn Val Tyr His Glu Ser Lys Leu Ala Ala Lys Glu Tyr Gln
        515                 520                 525

Ala Ala Lys Ala Arg Leu Phe Thr Ala Phe Ile Lys Ala Gly Leu Gly
    530                 535                 540

Ala Trp Val Glu Lys Pro Thr Glu Gln Asp Gln Phe Ser Leu Thr Pro
545                 550                 555                 560


<210> SEQ ID NO 75
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (491)..(492)
<223> OTHER INFORMATION: May or may not be present

<400> SEQUENCE: 75

Met Gly Asn Ala Arg Thr Arg Arg Arg Glu Arg Arg Ala Glu Lys Gln
1               5                   10                  15

Ala Gln Trp Lys Ala Ala Asn Gly Gly Gly Gly Thr Ser Gly Ser Gly
            20                  25                  30

Ser Gly Ser Pro Ala Gly Gly Gly Ala Pro Gly Ser Gly Gly Gly Ser
        35                  40                  45

Lys Ala Glu Arg Met Gly Phe Thr Glu Val Thr Pro Val Thr Gly Ala
    50                  55                  60

Ser Leu Arg Arg Thr Met Leu Leu Leu Ser Arg Ser Pro Glu Ala Gln
65                  70                  75                  80

Pro Lys Thr Leu Pro Leu Thr Gly Ser Thr Phe His Asp Gln Ile Ala
                85                  90                  95

Met Leu Ser His Arg Cys Phe Asn Thr Leu Thr Asn Ser Phe Gln Pro
            100                 105                 110

Ser Leu Leu Gly Arg Lys Ile Leu Ala Ala Ile Ile Met Lys Lys Asp
        115                 120                 125

Ser Glu Asp Met Gly Val Val Val Ser Leu Gly Thr Gly Asn Arg Cys
    130                 135                 140

Val Lys Gly Asp Ser Leu Ser Leu Lys Gly Glu Thr Val Asn Asp Cys
145                 150                 155                 160

His Ala Glu Ile Ile Ser Arg Arg Gly Phe Ile Arg Phe Leu Tyr Ser
                165                 170                 175

Glu Leu Met Lys Tyr Asn Ser Gln Thr Ala Lys Asp Ser Ile Phe Glu
            180                 185                 190

Pro Ala Lys Gly Gly Glu Lys Leu Gln Ile Lys Lys Thr Val Ser Phe
        195                 200                 205

His Leu Tyr Ile Ser Thr Ala Pro Cys Gly Asp Gly Ala Leu Phe Asp
    210                 215                 220

Lys Ser Cys Ser Asp Arg Ala Met Glu Ser Thr Glu Ser Arg His Tyr
225                 230                 235                 240

Pro Val Phe Glu Asn Pro Lys Gln Gly Lys Leu Arg Thr Lys Val Glu
                245                 250                 255

Asn Gly Glu Gly Thr Ile Pro Val Glu Ser Ser Asp Ile Val Pro Thr
            260                 265                 270
```

Trp Asp Gly Ile Arg Leu Gly Glu Arg Leu Arg Thr Met Ser Cys Ser
275 280 285

Asp Lys Ile Leu Arg Trp Asn Val Leu Gly Leu Gln Gly Ala Leu Leu
290 295 300

Thr His Phe Leu Gln Pro Ile Tyr Leu Lys Ser Val Thr Leu Gly Tyr
305 310 315 320

Leu Phe Ser Gln Gly His Leu Thr Arg Ala Ile Cys Cys Arg Val Thr
325 330 335

Arg Asp Gly Ser Ala Phe Glu Asp Gly Leu Arg His Pro Phe Ile Val
340 345 350

Asn His Pro Lys Val Gly Arg Val Ser Ile Tyr Asp Ser Lys Arg Gln
355 360 365

Ser Gly Lys Thr Lys Glu Thr Ser Val Asn Trp Cys Leu Ala Asp Gly
370 375 380

Tyr Asp Leu Glu Ile Leu Asp Gly Thr Arg Gly Thr Val Asp Gly Pro
385 390 395 400

Arg Asn Glu Leu Ser Arg Val Ser Lys Lys Asn Ile Phe Leu Leu Phe
405 410 415

Lys Lys Leu Cys Ser Phe Arg Tyr Arg Arg Asp Leu Leu Arg Leu Ser
420 425 430

Tyr Gly Glu Ala Lys Lys Ala Ala Arg Asp Tyr Glu Thr Ala Lys Asn
435 440 445

Tyr Phe Lys Lys Gly Leu Lys Asp Met Gly Tyr Gly Asn Trp Ile Ser
450 455 460

Lys Pro Gln Glu Glu Lys Asn Phe Tyr Leu Cys Pro Val Gly Ser Gly
465 470 475 480

Ser Gly Ser Gly Pro Lys Lys Arg Lys Val Ala Ala
485 490

<210> SEQ ID NO 76
<211> LENGTH: 469
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MISC_FEATURE
<222> LOCATION: (469)..(469)
<223> OTHER INFORMATION: May or may not be present

<400> SEQUENCE: 76

Met Gly Pro Lys Lys Lys Arg Lys Val Ala Ala Gly Ser Gly Ser Gly
1 5 10 15

Ser Met Gly Asn Ala Arg Thr Arg Arg Arg Glu Arg Arg Ala Glu Lys
20 25 30

Gln Ala Gln Trp Lys Ala Ala Asn Gly Gly Gly Gly Thr Ser Gly Ser
35 40 45

Gly Ser Gly Ser Pro Ala Gly Gly Gly Ala Pro Gly Ser Gly Gly Gly
50 55 60

Ser Met Leu His Leu Asp Gln Thr Pro Ser Arg Gln Pro Ile Pro Ser
65 70 75 80

Glu Gly Leu Gln Leu His Leu Pro Gln Val Leu Ala Asp Ala Val Ser
85 90 95

```
Arg Leu Val Leu Gly Lys Phe Gly Asp Leu Thr Asp Asn Phe Ser Ser
            100                 105                 110

Pro His Ala Arg Arg Lys Val Leu Ala Gly Val Val Met Thr Thr Gly
        115                 120                 125

Thr Asp Val Lys Asp Ala Lys Val Ile Ser Val Ser Thr Gly Thr Lys
    130                 135                 140

Cys Ile Asn Gly Glu Tyr Met Ser Asp Arg Gly Leu Ala Leu Asn Asp
145                 150                 155                 160

Cys His Ala Glu Ile Ile Ser Arg Arg Ser Leu Leu Arg Phe Leu Tyr
                165                 170                 175

Thr Gln Leu Glu Leu Tyr Leu Asn Asn Lys Asp Asp Gln Lys Arg Ser
            180                 185                 190

Ile Phe Gln Lys Ser Glu Arg Gly Gly Phe Arg Leu Lys Glu Asn Val
        195                 200                 205

Gln Phe His Leu Tyr Ile Ser Thr Ser Pro Cys Gly Asp Ala Arg Ile
    210                 215                 220

Phe Ser Pro His Glu Pro Ile Leu Glu Glu Pro Ala Asp Arg His Pro
225                 230                 235                 240

Asn Arg Lys Ala Arg Gly Gln Leu Arg Thr Lys Ile Glu Ser Gly Glu
                245                 250                 255

Gly Thr Ile Pro Val Arg Ser Asn Ala Ser Ile Gln Thr Trp Asp Gly
            260                 265                 270

Val Leu Gln Gly Glu Arg Leu Leu Thr Met Ser Cys Ser Asp Lys Ile
        275                 280                 285

Ala Arg Trp Asn Val Val Gly Ile Gln Gly Ser Leu Leu Ser Ile Phe
    290                 295                 300

Val Glu Pro Ile Tyr Phe Ser Ser Ile Ile Leu Gly Ser Leu Tyr His
305                 310                 315                 320

Gly Asp His Leu Ser Arg Ala Met Tyr Gln Arg Ile Ser Asn Ile Glu
                325                 330                 335

Asp Leu Pro Pro Leu Tyr Thr Leu Asn Lys Pro Leu Leu Ser Gly Ile
            340                 345                 350

Ser Asn Ala Glu Ala Arg Gln Pro Gly Lys Ala Pro Asn Phe Ser Val
        355                 360                 365

Asn Trp Thr Val Gly Asp Ser Ala Ile Glu Val Ile Asn Ala Thr Thr
    370                 375                 380

Gly Lys Asp Glu Leu Gly Arg Ala Ser Arg Leu Cys Lys His Ala Leu
385                 390                 395                 400

Tyr Cys Arg Trp Met Arg Val His Gly Lys Val Pro Ser His Leu Leu
                405                 410                 415

Arg Ser Lys Ile Thr Lys Pro Asn Val Tyr His Glu Ser Lys Leu Ala
            420                 425                 430

Ala Lys Glu Tyr Gln Ala Ala Lys Ala Arg Leu Phe Thr Ala Phe Ile
        435                 440                 445

Lys Ala Gly Leu Gly Ala Trp Val Glu Lys Pro Thr Glu Gln Asp Gln
    450                 455                 460

Phe Ser Leu Thr Pro
465
```

<210> SEQ ID NO 77
<211> LENGTH: 585
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MISC_FEATURE
<222> LOCATION: (584)..(585)
<223> OTHER INFORMATION: May or may not be present

<400> SEQUENCE: 77

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Lys Ala Glu
    130                 135                 140

Arg Met Gly Phe Thr Glu Val Thr Pro Val Thr Gly Ala Ser Leu Arg
145                 150                 155                 160

Arg Thr Met Leu Leu Leu Ser Arg Ser Pro Glu Ala Gln Pro Lys Thr
                165                 170                 175

Leu Pro Leu Thr Gly Ser Thr Phe His Asp Gln Ile Ala Met Leu Ser
            180                 185                 190

His Arg Cys Phe Asn Thr Leu Thr Asn Ser Phe Gln Pro Ser Leu Leu
        195                 200                 205

Gly Arg Lys Ile Leu Ala Ala Ile Ile Met Lys Lys Asp Ser Glu Asp
    210                 215                 220

Met Gly Val Val Val Ser Leu Gly Thr Gly Asn Arg Cys Val Lys Gly
225                 230                 235                 240

Asp Ser Leu Ser Leu Lys Gly Glu Thr Val Asn Asp Cys His Ala Glu
                245                 250                 255

Ile Ile Ser Arg Arg Gly Phe Ile Arg Phe Leu Tyr Ser Glu Leu Met
            260                 265                 270

Lys Tyr Asn Ser Gln Thr Ala Lys Asp Ser Ile Phe Glu Pro Ala Lys
        275                 280                 285

Gly Gly Glu Lys Leu Gln Ile Lys Lys Thr Val Ser Phe His Leu Tyr
    290                 295                 300

Ile Ser Thr Ala Pro Cys Gly Asp Gly Ala Leu Phe Asp Lys Ser Cys
305                 310                 315                 320

Ser Asp Arg Ala Met Glu Ser Thr Glu Ser Arg His Tyr Pro Val Phe
                325                 330                 335

Glu Asn Pro Lys Gln Gly Lys Leu Arg Thr Lys Val Glu Asn Gly Gln
            340                 345                 350

Gly Thr Ile Pro Val Glu Ser Ser Asp Ile Val Pro Thr Trp Asp Gly
        355                 360                 365

Ile Arg Leu Gly Glu Arg Leu Arg Thr Met Ser Cys Ser Asp Lys Ile
```

370 375 380

Leu Arg Trp Asn Val Leu Gly Leu Gln Gly Ala Leu Leu Thr His Phe
385 390 395 400

Leu Gln Pro Ile Tyr Leu Lys Ser Val Thr Leu Gly Tyr Leu Phe Ser
405 410 415

Gln Gly His Leu Thr Arg Ala Ile Cys Cys Arg Val Thr Arg Asp Gly
420 425 430

Ser Ala Phe Glu Asp Gly Leu Arg His Pro Phe Ile Val Asn His Pro
435 440 445

Lys Val Gly Arg Val Ser Ile Tyr Asp Ser Lys Arg Gln Ser Gly Lys
450 455 460

Thr Lys Glu Thr Ser Val Asn Trp Cys Leu Ala Asp Gly Tyr Asp Leu
465 470 475 480

Glu Ile Leu Asp Gly Thr Arg Gly Thr Val Asp Gly Pro Arg Asn Glu
485 490 495

Leu Ser Arg Val Ser Lys Lys Asn Ile Phe Leu Leu Phe Lys Lys Leu
500 505 510

Cys Ser Phe Arg Tyr Arg Arg Asp Leu Leu Arg Leu Ser Tyr Gly Glu
515 520 525

Ala Lys Lys Ala Ala Arg Asp Tyr Glu Thr Ala Lys Asn Tyr Phe Lys
530 535 540

Lys Gly Leu Lys Asp Met Gly Tyr Gly Asn Trp Ile Ser Lys Pro Gln
545 550 555 560

Glu Glu Lys Asn Phe Tyr Leu Cys Pro Val Gly Ser Gly Ser Gly Ser
565 570 575

Gly Pro Lys Lys Arg Lys Val Ala Ala
580 585

<210> SEQ ID NO 78
<211> LENGTH: 560
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MISC_FEATURE
<222> LOCATION: (560)..(560)
<223> OTHER INFORMATION: May or may not be present

<400> SEQUENCE: 78

Met Gly Pro Lys Lys Lys Arg Lys Val Ala Ala Gly Ser Gly Ser Gly
1 5 10 15

Ser Met Ala Ser Asn Phe Thr Gln Phe Val Leu Val Asp Asn Gly Gly
20 25 30

Thr Gly Asp Val Thr Val Ala Pro Ser Asn Phe Ala Asn Gly Val Ala
35 40 45

Glu Trp Ile Ser Ser Asn Ser Arg Ser Gln Ala Tyr Lys Val Thr Cys
50 55 60

Ser Val Arg Gln Ser Ser Ala Gln Lys Arg Lys Tyr Thr Ile Lys Val
65 70 75 80

Glu Val Pro Lys Val Ala Thr Gln Thr Val Gly Gly Val Glu Leu Pro
85 90 95

Val Ala Ala Trp Arg Ser Tyr Leu Asn Met Glu Leu Thr Ile Pro Ile

```
            100                 105                 110

Phe Ala Thr Asn Ser Asp Cys Glu Leu Ile Val Lys Ala Met Gln Gly
        115                 120                 125

Leu Leu Lys Asp Gly Asn Pro Ile Pro Ser Ala Ile Ala Ala Asn Ser
    130                 135                 140

Gly Ile Tyr Gly Gly Ser Gly Gly Ser Gly Gly Ser Met Leu His Leu
145                 150                 155                 160

Asp Gln Thr Pro Ser Arg Gln Pro Ile Pro Ser Glu Gly Leu Gln Leu
                165                 170                 175

His Leu Pro Gln Val Leu Ala Asp Ala Val Ser Arg Leu Val Leu Gly
            180                 185                 190

Lys Phe Gly Asp Leu Thr Asp Asn Phe Ser Ser Pro His Ala Arg Arg
        195                 200                 205

Lys Val Leu Ala Gly Val Val Met Thr Thr Gly Thr Asp Val Lys Asp
    210                 215                 220

Ala Lys Val Ile Ser Val Ser Thr Gly Thr Lys Cys Ile Asn Gly Glu
225                 230                 235                 240

Tyr Met Ser Asp Arg Gly Leu Ala Leu Asn Asp Cys His Ala Glu Ile
                245                 250                 255

Ile Ser Arg Arg Ser Leu Leu Arg Phe Leu Tyr Thr Gln Leu Glu Leu
            260                 265                 270

Tyr Leu Asn Asn Lys Asp Asp Gln Lys Arg Ser Ile Phe Gln Lys Ser
        275                 280                 285

Glu Arg Gly Gly Phe Arg Leu Lys Glu Asn Val Gln Phe His Leu Tyr
    290                 295                 300

Ile Ser Thr Ser Pro Cys Gly Asp Ala Arg Ile Phe Ser Pro His Glu
305                 310                 315                 320

Pro Ile Leu Glu Glu Pro Ala Asp Arg His Pro Asn Arg Lys Ala Arg
                325                 330                 335

Gly Gln Leu Arg Thr Lys Ile Glu Ser Gly Gln Gly Thr Ile Pro Val
            340                 345                 350

Arg Ser Asn Ala Ser Ile Gln Thr Trp Asp Gly Val Leu Gln Gly Glu
        355                 360                 365

Arg Leu Leu Thr Met Ser Cys Ser Asp Lys Ile Ala Arg Trp Asn Val
    370                 375                 380

Val Gly Ile Gln Gly Ser Leu Leu Ser Ile Phe Val Glu Pro Ile Tyr
385                 390                 395                 400

Phe Ser Ser Ile Ile Leu Gly Ser Leu Tyr His Gly Asp His Leu Ser
                405                 410                 415

Arg Ala Met Tyr Gln Arg Ile Ser Asn Ile Glu Asp Leu Pro Pro Leu
            420                 425                 430

Tyr Thr Leu Asn Lys Pro Leu Leu Ser Gly Ile Ser Asn Ala Glu Ala
        435                 440                 445

Arg Gln Pro Gly Lys Ala Pro Asn Phe Ser Val Asn Trp Thr Val Gly
    450                 455                 460

Asp Ser Ala Ile Glu Val Ile Asn Ala Thr Thr Gly Lys Asp Glu Leu
465                 470                 475                 480

Gly Arg Ala Ser Arg Leu Cys Lys His Ala Leu Tyr Cys Arg Trp Met
                485                 490                 495

Arg Val His Gly Lys Val Pro Ser His Leu Leu Arg Ser Lys Ile Thr
            500                 505                 510

Lys Pro Asn Val Tyr His Glu Ser Lys Leu Ala Ala Lys Glu Tyr Gln
        515                 520                 525
```

```
Ala Ala Lys Ala Arg Leu Phe Thr Ala Phe Ile Lys Ala Gly Leu Gly
    530                 535                 540

Ala Trp Val Glu Lys Pro Thr Glu Gln Asp Gln Phe Ser Leu Thr Pro
545                 550                 555                 560


<210> SEQ ID NO 79
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (491)..(492)
<223> OTHER INFORMATION: May or may not be present

<400> SEQUENCE: 79

Met Gly Asn Ala Arg Thr Arg Arg Arg Glu Arg Arg Ala Glu Lys Gln
1               5                   10                  15

Ala Gln Trp Lys Ala Ala Asn Gly Gly Gly Gly Thr Ser Gly Ser Gly
            20                  25                  30

Ser Gly Ser Pro Ala Gly Gly Gly Ala Pro Gly Ser Gly Gly Gly Ser
        35                  40                  45

Lys Ala Glu Arg Met Gly Phe Thr Glu Val Thr Pro Val Thr Gly Ala
    50                  55                  60

Ser Leu Arg Arg Thr Met Leu Leu Leu Ser Arg Ser Pro Glu Ala Gln
65                  70                  75                  80

Pro Lys Thr Leu Pro Leu Thr Gly Ser Thr Phe His Asp Gln Ile Ala
                85                  90                  95

Met Leu Ser His Arg Cys Phe Asn Thr Leu Thr Asn Ser Phe Gln Pro
            100                 105                 110

Ser Leu Leu Gly Arg Lys Ile Leu Ala Ala Ile Ile Met Lys Lys Asp
        115                 120                 125

Ser Glu Asp Met Gly Val Val Val Ser Leu Gly Thr Gly Asn Arg Cys
    130                 135                 140

Val Lys Gly Asp Ser Leu Ser Leu Lys Gly Glu Thr Val Asn Asp Cys
145                 150                 155                 160

His Ala Glu Ile Ile Ser Arg Arg Gly Phe Ile Arg Phe Leu Tyr Ser
                165                 170                 175

Glu Leu Met Lys Tyr Asn Ser Gln Thr Ala Lys Asp Ser Ile Phe Glu
            180                 185                 190

Pro Ala Lys Gly Gly Glu Lys Leu Gln Ile Lys Lys Thr Val Ser Phe
        195                 200                 205

His Leu Tyr Ile Ser Thr Ala Pro Cys Gly Asp Gly Ala Leu Phe Asp
    210                 215                 220

Lys Ser Cys Ser Asp Arg Ala Met Glu Ser Thr Glu Ser Arg His Tyr
225                 230                 235                 240

Pro Val Phe Glu Asn Pro Lys Gln Gly Lys Leu Arg Thr Lys Val Glu
                245                 250                 255

Asn Gly Gln Gly Thr Ile Pro Val Glu Ser Ser Asp Ile Val Pro Thr
            260                 265                 270

Trp Asp Gly Ile Arg Leu Gly Glu Arg Leu Arg Thr Met Ser Cys Ser
        275                 280                 285

Asp Lys Ile Leu Arg Trp Asn Val Leu Gly Leu Gln Gly Ala Leu Leu
    290                 295                 300
```

Thr His Phe Leu Gln Pro Ile Tyr Leu Lys Ser Val Thr Leu Gly Tyr
305 310 315 320

Leu Phe Ser Gln Gly His Leu Thr Arg Ala Ile Cys Cys Arg Val Thr
325 330 335

Arg Asp Gly Ser Ala Phe Glu Asp Gly Leu Arg His Pro Phe Ile Val
340 345 350

Asn His Pro Lys Val Gly Arg Val Ser Ile Tyr Asp Ser Lys Arg Gln
355 360 365

Ser Gly Lys Thr Lys Glu Thr Ser Val Asn Trp Cys Leu Ala Asp Gly
370 375 380

Tyr Asp Leu Glu Ile Leu Asp Gly Thr Arg Gly Thr Val Asp Gly Pro
385 390 395 400

Arg Asn Glu Leu Ser Arg Val Ser Lys Lys Asn Ile Phe Leu Leu Phe
405 410 415

Lys Lys Leu Cys Ser Phe Arg Tyr Arg Arg Asp Leu Leu Arg Leu Ser
420 425 430

Tyr Gly Glu Ala Lys Lys Ala Ala Arg Asp Tyr Glu Thr Ala Lys Asn
435 440 445

Tyr Phe Lys Lys Gly Leu Lys Asp Met Gly Tyr Gly Asn Trp Ile Ser
450 455 460

Lys Pro Gln Glu Glu Lys Asn Phe Tyr Leu Cys Pro Val Gly Ser Gly
465 470 475 480

Ser Gly Ser Gly Pro Lys Lys Arg Lys Val Ala Ala
485 490

<210> SEQ ID NO 80
<211> LENGTH: 469
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MISC_FEATURE
<222> LOCATION: (469)..(469)
<223> OTHER INFORMATION: May or may not be present

<400> SEQUENCE: 80

Met Gly Pro Lys Lys Lys Arg Lys Val Ala Ala Gly Ser Gly Ser Gly
1 5 10 15

Ser Met Gly Asn Ala Arg Thr Arg Arg Arg Glu Arg Arg Ala Glu Lys
20 25 30

Gln Ala Gln Trp Lys Ala Ala Asn Gly Gly Gly Gly Thr Ser Gly Ser
35 40 45

Gly Ser Gly Ser Pro Ala Gly Gly Gly Ala Pro Gly Ser Gly Gly Gly
50 55 60

Ser Met Leu His Leu Asp Gln Thr Pro Ser Arg Gln Pro Ile Pro Ser
65 70 75 80

Glu Gly Leu Gln Leu His Leu Pro Gln Val Leu Ala Asp Ala Val Ser
85 90 95

Arg Leu Val Leu Gly Lys Phe Gly Asp Leu Thr Asp Asn Phe Ser Ser
100 105 110

Pro His Ala Arg Arg Lys Val Leu Ala Gly Val Val Met Thr Thr Gly
115 120 125

-continued

```
Thr Asp Val Lys Asp Ala Lys Val Ile Ser Val Ser Thr Gly Thr Lys
    130                 135                 140

Cys Ile Asn Gly Glu Tyr Met Ser Asp Arg Gly Leu Ala Leu Asn Asp
145                 150                 155                 160

Cys His Ala Glu Ile Ile Ser Arg Arg Ser Leu Leu Arg Phe Leu Tyr
                165                 170                 175

Thr Gln Leu Glu Leu Tyr Leu Asn Asn Lys Asp Asp Gln Lys Arg Ser
            180                 185                 190

Ile Phe Gln Lys Ser Glu Arg Gly Gly Phe Arg Leu Lys Glu Asn Val
        195                 200                 205

Gln Phe His Leu Tyr Ile Ser Thr Ser Pro Cys Gly Asp Ala Arg Ile
    210                 215                 220

Phe Ser Pro His Glu Pro Ile Leu Glu Glu Pro Ala Asp Arg His Pro
225                 230                 235                 240

Asn Arg Lys Ala Arg Gly Gln Leu Arg Thr Lys Ile Glu Ser Gly Gln
                245                 250                 255

Gly Thr Ile Pro Val Arg Ser Asn Ala Ser Ile Gln Thr Trp Asp Gly
            260                 265                 270

Val Leu Gln Gly Glu Arg Leu Leu Thr Met Ser Cys Ser Asp Lys Ile
        275                 280                 285

Ala Arg Trp Asn Val Val Gly Ile Gln Gly Ser Leu Leu Ser Ile Phe
    290                 295                 300

Val Glu Pro Ile Tyr Phe Ser Ser Ile Ile Leu Gly Ser Leu Tyr His
305                 310                 315                 320

Gly Asp His Leu Ser Arg Ala Met Tyr Gln Arg Ile Ser Asn Ile Glu
                325                 330                 335

Asp Leu Pro Pro Leu Tyr Thr Leu Asn Lys Pro Leu Leu Ser Gly Ile
            340                 345                 350

Ser Asn Ala Glu Ala Arg Gln Pro Gly Lys Ala Pro Asn Phe Ser Val
        355                 360                 365

Asn Trp Thr Val Gly Asp Ser Ala Ile Glu Val Ile Asn Ala Thr Thr
    370                 375                 380

Gly Lys Asp Glu Leu Gly Arg Ala Ser Arg Leu Cys Lys His Ala Leu
385                 390                 395                 400

Tyr Cys Arg Trp Met Arg Val His Gly Lys Val Pro Ser His Leu Leu
                405                 410                 415

Arg Ser Lys Ile Thr Lys Pro Asn Val Tyr His Glu Ser Lys Leu Ala
            420                 425                 430

Ala Lys Glu Tyr Gln Ala Ala Lys Ala Arg Leu Phe Thr Ala Phe Ile
        435                 440                 445

Lys Ala Gly Leu Gly Ala Trp Val Glu Lys Pro Thr Glu Gln Asp Gln
    450                 455                 460

Phe Ser Leu Thr Pro
465
```

<210> SEQ ID NO 81
<211> LENGTH: 392
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MISC_FEATURE
<222> LOCATION: (1)..(2)
<223> OTHER INFORMATION: May or may not be present

<400> SEQUENCE: 81

```
Met Gly Pro Lys Lys Lys Arg Lys Val Ala Ala Gly Ser Gly Ser Gly
1               5                   10                  15

Ser Met Ala Ser Asn Phe Thr Gln Phe Val Leu Val Asp Asn Gly Gly
            20                  25                  30

Thr Gly Asp Val Thr Val Ala Pro Ser Asn Phe Ala Asn Gly Val Ala
        35                  40                  45

Glu Trp Ile Ser Ser Asn Ser Arg Ser Gln Ala Tyr Lys Val Thr Cys
    50                  55                  60

Ser Val Arg Gln Ser Ser Ala Gln Lys Arg Lys Tyr Thr Ile Lys Val
65                  70                  75                  80

Glu Val Pro Lys Val Ala Thr Gln Thr Val Gly Gly Val Glu Leu Pro
                85                  90                  95

Val Ala Ala Trp Arg Ser Tyr Leu Asn Met Glu Leu Thr Ile Pro Ile
            100                 105                 110

Phe Ala Thr Asn Ser Asp Cys Glu Leu Ile Val Lys Ala Met Gln Gly
        115                 120                 125

Leu Leu Lys Asp Gly Asn Pro Ile Pro Ser Ala Ile Ala Ala Asn Ser
    130                 135                 140

Gly Ile Tyr Gly Gly Ser Gly Gly Ser Gly Gly Ser Met Thr Ser Glu
145                 150                 155                 160

Lys Gly Pro Ser Thr Gly Asp Pro Thr Leu Arg Arg Arg Ile Glu Pro
                165                 170                 175

Trp Glu Phe Asp Val Phe Tyr Asp Pro Arg Glu Leu Arg Lys Glu Ala
            180                 185                 190

Cys Leu Leu Tyr Glu Ile Lys Trp Gly Met Ser Arg Lys Ile Trp Arg
        195                 200                 205

Ser Ser Gly Lys Asn Thr Thr Asn His Val Glu Val Asn Phe Ile Lys
    210                 215                 220

Lys Phe Thr Ser Glu Arg Asp Phe His Pro Ser Met Ser Cys Ser Ile
225                 230                 235                 240

Thr Trp Phe Leu Ser Trp Ser Pro Cys Trp Glu Cys Ser Gln Ala Ile
                245                 250                 255

Arg Glu Phe Leu Ser Arg His Pro Gly Val Thr Leu Val Ile Tyr Val
            260                 265                 270

Ala Arg Leu Phe Trp His Met Asp Gln Gln Asn Arg Gln Gly Leu Arg
        275                 280                 285

Asp Leu Val Asn Ser Gly Val Thr Ile Gln Ile Met Arg Ala Ser Glu
    290                 295                 300

Tyr Tyr His Cys Trp Arg Asn Phe Val Asn Tyr Pro Pro Gly Asp Glu
305                 310                 315                 320

Ala His Trp Pro Gln Tyr Pro Pro Leu Trp Met Met Leu Tyr Ala Leu
                325                 330                 335

Glu Leu His Cys Ile Ile Leu Ser Leu Pro Pro Cys Leu Lys Ile Ser
            340                 345                 350

Arg Arg Trp Gln Asn His Leu Thr Phe Phe Arg Leu His Leu Gln Asn
        355                 360                 365

Cys His Tyr Gln Thr Ile Pro Pro His Ile Leu Leu Ala Thr Gly Leu
    370                 375                 380

Ile His Pro Ser Val Ala Trp Arg
385                 390
```

<210> SEQ ID NO 82

```
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2)
<223> OTHER INFORMATION: May or may not be present

<400> SEQUENCE: 82

Met Gly Pro Lys Lys Lys Arg Lys Val Ala Ala Gly Ser Gly Ser Gly
1               5                   10                  15

Ser Met Ala Ser Asn Phe Thr Gln Phe Val Leu Val Asp Asn Gly Gly
            20                  25                  30

Thr Gly Asp Val Thr Val Ala Pro Ser Asn Phe Ala Asn Gly Val Ala
        35                  40                  45

Glu Trp Ile Ser Ser Asn Ser Arg Ser Gln Ala Tyr Lys Val Thr Cys
    50                  55                  60

Ser Val Arg Gln Ser Ser Ala Gln Lys Arg Lys Tyr Thr Ile Lys Val
65                  70                  75                  80

Glu Val Pro Lys Val Ala Thr Gln Thr Val Gly Gly Val Glu Leu Pro
                85                  90                  95

Val Ala Ala Trp Arg Ser Tyr Leu Asn Met Glu Leu Thr Ile Pro Ile
            100                 105                 110

Phe Ala Thr Asn Ser Asp Cys Glu Leu Ile Val Lys Ala Met Gln Gly
        115                 120                 125

Leu Leu Lys Asp Gly Asn Pro Ile Pro Ser Ala Ile Ala Ala Asn Ser
    130                 135                 140

Gly Ile Tyr Gly Gly Ser Gly Gly Ser Gly Gly Ser Met Ser Ser Glu
145                 150                 155                 160

Thr Gly Pro Val Ala Val Asp Pro Thr Leu Arg Arg Arg Ile Glu Pro
                165                 170                 175

His Glu Phe Glu Val Phe Phe Asp Pro Arg Glu Leu Arg Lys Glu Thr
            180                 185                 190

Cys Leu Leu Tyr Glu Ile Asn Trp Gly Gly Arg His Ser Ile Trp Arg
        195                 200                 205

His Thr Ser Gln Asn Thr Asn Lys His Val Glu Val Asn Phe Ile Glu
    210                 215                 220

Lys Phe Thr Thr Glu Arg Tyr Phe Cys Pro Asn Thr Arg Cys Ser Ile
225                 230                 235                 240

Thr Trp Phe Leu Ser Trp Ser Pro Cys Gly Glu Cys Ser Arg Ala Ile
                245                 250                 255

Thr Glu Phe Leu Ser Arg Tyr Pro His Val Thr Leu Phe Ile Tyr Ile
            260                 265                 270

Ala Arg Leu Tyr His His Ala Asp Pro Arg Asn Arg Gln Gly Leu Arg
        275                 280                 285

Asp Leu Ile Ser Ser Gly Val Thr Ile Gln Ile Met Thr Glu Gln Glu
    290                 295                 300

Ser Gly Tyr Cys Trp Arg Asn Phe Val Asn Tyr Ser Pro Ser Asn Glu
305                 310                 315                 320

Ala His Trp Pro Arg Tyr Pro His Leu Trp Val Arg Leu Tyr Val Leu
                325                 330                 335

Glu Leu Tyr Cys Ile Ile Leu Gly Leu Pro Pro Cys Leu Asn Ile Leu
            340                 345                 350
```

```
Arg Arg Lys Gln Pro Gln Leu Thr Phe Phe Thr Ile Ala Leu Gln Ser
        355                 360                 365

Cys His Tyr Gln Arg Leu Pro Pro His Ile Leu Trp Ala Thr Gly Leu
    370                 375                 380

Lys
385


<210> SEQ ID NO 83
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Asp Ile Glu Asp Glu Glu Asn Met Ser Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly Gly
        35                  40                  45

Pro Gly Arg Lys Arg Pro Leu Glu Glu Gly Ser Asn Gly His Ser Lys
    50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Gly Gly Ser Gly Gly Ser
    290                 295                 300

Gly Gly Ser Met Ser Ser Glu Thr Gly Pro Val Ala Val Asp Pro Thr
305                 310                 315                 320
```

Leu Arg Arg Arg Ile Glu Pro His Glu Phe Glu Val Phe Phe Asp Pro
325 330 335

Arg Glu Leu Arg Lys Glu Thr Cys Leu Leu Tyr Glu Ile Asn Trp Gly
340 345 350

Gly Arg His Ser Ile Trp Arg His Thr Ser Gln Asn Thr Asn Lys His
355 360 365

Val Glu Val Asn Phe Ile Glu Lys Phe Thr Thr Glu Arg Tyr Phe Cys
370 375 380

Pro Asn Thr Arg Cys Ser Ile Thr Trp Phe Leu Ser Trp Ser Pro Cys
385 390 395 400

Gly Glu Cys Ser Arg Ala Ile Thr Glu Phe Leu Ser Arg Tyr Pro His
405 410 415

Val Thr Leu Phe Ile Tyr Ile Ala Arg Leu Tyr His His Ala Asp Pro
420 425 430

Arg Asn Arg Gln Gly Leu Arg Asp Leu Ile Ser Ser Gly Val Thr Ile
435 440 445

Gln Ile Met Thr Glu Gln Glu Ser Gly Tyr Cys Trp Arg Asn Phe Val
450 455 460

Asn Tyr Ser Pro Ser Asn Glu Ala His Trp Pro Arg Tyr Pro His Leu
465 470 475 480

Trp Val Arg Leu Tyr Val Leu Glu Leu Tyr Cys Ile Ile Leu Gly Leu
485 490 495

Pro Pro Cys Leu Asn Ile Leu Arg Arg Lys Gln Pro Gln Leu Thr Phe
500 505 510

Phe Thr Ile Ala Leu Gln Ser Cys His Tyr Gln Arg Leu Pro Pro His
515 520 525

Ile Leu Trp Ala Thr Gly Leu Lys
530 535

<210> SEQ ID NO 84
<211> LENGTH: 543
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

Met Asp Ile Glu Asp Glu Glu Asn Met Ser Ser Ser Ser Thr Asp Val
1 5 10 15

Lys Glu Asn Arg Asn Leu Asp Asn Val Ser Pro Lys Asp Gly Ser Thr
20 25 30

Pro Gly Pro Gly Glu Gly Ser Gln Leu Ser Asn Gly Gly Gly Gly Gly
35 40 45

Pro Gly Arg Lys Arg Pro Leu Glu Glu Gly Ser Asn Gly His Ser Lys
50 55 60

Tyr Arg Leu Lys Lys Arg Arg Lys Thr Pro Gly Pro Val Leu Pro Lys
65 70 75 80

Asn Ala Leu Met Gln Leu Asn Glu Ile Lys Pro Gly Leu Gln Tyr Thr
85 90 95

Leu Leu Ser Gln Thr Gly Pro Val His Ala Pro Leu Phe Val Met Ser
100 105 110

Val Glu Val Asn Gly Gln Val Phe Glu Gly Ser Gly Pro Thr Lys Lys
115 120 125

Lys Ala Lys Leu His Ala Ala Glu Lys Ala Leu Arg Ser Phe Val Gln

```
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Gly Gly Ser Gly Gly Ser
    290                 295                 300

Gly Gly Ser Met Thr Ser Glu Lys Gly Pro Ser Thr Gly Asp Pro Thr
305                 310                 315                 320

Leu Arg Arg Arg Ile Glu Pro Trp Glu Phe Asp Val Phe Tyr Asp Pro
                325                 330                 335

Arg Glu Leu Arg Lys Glu Ala Cys Leu Leu Tyr Glu Ile Lys Trp Gly
            340                 345                 350

Met Ser Arg Lys Ile Trp Arg Ser Ser Gly Lys Asn Thr Thr Asn His
        355                 360                 365

Val Glu Val Asn Phe Ile Lys Lys Phe Thr Ser Glu Arg Asp Phe His
    370                 375                 380

Pro Ser Met Ser Cys Ser Ile Thr Trp Phe Leu Ser Trp Ser Pro Cys
385                 390                 395                 400

Trp Glu Cys Ser Gln Ala Ile Arg Glu Phe Leu Ser Arg His Pro Gly
                405                 410                 415

Val Thr Leu Val Ile Tyr Val Ala Arg Leu Phe Trp His Met Asp Gln
            420                 425                 430

Gln Asn Arg Gln Gly Leu Arg Asp Leu Val Asn Ser Gly Val Thr Ile
        435                 440                 445

Gln Ile Met Arg Ala Ser Glu Tyr Tyr His Cys Trp Arg Asn Phe Val
    450                 455                 460

Asn Tyr Pro Pro Gly Asp Glu Ala His Trp Pro Gln Tyr Pro Pro Leu
465                 470                 475                 480

Trp Met Met Leu Tyr Ala Leu Glu Leu His Cys Ile Ile Leu Ser Leu
                485                 490                 495

Pro Pro Cys Leu Lys Ile Ser Arg Arg Trp Gln Asn His Leu Thr Phe
            500                 505                 510

Phe Arg Leu His Leu Gln Asn Cys His Tyr Gln Thr Ile Pro Pro His
        515                 520                 525

Ile Leu Leu Ala Thr Gly Leu Ile His Pro Ser Val Ala Trp Arg
    530                 535                 540
```

<210> SEQ ID NO 85

<211> LENGTH: 585
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Lys Ala Glu
    130                 135                 140

Arg Met Gly Phe Thr Glu Val Thr Pro Val Thr Gly Ala Ser Leu Arg
145                 150                 155                 160

Arg Thr Met Leu Leu Leu Ser Arg Ser Pro Glu Ala Gln Pro Lys Thr
                165                 170                 175

Leu Pro Leu Thr Gly Ser Thr Phe His Asp Gln Ile Ala Met Leu Ser
            180                 185                 190

His Arg Cys Phe Asn Thr Leu Thr Asn Ser Phe Gln Pro Ser Leu Leu
        195                 200                 205

Gly Arg Lys Ile Leu Ala Ala Ile Ile Met Lys Lys Asp Ser Glu Asp
    210                 215                 220

Met Gly Val Val Val Ser Leu Gly Thr Gly Asn Arg Cys Val Lys Gly
225                 230                 235                 240

Asp Ser Leu Ser Leu Lys Gly Glu Thr Val Asn Asp Cys His Ala Glu
                245                 250                 255

Ile Ile Ser Arg Arg Gly Phe Ile Arg Phe Leu Tyr Ser Glu Leu Met
            260                 265                 270

Lys Tyr Asn Ser Gln Thr Ala Lys Asp Ser Ile Phe Glu Pro Ala Lys
        275                 280                 285

Gly Gly Glu Lys Leu Gln Ile Lys Lys Thr Val Ser Phe His Leu Tyr
    290                 295                 300

Ile Ser Thr Ala Pro Cys Gly Asp Gly Ala Leu Phe Asp Lys Ser Cys
305                 310                 315                 320

Ser Asp Arg Ala Met Glu Ser Thr Glu Ser Arg His Tyr Pro Val Phe
                325                 330                 335

Glu Asn Pro Lys Gln Gly Lys Leu Arg Thr Lys Val Glu Asn Gly Glu
            340                 345                 350

Gly Thr Ile Pro Val Glu Ser Ser Asp Ile Val Pro Thr Trp Asp Gly
        355                 360                 365

Ile Arg Leu Gly Glu Arg Leu Arg Thr Met Ser Cys Ser Asp Lys Ile

-continued

```
    370                 375                 380

Leu Arg Trp Asn Val Leu Gly Leu Gln Gly Ala Leu Leu Thr His Phe
385                 390                 395                 400

Leu Gln Pro Ile Tyr Leu Lys Ser Val Thr Leu Gly Tyr Leu Phe Ser
                405                 410                 415

Gln Gly His Leu Thr Arg Ala Ile Cys Cys Arg Val Thr Arg Asp Gly
            420                 425                 430

Ser Ala Phe Glu Asp Gly Leu Arg His Pro Phe Ile Val Asn His Pro
        435                 440                 445

Lys Val Gly Arg Val Ser Ile Tyr Asp Ser Lys Arg Gln Ser Gly Lys
    450                 455                 460

Thr Lys Glu Thr Ser Val Asn Trp Cys Leu Ala Asp Gly Tyr Asp Leu
465                 470                 475                 480

Glu Ile Leu Asp Gly Thr Arg Gly Thr Val Asp Gly Pro Arg Asn Glu
                485                 490                 495

Leu Ser Arg Val Ser Lys Lys Asn Ile Phe Leu Leu Phe Lys Lys Leu
            500                 505                 510

Cys Ser Phe Arg Tyr Arg Arg Asp Leu Leu Arg Leu Ser Tyr Gly Glu
        515                 520                 525

Ala Lys Lys Ala Ala Arg Asp Tyr Glu Thr Ala Lys Asn Tyr Phe Lys
    530                 535                 540

Lys Gly Leu Lys Asp Met Gly Tyr Gly Asn Trp Ile Ser Lys Pro Gln
545                 550                 555                 560

Glu Glu Lys Asn Phe Tyr Leu Cys Pro Val Gly Ser Gly Ser Gly Ser
                565                 570                 575

Leu Pro Pro Leu Glu Arg Leu Thr Leu
            580                 585


<210> SEQ ID NO 86
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Gln Leu His
    130                 135                 140
```

-continued

```
Leu Pro Gln Val Leu Ala Asp Ala Val Ser Arg Leu Val Leu Gly Lys
145                 150                 155                 160

Phe Gly Asp Leu Thr Asp Asn Phe Ser Ser Pro His Ala Arg Arg Lys
                165                 170                 175

Val Leu Ala Gly Val Val Met Thr Thr Gly Thr Asp Val Lys Asp Ala
            180                 185                 190

Lys Val Ile Ser Val Ser Thr Gly Thr Lys Cys Ile Asn Gly Glu Tyr
        195                 200                 205

Met Ser Asp Arg Gly Leu Ala Leu Asn Asp Cys His Ala Glu Ile Ile
    210                 215                 220

Ser Arg Arg Ser Leu Leu Arg Phe Leu Tyr Thr Gln Leu Glu Leu Tyr
225                 230                 235                 240

Leu Asn Asn Lys Asp Asp Gln Lys Arg Ser Ile Phe Gln Lys Ser Glu
                245                 250                 255

Arg Gly Gly Phe Arg Leu Lys Glu Asn Val Gln Phe His Leu Tyr Ile
            260                 265                 270

Ser Thr Ser Pro Cys Gly Asp Ala Arg Ile Phe Ser Pro His Glu Pro
        275                 280                 285

Ile Leu Glu Glu Pro Ala Asp Arg His Pro Asn Arg Lys Ala Arg Gly
    290                 295                 300

Gln Leu Arg Thr Lys Ile Glu Ser Gly Glu Gly Thr Ile Pro Val Arg
305                 310                 315                 320

Ser Asn Ala Ser Ile Gln Thr Trp Asp Gly Val Leu Gln Gly Glu Arg
                325                 330                 335

Leu Leu Thr Met Ser Cys Ser Asp Lys Ile Ala Arg Trp Asn Val Val
            340                 345                 350

Gly Ile Gln Gly Ser Leu Leu Ser Ile Phe Val Glu Pro Ile Tyr Phe
        355                 360                 365

Ser Ser Ile Ile Leu Gly Ser Leu Tyr His Gly Asp His Leu Ser Arg
    370                 375                 380

Ala Met Tyr Gln Arg Ile Ser Asn Ile Glu Asp Leu Pro Pro Leu Tyr
385                 390                 395                 400

Thr Leu Asn Lys Pro Leu Leu Ser Gly Ile Ser Asn Ala Glu Ala Arg
                405                 410                 415

Gln Pro Gly Lys Ala Pro Asn Phe Ser Val Asn Trp Thr Val Gly Asp
            420                 425                 430

Ser Ala Ile Glu Val Ile Asn Ala Thr Thr Gly Lys Asp Glu Leu Gly
        435                 440                 445

Arg Ala Ser Arg Leu Cys Lys His Ala Leu Tyr Cys Arg Trp Met Arg
    450                 455                 460

Val His Gly Lys Val Pro Ser His Leu Leu Arg Ser Lys Ile Thr Lys
465                 470                 475                 480

Pro Asn Val Tyr His Glu Ser Lys Leu Ala Ala Lys Glu Tyr Gln Ala
                485                 490                 495

Ala Lys Ala Arg Leu Phe Thr Ala Phe Ile Lys Ala Gly Leu Gly Ala
            500                 505                 510

Trp Val Glu Lys Pro Thr Glu Gln Asp Gln Phe Ser Leu Thr Gly Ser
        515                 520                 525

Gly Ser Gly Ser Pro Lys Lys Lys Arg Lys Val
    530                 535
```

<210> SEQ ID NO 87
<211> LENGTH: 541
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 87

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Gln Leu His
    130                 135                 140

Leu Pro Gln Val Leu Ala Asp Ala Val Ser Arg Leu Val Leu Gly Lys
145                 150                 155                 160

Phe Gly Asp Leu Thr Asp Asn Phe Ser Ser Pro His Ala Arg Arg Lys
                165                 170                 175

Val Leu Ala Gly Val Val Met Thr Thr Gly Thr Asp Val Lys Asp Ala
            180                 185                 190

Lys Val Ile Ser Val Ser Thr Gly Thr Lys Cys Ile Asn Gly Glu Tyr
        195                 200                 205

Met Ser Asp Arg Gly Leu Ala Leu Asn Asp Cys His Ala Glu Ile Ile
    210                 215                 220

Ser Arg Arg Ser Leu Leu Arg Phe Leu Tyr Thr Gln Leu Glu Leu Tyr
225                 230                 235                 240

Leu Asn Asn Lys Asp Asp Gln Lys Arg Ser Ile Phe Gln Lys Ser Glu
                245                 250                 255

Arg Gly Gly Phe Arg Leu Lys Glu Asn Val Gln Phe His Leu Tyr Ile
            260                 265                 270

Ser Thr Ser Pro Cys Gly Asp Ala Arg Ile Phe Ser Pro His Glu Pro
        275                 280                 285

Ile Leu Glu Glu Pro Ala Asp Arg His Pro Asn Arg Lys Ala Arg Gly
    290                 295                 300

Gln Leu Arg Thr Lys Ile Glu Ser Gly Glu Gly Thr Ile Pro Val Arg
305                 310                 315                 320

Ser Asn Ala Ser Ile Gln Thr Trp Asp Gly Val Leu Gln Gly Glu Arg
                325                 330                 335

Leu Leu Thr Met Ser Cys Ser Asp Lys Ile Ala Arg Trp Asn Val Val
            340                 345                 350

Gly Ile Gln Gly Ser Leu Leu Ser Ile Phe Val Glu Pro Ile Tyr Phe
        355                 360                 365

Ser Ser Ile Ile Leu Gly Ser Leu Tyr His Gly Asp His Leu Ser Arg
    370                 375                 380
```

```
Ala Met Tyr Gln Arg Ile Ser Asn Ile Glu Asp Leu Pro Pro Leu Tyr
385                 390                 395                 400

Thr Leu Asn Lys Pro Leu Leu Ser Gly Ile Ser Asn Ala Glu Ala Arg
                405                 410                 415

Gln Pro Gly Lys Ala Pro Asn Phe Ser Val Asn Trp Thr Val Gly Asp
            420                 425                 430

Ser Ala Ile Glu Val Ile Asn Ala Thr Thr Gly Lys Asp Glu Leu Gly
        435                 440                 445

Arg Ala Ser Arg Leu Cys Lys His Ala Leu Tyr Cys Arg Trp Met Arg
    450                 455                 460

Val His Gly Lys Val Pro Ser His Leu Leu Arg Ser Lys Ile Thr Lys
465                 470                 475                 480

Pro Asn Val Tyr His Glu Ser Lys Leu Ala Ala Lys Glu Tyr Gln Ala
                485                 490                 495

Ala Lys Ala Arg Leu Phe Thr Ala Phe Ile Lys Ala Gly Leu Gly Ala
            500                 505                 510

Trp Val Glu Lys Pro Thr Glu Gln Asp Gln Phe Ser Leu Thr Gly Ser
        515                 520                 525

Gly Ser Gly Ser Leu Pro Pro Leu Glu Arg Leu Thr Leu
    530                 535                 540


<210> SEQ ID NO 88
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Ser Gly Ser
    130                 135                 140

Glu Thr Pro Gly Thr Ser Glu Ser Ala Thr Pro Glu Ser Met Ser Ser
145                 150                 155                 160

Glu Thr Gly Pro Val Ala Val Asp Pro Thr Leu Arg Arg Arg Ile Glu
                165                 170                 175

Pro His Glu Phe Glu Val Phe Phe Asp Pro Arg Glu Leu Arg Lys Glu
            180                 185                 190

Thr Cys Leu Leu Tyr Glu Ile Asn Trp Gly Gly Arg His Ser Ile Trp
        195                 200                 205
```

```
Arg His Thr Ser Gln Asn Thr Asn Lys His Val Glu Val Asn Phe Ile
    210                 215                 220

Glu Lys Phe Thr Thr Glu Arg Tyr Phe Cys Pro Asn Thr Arg Cys Ser
225                 230                 235                 240

Ile Thr Trp Phe Leu Ser Trp Ser Pro Cys Gly Glu Cys Ser Arg Ala
                245                 250                 255

Ile Thr Glu Phe Leu Ser Arg Tyr Pro His Val Thr Leu Phe Ile Tyr
            260                 265                 270

Ile Ala Arg Leu Tyr His His Ala Asp Pro Arg Asn Arg Gln Gly Leu
        275                 280                 285

Arg Asp Leu Ile Ser Ser Gly Val Thr Ile Gln Ile Met Thr Glu Gln
    290                 295                 300

Glu Ser Gly Tyr Cys Trp Arg Asn Phe Val Asn Tyr Ser Pro Ser Asn
305                 310                 315                 320

Glu Ala His Trp Pro Arg Tyr Pro His Leu Trp Val Arg Leu Tyr Val
                325                 330                 335

Leu Glu Leu Tyr Cys Ile Ile Leu Gly Leu Pro Pro Cys Leu Asn Ile
            340                 345                 350

Leu Arg Arg Lys Gln Pro Gln Leu Thr Phe Phe Thr Ile Ala Leu Gln
        355                 360                 365

Ser Cys His Tyr Gln Arg Leu Pro Pro His Ile Leu Trp Ala Thr Gly
    370                 375                 380

Leu Lys Gly Ser Gly Ser Gly Ser Pro Lys Lys Lys Arg Lys Val
385                 390                 395


<210> SEQ ID NO 89
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Ser Gly Ser
    130                 135                 140

Glu Thr Pro Gly Thr Ser Glu Ser Ala Thr Pro Glu Ser Met Ser Ser
145                 150                 155                 160

Glu Thr Gly Pro Val Ala Val Asp Pro Thr Leu Arg Arg Arg Ile Glu
```

```
                165                 170                 175

Pro His Glu Phe Glu Val Phe Phe Asp Pro Arg Glu Leu Arg Lys Glu
            180                 185                 190

Thr Cys Leu Leu Tyr Glu Ile Asn Trp Gly Gly Arg His Ser Ile Trp
        195                 200                 205

Arg His Thr Ser Gln Asn Thr Asn Lys His Val Glu Val Asn Phe Ile
    210                 215                 220

Glu Lys Phe Thr Thr Glu Arg Tyr Phe Cys Pro Asn Thr Arg Cys Ser
225                 230                 235                 240

Ile Thr Trp Phe Leu Ser Trp Ser Pro Cys Gly Glu Cys Ser Arg Ala
                245                 250                 255

Ile Thr Glu Phe Leu Ser Arg Tyr Pro His Val Thr Leu Phe Ile Tyr
            260                 265                 270

Ile Ala Arg Leu Tyr His His Ala Asp Pro Arg Asn Arg Gln Gly Leu
        275                 280                 285

Arg Asp Leu Ile Ser Ser Gly Val Thr Ile Gln Ile Met Thr Glu Gln
    290                 295                 300

Glu Ser Gly Tyr Cys Trp Arg Asn Phe Val Asn Tyr Ser Pro Ser Asn
305                 310                 315                 320

Glu Ala His Trp Pro Arg Tyr Pro His Leu Trp Val Arg Leu Tyr Val
                325                 330                 335

Leu Glu Leu Tyr Cys Ile Ile Leu Gly Leu Pro Pro Cys Leu Asn Ile
            340                 345                 350

Leu Arg Arg Lys Gln Pro Gln Leu Thr Phe Phe Thr Ile Ala Leu Gln
        355                 360                 365

Ser Cys His Tyr Gln Arg Leu Pro Pro His Ile Leu Trp Ala Thr Gly
    370                 375                 380

Leu Lys Gly Ser Gly Ser Gly Ser Leu Pro Pro Leu Glu Arg Leu Thr
385                 390                 395                 400

Leu


<210> SEQ ID NO 90
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
```

```
        115                 120                 125

Pro Ala Gly Gly Gly Ala Pro Gly Ser Gly Gly Gly Ser Ser Gly Ser
    130                 135                 140

Glu Thr Pro Gly Thr Ser Glu Ser Ala Thr Pro Glu Ser Met Thr Ser
145                 150                 155                 160

Glu Lys Gly Pro Ser Thr Gly Asp Pro Thr Leu Arg Arg Arg Ile Glu
                165                 170                 175

Pro Trp Glu Phe Asp Val Phe Tyr Asp Pro Arg Glu Leu Arg Lys Glu
            180                 185                 190

Ala Cys Leu Leu Tyr Glu Ile Lys Trp Gly Met Ser Arg Lys Ile Trp
        195                 200                 205

Arg Ser Ser Gly Lys Asn Thr Thr Asn His Val Glu Val Asn Phe Ile
    210                 215                 220

Lys Lys Phe Thr Ser Glu Arg Asp Phe His Pro Ser Met Ser Cys Ser
225                 230                 235                 240

Ile Thr Trp Phe Leu Ser Trp Ser Pro Cys Trp Glu Cys Ser Gln Ala
                245                 250                 255

Ile Arg Glu Phe Leu Ser Arg His Pro Gly Val Thr Leu Val Ile Tyr
            260                 265                 270

Val Ala Arg Leu Phe Trp His Met Asp Gln Gln Asn Arg Gln Gly Leu
        275                 280                 285

Arg Asp Leu Val Asn Ser Gly Val Thr Ile Gln Ile Met Arg Ala Ser
    290                 295                 300

Glu Tyr Tyr His Cys Trp Arg Asn Phe Val Asn Tyr Pro Pro Gly Asp
305                 310                 315                 320

Glu Ala His Trp Pro Gln Tyr Pro Pro Leu Trp Met Met Leu Tyr Ala
                325                 330                 335

Leu Glu Leu His Cys Ile Ile Leu Ser Leu Pro Pro Cys Leu Lys Ile
            340                 345                 350

Ser Arg Arg Trp Gln Asn His Leu Thr Phe Phe Arg Leu His Leu Gln
        355                 360                 365

Asn Cys His Tyr Gln Thr Ile Pro Pro His Ile Leu Leu Ala Thr Gly
    370                 375                 380

Leu Ile His Pro Ser Val Ala Trp Arg Gly Ser Gly Ser Gly Ser Pro
385                 390                 395                 400

Lys Lys Lys Arg Lys Val
                405
```

<210> SEQ ID NO 91
<211> LENGTH: 408
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60
```

-continued

```
Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Ser Gly Ser Gly Ala Gly Ser Gly Ser
        115                 120                 125

Pro Ala Gly Gly Gly Ala Pro Gly Ser Gly Gly Gly Ser Ser Gly Ser
    130                 135                 140

Glu Thr Pro Gly Thr Ser Glu Ser Ala Thr Pro Glu Ser Met Thr Ser
145                 150                 155                 160

Glu Lys Gly Pro Ser Thr Gly Asp Pro Thr Leu Arg Arg Arg Ile Glu
                165                 170                 175

Pro Trp Glu Phe Asp Val Phe Tyr Asp Pro Arg Glu Leu Arg Lys Glu
            180                 185                 190

Ala Cys Leu Leu Tyr Glu Ile Lys Trp Gly Met Ser Arg Lys Ile Trp
        195                 200                 205

Arg Ser Ser Gly Lys Asn Thr Thr Asn His Val Glu Val Asn Phe Ile
    210                 215                 220

Lys Lys Phe Thr Ser Glu Arg Asp Phe His Pro Ser Met Ser Cys Ser
225                 230                 235                 240

Ile Thr Trp Phe Leu Ser Trp Ser Pro Cys Trp Glu Cys Ser Gln Ala
                245                 250                 255

Ile Arg Glu Phe Leu Ser Arg His Pro Gly Val Thr Leu Val Ile Tyr
            260                 265                 270

Val Ala Arg Leu Phe Trp His Met Asp Gln Gln Asn Arg Gln Gly Leu
        275                 280                 285

Arg Asp Leu Val Asn Ser Gly Val Thr Ile Gln Ile Met Arg Ala Ser
    290                 295                 300

Glu Tyr Tyr His Cys Trp Arg Asn Phe Val Asn Tyr Pro Pro Gly Asp
305                 310                 315                 320

Glu Ala His Trp Pro Gln Tyr Pro Pro Leu Trp Met Met Leu Tyr Ala
                325                 330                 335

Leu Glu Leu His Cys Ile Ile Leu Ser Leu Pro Pro Cys Leu Lys Ile
            340                 345                 350

Ser Arg Arg Trp Gln Asn His Leu Thr Phe Phe Arg Leu His Leu Gln
        355                 360                 365

Asn Cys His Tyr Gln Thr Ile Pro Pro His Ile Leu Leu Ala Thr Gly
    370                 375                 380

Leu Ile His Pro Ser Val Ala Trp Arg Gly Ser Gly Ser Gly Ser Leu
385                 390                 395                 400

Pro Pro Leu Glu Arg Leu Thr Leu
                405
```

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

```
Gly Gly Ser Gly Gly Ser Gly Gly Ser
1               5
```

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Ser Gly Ser Glu Thr Pro Gly Thr Ser Glu Ser Ala Thr Pro Glu Ser
1 5 10 15

<210> SEQ ID NO 94
<211> LENGTH: 569
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

Met Pro Lys Lys Lys Arg Lys Val Asp Pro Lys Lys Lys Arg Lys Val
1 5 10 15

Asp Pro Lys Lys Lys Arg Lys Val Gly Ser Tyr Pro Tyr Asp Val Pro
20 25 30

Asp Tyr Ala Gly Ser Asn Ala Arg Thr Arg Arg Arg Glu Arg Arg Ala
35 40 45

Glu Lys Gln Ala Gln Trp Lys Ala Ala Asn Gly Gly Gly Gly Ser Gly
50 55 60

Gly Gly Gly Ser Gly Gly Gly Gly Ser Asn Ala Arg Thr Arg Arg Arg
65 70 75 80

Glu Arg Arg Ala Glu Lys Gln Ala Gln Trp Lys Ala Ala Asn Gly Gly
85 90 95

Gly Gly Ser Gly Gly Gly Gly Ser Gly Gly Gly Gly Ser Asn Ala Arg
100 105 110

Thr Arg Arg Arg Glu Arg Arg Ala Glu Lys Gln Ala Gln Trp Lys Ala
115 120 125

Ala Asn Gly Gly Gly Gly Ser Gly Gly Gly Gly Ser Gly Gly Gly Gly
130 135 140

Ser Asn Ala Arg Thr Arg Arg Arg Glu Arg Arg Ala Glu Lys Gln Ala
145 150 155 160

Gln Trp Lys Ala Ala Asn Leu His Leu Asp Gln Thr Pro Ser Arg Gln
165 170 175

Pro Ile Pro Ser Glu Gly Leu Gln Leu His Leu Pro Gln Val Leu Ala
180 185 190

Asp Ala Val Ser Arg Leu Val Leu Gly Lys Phe Gly Asp Leu Thr Asp
195 200 205

Asn Phe Ser Ser Pro His Ala Arg Arg Lys Val Leu Ala Gly Val Val
210 215 220

Met Thr Thr Gly Thr Asp Val Lys Asp Ala Lys Val Ile Ser Val Ser
225 230 235 240

Thr Gly Thr Lys Cys Ile Asn Gly Glu Tyr Met Ser Asp Arg Gly Leu
245 250 255

Ala Leu Asn Asp Cys His Ala Glu Ile Ile Ser Arg Arg Ser Leu Leu
260 265 270

Arg Phe Leu Tyr Thr Gln Leu Glu Leu Tyr Leu Asn Asn Lys Asp Asp
275 280 285

```
Gln Lys Arg Ser Ile Phe Gln Lys Ser Glu Arg Gly Gly Phe Arg Leu
    290                 295                 300

Lys Glu Asn Val Gln Phe His Leu Tyr Ile Ser Thr Ser Pro Cys Gly
305                 310                 315                 320

Asp Ala Arg Ile Phe Ser Pro His Glu Pro Ile Leu Glu Glu Pro Ala
                325                 330                 335

Asp Arg His Pro Asn Arg Lys Ala Arg Gly Gln Leu Arg Thr Lys Ile
            340                 345                 350

Glu Ser Gly Glu Gly Thr Ile Pro Val Arg Ser Asn Ala Ser Ile Gln
        355                 360                 365

Thr Trp Asp Gly Val Leu Gln Gly Glu Arg Leu Leu Thr Met Ser Cys
    370                 375                 380

Ser Asp Lys Ile Ala Arg Trp Asn Val Val Gly Ile Gln Gly Ser Leu
385                 390                 395                 400

Leu Ser Ile Phe Val Glu Pro Ile Tyr Phe Ser Ser Ile Ile Leu Gly
                405                 410                 415

Ser Leu Tyr His Gly Asp His Leu Ser Arg Ala Met Tyr Gln Arg Ile
            420                 425                 430

Ser Asn Ile Glu Asp Leu Pro Pro Leu Tyr Thr Leu Asn Lys Pro Leu
        435                 440                 445

Leu Ser Gly Ile Ser Asn Ala Glu Ala Arg Gln Pro Gly Lys Ala Pro
    450                 455                 460

Asn Phe Ser Val Asn Trp Thr Val Gly Asp Ser Ala Ile Glu Val Ile
465                 470                 475                 480

Asn Ala Thr Thr Gly Lys Asp Glu Leu Gly Arg Ala Ser Arg Leu Cys
                485                 490                 495

Lys His Ala Leu Tyr Cys Arg Trp Met Arg Val His Gly Lys Val Pro
            500                 505                 510

Ser His Leu Leu Arg Ser Lys Ile Thr Lys Pro Asn Val Tyr His Glu
        515                 520                 525

Ser Lys Leu Ala Ala Lys Glu Tyr Gln Ala Ala Lys Ala Arg Leu Phe
    530                 535                 540

Thr Ala Phe Ile Lys Ala Gly Leu Gly Ala Trp Val Glu Lys Pro Thr
545                 550                 555                 560

Glu Gln Asp Gln Phe Ser Leu Thr Pro
                565


<210> SEQ ID NO 95
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Pro Lys Lys Lys Arg Lys Val Asp Gly Ser Gly Asn Ala Arg Thr
1               5                   10                  15

Arg Arg Arg Glu Arg Arg Ala Glu Lys Gln Ala Gln Trp Lys Ala Ala
            20                  25                  30

Asn Gly Gly Gly Gly Thr Ser Gly Ser Gly Ser Gly Ser Pro Ala Gly
        35                  40                  45

Gly Gly Ala Pro Gly Ser Gly Gly Gly Ser Met Thr Ser Glu Lys Gly
    50                  55                  60

Pro Ser Thr Gly Asp Pro Thr Leu Arg Arg Arg Ile Glu Pro Trp Glu
```

-continued

```
65                  70                  75                  80

Phe Asp Val Phe Tyr Asp Pro Arg Glu Leu Arg Lys Glu Ala Cys Leu
                85                  90                  95

Leu Tyr Glu Ile Lys Trp Gly Met Ser Arg Lys Ile Trp Arg Ser Ser
            100                 105                 110

Gly Lys Asn Thr Thr Asn His Val Glu Val Asn Phe Ile Lys Lys Phe
        115                 120                 125

Thr Ser Glu Arg Asp Phe His Pro Ser Met Ser Cys Ser Ile Thr Trp
    130                 135                 140

Phe Leu Ser Trp Ser Pro Cys Trp Glu Cys Ser Gln Ala Ile Arg Glu
145                 150                 155                 160

Phe Leu Ser Arg His Pro Gly Val Thr Leu Val Ile Tyr Val Ala Arg
                165                 170                 175

Leu Phe Trp His Met Asp Gln Gln Asn Arg Gln Gly Leu Arg Asp Leu
            180                 185                 190

Val Asn Ser Gly Val Thr Ile Gln Ile Met Arg Ala Ser Glu Tyr Tyr
        195                 200                 205

His Cys Trp Arg Asn Phe Val Asn Tyr Pro Pro Gly Asp Glu Ala His
    210                 215                 220

Trp Pro Gln Tyr Pro Pro Leu Trp Met Met Leu Tyr Ala Leu Glu Leu
225                 230                 235                 240

His Cys Ile Ile Leu Ser Leu Pro Pro Cys Leu Lys Ile Ser Arg Arg
                245                 250                 255

Trp Gln Asn His Leu Thr Phe Phe Arg Leu His Leu Gln Asn Cys His
            260                 265                 270

Tyr Gln Thr Ile Pro Pro His Ile Leu Leu Ala Thr Gly Leu Ile His
        275                 280                 285

Pro Ser Val Ala Trp Arg
    290


<210> SEQ ID NO 96
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Pro Lys Lys Lys Arg Lys Val Asp Pro Lys Lys Lys Arg Lys Val
1               5                   10                  15

Asp Pro Lys Lys Lys Arg Lys Val Gly Ser Tyr Pro Tyr Asp Val Pro
            20                  25                  30

Asp Tyr Ala Gly Ser Asn Ala Arg Thr Arg Arg Arg Glu Arg Arg Ala
        35                  40                  45

Glu Lys Gln Ala Gln Trp Lys Ala Ala Asn Gly Gly Gly Gly Ser Gly
    50                  55                  60

Gly Gly Gly Ser Gly Gly Gly Gly Ser Asn Ala Arg Thr Arg Arg Arg
65                  70                  75                  80

Glu Arg Arg Ala Glu Lys Gln Ala Gln Trp Lys Ala Ala Asn Gly Gly
                85                  90                  95

Gly Gly Ser Gly Gly Gly Gly Ser Gly Gly Gly Gly Ser Asn Ala Arg
            100                 105                 110

Thr Arg Arg Arg Glu Arg Arg Ala Glu Lys Gln Ala Gln Trp Lys Ala
        115                 120                 125
```

```
Ala Asn Gly Gly Gly Gly Ser Gly Gly Gly Gly Ser Gly Gly Gly Gly
    130                 135                 140

Ser Asn Ala Arg Thr Arg Arg Arg Glu Arg Arg Ala Glu Lys Gln Ala
145                 150                 155                 160

Gln Trp Lys Ala Ala Asn Met Thr Ser Glu Lys Gly Pro Ser Thr Gly
                165                 170                 175

Asp Pro Thr Leu Arg Arg Arg Ile Glu Pro Trp Glu Phe Asp Val Phe
            180                 185                 190

Tyr Asp Pro Arg Glu Leu Arg Lys Glu Ala Cys Leu Leu Tyr Glu Ile
        195                 200                 205

Lys Trp Gly Met Ser Arg Lys Ile Trp Arg Ser Ser Gly Lys Asn Thr
    210                 215                 220

Thr Asn His Val Glu Val Asn Phe Ile Lys Lys Phe Thr Ser Glu Arg
225                 230                 235                 240

Asp Phe His Pro Ser Met Ser Cys Ser Ile Thr Trp Phe Leu Ser Trp
                245                 250                 255

Ser Pro Cys Trp Glu Cys Ser Gln Ala Ile Arg Glu Phe Leu Ser Arg
            260                 265                 270

His Pro Gly Val Thr Leu Val Ile Tyr Val Ala Arg Leu Phe Trp His
        275                 280                 285

Met Asp Gln Gln Asn Arg Gln Gly Leu Arg Asp Leu Val Asn Ser Gly
    290                 295                 300

Val Thr Ile Gln Ile Met Arg Ala Ser Glu Tyr Tyr His Cys Trp Arg
305                 310                 315                 320

Asn Phe Val Asn Tyr Pro Pro Gly Asp Glu Ala His Trp Pro Gln Tyr
                325                 330                 335

Pro Pro Leu Trp Met Met Leu Tyr Ala Leu Glu Leu His Cys Ile Ile
            340                 345                 350

Leu Ser Leu Pro Pro Cys Leu Lys Ile Ser Arg Arg Trp Gln Asn His
        355                 360                 365

Leu Thr Phe Phe Arg Leu His Leu Gln Asn Cys His Tyr Gln Thr Ile
    370                 375                 380

Pro Pro His Ile Leu Leu Ala Thr Gly Leu Ile His Pro Ser Val Ala
385                 390                 395                 400

Trp Arg


<210> SEQ ID NO 97
<211> LENGTH: 564
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Leu Arg Ser Phe Val Gln Phe Pro Asn Ala Ser Glu Ala His Leu
1               5                   10                  15

Ala Met Gly Arg Thr Leu Ser Val Asn Thr Asp Phe Thr Ser Asp Gln
            20                  25                  30

Ala Asp Phe Pro Asp Thr Leu Phe Asn Gly Phe Glu Thr Pro Asp Lys
        35                  40                  45

Ala Glu Pro Pro Phe Tyr Val Gly Ser Asn Gly Asp Asp Ser Phe Ser
    50                  55                  60

Ser Ser Gly Asp Leu Ser Leu Ser Ala Ser Pro Val Pro Ala Ser Leu
65                  70                  75                  80
```

```
Ala Gln Pro Pro Leu Pro Val Leu Pro Pro Phe Pro Pro Pro Ser Gly
                85                  90                  95

Lys Asn Pro Val Met Ile Leu Asn Glu Leu Arg Pro Gly Leu Lys Tyr
            100                 105                 110

Asp Phe Leu Ser Glu Ser Gly Glu Ser His Ala Lys Ser Phe Val Met
        115                 120                 125

Ser Val Val Val Asp Gly Gln Phe Phe Glu Gly Ser Gly Arg Asn Lys
    130                 135                 140

Lys Leu Ala Lys Ala Arg Ala Ala Gln Ser Ala Leu Ala Ala Ile Phe
145                 150                 155                 160

Asn Leu His Leu Asp Gln Thr Pro Ser Arg Gln Pro Ile Pro Ser Glu
                165                 170                 175

Gly Leu Gln Leu His Leu Pro Gln Val Leu Ala Asp Ala Val Ser Arg
            180                 185                 190

Leu Val Leu Gly Lys Phe Gly Asp Leu Thr Asp Asn Phe Ser Ser Pro
        195                 200                 205

His Ala Arg Arg Lys Val Leu Ala Gly Val Val Met Thr Thr Gly Thr
    210                 215                 220

Asp Val Lys Asp Ala Lys Val Ile Ser Val Ser Thr Gly Thr Lys Cys
225                 230                 235                 240

Ile Asn Gly Glu Tyr Met Ser Asp Arg Gly Leu Ala Leu Asn Asp Cys
                245                 250                 255

His Ala Glu Ile Ile Ser Arg Arg Ser Leu Leu Arg Phe Leu Tyr Thr
            260                 265                 270

Gln Leu Glu Leu Tyr Leu Asn Asn Lys Asp Asp Gln Lys Arg Ser Ile
        275                 280                 285

Phe Gln Lys Ser Glu Arg Gly Gly Phe Arg Leu Lys Glu Asn Val Gln
    290                 295                 300

Phe His Leu Tyr Ile Ser Thr Ser Pro Cys Gly Asp Ala Arg Ile Phe
305                 310                 315                 320

Ser Pro His Glu Pro Ile Leu Glu Glu Pro Ala Asp Arg His Pro Asn
                325                 330                 335

Arg Lys Ala Arg Gly Gln Leu Arg Thr Lys Ile Glu Ser Gly Glu Gly
            340                 345                 350

Thr Ile Pro Val Arg Ser Asn Ala Ser Ile Gln Thr Trp Asp Gly Val
        355                 360                 365

Leu Gln Gly Glu Arg Leu Leu Thr Met Ser Cys Ser Asp Lys Ile Ala
    370                 375                 380

Arg Trp Asn Val Val Gly Ile Gln Gly Ser Leu Leu Ser Ile Phe Val
385                 390                 395                 400

Glu Pro Ile Tyr Phe Ser Ser Ile Ile Leu Gly Ser Leu Tyr His Gly
                405                 410                 415

Asp His Leu Ser Arg Ala Met Tyr Gln Arg Ile Ser Asn Ile Glu Asp
            420                 425                 430

Leu Pro Pro Leu Tyr Thr Leu Asn Lys Pro Leu Leu Ser Gly Ile Ser
        435                 440                 445

Asn Ala Glu Ala Arg Gln Pro Gly Lys Ala Pro Asn Phe Ser Val Asn
    450                 455                 460

Trp Thr Val Gly Asp Ser Ala Ile Glu Val Ile Asn Ala Thr Thr Gly
465                 470                 475                 480

Lys Asp Glu Leu Gly Arg Ala Ser Arg Leu Cys Lys His Ala Leu Tyr
                485                 490                 495

Cys Arg Trp Met Arg Val His Gly Lys Val Pro Ser His Leu Leu Arg
```

500 505 510

Ser Lys Ile Thr Lys Pro Asn Val Tyr His Glu Ser Lys Leu Ala Ala
515 520 525

Lys Glu Tyr Gln Ala Ala Lys Ala Arg Leu Phe Thr Ala Phe Ile Lys
530 535 540

Ala Gly Leu Gly Ala Trp Val Glu Lys Pro Thr Glu Gln Asp Gln Phe
545 550 555 560

Ser Leu Thr Pro

<210> SEQ ID NO 98
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 98
nnnnnnnnnn nnnnnnnnnn ggccaacatg aggatcaccc atgtctgcag ggcc 54

<210> SEQ ID NO 99
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (22)..(41)
<223> OTHER INFORMATION: a, c, t, g, unknown or other

<400> SEQUENCE: 99
aacatgagga tcacccatgt cnnnnnnnnn nnnnnnnnnn naacatgagg atcacccatg 60
tc 62

<210> SEQ ID NO 100
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 100
nnnnnnnnnn nnnnnnnnnn gggccctgaa gaagggccc 39

<210> SEQ ID NO 101
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(39)
<223> OTHER INFORMATION: a, c, t, g, unknown or other

<400> SEQUENCE: 101
gggccctgaa gaagggcccn nnnnnnnnnn nnnnnnnnng ggccctgaag aagggccc 58

<210> SEQ ID NO 102
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 102
nnnnnnnnnn nnnnnnnnnn ccggagcaga cgatatggcg tcgctccgg 49

<210> SEQ ID NO 103
<211> LENGTH: 109
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (45)..(64)
<223> OTHER INFORMATION: a, c, t, g, unknown or other

<400> SEQUENCE: 103
tggaatagta taacaatatg ctaaatgttg ttatagtatc ccacnnnnnn nnnnnnnnnn 60
nnnngtggaa tagtataaca atatgctaaa tgttgttata gtatcccac 109

<210> SEQ ID NO 104
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (50)..(52)
<223> OTHER INFORMATION: a, c, t, g, unknown or other
<220> FEATURE:
<221> NAME/KEY: modified_base
<222> LOCATION: (54)..(68)
<223> OTHER INFORMATION: a, c, t, g, unknown or other

<400> SEQUENCE: 104
gggtggaata gtataacaat atgctaaatg ttgttatagt atcccacctn nncnnnnnnn 60 nnnnnnnn 68

<210> SEQ ID NO 105
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (46)..(51)
<223> OTHER INFORMATION: a, c, t, g, unknown or other
<220> FEATURE:
<221> NAME/KEY: modified_base
<222> LOCATION: (53)..(65)
<223> OTHER INFORMATION: a, c, t, g, unknown or other

<400> SEQUENCE: 105
gtggaatagt ataacaatat gctaaatgtt gttatagtat cccacnnnnn ncnnnnnnnn 60 nnnnn 65

<210> SEQ ID NO 106
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (46)..(51)
<223> OTHER INFORMATION: a, c, t, g, unknown or other
<220> FEATURE:
<221> NAME/KEY: modified_base
<222> LOCATION: (53)..(66)
<223> OTHER INFORMATION: a, c, t, g, unknown or other

<400> SEQUENCE: 106
gtggaagagg agaacaatat gctaaatgtt gttctcgtct cccacnnnnn ncnnnnnnnn 60 nnnnnn 66

<210> SEQ ID NO 107
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (50)..(52)
<223> OTHER INFORMATION: a, c, t, g, unknown or other
<220> FEATURE:
<221> NAME/KEY: modified_base
<222> LOCATION: (54)..(68)
<223> OTHER INFORMATION: a, c, t, g, unknown or other

<400> SEQUENCE: 107
gggtggaaga ggagaacaat atgctaaatg ttgttctcgt ctcccacctn nncnnnnnnn 60 nnnnnnnn 68

<210> SEQ ID NO 108
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (46)..(51)
<223> OTHER INFORMATION: a, c, t, g, unknown or other
<220> FEATURE:
<221> NAME/KEY: modified_base
<222> LOCATION: (53)..(66)
<223> OTHER INFORMATION: a, c, t, g, unknown or other

<400> SEQUENCE: 108
ggtgaagagg agaacaatat gctaaatgtt gttctcgtct ccaccnnnnn ncnnnnnnnn 60 nnnnnn 66

<210> SEQ ID NO 109
<211> LENGTH: 66

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (46)..(52)
<223> OTHER INFORMATION: a, c, t, g, unknown or other
<220> FEATURE:
<221> NAME/KEY: modified_base
<222> LOCATION: (54)..(66)
<223> OTHER INFORMATION: a, c, t, g, unknown or other

<400> SEQUENCE: 109
ggtgaagagg agaacaatat gctaaatgtt gttctcgtct ccaccnnnnn nncnnnnnnn 60 nnnnnn 66

<210> SEQ ID NO 110
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (46)..(51)
<223> OTHER INFORMATION: a, c, t, g, unknown or other
<220> FEATURE:
<221> NAME/KEY: modified_base
<222> LOCATION: (53)..(66)
<223> OTHER INFORMATION: a, c, t, g, unknown or other

<400> SEQUENCE: 110
gtggaagagg agaacaatag gctaaacgtt gttctcgtct cccacnnnnn ncnnnnnnnn 60 nnnnnn 66

<210> SEQ ID NO 111
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (50)..(52)
<223> OTHER INFORMATION: a, c, t, g, unknown or other
<220> FEATURE:
<221> NAME/KEY: modified_base
<222> LOCATION: (54)..(68)
<223> OTHER INFORMATION: a, c, t, g, unknown or other

<400> SEQUENCE: 111
gggtggaaga ggagaacaat aggctaaacg ttgttctcgt ctcccacctn nncnnnnnnn 60 nnnnnnnn 68

<210> SEQ ID NO 112
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (46)..(51)
<223> OTHER INFORMATION: a, c, t, g, unknown or other
<220> FEATURE:

<221> NAME/KEY: modified_base
<222> LOCATION: (53)..(66)
<223> OTHER INFORMATION: a, c, t, g, unknown or other

<400> SEQUENCE: 112
ggtgaagagg agaacaatag gctaaacgtt gttctcgtct ccaccnnnnn ncnnnnnnnn 60 nnnnnn 66

<210> SEQ ID NO 113
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (46)..(52)
<223> OTHER INFORMATION: a, c, t, g, unknown or other
<220> FEATURE:
<221> NAME/KEY: modified_base
<222> LOCATION: (54)..(66)
<223> OTHER INFORMATION: a, c, t, g, unknown or other

<400> SEQUENCE: 113
ggtgaagagg agaacaatag gctaaacgtt gttctcgtct ccaccnnnnn nncnnnnnnn 60 nnnnnn 66

<210> SEQ ID NO 114
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (56)..(62)
<223> OTHER INFORMATION: a, c, t, g, unknown or other
<220> FEATURE:
<221> NAME/KEY: modified_base
<222> LOCATION: (64)..(73)
<223> OTHER INFORMATION: a, c, t, g, unknown or other

<400> SEQUENCE: 114
ggtgtcgaga atagtataac aatatgctaa atgttgttat agtatcctcg acaccnnnnn 60
nncnnnnnnn nnn 73

<210> SEQ ID NO 115
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (56)..(62)
<223> OTHER INFORMATION: a, c, t, g, unknown or other
<220> FEATURE:
<221> NAME/KEY: modified_base
<222> LOCATION: (64)..(73)
<223> OTHER INFORMATION: a, c, t, g, unknown or other

<400> SEQUENCE: 115
ggtgtcgaga agaggagaac aatatgctaa atgttgttct cgtctcctcg acaccnnnnn 60
nncnnnnnnn nnn 73

<210> SEQ ID NO 116
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (56)..(62)
<223> OTHER INFORMATION: a, c, t, g, unknown or other
<220> FEATURE:
<221> NAME/KEY: modified_base
<222> LOCATION: (64)..(73)
<223> OTHER INFORMATION: a, c, t, g, unknown or other

<400> SEQUENCE: 116
ggtgtcgaga agaggagaac aataggctaa acgttgttct cgtctcctcg acaccnnnnn 60
nncnnnnnnn nnn 73

<210> SEQ ID NO 117
<211> LENGTH: 1387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

Met Ala Arg Ile Leu Ala Phe Ala Ile Gly Ile Ser Ser Ile Gly Trp
1 5 10 15

Ala Phe Ser Glu Asn Asp Glu Leu Lys Asp Cys Gly Val Arg Ile Phe
20 25 30

Thr Lys Val Glu Asn Pro Lys Thr Gly Glu Ser Leu Ala Leu Pro Arg
35 40 45

Arg Leu Ala Arg Ser Ala Arg Lys Arg Leu Ala Arg Arg Lys Ala Arg
50 55 60

Leu Asn His Leu Lys His Leu Ile Ala Asn Glu Phe Lys Leu Asn Tyr
65 70 75 80

Glu Asp Tyr Gln Ser Phe Asp Glu Ser Leu Ala Lys Ala Tyr Lys Gly
85 90 95

Ser Leu Ile Ser Pro Tyr Glu Leu Arg Phe Arg Ala Leu Asn Glu Leu
100 105 110

Leu Ser Lys Gln Asp Phe Ala Arg Val Ile Leu His Ile Ala Lys Arg
115 120 125

Arg Gly Tyr Asp Asp Ile Lys Asn Ser Asp Asp Lys Glu Lys Gly Ala
130 135 140

Ile Leu Lys Ala Ile Lys Gln Asn Glu Glu Lys Leu Ala Asn Tyr Gln
145 150 155 160

Ser Val Gly Glu Tyr Leu Tyr Lys Glu Tyr Phe Gln Lys Phe Lys Glu
165 170 175

Asn Ser Lys Glu Phe Thr Asn Val Arg Asn Lys Lys Glu Ser Tyr Glu
180 185 190

Arg Cys Ile Ala Gln Ser Phe Leu Lys Asp Glu Leu Lys Leu Ile Phe
195 200 205

Lys Lys Gln Arg Glu Phe Gly Phe Ser Phe Ser Lys Lys Phe Glu Glu
210 215 220

Glu Val Leu Ser Val Ala Phe Tyr Lys Arg Ala Leu Lys Asp Phe Ser
225 230 235 240

```
His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
    370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
        515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp Ala Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
    610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
```

```
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
    690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
    770                 775                 780

Gly Ala Leu His Glu Glu Thr Phe Arg Lys Glu Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
    850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys Ser Gly Leu Pro Pro Leu Glu Arg
            980                 985                 990

Leu Thr Leu Gly Ser Gly Gly Gly  Gly Ser Gln Leu His  Leu Pro Gln
        995                 1000                1005

Val Leu  Ala Asp Ala Val Ser  Arg Leu Val Leu Gly  Lys Phe Gly
    1010                1015                1020

Asp Leu  Thr Asp Asn Phe Ser  Ser Pro His Ala Arg  Arg Lys Val
    1025                1030                1035

Leu Ala  Gly Val Val Met Thr  Thr Gly Thr Asp Val  Lys Asp Ala
    1040                1045                1050

Lys Val  Ile Ser Val Ser Thr  Gly Thr Lys Cys Ile  Asn Gly Glu
    1055                1060                1065

Tyr Met  Ser Asp Arg Gly Leu  Ala Leu Asn Asp Cys  His Ala Glu
    1070                1075                1080
```

```
Ile Ile  Ser Arg Arg Ser Leu  Leu Arg Phe Leu Tyr  Thr Gln Leu
    1085                 1090                 1095

Glu Leu  Tyr Leu Asn Asn Lys  Asp Asp Gln Lys Arg  Ser Ile Phe
    1100                 1105                 1110

Gln Lys  Ser Glu Arg Gly Gly  Phe Arg Leu Lys Glu  Asn Val Gln
    1115                 1120                 1125

Phe His  Leu Tyr Ile Ser Thr  Ser Pro Cys Gly Asp  Ala Arg Ile
    1130                 1135                 1140

Phe Ser  Pro His Glu Pro Ile  Leu Glu Glu Pro Ala  Asp Arg His
    1145                 1150                 1155

Pro Asn  Arg Lys Ala Arg Gly  Gln Leu Arg Thr Lys  Ile Glu Ser
    1160                 1165                 1170

Gly Gln  Gly Thr Ile Pro Val  Arg Ser Asn Ala Ser  Ile Gln Thr
    1175                 1180                 1185

Trp Asp  Gly Val Leu Gln Gly  Glu Arg Leu Leu Thr  Met Ser Cys
    1190                 1195                 1200

Ser Asp  Lys Ile Ala Arg Trp  Asn Val Val Gly Ile  Gln Gly Ser
    1205                 1210                 1215

Leu Leu  Ser Ile Phe Val Glu  Pro Ile Tyr Phe Ser  Ser Ile Ile
    1220                 1225                 1230

Leu Gly  Ser Leu Tyr His Gly  Asp His Leu Ser Arg  Ala Met Tyr
    1235                 1240                 1245

Gln Arg  Ile Ser Asn Ile Glu  Asp Leu Pro Pro Leu  Tyr Thr Leu
    1250                 1255                 1260

Asn Lys  Pro Leu Leu Ser Gly  Ile Ser Asn Ala Glu  Ala Arg Gln
    1265                 1270                 1275

Pro Gly  Lys Ala Pro Asn Phe  Ser Val Asn Trp Thr  Val Gly Asp
    1280                 1285                 1290

Ser Ala  Ile Glu Val Ile Asn  Ala Thr Thr Gly Lys  Asp Glu Leu
    1295                 1300                 1305

Gly Arg  Ala Ser Arg Leu Cys  Lys His Ala Leu Tyr  Cys Arg Trp
    1310                 1315                 1320

Met Arg  Val His Gly Lys Val  Pro Ser His Leu Leu  Arg Ser Lys
    1325                 1330                 1335

Ile Thr  Lys Pro Asn Val Tyr  His Glu Ser Lys Leu  Ala Ala Lys
    1340                 1345                 1350

Glu Tyr  Gln Ala Ala Lys Ala  Arg Leu Phe Thr Ala  Phe Ile Lys
    1355                 1360                 1365

Ala Gly  Leu Gly Ala Trp Val  Glu Lys Pro Thr Glu  Gln Asp Gln
    1370                 1375                 1380

Phe Ser  Leu Thr
    1385
```

<210> SEQ ID NO 118
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118

```
gtggaatagt ataacaatat gctaaatgtt gttatagtat cccacacaaa ccgagcggtg     60

tctgt                                                                 65
```

<210> SEQ ID NO 119
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 119
gtggaatagt ataacaatat gctaaatgtt gttatagtat cccaccaaac cgagcggtgt 60
ctgtggtgga atagtataac aatatgctaa atgttgttat agtatcccac 110

<210> SEQ ID NO 120
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120
gtggaatagt ataacaatat gctaaatgtt gttatagtat cccactacaa accgagcggt 60
gtctggtgga atagtataac aatatgctaa atgttgttat agtatcccac 110

<210> SEQ ID NO 121
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 121
gtggaatagt ataacaatat gctaaatgtt gttatagtat cccactttac aaaccgagcg 60
gtgtcgtgga atagtataac aatatgctaa atgttgttat agtatcccac 110

<210> SEQ ID NO 122
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 122
gtggaatagt ataacaatat gctaaatgtt gttatagtat cccacgtttt acaaaccgag 60
cggtggtgga atagtataac aatatgctaa atgttgttat agtatcccac 110

<210> SEQ ID NO 123
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 123
gtggaatagt ataacaatat gctaaatgtt gttatagtat cccacaagtt ttacaaaccg 60
agcgggtgga atagtataac aatatgctaa atgttgttat agtatcccac 110

<210> SEQ ID NO 124
<211> LENGTH: 429
<212> TYPE: PRT

<213> ORGANISM: Unknown
<220> FEATURE:
<223> OTHER INFORMATION: Description of Unknown:
ADAR1 catalytic domain sequence

<400> SEQUENCE: 124

```
Lys Ala Glu Arg Met Gly Phe Thr Glu Val Thr Pro Val Thr Gly Ala
1               5                   10                  15

Ser Leu Arg Arg Thr Met Leu Leu Leu Ser Arg Ser Pro Glu Ala Gln
            20                  25                  30

Pro Lys Thr Leu Pro Leu Thr Gly Ser Thr Phe His Asp Gln Ile Ala
        35                  40                  45

Met Leu Ser His Arg Cys Phe Asn Thr Leu Thr Asn Ser Phe Gln Pro
    50                  55                  60

Ser Leu Leu Gly Arg Lys Ile Leu Ala Ala Ile Ile Met Lys Lys Asp
65                  70                  75                  80

Ser Glu Asp Met Gly Val Val Val Ser Leu Gly Thr Gly Asn Arg Cys
                85                  90                  95

Val Lys Gly Asp Ser Leu Ser Leu Lys Gly Glu Thr Val Asn Asp Cys
            100                 105                 110

His Ala Glu Ile Ile Ser Arg Arg Gly Phe Ile Arg Phe Leu Tyr Ser
        115                 120                 125

Glu Leu Met Lys Tyr Asn Ser Gln Thr Ala Lys Asp Ser Ile Phe Glu
    130                 135                 140

Pro Ala Lys Gly Gly Glu Lys Leu Gln Ile Lys Lys Thr Val Ser Phe
145                 150                 155                 160

His Leu Tyr Ile Ser Thr Ala Pro Cys Gly Asp Gly Ala Leu Phe Asp
                165                 170                 175

Lys Ser Cys Ser Asp Arg Ala Met Glu Ser Thr Glu Ser Arg His Tyr
            180                 185                 190

Pro Val Phe Glu Asn Pro Lys Gln Gly Lys Leu Arg Thr Lys Val Glu
        195                 200                 205

Asn Gly Glu Gly Thr Ile Pro Val Glu Ser Ser Asp Ile Val Pro Thr
    210                 215                 220

Trp Asp Gly Ile Arg Leu Gly Glu Arg Leu Arg Thr Met Ser Cys Ser
225                 230                 235                 240

Asp Lys Ile Leu Arg Trp Asn Val Leu Gly Leu Gln Gly Ala Leu Leu
                245                 250                 255

Thr His Phe Leu Gln Pro Ile Tyr Leu Lys Ser Val Thr Leu Gly Tyr
            260                 265                 270

Leu Phe Ser Gln Gly His Leu Thr Arg Ala Ile Cys Cys Arg Val Thr
        275                 280                 285

Arg Asp Gly Ser Ala Phe Glu Asp Gly Leu Arg His Pro Phe Ile Val
    290                 295                 300

Asn His Pro Lys Val Gly Arg Val Ser Ile Tyr Asp Ser Lys Arg Gln
305                 310                 315                 320

Ser Gly Lys Thr Lys Glu Thr Ser Val Asn Trp Cys Leu Ala Asp Gly
                325                 330                 335

Tyr Asp Leu Glu Ile Leu Asp Gly Thr Arg Gly Thr Val Asp Gly Pro
            340                 345                 350

Arg Asn Glu Leu Ser Arg Val Ser Lys Lys Asn Ile Phe Leu Leu Phe
        355                 360                 365

Lys Lys Leu Cys Ser Phe Arg Tyr Arg Arg Asp Leu Leu Arg Leu Ser
    370                 375                 380
```

Tyr Gly Glu Ala Lys Lys Ala Ala Arg Asp Tyr Glu Thr Ala Lys Asn
385 390 395 400

Tyr Phe Lys Lys Gly Leu Lys Asp Met Gly Tyr Gly Asn Trp Ile Ser
405 410 415

Lys Pro Gln Glu Glu Lys Asn Phe Tyr Leu Cys Pro Val
420 425

<210> SEQ ID NO 125
<211> LENGTH: 385
<212> TYPE: PRT
<213> ORGANISM: Unknown
<220> FEATURE:
<223> OTHER INFORMATION: Description of Unknown:
ADAR2 catalytic domain sequence

<400> SEQUENCE: 125

Gln Leu His Leu Pro Gln Val Leu Ala Asp Ala Val Ser Arg Leu Val
1 5 10 15

Leu Gly Lys Phe Gly Asp Leu Thr Asp Asn Phe Ser Ser Pro His Ala
20 25 30

Arg Arg Lys Val Leu Ala Gly Val Val Met Thr Thr Gly Thr Asp Val
35 40 45

Lys Asp Ala Lys Val Ile Ser Val Ser Thr Gly Thr Lys Cys Ile Asn
50 55 60

Gly Glu Tyr Met Ser Asp Arg Gly Leu Ala Leu Asn Asp Cys His Ala
65 70 75 80

Glu Ile Ile Ser Arg Arg Ser Leu Leu Arg Phe Leu Tyr Thr Gln Leu
85 90 95

Glu Leu Tyr Leu Asn Asn Lys Asp Asp Gln Lys Arg Ser Ile Phe Gln
100 105 110

Lys Ser Glu Arg Gly Gly Phe Arg Leu Lys Glu Asn Val Gln Phe His
115 120 125

Leu Tyr Ile Ser Thr Ser Pro Cys Gly Asp Ala Arg Ile Phe Ser Pro
130 135 140

His Glu Pro Ile Leu Glu Glu Pro Ala Asp Arg His Pro Asn Arg Lys
145 150 155 160

Ala Arg Gly Gln Leu Arg Thr Lys Ile Glu Ser Gly Glu Gly Thr Ile
165 170 175

Pro Val Arg Ser Asn Ala Ser Ile Gln Thr Trp Asp Gly Val Leu Gln
180 185 190

Gly Glu Arg Leu Leu Thr Met Ser Cys Ser Asp Lys Ile Ala Arg Trp
195 200 205

Asn Val Val Gly Ile Gln Gly Ser Leu Leu Ser Ile Phe Val Glu Pro
210 215 220

Ile Tyr Phe Ser Ser Ile Ile Leu Gly Ser Leu Tyr His Gly Asp His
225 230 235 240

Leu Ser Arg Ala Met Tyr Gln Arg Ile Ser Asn Ile Glu Asp Leu Pro
245 250 255

Pro Leu Tyr Thr Leu Asn Lys Pro Leu Leu Ser Gly Ile Ser Asn Ala
260 265 270

Glu Ala Arg Gln Pro Gly Lys Ala Pro Asn Phe Ser Val Asn Trp Thr
275 280 285

Val Gly Asp Ser Ala Ile Glu Val Ile Asn Ala Thr Thr Gly Lys Asp
290 295 300

Glu Leu Gly Arg Ala Ser Arg Leu Cys Lys His Ala Leu Tyr Cys Arg
305 310 315 320

```
Trp Met Arg Val His Gly Lys Val Pro Ser His Leu Leu Arg Ser Lys
                325                 330                 335

Ile Thr Lys Pro Asn Val Tyr His Glu Ser Lys Leu Ala Ala Lys Glu
            340                 345                 350

Tyr Gln Ala Ala Lys Ala Arg Leu Phe Thr Ala Phe Ile Lys Ala Gly
        355                 360                 365

Leu Gly Ala Trp Val Glu Lys Pro Thr Glu Gln Asp Gln Phe Ser Leu
    370                 375                 380

Thr
385


<210> SEQ ID NO 126
<211> LENGTH: 298
<212> TYPE: PRT
<213> ORGANISM: Unknown
<220> FEATURE:
<223> OTHER INFORMATION: Description of Unknown:
      ADAR dsRBD sequence

<400> SEQUENCE: 126

Met Asp Ile Glu Asp Glu Glu Asn Met Ser Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly Gly
        35                  40                  45

Pro Gly Arg Lys Arg Pro Leu Glu Glu Gly Ser Asn Gly His Ser Lys
    50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
            260                 265                 270

Phe Phe Glu Gly Ser Gly Arg Asn Lys Lys Leu Ala Lys Ala Arg Ala
```

```
        275                 280                 285

Ala Gln Ser Ala Leu Ala Ala Ile Phe Asn
    290                 295


<210> SEQ ID NO 127
<211> LENGTH: 564
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Leu Arg Ser Phe Val Gln Phe Pro Asn Ala Ser Glu Ala His Leu
1               5                   10                  15

Ala Met Gly Arg Thr Leu Ser Val Asn Thr Asp Phe Thr Ser Asp Gln
            20                  25                  30

Ala Asp Phe Pro Asp Thr Leu Phe Asn Gly Phe Glu Thr Pro Asp Lys
        35                  40                  45

Ala Glu Pro Pro Phe Tyr Val Gly Ser Asn Gly Asp Asp Ser Phe Ser
    50                  55                  60

Ser Ser Gly Asp Leu Ser Leu Ser Ala Ser Pro Val Pro Ala Ser Leu
65                  70                  75                  80

Ala Gln Pro Pro Leu Pro Val Leu Pro Pro Phe Pro Pro Pro Ser Gly
                85                  90                  95

Lys Asn Pro Val Met Ile Leu Asn Glu Leu Arg Pro Gly Leu Lys Tyr
            100                 105                 110

Asp Phe Leu Ser Glu Ser Gly Glu Ser His Ala Lys Ser Phe Val Met
        115                 120                 125

Ser Val Val Val Asp Gly Gln Phe Phe Glu Gly Ser Gly Arg Asn Lys
    130                 135                 140

Lys Leu Ala Lys Ala Arg Ala Ala Gln Ser Ala Leu Ala Ala Ile Phe
145                 150                 155                 160

Asn Leu His Leu Asp Gln Thr Pro Ser Arg Gln Pro Ile Pro Ser Glu
                165                 170                 175

Gly Leu Gln Leu His Leu Pro Gln Val Leu Ala Asp Ala Val Ser Arg
            180                 185                 190

Leu Val Leu Gly Lys Phe Gly Asp Leu Thr Asp Asn Phe Ser Ser Pro
        195                 200                 205

His Ala Arg Arg Lys Val Leu Ala Gly Val Val Met Thr Thr Gly Thr
    210                 215                 220

Asp Val Lys Asp Ala Lys Val Ile Ser Val Ser Thr Gly Thr Lys Cys
225                 230                 235                 240

Ile Asn Gly Glu Tyr Met Ser Asp Arg Gly Leu Ala Leu Asn Asp Cys
                245                 250                 255

His Ala Glu Ile Ile Ser Arg Arg Ser Leu Leu Arg Phe Leu Tyr Thr
            260                 265                 270

Gln Leu Glu Leu Tyr Leu Asn Asn Lys Asp Asp Gln Lys Arg Ser Ile
        275                 280                 285

Phe Gln Lys Ser Glu Arg Gly Gly Phe Arg Leu Lys Glu Asn Val Gln
    290                 295                 300

Phe His Leu Tyr Ile Ser Thr Ser Pro Cys Gly Asp Ala Arg Ile Phe
305                 310                 315                 320

Ser Pro His Glu Pro Ile Leu Glu Glu Pro Ala Asp Arg His Pro Asn
                325                 330                 335
```

```
Arg Lys Ala Arg Gly Gln Leu Arg Thr Lys Ile Glu Ser Gly Glu Gly
            340                 345                 350

Thr Ile Pro Val Arg Ser Asn Ala Ser Ile Gln Thr Trp Asp Gly Val
        355                 360                 365

Leu Gln Gly Glu Arg Leu Leu Thr Met Ser Cys Ser Asp Lys Ile Ala
    370                 375                 380

Arg Trp Asn Val Val Gly Ile Gln Gly Ser Leu Leu Ser Ile Phe Val
385                 390                 395                 400

Glu Pro Ile Tyr Phe Ser Ser Ile Ile Leu Gly Ser Leu Tyr His Gly
                405                 410                 415

Asp His Leu Ser Arg Ala Met Tyr Gln Arg Ile Ser Asn Ile Glu Asp
            420                 425                 430

Leu Pro Pro Leu Tyr Thr Leu Asn Lys Pro Leu Leu Ser Gly Ile Ser
        435                 440                 445

Asn Ala Glu Ala Arg Gln Pro Gly Lys Ala Pro Asn Phe Ser Val Asn
    450                 455                 460

Trp Thr Val Gly Asp Ser Ala Ile Glu Val Ile Asn Ala Thr Thr Gly
465                 470                 475                 480

Lys Asp Glu Leu Gly Arg Ala Ser Arg Leu Cys Lys His Ala Leu Tyr
                485                 490                 495

Cys Arg Trp Met Arg Val His Gly Lys Val Pro Ser His Leu Leu Arg
            500                 505                 510

Ser Lys Ile Thr Lys Pro Asn Val Tyr His Glu Ser Lys Leu Ala Ala
        515                 520                 525

Lys Glu Tyr Gln Ala Ala Lys Ala Arg Leu Phe Thr Ala Phe Ile Lys
    530                 535                 540

Ala Gly Leu Gly Ala Trp Val Glu Lys Pro Thr Glu Gln Asp Gln Phe
545                 550                 555                 560

Ser Leu Thr Pro
```

<210> SEQ ID NO 128
<211> LENGTH: 36
<212> TYPE: DNA
<213> ORGANISM: Mus sp.

<400> SEQUENCE: 128
ctcacagaca ccgctcggtt tgtaaaactt ttcttc 36

<210> SEQ ID NO 129
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
ctcacagaca ccgctcagtt tgtaaaactt ttcttc 36

<210> SEQ ID NO 130
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
ctcacagaca ccgctcagtt tgtaaaactt ttcttc 36

<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ctcacagaca ccgctcatgt cttatctagc atgaca 36

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctcacagaca ccgctcgtgt cttatctagc atgaca 36

<210> SEQ ID NO 133
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (17)..(19)
<223> OTHER INFORMATION: a, c, t, g, unknown or other

<400> SEQUENCE: 133
nnnnnnnnnn nnnnncnnnt ccaccctatg atattgttgt aaatcgtata acaatatgat 60
aaggtggg 68

<210> SEQ ID NO 134
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, t, g, unknown or other
<220> FEATURE:
<221> NAME/KEY: modified_base
<222> LOCATION: (15)..(20)
<223> OTHER INFORMATION: a, c, t, g, unknown or other

<400> SEQUENCE: 134
nnnnnnnnnn nnncnnnnnn caccctatga tattgttgta aatcgtataa caatatgata 60
aggtg 65

<210> SEQ ID NO 135
<211> LENGTH: 66
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<221> NAME/KEY: modified_base
<222> LOCATION: (1)..(14)
<223> OTHER INFORMATION: a, c, t, g, unknown or other
<220> FEATURE:
<221> NAME/KEY: modified_base
<222> LOCATION: (16)..(21)
<223> OTHER INFORMATION: a, c, t, g, unknown or other

<400> SEQUENCE: 135
nnnnnnnnnn nnnncnnnnn ncaccctctg ctcttgttgt aaatcgtata acaagaggag 60
aaggtg 66

<210> SEQ ID NO 136
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (17)..(19)
<223> OTHER INFORMATION: a, c, t, g, unknown or other

<400> SEQUENCE: 136
nnnnnnnnnn nnnnncnnnt ccaccctctg ctcttgttgt aaatcgtata acaagaggag 60
aaggtggg 68

<210> SEQ ID NO 137
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(14)
<223> OTHER INFORMATION: a, c, t, g, unknown or other
<220> FEATURE:
<221> NAME/KEY: modified_base
<222> LOCATION: (16)..(21)
<223> OTHER INFORMATION: a, c, t, g, unknown or other

<400> SEQUENCE: 137
nnnnnnnnnn nnnncnnnnn nccacctctg ctcttgttgt aaatcgtata acaagaggag 60
aagtgg 66

<210> SEQ ID NO 138
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(13)
<223> OTHER INFORMATION: a, c, t, g, unknown or other
<220> FEATURE:
<221> NAME/KEY: modified_base
<222> LOCATION: (15)..(21)
<223> OTHER INFORMATION: a, c, t, g, unknown or other

<400> SEQUENCE: 138
nnnnnnnnnn nnncnnnnnn nccacctctg ctcttgttgt aaatcgtata acaagaggag 60
aagtgg 66

<210> SEQ ID NO 139
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(14)
<223> OTHER INFORMATION: a, c, t, g, unknown or other
<220> FEATURE:
<221> NAME/KEY: modified_base
<222> LOCATION: (16)..(21)
<223> OTHER INFORMATION: a, c, t, g, unknown or other

<400> SEQUENCE: 139
nnnnnnnnnn nnnncnnnnn ncaccctctg ctcttgttgc aaatcggata acaagaggag 60
aaggtg 66

<210> SEQ ID NO 140
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (17)..(19)
<223> OTHER INFORMATION: a, c, t, g, unknown or other

<400> SEQUENCE: 140
nnnnnnnnnn nnnnncnnnt ccaccctctg ctcttgttgc aaatcggata acaagaggag 60
aaggtggg 68

<210> SEQ ID NO 141
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(14)
<223> OTHER INFORMATION: a, c, t, g, unknown or other
<220> FEATURE:
<221> NAME/KEY: modified_base
<222> LOCATION: (16)..(21)
<223> OTHER INFORMATION: a, c, t, g, unknown or other

<400> SEQUENCE: 141
nnnnnnnnnn nnnncnnnnn nccacctctg ctcttgttgc aaatcggata acaagaggag 60
aagtgg 66

<210> SEQ ID NO 142
<211> LENGTH: 66

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(13)
<223> OTHER INFORMATION: a, c, t, g, unknown or other
<220> FEATURE:
<221> NAME/KEY: modified_base
<222> LOCATION: (15)..(21)
<223> OTHER INFORMATION: a, c, t, g, unknown or other

<400> SEQUENCE: 142
nnnnnnnnnn nnncnnnnnn nccacctctg ctcttgttgc aaatcggata acaagaggag 60
aagtgg 66

<210> SEQ ID NO 143
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (12)..(18)
<223> OTHER INFORMATION: a, c, t, g, unknown or other

<400> SEQUENCE: 143
nnnnnnnnnn cnnnnnnncc acagctcctc tgctcttgtt gcaaatcgga taacaagagg 60
agaagagctg tgg 73

<210> SEQ ID NO 144
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (12)..(18)
<223> OTHER INFORMATION: a, c, t, g, unknown or other

<400> SEQUENCE: 144
nnnnnnnnnn cnnnnnnncc acagctcctc tgctcttgtt gtaaatcgta taacaagagg 60
agaagagctg tgg 73

<210> SEQ ID NO 145
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(10)
<223> OTHER INFORMATION: a, c, t, g, unknown or other
<220> FEATURE:

```
<221> NAME/KEY: modified_base
<222> LOCATION: (12)..(18)
<223> OTHER INFORMATION: a, c, t, g, unknown or other

<400> SEQUENCE: 145

nnnnnnnnnn cnnnnnnncc acagctccta tgatattgtt gtaaatcgta taacaatatg     60

ataagagctg tgg                                                        73


<210> SEQ ID NO 146
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (45)..(64)
<223> OTHER INFORMATION: a, c, t, g, unknown or other

<400> SEQUENCE: 146

tggaatagta taacaatatg ctaaatgttg ttatagtatc ccacnnnnnn nnnnnnnnnn     60

nnnngtggaa tagtataaca atatgctaaa tgttgttata gtatcccac                109


<210> SEQ ID NO 147
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(86)
<223> OTHER INFORMATION: a, c, t, g, unknown or other

<400> SEQUENCE: 147

caacattatc ggggagtttt gacctccaag gtgttgnnnn nnnnnnnnnn nnnnnnnnnn     60

nnnnnnnnnn nnnnnnnnnn nnnnnn                                          86


<210> SEQ ID NO 148
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(22)
<223> OTHER INFORMATION: a, c, t, g, unknown or other

<400> SEQUENCE: 148

nnnnnnnnnn nnnnnnnnnn nngttttagt ccctgaaaag ggactaaaat aaagagtttg     60

cgggactctg cggggttaca atcccctaaa accgcttttt tt                       102


<210> SEQ ID NO 149
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149

aaagtctcac agacaccgct cagtttgtaa aacttttctt c                         41
```

<210> SEQ ID NO 150
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
gtggaatagt ataacaatat gctaaatgtt gttatagtat cccactgtct gtggcgagcc 60
aaaca 65

<210> SEQ ID NO 151
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
gtggaatagt ataacaatat gctaaatgtt gttatagtat cccacgtgtc tgtggcgagc 60
caaaca 66

<210> SEQ ID NO 152
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
aagttttaca aaccgagcgg caccctatga tattgttgta aatcgtataa caatatgata 60
aggtg 65

<210> SEQ ID NO 153
<211> LENGTH: 109
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153
tggaatagta taacaatatg ctaaatgttg ttatagtatc ccaccaaacc gagcggtgtc 60
tgtggtggaa tagtataaca atatgctaaa tgttgttata gtatcccac 109

<210> SEQ ID NO 154
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
caaaccgagc ggtgtctgtg ggccaacatg aggatcaccc atgtctgcag ggcc 54

<210> SEQ ID NO 155
<211> LENGTH: 62
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 155
aacatgagga tcacccatgt ccaaaccgag cggtgtctgt gaacatgagg atcacccatg 60
tc 62

<210> SEQ ID NO 156
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 156
caaaccgagc ggtgtctgtg gggccctgaa gaagggccc 39

<210> SEQ ID NO 157
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 157
gggccctgaa gaagggcccc aaaccgagcg gtgtctgtgg ggccctgaag aagggccc 58

<210> SEQ ID NO 158
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 158
cggcctcagt gagcga 16

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 159
ggaaccccta gtgatggagt t 21

<210> SEQ ID NO 160
<211> LENGTH: 20
<212> TYPE: DNA
<213> ORGANISM: Unknown
<220> FEATURE:
<223> OTHER INFORMATION: Description of Unknown:
target sequence

<400> SEQUENCE: 160
gggaaatcca gctagcggca 20

<210> SEQ ID NO 161
<211> LENGTH: 20
<212> TYPE: DNA

<213> ORGANISM: Unknown
<220> FEATURE:
<223> OTHER INFORMATION: Description of Unknown:
target sequence

<400> SEQUENCE: 161
gggaaaactg tctagttccc 20

<210> SEQ ID NO 162
<211> LENGTH: 20
<212> TYPE: DNA
<213> ORGANISM: Unknown
<220> FEATURE:
<223> OTHER INFORMATION: Description of Unknown:
target sequence

<400> SEQUENCE: 162
taattgactg gctagtacag 20

<210> SEQ ID NO 163
<211> LENGTH: 20
<212> TYPE: DNA
<213> ORGANISM: Unknown
<220> FEATURE:
<223> OTHER INFORMATION: Description of Unknown:
target sequence

<400> SEQUENCE: 163
gagctttttg cttagcactg 20

<210> SEQ ID NO 164
<211> LENGTH: 1884
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 164
atggataaaa aaccattaga tgttttaata tctgcgaccg ggctctggat gtccaggact 60
ggcacgctcc acaaaatcaa gcaccatgag gtctcaagaa gtaaaatata cattgaaatg 120
gcgtgtggag accatcttgt tgtgaataat tccaggagtt gtagaacagc cagagcattc 180
agacatcata agtacagaaa aacctgcaaa cgatgtaggg tttcggacga ggatatcaat 240
aattttctca caagatcaac cgaaagcaaa aacagtgtga aagttagggt agtttctgct 300
ccaaaggtca aaaaagctat gccgaaatca gtttcaaggg ctccgaagcc tctggaaaat 360
tctgtttctg caaaggcatc aacgaacaca tccagatctg taccttcgcc tgcaaaatca 420
actccaaatt cgtctgttcc cgcatcggct cctgctcctt cacttacaag aagccagctt 480
gatagggttg aggctctctt aagtccagag gataaaattt ctctaaatat ggcaaagcct 540
ttcagggaac ttgagcctga acttgtgaca agaagaaaaa acgattttca gcggctctat 600
accaatgata gagaagacta cctcggtaaa ctcgaacgtg atattacgaa atttttcgta 660
gaccggggtt ttctggagat aaagtctcct atccttattc cggcggaata cgtggagaga 720
atgggtatta ataatgatac tgaactttca aaacagatct tccgggtgga taaaaatctc 780
tgcttgaggc caatgcttgc cccgactctt tacaactatc tgcgaaaact cgataggatt 840
ttaccaggcc caataaaaat tttcgaagtc ggaccttgtt accggaaaga gtctgacggc 900
aaagagcacc tggaagaatt tactatggtg aacttctgtc agatgggttc gggatgtact 960
cgggaaaatc ttgaagctct catcaaagag tttctggact atctggaaat cgacttcgaa 1020
atcgtaggag attcctgtat ggtctttggg gatactcttg atataatgca cggggacctg 1080
gagctttctt cggcagtcgt cgggccagtt tctcttgata gagaatgggg tattgacaaa 1140
ccatggatag gtgcaggttt tggtcttgaa cgcttgctca aggttatgca cggctttaaa 1200
aacattaaga gggcatcaag gtccgaatct tactataatg ggatttcaac caatctgtta 1260
taaagcggcc gcgtcgacgg gcccgcggaa ttccgccccc ccccccctctc cctccccccc 1320 ccctaacgtt actggccgaa gccgcttgga ataaggccgg tgtgcgtttg tctatatgtt 1380
attttccacc atattgccgt cttttggcaa tgtgagggcc cggaaacctg gccctgtctt 1440
cttgacgagc attcctaggg gtctttcccc tctcgccaaa ggaatgcaag gtctgttgaa 1500
tgtcgtgaag gaagcagttc ctctggaagc ttcttgaaga caaacaacgt ctgtagcgac 1560 ccctttgcagg cagcggaacc ccccacctgg cgacaggtgc ctctgcggcc aaaagccacg 1620
tgtataagat acacctgcaa aggcggcaca accccagtgc cacgttgtga gttggatagt 1680
tgtggaaaga gtcaaatggc tctcctcaag cgtattcaac aaggggctga aggatgccca 1740
gaaggtaccc cattgtatgg gatctgatct ggggcctcgg tgcacatgct ttacatgtgt 1800
ttagtcgagg ttaaaaaaac gtctaggccc cccgaaccac ggggacgtgg ttttcctttg 1860
aaaaacacga tgataatatg gcca 1884

<210> SEQ ID NO 165
<211> LENGTH: 2106
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 165
atggatatag aagatgaaga aaacatgagt tccagcagca ctgatctgaa ggaaaaccgc 60
aatctggaca acgtgtcccc caaggatggc agcacacctg ggcctggcga gggctctcag 120
ctctccaatg gggtggtgg tggccccggc agaaagcggc ccctggagga gggcagcaat 180
ggccactcca agtaccgcct gaagaaaagg aggaaaacac cagggcccgt cctccccaag 240
aacgccctga tgcagctgaa tgagatcaag cctggtttgc agtacacact cctgtcccag 300
actgggcccg tgcacgcgcc tttgtttgtc atgtctgtgg aggtgaatgg ccaggttttt 360
gagggctctg gtcccacaaa gaaaaaggca aaactccatg ctgctgagaa ggccttgagg 420
tctttcgttc agtttcctaa tgcctctgag gcccacctgg ccatggggag gaccctgtct 480
gtcaacacgg acttcacatc tgaccaggcc gacttccctg acacgctctt caatggtttt 540
gaaactcctg acaaggcgga gcctcccttt tacgtgggct ccaatgggga tgactccttc 600
agttccagcg gggacctcag cttgtctgct tccccggtgc ctgccagcct agcccagcct 660
cctctccctg tcttaccacc attcccaccc ccgagtggga agaatcccgt gatgatcttg 720
aacgaactgc gcccaggact caagtatgac ttcctctccg agagcgggga gagccatgcc 780
aagagcttcg tcatgtctgt ggtcgtggat ggtcagttct ttgaaggctc ggggagaaac 840
aagaagcttg ccaaggcccg ggctgcgcag tctgccctgg ccgccatttt taacttgcac 900
ttggatcaga cgccatctcg ccagcctatt cccagtgagg gtcttcagct gcatttaccg 960
caggttttag ctgacgctgt ctcacgcctg gtcctgggta agtttggtga cctgaccgac 1020
aacttctcct cccctcacgc tcgcagaaaa gtgctggctg gagtcgtcat gacaacaggc 1080
acagatgtta aagatgccaa ggtgataagt gtttctacag gaacaaaatg tattaatggt 1140

```
gaatacatga gtgatcgtgg ccttgcatta aatgactgcc atgcagaaat aatatctcgg   1200
agatccttgc tcagatttct ttatacacaa cttgagcttt acttaaataa caaagatgat   1260
caaaaaagat ccatctttca gaaatcagag cgaggggggt ttaggctgaa ggagaatgtc   1320
cagtttcatc tgtacatcag cacctctccc tgtggagatg ccagaatctt ctcaccacat   1380
gagccaatcc tggaagaacc agcagataga cacccaaatc gtaaagcaag aggacagcta   1440
cggaccaaaa tagagtctgg tgaggggacg attccagtgc gctccaatgc gagcatccaa   1500
acgtgggacg gggtgctgca aggggagcgg ctgctcacca tgtcctgcag tgacaagatt   1560
gcacgctgga acgtggtggg catccaggga tccctgctca gcattttcgt ggagcccatt   1620
tacttctcga gcatcatcct gggcagcctt taccacgggg accacctttc cagggccatg   1680
taccagcgga tctccaacat agaggacctg ccacctctct acaccctcaa caagcctttg   1740
ctcagtggca tcagcaatgc agaagcacgg cagccaggga aggcccccaa cttcagtgtc   1800
aactggacgg taggcgactc cgctattgag gtcatcaacg ccacgactgg gaaggatgag   1860
ctgggccgcg cgtcccgcct gtgtaagcac gcgttgtact gtcgctggat gcgtgtgcac   1920
ggcaaggttc cctcccactt actacgctcc aagattacca agcccaacgt gtaccatgag   1980
tccaagctgg cggcaaagga gtaccaggcc gccaaggcgc gtctgttcac agccttcatc   2040
aaggcggggc tgggggcctg ggtggagaag cccaccgagc aggaccagtt ctcactcacg   2100
ccctga                                                              2106
```

<210> SEQ ID NO 166
<211> LENGTH: 632
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166

```
accggtttta gtccctgaag gaagggacta aaataaagag tttgcgggac tctgcggggt     60
tacaatcccc taaaaccgct aaggctagtc cgttatcaac ttgaaaaagt ggcaccgagt    120
cggtgctttt ttgctagcct agacccagct ttcttgtaca aagttggcat taatacgcgt    180
tgacattgat tattgactag ttattaatag taatcaatta cggggtcatt agttcatagc    240
ccatatatgg agttccgcgt tacataactt acggtaaatg gcccgcctgg ctgaccgccc    300
aacgaccccc gcccattgac gtcaataatg acgtatgttc ccatagtaac gccaataggg    360
actttccatt gacgtcaatg ggtggagtat ttacggtaaa ctgcccactt ggcagtacat    420
caagtgtatc atatgccaag tacgccccct attgacgtca atgacggtaa atggcccgcc    480
tggcattatg cccagtacat gaccttatgg gactttccta cttggcagta catctacgta    540
ttagtcatcg ctattaccat ggtgatgcgg ttttggcagt acatcaatgg gcgtggatag    600
cggtttgact cacggggatt tccaagtctc ca                                  632
```

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
agggcgatgc cacctgggg 19

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 168
agggcgatgc gacctgggg 19

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 169
agggcgatgg gacctgggg 19

<210> SEQ ID NO 170
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
atcgccctga aaagggcgat gccacctggg g 31

<210> SEQ ID NO 171
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
atcgccctga aaagggcgat gcgacctggg g 31

<210> SEQ ID NO 172
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
atcgccctga aaagggcgat gggacctggg g 31

<210> SEQ ID NO 173
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 173
accgctcagt ttntaa 16

<210> SEQ ID NO 174
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 174
ccgctcnntt tntaaa 16

<210> SEQ ID NO 175
<211> LENGTH: 31
<212> TYPE: DNA
<213> ORGANISM: Unknown
<220> FEATURE:
<223> OTHER INFORMATION: Description of Unknown:
target sequence

<400> SEQUENCE: 175
gggcgatgcc acctaaggca agctgaccct g 31

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
gccctaggtg gcatcgccc 19

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
cagggtcagc ttgccctag 19

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
gccccaggtg gcatcgccc 19

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
agggtcagct tgccccagg 19

<210> SEQ ID NO 180
<211> LENGTH: 66
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (46)..(51)
<223> OTHER INFORMATION: a, c, u, g, unknown or other
<220> FEATURE:
<221> NAME/KEY: modified_base
<222> LOCATION: (53)..(66)
<223> OTHER INFORMATION: a, c, u, g, unknown or other

<400> SEQUENCE: 180
guggaauagu auaacaauau gcuaaauguu guuauaguau cccacnnnnn ncnnnnnnnn 60 nnnnnn 66

<210> SEQ ID NO 181
<211> LENGTH: 68
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (50)..(52)
<223> OTHER INFORMATION: a, c, u, g, unknown or other
<220> FEATURE:
<221> NAME/KEY: modified_base
<222> LOCATION: (54)..(68)
<223> OTHER INFORMATION: a, c, u, g, unknown or other

<400> SEQUENCE: 181
ggguggaaua guauaacaau augcuaaaug uuguuauagu aucccaccun nncnnnnnnn 60 nnnnnnnn 68

<210> SEQ ID NO 182
<211> LENGTH: 24
<212> TYPE: DNA
<213> ORGANISM: Unknown
<220> FEATURE:
<223> OTHER INFORMATION: Description of Unknown:
target sequence

<400> SEQUENCE: 182
tcacagacac cgctcagttt gtaa 24

<210> SEQ ID NO 183
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
caaaccgagc ggtgtc 16

<210> SEQ ID NO 184
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 184
acaaaccgag cggtgt 16

<210> SEQ ID NO 185
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 185
tacaaaccga gcggtg 16

<210> SEQ ID NO 186
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 186
ttacaaaccg agcggt 16

<210> SEQ ID NO 187
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 187
caaaccgagc ggtgtct 17

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 188
acaaaccgag cggtgtc 17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 189
tacaaaccga gcggtgt 17

<210> SEQ ID NO 190
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 190
ttacaaaccg agcggtg 17

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 191
caaaccgagc ggtgtctg 18

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
acaaaccgag cggtgtct 18

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193
tacaaaccga gcggtgtc 18

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 194
ttacaaaccg agcggtgt 18

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
caaaccgagc ggtgtctgt 19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
acaaaccgag cggtgtctg 19

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
tacaaaccga gcggtgtct 19

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
ttacaaaccg agcggtgtc 19

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
caaaccgagc ggtgtctgtg 20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
acaaaccgag cggtgtctgt 20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
tacaaaccga gcggtgtctg 20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
ttacaaaccg agcggtgtct 20

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 203
caaaccgagc ggtgtctgtg a 21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 204
acaaaccgag cggtgtctgt g 21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 205
tacaaaccga gcggtgtctg t 21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 206
ttacaaaccg agcggtgtct g 21

<210> SEQ ID NO 207
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 207
agcaataaaa tggc 14

<210> SEQ ID NO 208
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 208
agcaataaaa tggc 14

<210> SEQ ID NO 209
<211> LENGTH: 39
<212> TYPE: DNA
<213> ORGANISM: Mus sp.

<400> SEQUENCE: 209
gagcaataaa atggcttcaa ctatctgagt gacactgtg 39

<210> SEQ ID NO 210
<211> LENGTH: 39
<212> TYPE: DNA
<213> ORGANISM: Mus sp.

<400> SEQUENCE: 210
gagcaataaa atggcttcaa ctatctgagt gacactgtg 39

<210> SEQ ID NO 211
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 211
gagccataaa atggcttcaa ctatctgagt gacactgtg 39

<210> SEQ ID NO 212
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 212
gagcaataaa attgcttcaa ctatctgagt gacactgtg 39

<210> SEQ ID NO 213
<211> LENGTH: 39
<212> TYPE: DNA
<213> ORGANISM: Mus sp.

<400> SEQUENCE: 213
gagcaataaa atggcttcaa ctatctgagt gacactgtg 39

<210> SEQ ID NO 214
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 214
gagcaatgga atggcttcaa ctatctgagt gacactgtg 39

<210> SEQ ID NO 215
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 215
gagccataaa atggcttcaa ctatctgagt gacactgtg 39

<210> SEQ ID NO 216
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 216
gagcaataaa attgcttcaa ctatctgagt gacactgtg 39

<210> SEQ ID NO 217
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 217
ccgctcagtt tnt 13

<210> SEQ ID NO 218
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 218
ccgctcnntt tnt 13

<210> SEQ ID NO 219
<211> LENGTH: 40
<212> TYPE: DNA
<213> ORGANISM: Mus sp.

<400> SEQUENCE: 219
tgaaagtctc acagacaccg ctcatgtctt atctagcatg 40

<210> SEQ ID NO 220
<211> LENGTH: 40
<212> TYPE: DNA
<213> ORGANISM: Mus sp.

<400> SEQUENCE: 220
tgaaagtctc acagacaccg ctcatgtctt atctagcatg 40

<210> SEQ ID NO 221
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 221
tgaaagtctc ccagacaccg ctcatgtctt atctagcatg 40

<210> SEQ ID NO 222
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 222
tgcaagtctc acagacaccg ctcatgtctt atctagcatg 40

<210> SEQ ID NO 223
<211> LENGTH: 40
<212> TYPE: DNA
<213> ORGANISM: Mus sp.

<400> SEQUENCE: 223
tgaaagtctc acagacaccg ctcatgtctt atctagcatg 40

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 224
tgaaagtctc acagacaccg ctcgtgtctt atctagcatg 40

<210> SEQ ID NO 225
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 225
tgaaagtctc ccagacaccg ctcatgtctt atctagcatg 40

<210> SEQ ID NO 226
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 226
tgcaagtctc acagacaccg ctcatgtctt atctagcatg 40

<210> SEQ ID NO 227
<211> LENGTH: 66
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (46)..(51)
<223> OTHER INFORMATION: a, c, u, g, unknown or other
<220> FEATURE:
<221> NAME/KEY: modified_base
<222> LOCATION: (53)..(66)
<223> OTHER INFORMATION: a, c, u, g, unknown or other

<400> SEQUENCE: 227
guggaauagu auaacaauau gcuaaauguu guuauaguau cccacnnnnn ncnnnnnnnn 60 nnnnnn 66

<210> SEQ ID NO 228
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
gccacctgag gcaagctgac cctgaagttc atctgcacc 39

<210> SEQ ID NO 229
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 229
gccacctgag gcaagctgac cctgaagttc atctgcacc 39

<210> SEQ ID NO 230
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 230
gccccctgag gcaagctgac cctgaagttc atctgcacc 39

<210> SEQ ID NO 231
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 231
gccacctgag gcaagctgac cctgcagttc atctgcacc 39

<210> SEQ ID NO 232
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 232
gccacctgag gccagctgac cctgaagttc atctgcacc 39

<210> SEQ ID NO 233
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 233
gccacctgag gcaggctgac cctgaagttc atctgcacc 39

<210> SEQ ID NO 234
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 234
gccacctgag gcaagctgac cctgaagttc atctgcacc 39

<210> SEQ ID NO 235
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
gccacctgag gcaagctgac cctgaggttc atctgcacc 39

<210> SEQ ID NO 236
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
gccgcctgag gcaagctgac cctgaagttc atctgcacc 39

<210> SEQ ID NO 237
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 237
gccacctggg gcaagctgac cctgaagttc atctgcacc 39

<210> SEQ ID NO 238
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 238
gccacctgag gcaggctgac cctgaagttc atctgcacc 39

<210> SEQ ID NO 239
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 239
gccacctgag gcgagctgac cctgaagttc atctgcacc 39

<210> SEQ ID NO 240
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
gccgcctgag gcaagctgac cctgaggttc atctgcacc 39

<210> SEQ ID NO 241
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
gccgcctgag gcaggctgac cctgaagttc atctgcacc 39

<210> SEQ ID NO 242
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
gccacctgag gcaagctgac cctgaagttc atctgcacc 39

<210> SEQ ID NO 243
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 243
gccacctggg gcaagctgac cctgaagttc atctgcacc 39

<210> SEQ ID NO 244
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 244
gccacctgag gccagctgac cctgaagttc atctgcacc 39

<210> SEQ ID NO 245
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 245
cagacaccgc tcagtttgta aaacttttct tccttccaaa 40

<210> SEQ ID NO 246
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 246
cagacaccgc tcagtttgta aaacttttct tccttccaaa 40

<210> SEQ ID NO 247
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 247
cagacaccgc tcagtttgta aaacttttct tccttccaca 40

<210> SEQ ID NO 248
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 248
cagacaccgc tcagtttgta aaacttttct tccttccaac 40

<210> SEQ ID NO 249
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 249
cagacaccgc tcagtttgtg aaacttttct tccttccaaa 40

<210> SEQ ID NO 250

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250

cagacaccgc tcagtttgta acacttttct tccttccaaa                         40


<210> SEQ ID NO 251
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251

cagacaccgc tcagtttgta aaccttttct tccttccaaa                         40


<210> SEQ ID NO 252
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252

cagacaccgc tcagtttgta aaacttttct tccttccaaa                         40


<210> SEQ ID NO 253
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253

cagacaccgc tcggtttgta aaacttttct tccttccaaa                         40


<210> SEQ ID NO 254
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254

cagacaccgc tcagtttgtg aaacttttct tccttccaaa                         40


<210> SEQ ID NO 255
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255

cagacaccgc tcggtttgtg aaacttttct tccttccaaa                         40


<210> SEQ ID NO 256
<211> LENGTH: 40
```

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 256
cagacaccgc tcagtttgta gaacttttct tccttccaaa 40

<210> SEQ ID NO 257
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 257
cagacaccgc tcagtttgta aaacttttct tccttccaga 40

<210> SEQ ID NO 258
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 258
cagacaccgc tcagtttgta aaacttttct tccttccaaa 40

<210> SEQ ID NO 259
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 259
cagacaccgc tcggtttgta aaacttttct tccttccaaa 40

<210> SEQ ID NO 260
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 260
cagacaccgc tcagtttgta aaacttttct tccttccaca 40

<210> SEQ ID NO 261
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 261
cagacaccgc tcagtttgta aaacttttct tccttccaac 40

<210> SEQ ID NO 262
<211> LENGTH: 40
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 262

cagacaccgc tcggtttgtg aaacttttct tccttccaaa                        40


<210> SEQ ID NO 263
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263

cagacaccgc tcagtttgta acacttttct tccttccaaa                        40


<210> SEQ ID NO 264
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264

cagacaccgc tcagtttgtg aaacttttct tccttccaaa                        40


<210> SEQ ID NO 265
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265

aacatgagga tcacccatgt ccaaaccgag cggtgtctgt gaacatgagg atcacccatg     60

tc                                                                    62


<210> SEQ ID NO 266
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266

aacatgagga tcacccatgt ctacaaaccg agcggtgtct gaacatgagg atcacccatg     60

tc                                                                    62


<210> SEQ ID NO 267
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267

aacatgagga tcacccatgt ctttacaaac cgagcggtgt caacatgagg atcacccatg     60

tc                                                                    62
```

<210> SEQ ID NO 268
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268
aacatgagga tcacccatgt cgttttacaa accgagcggt gaacatgagg atcacccatg 60
tc 62

<210> SEQ ID NO 269
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 269
aacatgagga tcacccatgt caagttttac aaaccgagcg gaacatgagg atcacccatg 60
tc 62

<210> SEQ ID NO 270
<211> LENGTH: 5
<212> TYPE: PRT
<213> ORGANISM: Mus sp.

<400> SEQUENCE: 270

Thr Ala Arg Val Leu
1 5

<210> SEQ ID NO 271
<211> LENGTH: 15
<212> TYPE: DNA
<213> ORGANISM: Mus sp.
<220> FEATURE:
<221> NAME/KEY: CDS
<222> LOCATION: (1)..(15)

<400> SEQUENCE: 271 acc gct cgt gtc tta 15
Thr Ala Arg Val Leu
1 5

<210> SEQ ID NO 272
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Thr Ala His Val Leu
1 5

<210> SEQ ID NO 273
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide -continued

```
<220> FEATURE:
<221> NAME/KEY: CDS
<222> LOCATION: (1)..(15)

<400> SEQUENCE: 273

acc gct cat gtc tta                                                 15
Thr Ala His Val Leu
1               5


<210> SEQ ID NO 274
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Thr Ala Gln Phe Val Lys Leu Phe Phe Leu Pro Lys Phe Ile Ser Asn
1               5                   10                  15

Ser Asp Gly Val Leu
            20


<210> SEQ ID NO 275
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(63)

<400> SEQUENCE: 275

acc gct cag ttt gta aaa ctt ttc ttc ctt cca aag ttt att tca aac       48
Thr Ala Gln Phe Val Lys Leu Phe Phe Leu Pro Lys Phe Ile Ser Asn
1               5                   10                  15

tct gat ggt gtc tta                                                 63
Ser Asp Gly Val Leu
            20
```